(12) United States Patent
Lavoie et al.

(10) Patent No.: US 10,287,555 B2
(45) Date of Patent: May 14, 2019

(54) ROTAVIRUS-LIKE PARTICLE PRODUCTION IN PLANTS

(71) Applicants: MEDICAGO, INC., Quebec (CA); MITSUBISHI TANABE PHARMA CORPORATION, Osaka (JP)

(72) Inventors: Pierre-Olivier Lavoie, Quebec (CA); Marc-Andre D'Aoust, Quebec (CA)

(73) Assignee: MITSUBISHI TANABE PHARMA CORPORATION (JP)

(*) Notice: Subject to any disclaimer, the term of this patent is extended or adjusted under 35 U.S.C. 154(b) by 0 days.

(21) Appl. No.: 15/545,362

(22) PCT Filed: Jan. 21, 2016

(86) PCT No.: PCT/CA2016/050043
§ 371 (c)(1),
(2) Date: Jul. 21, 2017

(87) PCT Pub. No.: WO2016/115630
PCT Pub. Date: Jul. 28, 2016

(65) Prior Publication Data
US 2018/0016561 A1     Jan. 18, 2018

Related U.S. Application Data

(60) Provisional application No. 62/106,941, filed on Jan. 23, 2015.

(51) Int. Cl.
| | | |
|---|---|---|
| *C12N 7/04* | (2006.01) | |
| *A61K 39/12* | (2006.01) | |
| *C12N 7/02* | (2006.01) | |
| *C12N 15/82* | (2006.01) | |
| *C12N 15/86* | (2006.01) | |
| *A61K 39/00* | (2006.01) | |

(52) U.S. Cl.
CPC ............. *C12N 7/04* (2013.01); *A61K 39/12* (2013.01); *C12N 7/02* (2013.01); *C12N 15/8257* (2013.01); *C12N 15/86* (2013.01); *A61K 2039/5258* (2013.01); *C12N 2720/12322* (2013.01); *C12N 2720/12323* (2013.01); *C12N 2720/12334* (2013.01); *C12N 2720/12351* (2013.01)

(58) Field of Classification Search
None
See application file for complete search history.

(56) References Cited

U.S. PATENT DOCUMENTS

| | | | |
|---|---|---|---|
| 4,624,850 A | 11/1986 | Albert et al. | |
| 4,636,385 A | 1/1987 | Plotkin et al. | |
| 4,704,275 A | 11/1987 | Wyatt et al. | |
| 4,751,080 A | 6/1988 | Wyatt et al. | |
| 4,927,628 A | 5/1990 | Chanock et al. | |
| 5,474,773 A | 12/1995 | Ward | |
| 5,695,767 A | 12/1997 | Ward | |
| 8,674,084 B2 | 3/2014 | Sainsbury et al. | |
| 2003/0175301 A1 | 9/2003 | Cohen et al. | |
| 2003/0175303 A1 | 9/2003 | Kim et al. | |
| 2005/0186219 A1 | 8/2005 | Langridge et al. | |
| 2010/0239610 A1 | 9/2010 | D'Aoust et al. | |
| 2013/0295609 A1 | 11/2013 | D'Aoust et al. | |

FOREIGN PATENT DOCUMENTS

| | | |
|---|---|---|
| CN | 101978066 A | 2/2011 |
| WO | 01/59070 A1 | 8/2001 |
| WO | 2007081447 A2 | 7/2007 |
| WO | 2007135480 A1 | 11/2007 |
| WO | 2009076778 A1 | 6/2009 |
| WO | 2009087391 A1 | 7/2009 |
| WO | 2009148964 A2 | 12/2009 |
| WO | 2013166609 A1 | 11/2013 |

OTHER PUBLICATIONS

Kavanagh et al. Rotavirus enterotoxin NSP4 has mucosal adjuvant properties. Vaccine 28 (2010) 3106-3111.*
Kim et al. Production of Hybrid Double- or Triple-Layered Virus-Like Particles of Group A and C Rotaviruses Using a Baculovirus Expression System. Virology 302, 1-8 (2002).*
Marashi et al. Intra-peritoneal and intra-rectal immunogenicity induced by rotavirus virus like particles 2/6/7 in mice. Microbial Pathogenesis 67-68 (2014) 48e54.*
Meshcheriakova et al. Fine-tuning levels of heterologous gene expression in plants by orthogonal variation of the untranslated regions of a nonreplicating transient expression system. Plant Biotechnology Journal (2014) 12, pp. 718-727.*
Written Opinion dated Aug. 26, 2016 re SG 11201406996V.
Invitation to Respond to Written Opinion re Singapore application 11201406996V dated Aug. 21, 2017.
Office Action dated Feb. 9, 2017 re TW 102116731 (associates translation).

(Continued)

*Primary Examiner* — Nianxiang Zou
(74) *Attorney, Agent, or Firm* — J.A. Lindeman & Co., PLLC

(57) ABSTRACT

A method of producing a rotavirus-like particle (RLP) in a plant is provided. The method comprises expressing within a host or host cell for example a plant, portion of a plant or plant cell one or more nucleic acid comprising one or more regulatory region operatively linked to a first, second and third nucleotide sequence, the regulatory region active in the host or host cell. The first nucleotide sequence encoding a first rotavirus protein, the second nucleotide sequence encoding a second rotavirus protein and the third nucleotide sequence encoding a third rotavirus protein. The first, second and third encode rotavirus protein NSP4 and VP2 or VP6 and VP4 or VP7. The host or host cell is incubated under conditions that permit the expression of the nucleic acids, so that NSP4 and either VP2 of VP6 and VP4 or VP7 are expressed, thereby producing the RLP. Hosts comprising the RLP, compositions comprising the RLP and method for using the composition are also provided.

25 Claims, 32 Drawing Sheets

Specification includes a Sequence Listing.

(56) References Cited

OTHER PUBLICATIONS

Office Action dated Sep. 3, 2017 re TW 102116731 (associates translation).
Restriction Requirement dated Jun. 6, 2017 in related U.S. Appl. No. 14/398,650.
Office Action dated Oct. 5, 2017 in related U.S. Appl. No. 14/398,650.
Angel, J., Franco, M.A. and Greenberg, H.B. (2007). Rotavirus vaccines: recent developments and future considerations. Nature reviews: Microbiology 5, 529-539.
Arakawa, T., et al. Synthesis of a coltera toxin B subunit-rotavirus NSP4 fusion protein in potato. Plant Cell Reports, 2001, vol. 20:4, pp. 343-348.
Crawford, S.E. et al. Characterization of virus-like particles produced by the expression of rotavirus capsid proteins in insect cells. Journal of Virology. Sep. 1994. vol. 68, No. 9, pp. 5945-5952.
Denisova, E.R., Dowling, W., LaMonica, R., Shaw, R., Scarlata, S., Ruggeri, F. and Mackow, E.R. (1999). Rotavirus Capsid Protein VP5* Permeabilizes Membranes. Journal of Virology 73 3147-3153.
Dennehy, P.H. (2007). Rotavirus vaccines—An update. Vaccine 25, 3137-3141.
Desselberger, U. Rotaviruses. Virus Research vol. 190 (2014) 75-96.
Estes, Mary K. Advances in Molecular Biology : Impact on Rotavirus Vaccine Development. the Journal of Infectious Diseases, 1996, 174 Supplement 1) 537-46.
Fernandez, et al., Passive Immunity to Bovine Rotavirus in Newborn Calves Fed Colostrum Supplements From Cows Immunized with Recombinant SA11 rotavirus core-like particle (CLP) or virus-like particle (VLP) vaccines. Vaccine, 16 (5):507-516 (1998).
Glass, R.I., et al.(2006). Rotavirus vaccines: current prospects and future challenges. Lancet 368, 323-32.
González, A.M., (2004). Antibody responses to human rotavirus (HRV) in gnotobiotic pigs following a new prime/boost vaccine strategy using oral attenuated HRV priming and intranasal VP2/6 rotavirus-like particle (VLP) boosting with ISCOM. Clinical & Experimental Immunology 135 361-372.
González, R.A., (2000). Relative localization of viroplasmic and endoplasmic reticulum-resident rotavirus proteins in infected cells. Archives of Virology 145, 1963-1973.
Greenberg HB, Estes MK (2009) Rotaviruses: from pathogenesis to vaccination. Gastroenterology 136: 1939-1951.
Li, J., et al. Immunogenicity of a plant-derived edible rotavirus subunit vaccine transformed over fifty generations. Virology vol. 356, pp. 171-178. 2006.
Libersou, S., et al. Geometric Mismatches within the Concentric Layers of Rotavirus Particles: a Potential Regulatory Switch of Viral Particle Transcription Activity. J. Virol, Mar. 2008, 82(6), pp. 2844-2852.
Lopez, T., (2005). Silencing the Morphogenesis of Rotavirus. Journal of Virology 79, 184-92.
Lundgren, O. and Svensson, L. (2001). Pathogenesis of Rotavirus diarrhea. Microbes and Infection 3 1145-1156.
Martin, S., et al al. (2002) Ionic Strength- and Temperature-Induced Kca Shifts in the Uncoating Reaction of Rotavirus Strains RF and SA11: Correlation with Membrane Permeabilization. Journal of Virology, 552-559.
Matsumura, T., Itchoda, N. and Tsunemitsu, H. (2002). Production of immunogenic VP6 protein of bovine group A rotavirus in transgenic potato plants. Archives of Virology 147, 1263-1270.
O'Brien, G.J., Bryant, C.J., Voogd, C., Greenberg, H.B., Gardner, R.C. and Bellamy, A.R. (2000). Rotavirus VP6 expressed by PVX vectors in Nicotiana benthamiana coats PVX rods and also assembles into virus-like particles. Virology 270, 444-453.
O'Neal et al. ("Rotavirus Virus-like Particles Administered Mucosally Induce Protective Immunity," J. Virology, 71 (11):8707-8717 (1997).
Palombo, E.A. (1999). Genetic and antigenic diversity of human rotaviruses: potential impact on the success of candidate vaccines. FEMS Microbiology Letters 181, 1-8.

Rahman, M.,et al. Genetic Characterization of a Novel, Naturally Occurring Recombinant Human G6P[6] Rotavrus. J. Clin Microbiol. 41: 2088-2095 (2003).
Rangan, L., et al. Analysis of Context Sequence Surrounding Translation Initiation Site from Complete Genome of Model Plants. Mol. Biotechnol., 2008, vol. 39, pp. 207-213.
Rodriguez-Diaz, J., et al. Oral immunization of mice with Lactococcus lactis expressing the rotavirus VP8* protein. Biotechnology Letters, 2011, vol. 33(6), pp. 1169-1175.
Rodriguez-Diaz, J., et al. Expression and purification of pôlyhistidine-tagged rotavirus NSP4 proteins in insect cells. Protein Expr. Purif. 2003, 31(2), 207-12.
Sainsbury, F., et al. Expression of multiple proteins using full-length and deleted versions of cowpea mosaic virus RNA-2. Plant Biotechnology Journal, vol. 6, 2008, pp. 82-92.
Sainsbury Extremely high-level and rapid transient protein production in plants without the use of viral replication. Plant Physiology. (2008) vol. 148, 1212-1218.
Sainsbury, F., et al. pEAQ: versatile expression vectors for easy and quick transient expression of heterologous proteins in plants. Plant Biotechnology Journal (2009), 7, pp. 682-693.
Sainsbury F. et al. 2009, Methods in Molecular Biology, Recombinant Proteins From Plants, vol. 483: 25-39.
Saldana, S., et al. (2006). Production of rotavirus-like particles in tomato (Lycopersicon esculentum L.) fruit by expression of capsid proteins VP2 and VP6 and immunological studies. Viral Immunology 19, 42-53.
Sanchez-Padilla et al., 2009 Burden of disease and circulating serotypes of rotavirus infection in sub-Saharan Africa: Systematic review and meta-analysis. the Lancet Infectious Diseases., pp 567-576.
Sharifi, Z., et al. Expression of Nonstructural Glycoprotein NSP4 of SA11 simian rotavirus in Escherichia coli and Production of Antibody Against It. Medical Journal of the Islamic Republic of Iren, vol. 17:3, 2003, pp. 217-224.
Thongprachum, A., et al. A noval multiplex RT-PCR for identification of VP6 subgroups of human and porcine rotaviruses. Journal of Virological Methods, vol. 168 (2010) pp. 191-196.
Tian, P., et al. The Rotavirus Nonstructural Glycoprotein NSP4 Mobilizes Ca2+ from the Endoplasmic Reticulum. Journal of Virology, 1995, pp. 5763-5772.
Tian, P., et al. (1996). The Rotavirus Nonstructural Glycoprotein NSP4 Possesses Membrane Destabilization Activity. Journal of Virology 70, 6973-6981.
Varani, G. and Allain, F.H-T. (2002). How a rotavirus hijacks the human protein synthesis machinery. Nature Structural Biology 9, 158-160.
Xu, A., et al. Immobilization of the early secretory pathway by a virus glycoprotein that binds to microtubules. EMBO Journal, 2000, vol. 19:23, pp. 6465-6474.
Yang, Y.M. et al. Immunogenicity and virus-like particle formation of rotavirus capsid proteins produced in transgenic plants. Science China Life Sciences. Jan. 2011. vol. 54, No. 1, pp. 82-89.
Yu, Jie, et al. (2001) A plant-based multicomponent vaccine protects mice from enteric diseases. Nature Biotechnology, vol. 19, 548-552.
Zhou B. et al.(2010). Oral administration of plant-based rotavirus VP6 induces antigen-specific IgAs, IgGs and passive protection in mice. Vaccine 28, 6021-6027.
Aoki, S., et al. Structure of rotavirus outer-layer protein VP7 bound with a neutralizing Fab. Science, 2009, vol. 324:5933, pp. 1444-1447.
Mitsubishi Tanabe Pharma Corporation, Conclusion of Research Collaboration Agreement for Next-Generation Vaccines. Mar. 2012.
Rongxiang Fang, Carrot as a bioreactor to produce vaccines against rotavirus and enteropathogenic E coli. Annual Report 2005.
Choi, A., et al. Intranassal administration of an Escherichia coli-expressed codon-optimized rotavirus VP6 protein induces protection in mice. Protein Expression and Purification 38 (2004), pp. 205-216.
Cortez-Perez, N., et al. Rotavirus-like particles: A novel nanocarrier for the Gut. Journal of Biomedicine and Biotechnology, 2010, vol. 317545, pp. 1-10.

(56) References Cited

OTHER PUBLICATIONS

Desselberger, U. et al. Immune responses to rotavirus infection and vaccination and associated correlates of protection. J. Infect Dis., 2011, vol. 203:2, pp. 188-195.
Emslie, Kerry R., et al. Expression of the Rotavirus SA11 Protein VP7 in the Simple Eukaryote Dictyostelium discoideum. J. of Virology, 1995, pp. 1747-1754.
Estes, M.K., et al. Rotavirus gene structure and function. Microbiology Rev. 1989, vol. 53:4, pp. 410-449.
GenBank P11231.1 (2008) from related U.S. Appl. No. 14/398,650.
GenBank P03530.1 (2008) from related U.S. Appl. No. 14/398,650.
GenBank ADO078484 (2010) from related U.S. Appl. No. 14/398,650.
GenBank ADD22465.1 (2010) from related U.S. Appl. No. 14/398,650.
Gomord, V., et al. Posttranslational modification of therapeutic proteins in plants. Current Opinion in Plant Biology, 2004, vol. 7:2, pp. 171-181.
Madore, H.P., et al. (1999). Biochemical and immunologic comparison of virus-like particles for a rotavirus subunit vaccine. Vaccine 17, 2461-2471.
Mathis, P.K., et al. Separation of rotavirus double-layered particles and triple-layered particles by capillary zone electrophoresis. J. Virol Methods., 2010, vol. 169:1, pp. 13-21.
MacLean, J., et al. Optimization of h uman papillomavirus type 16 (HPV-16) L1 expression in plants: comparison of the suitability of different HPV-16 L1 gene variants and different cell-compartment localization. Journal of General Virology (2007), vol. 88, pp. 1460-1469.
Nagels, B., et al. Production of Plant Made Pharmaceuticals: From Plant Host to Functional Protein. Critical Reviews in Plant Sciences, 2015, vol. 31:2, pp. 148-180.
Redmond, M.J., et al. Assembly of recombinant rotavirus proteins into virus-like particles and assessment of vaccine potential. Vaccine, vol. 11:2, 1993, pp. 273-281.
Rodriguez-Limas, W.A., Tyo, K.E.J., Nielsen, J., Ramirez, O.T. and Palomares, L.A. (2011). Molecular and process design for rotavirus-like particle production in *Saccharomyces cerevisiae*. Microb Cell Fact. 10, 33.
Trask, S., et al. Assembly of Highly Infectious Rotavirus Particles Recoated with Recombinant Outer Capsid Proteins. Journal of Virology, vol. 80:22, 2006, pp. 11293-11304.
Vieira, H., et al. Triple Layers Rotavirus VLP Production: Kinetics of Vector Replication, mRNA stability and recombinant protein production. Journal of Biotechnology, 2005, vol. 120:1, pp. 72-82.
CA 2,872,803 Office Action dated Jan. 27, 2015.
CA 2,872,803 Office Action dated May 29, 2015.
CA 2,872,803 Office Action dated Sep. 8, 2015.
CA 2,872,803 Office Action dated Jan. 26, 2016.
Office Action dated Sep. 18, 2015 re CN 201380024759.7 (associate's translation).
Office Action dated Jul. 20, 2016 re CN 2013800247597 (associate's translation).
Office Action dated Apr. 13, 2017 re CN 2017041001329450 (associate's translation).
Office Action dated Feb. 17, 2016 re EA 201492014 (associate's translation).
Office Action dated Apr. 3, 2017 re EA 201492014 (associate's translation).
Partial Supp. Search report Dec. 2, 2015 re EP 13787880.
Extended Search Report dated Feb. 22, 2016 re EP 13787880.7.
Office Action dated Nov. 18, 2016 re EP 13787880.7.
Office Action dated Mar. 24, 2017 re EP 13 787 880.7.
Intent to Grant EP 13787880.7 dated Jul. 19, 2017.
Office Action dated Feb. 19, 2017 re IL235290 (associate's translation).
International Search Report and Written Opinion in International Application No. PCT/CA2013/050364 dated Aug. 5, 2013.
JP 2015-510591 Office Action dated Apr. 18, 2017 (associate's translation).
Office Action dated Jun. 11, 2016 re MX/a/014/013671 (associate's translation).
Office Action dated Feb. 1, 2017 re MX/a/2014/013671 (associate's translation).
Office Action dated Oct. 4, 2017 re MX/a/2014/013671.
Written Opinion dated Dec. 8, 2015 re SG 11201406996V.

\* cited by examiner

Figure 6
A) CPMV-HT
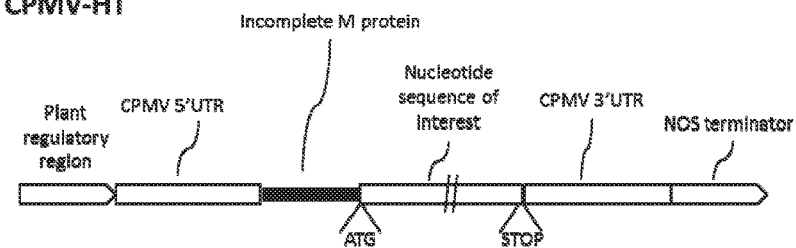
B) CPMV-HT+
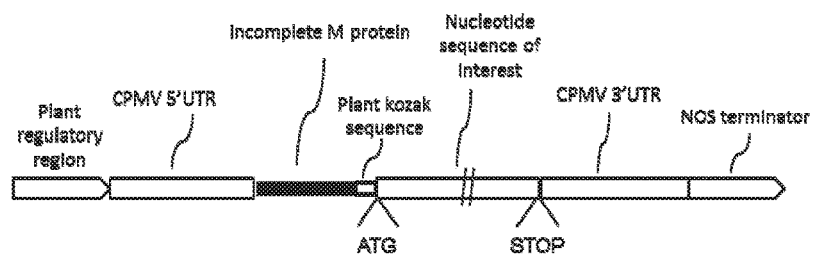
C) Construct comprising CPMV160
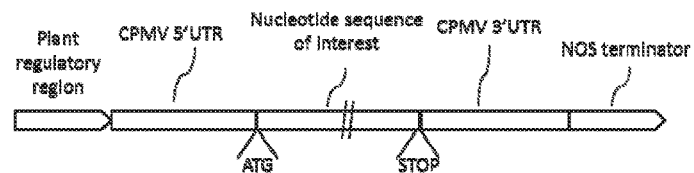
D) Construct comprising CPMV160+
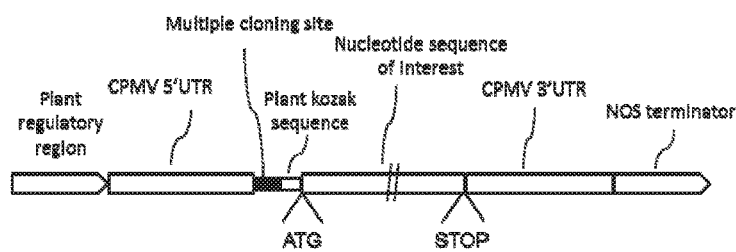

1. 2X35S/CPMV-HT/ RVA(WA) VP2(opt)/ NOS (Construct number 1710)

Figure 7A, SEQ ID NO: 19

IF-WA_VP2(opt).s1+3c

AAATTTGTCGGGCCCATGGCATACCGGAAGAGAGGAGCAAAGCGCGAA

Figure 7B, SEQ ID NO: 20

IF-WA_VP2(opt).s1-4r

ACTAAAGAAAATAGGCCTTTAAAGCTCGTTCATTATTCGCATATTGTCGA

Figure 7C, SEQ ID NO: 21

Optimized coding sequence of Rotavirus A VP2 from strain WA

ATGGCATACCGGAAGAGAGGAGCAAAGCGCGAAAACCTGCCGCAACAGAACGAGAGACTGCAAGAAAAAGAGAT
AGAGAAAGATGTCGACGTAACAATGGAAAACAAGAATAACAATAGGAAACAACAGCTGTCCGACAAAGTTCTGTCC
CAGAAGGAGGAAATTATCACTGACGCCCAGGACGATATTAAAATTGCCGGAGAAATAAAGAAGAGCTCGAAAGAA
GAATCTAAACAGCTGCTCGAAATTCTGAAAACAAAAGAAGACCATCAGAAAGAGATTCAATATGAAATTTTGCAAAA
AACAATACCTACATTTGAGTCCAAAGAAAGTATCCTCAAGAAGCTTGAAGACATAAGACCGGAGCAGGCAAAAAAA
CAGATGAAACTCTTTCGCATTTTCGAGCCAAAACAGCTCCCTATATATCGCGCCAATGGCGAGAAGGAGCTACGCAA
CCGGTGGTACTGGAAGTTGAAAAAGACACCCTGCCAGATGGAGATTATGACGTCCGGAGTATTTCCTCAATCTCT
ATGATCAGATCCTCATCGAAATGCCGGACTATCTGCTCCTCAAGGACATGGCCGTGGAGAACAAAAATAGCAGAGA
CGCCGGCAAAGTTGTCGACTCTGAGACTGCCAATATTTGTGATGCCATCTTCCAGGATGAGGAGACCGAGGGAGTC
GTCCGTAGATTCATCGCTGATATGCGGCAACAGGTCCAGGCTGATCGTAACATTGTCAATTACCCTTCCATCCTTCAC
CCTATTGATCATGCATTCAATGAGTATTTTCTTAACCACCAGTTGGTGGAGCCGCTGAACAATGAGATAATCTTCAAT
TACATACCAGAGAGGATAAGGAATGACGTGAATTACATCCTGAACATGGATATGAATCTGCCATCTACAGCCAGGT
ATATCAGGCCAAACTTGTTGCAGGATAGACTGAATCTTCACGATAATTTTGAGTCCCTGTGGGATACCATCACAACAT
CCAACTACATTCTGGCCAGGTCCGTCGTTCCCGATTTGAAGGAGAAGGAGCTGGTCTCCACCGAAGCACAGATCCAG
AAAATGAGCCAGGACCTGCAGCTGGAGGCCCTCACTATTCAGAGCGAGACACAGTTTTTAGCCGGGATTAACAGTC
AGGCTGCCAATGATTGTTTCAAGACCCTCATAGCCGCCATGCTGTCTCAAAGAACCATGTCTTTGGACTTTGTGACCA
CGAACTATATGAGCCTAATCTCCGGAATGTGGCTACTTACAGTGATTCCCAACGATATGTTCCTCCGGGAGTCACTAG
TGGCCTGTGAGCTGGCGATCATCAACACCATCGTGTATCCAGCATTCGGAATGCAGAGAATGCATTACCGGAATGG
CGACCCTCAGACACCCTTCCAGATCGCAGAACAGCAGATCCAGAATTTCCAGGTGGCGAACTGGCTCCATTTTATTA
ACAATAACAGATTCAGGCAAGTTGTGATTGATGGAGTTCTGAATCAGACTCTGAACGACAATATACGGAATGGACA
GGTCATCAACCAGCTGATGGAAGCATTGATGCAACTCAGCAGACAGCAGTTCCCCACGATGCCTGTGGATTACAAAC
GGAGCATCCAACGGGGCATTCTGCTTCTCTCCAATAGGCTGGGGCAGCTTGTCGACTTAACCCGACTGGTCTCCTAT
AACTACGAGACGCTAATGGCTTGTGTGACCATGAACATGCAGCACGTGCAAACCCTGACAACTGAGAAGTTGCAGC
TCACTTCTGTGACTTCGCTTTGTATGTTAATTGGTAACACAACCGTGATTCCGTCCCCACAGACACTGTTCCACTACTA
CAACATCAACGTGAATTTCCACTCCAATTATAATGAGCGGATCAACGACGCCGTCGCCATAATTACCGCAGCAAATA
GGCTGAATCTTTATCAGAAAAAAATGAAGTCCATAGTGGAAGACTTTCTGAAACGGCTCCAGATTTTCGACGTACCA
CGAGTGCCTGACGACCAAATGTACAGGCTGAGGGATCGCCTTCGGCTCTTACCCGTTGAACGGAGACGGCTTGACA
TATTCAACTTGATCCTGATGAATATGGAGCAGATCGAACGCGCTTCTGATAAGATTGCTCAGGGGGTTATCATCGCA
TACCGAGATATGCAGCTGGAACGCGACGAGATGTACGGATATGTTAATATTGCACGGAATCTTGATGGCTACCAGC

Figure 7C continued

AAATTAACTTGGAGGAACTCATGCGCACCGGTGATTACGGACAAATTACGAACATGCTTCTCAACAATCAACCCGTT
GCCCTTGTGGGTGCATTGCCCTTCGTTACGGACTCATCCGTGATCAGTCTAATCGCCAAGCTCGACGCAACCGTCTTC
GCTCAGATAGTGAAGCTCAGGAAAGTTGACACACTGAAGCCCATACTGTACAAAATAAACTCGGATTCCAATGACTT
TTACCTTGTGGCCAACTACGACTGGATCCCCACAAGTACAACTAAGGTCTACAAACAGGTGCCACAACCATTCGACTT
TAGAGCCAGCATGCACATGCTGACTTCTAACCTTACGTTTACCGTCTACTCTGACCTACTGTCATTTGTTTCAGCGGAC
ACGGTAGAGCCCATTAACGCAGTCGCATTCGACAATATGCGAATAATGAACGAGCTTTAA

Figure 7D

Schematic representation of construct 1191. SacII and StuI restriction enzyme sites used for plasmid linearization are annotated on the representation.

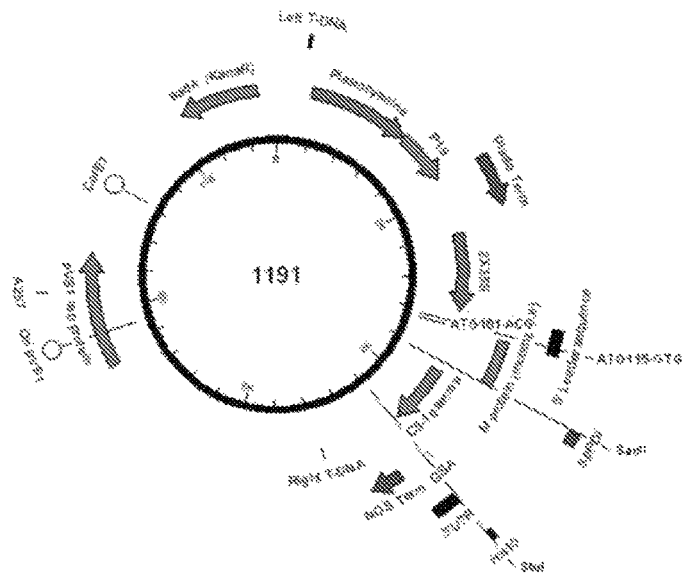

Figure 7E, SEQ ID NO: 22

Construct 1191 from left to right t-DNA borders (underlined). 2X35S/CPMV-HT/NOS with Plastocyanine-P19-Plastocyanine silencing inhibitor expression cassette <u>TGGCAGGATATATTGTGGTGTAAAC</u>AAATTGACGCTTAGACAACTTAATAACACATTGCGGACGTTTTTAATGTACTGAATTAACG
CCGAATCCCGGGCTGGTATATTTATATGTTGTCAAATAACTCAAAAACCATAAAAGTTTAAGTTAGCAAGTGTGTACATTTTTACTT
GAACAAAAATATTCACCTACTACTGTTATAAATCATTATTAAACATTAGAGTAAAGAAATATGGATGATAAGAACAAGAGTAGTGA
TATTTTGACAACAATTTTGTTGCAACATTTGAGAAAATTTTGTTGTTCTCTCTTTTCATTGGTCAAAAACAATAGAGAGAGAAAAAG
GAAGAGGGAGAATAAAAACATAATGTGAGTATGAGAGAGAAAGTTGTACAAAAGTTGTACCAAAATAGTTGTACAAATATCATT
GAGGAATTTGACAAAAGCTACACAAATAAGGGTTAATTGCTGTAAATAAATAAGGATGACGCATTAGAGAGATGTACCATTAGAG
AATTTTTGGCAAGTCATTAAAAAGAAAGAATAAATTATTTTTAAAATTAAAAGTTGAGTCATTTGATTAAACATGTGATTATTTAAT
GAATTGATGAAAGAGTTGGATTAAAGTTGTATTAGTAATTAGAATTTGGTGTCAAATTTAATTTGACATTTGATCTTTTCCTATATA
TTGCCCCATAGAGTCAGTTAACTCATTTTTATATTTCATAGATCAAATAAGAGAAATAACGGTATATTAATCCCTCCAAAAAAAAAA
AACGGTATATTTACTAAAAAATCTAAGCCACGTAGGAGGATAACAGGATCCCCGTAGGAGGATAACATCCAATCCAACCAATCAC
AACAATCCTGATGAGATAACCCACTTTAAGCCCACGCATCTGTGGCACATCTACATTATCTAAATCACACATTCTTCCACACATCTG

Figure 7E continued

```
AGCCACACAAAAACCAATCCACATCTTTATCACCCATTCTATAAAAAATCACACTTTGTGAGTCTACACTTTGATTCCCTTCAAACAC
ATACAAAGAGAAGAGACTAATTAATTAATTAATCATCTTGAGAGAAAATGGAACGAGCTATACAAGGAAACGACGCTAGGGAAC
AAGCTAACAGTGAACGTTGGGATGGAGGATCAGGAGGTACCACTTCTCCCTTCAAACTTCCTGACGAAAGTCCGAGTTGGACTGA
GTGGCGGCTACATAACGATGAGACGAATTCGAATCAAGATAATCCCCTTGGTTTCAAGGAAAGCTGGGGTTTCGGGAAAGTTGTA
TTTAAGAGATATCTCAGATACGACAGGACGGAAGCTTCACTGCACAGAGTCCTTGGATCTTGGACGGGAGATTCGGTTAACTATG
CAGCATCTCGATTTTTCGGTTTCGACCAGATCGGATGTACCTATAGTATTCGGTTTCGAGGAGTTAGTATCACCGTTTCTGGAGGG
TCGCGAACTCTTCAGCATCTCTGTGAGATGGCAATTCGGTCTAAGCAAGAACTGCTACAGCTTGCCCCAATCGAAGTGGAAAGTA
ATGTATCAAGAGGATGCCCTGAAGGTACTCAAACCTTCGAAAAAGAAAGCGAGTAAGTTAAAATGCTTCTTCGTCTCCTATTTATA
ATATGGTTTGTTATTGTTAATTTTGTTCTTGTAGAAGAGCTTAATTAATCGTTGTTGTTATGAAATACTATTTGTATGAGATGAACTG
GTGTAATGTAATTCATTTACATAAGTGGAGTCAGAATCAGAATGTTTCCTCCATAACTAACTAGACATGAAGACCTGCCGCGTACA
ATTGTCTTATATTTGAACAACTAAAATTGAACATCTTTTGCCACAACTTTATAAGTGGTTAATATAGCTCAAATATATGGTCAAGTTC
AATAGATTAATAATGGAAATATCAGTTATCGAAATTCATTAACAATCAACTTAACGTTATTAACTACTAATTTTATATCATCCCCTTT
GATAAATGATAGTACACCAATTAGGAAGGAGCATGCTCGCCTAGGAGATTGTCGTTTCCCGCCTTCAGTTTGCAAGCTGCTCTAGC
CGTGTAGCCAATACGCAAACCGCCTCTCCCCGCGCGTTGGGAATTACTAGCGCGTGTCGACAAGCTTGCATGCCGGTCAACATGG
TGGAGCACGACACACTTGTCTACTCCAAAAATATCAAAGATACAGTCTCAGAAGACCAAAGGGCAATTGAGACTTTTCAACAAAG
GGTAATATCCGGAAACCTCCTCGGATTCCATTGCCCAGCTATCTGTCACTTTATTGTGAAGATAGTGGAAAAGGAAGGTGGCTCCT
ACAAATGCCATCATTGCGATAAAGGAAAGGCCATCGTTGAAGATGCCTCTGCCGACAGTGGTCCCAAAGATGGACCCCCACCCAC
GAGGAGCATCGTGGAAAAAGAAGACGTTCCAACCACGTCTTCAAAGCAAGTGGATTGATGTGATAACATGGTGGAGCACGACAC
ACTTGTCTACTCCAAAAATATCAAAGATACAGTCTCAGAAGACCAAAGGGCAATTGAGACTTTTCAACAAAGGGTAATATCCGGA
AACCTCCTCGGATTCCATTGCCCAGCTATCTGTCACTTTATTGTGAAGATAGTGGAAAAGGAAGGTGGCTCCTACAAATGCCATCA
TTGCGATAAAGGAAAGGCCATCGTTGAAGATGCCTCTGCCGACAGTGGTCCCAAAGATGGACCCCCACCCACGAGGAGCATCGT
GGAAAAAGAAGACGTTCCAACCACGTCTTCAAAGCAAGTGGATTGATGTGATATCTCCACTGACGTAAGGGATGACGCACAATCC
CACTATCCTTCGCAAGACCCTTCCTCTATATAAGGAAGTTCATTTCATTTGGAGAGGTATTAAAATCTTAATAGGTTTTGATAAAAG
CGAACGTGGGGAAACCCGAACCAAACCTTCTTCTAAACTCTCTCTCATCTCTCTTAAAGCAAACTTCTCTCTTGTCTTTCTTGCGTGA
GCGATCTTCAACGTTGTCAGATCGTGCTTCGGCACCAGTACAACGTTTTCTTTCACTGAAGCGAAATCAAAGATCTCTTTGTGGACA
CGTAGTGCGGCGCCATTAAATAACGTGTACTTGTCCTATTCTTGTCGGTGTGGTCTTGGGAAAAGAAAGCTTGCTGGAGGCTGCT
GTTCAGCCCCATACATTACTTGTTACGATTCTGCTGACTTTCGGCGGGTGCAATATCTCTACTTCTGCTTGACGAGGTATTGTTGCCT
GTACTTCTTTCTTCTTCTTCTTGCTGATTGGTTCTATAAGAAATCTAGTATTTTCTTTGAAACAGAGTTTTCCCGTGGTTTTCGAACTT
GGGAGAAAGATTGTTAAGCTTCTGTATATTCTGCCCAAATTTGTCGGGCCCGCGGATGGCGAAAAACGTTGCGATTTTCGGCTTATT
GTTTTCTCTTCTTGTGTTGGTTCCTTCTCAGATCTTCGCCTGCAGGCTCCTCAGCCAAAACGACACCCCCATCTGTCTATCCACTGGC
CCCTGGATCTGCTGCCCAAACTAACTCCATGGTGACCCTGGGATGCCTGGTCAAGGGCTATTTCCCTGAGCCAGTGACAGTGACCT
GGAACTCTGGATCCCTGTCCAGCGGTGTGCACACCTTCCCAGCTGTCCTGCAGTCTGACCTCTACACTCTGAGCAGCTCAGTGACT
GTCCCCTCCAGCACCTGGCCCAGCGAGACCGTCACCTGCAACGTTGCCCACCCGGCCAGCAGCACCAAGGTGGACAAGAAAATTG
TGCCCAGGGATTGTGGTTGTAAGCCTTGCATATGTACAGTCCCAGAAGTATCATCTGTCTTCATCTTCCCCCCAAAGCCCAAGGAT
GTGCTCACCATTACTCTGACTCCTAAGGTCACGTGTGTTGTGGTAGACATCAGCAAGGATGATCCCGAGGTCCAGTTCAGCTGGTT
TGTAGATGATGTGGAGGTGCACACAGCTCAGACGCAACCCCGGGAGGAGCAGTTCAACAGCACTTTCCGCTCAGTCAGTGAACTT
CCCATCATGCACCAGGACTGGCTCAATGGCAAGGAGCGATCGCTCACCATCACCATCACCATCACCATCACCATTAAAGGCCTATT
TTCTTTAGTTTGAATTTACTGTTATTCGGTGTGCATTTCTATGTTTGGTGAGCGGTTTTCTGTGCTCAGAGTGTGTTTATTTTATGTA
ATTTAATTTCTTTGTGAGCTCCTGTTTAGCAGGTCGTCCCTTCAGCAAGGACACAAAAAGATTTTAATTTTATTAAAAAAAAAAAAA
AAAAAGACCGGGAATTCGATATCAAGCTTATCGACCTGCAGATCGTTCAAACATTTGGCAATAAAGTTTCTTAAGATTGAATCCTG
TTGCCGGTCTTGCGATGATTATCATATAATTTCTGTTGAATTACGTTAAGCATGTAATAATTAACATGTAATGCATGACGTTATTTAT
GAGATGGGTTTTTATGATTAGAGTCCCGCAATTATACATTTAATACGCGATAGAAAACAAAATATAGCGCGCAAACTAGGATAAA
TTATCGCGCGCGGTGTCATCTATGTTACTAGATCTCTAGAGTCTCAAGCTTGGCGCGCCCACGTGACTAGTGGCACTGGCCGTCGT
TTTACAACGTCGTGACTGGGAAAACCCTGGCGTTACCCAACTTAATCGCCTTGCAGCACATCCCCCTTTCGCCAGCTGGCGTAATA
GCGAAGAGGCCCGCACCGATCGCCCTTCCCAACAGTTGCGCAGCCTGAATGGCGAATGCTAGAGCAGCTTGAGCTTGGATCAGAT
TGTCGTTTCCCGCCTTCAGTTTAAACTATCAGTGTTTGACAGGATATATTGGCGGGTAAACCTAAGAGAAAAGAGCGTTTA
```

Figure 7F, SEQ ID NO: 23

Expression cassette number 1710 from 2X35S promoter to NOS terminator. VP2(opt) from Rotavirus A WA strain is underlined.

GTCAACATGGTGGAGCACGACACACTTGTCTACTCCAAAAATATCAAAGATACAGTCTCAGAAGACCAAAGGGCAATTGAGACTT
TTCAACAAAGGGTAATATCCGGAAACCTCCTCGGATTCCATTGCCCAGCTATCTGTCACTTTATTGTGAAGATAGTGGAAAAGGAA
GGTGGCTCCTACAAATGCCATCATTGCGATAAAGGAAAGGCCATCGTTGAAGATGCCTCTGCCGACAGTGGTCCCAAAGATGGAC
CCCCACCCACGAGGAGCATCGTGGAAAAAGAAGACGTTCCAACCACGTCTTCAAAGCAAGTGGATTGATGTGATAACATGGTGG
AGCACGACACACTTGTCTACTCCAAAAATATCAAAGATACAGTCTCAGAAGACCAAAGGGCAATTGAGACTTTTCAACAAAGGGT
AATATCCGGAAACCTCCTCGGATTCCATTGCCCAGCTATCTGTCACTTTATTGTGAAGATAGTGGAAAAGGAAGGTGGCTCCTACA
AATGCCATCATTGCGATAAAGGAAAGGCCATCGTTGAAGATGCCTCTGCCGACAGTGGTCCCAAAGATGGACCCCCACCCACGAG
GAGCATCGTGGAAAAAGAAGACGTTCCAACCACGTCTTCAAAGCAAGTGGATTGATGTGATATCTCCACTGACGTAAGGGATGAC
GCACAATCCCACTATCCTTCGCAAGACCCTTCCTCTATATAAGGAAGTTCATTTCATTTGGAGAGGTATTAAAATCTTAATAGGTTTT
GATAAAAGCGAACGTGGGGAAACCCGAACCAAACCTTCTTCTAAACTCTCTCTCATCTCTCTTAAAGCAAACTTCTCTCTTGTCTTTC
TTGCGTGAGCGATCTTCAACGTTGTCAGATCGTGCTTCGGCACCAGTACAACGTTTTCTTTCACTGAAGCGAAATCAAAGATCTCTT
TGTGGACACGTAGTGCGGCGCCATTAAATAACGTGTACTTGTCCTATTCTTGTCGGTGTGGTCTTGGGAAAAGAAAGCTTGCTGG
AGGCTGCTGTTCAGCCCCATACATTACTTGTTACGATTCTGCTGACTTTCGGCGGGTGCAATATCTCTACTTCTGCTTGACGAGGTA
TTGTTGCCTGTACTTCTTTCTTCTTCTTCTTGCTGATTGGTTCTATAAGAAATCTAGTATTTTCTTTGAAACAGAGTTTTCCCGTGGTT
TTCGAACTTGGAGAAAGATTGTTAAGCTTCTGTATATTCTGCCCAAATTTGTCGGGCCC<u>ATGGCATACCGGAAGAGAGGAGCAAA
GCGCGAAAACCTGCCGCAACAGAACGAGAGACTGCAAGAAAAAGAGATAGAGAAAGATGTCGACGTAACAATGGAAAACAAGA
ATAACAATAGGAAACAACAGCTGTCCGACAAAGTTCTGTCCCAGAAGGAGGAAATTATCACTGACGCCCAGGACGATATTAAAAT
TGCCGGAGAAATAAAGAAGAGCTCGAAAGAAGAATCTAAACAGCTGCTCGAAATTCTGAAAACAAAAGAAGACCATCAGAAAGA
GATTCAATATGAAATTTTGCAAAAAACAATACCTACATTTGAGTCCAAAGAAAGTATCCTCAAGAAGCTTGAAGACATAAGACCGG
AGCAGGCAAAAAAACAGATGAAACTCTTTCGCATTTTCGAGCCAAAACAGCTCCCTATATATCGCGCCAATGGCGAGAAGGAGCT
ACGCAACCGGTGGTACTGGAAGTTGAAAAAAGACACCCTGCCAGATGGAGATTATGACGTCCGGGAGTATTTCCTCAATCTCTAT
GATCAGATCCTCATCGAAATGCCGGACTATCTGCTCCTCAAGGACATGGCCGTGGAGAACAAAAATAGCAGAGACGCCGGCAAA
GTTGTCGACTCTGAGACTGCCAATATTTGTGATGCCATCTTCCAGGATGAGGAGACCGAGGGAGTCGTCCGTAGATTCATCGCTG
ATATGCGGCAACAGGTCCAGGCTGATCGTAACATTGTCAATTACCCTTCCATCCTTCACCCTATTGATCATGCATTCAATGAGTATT
TTCTTAACCACCAGTTGGTGGAGCCGCTGAACAATGAGATAATCTTCAATTACATACCAGAGAGGATAAGGAATGACGTGAATTA
CATCCTGAACATGGATATGAATCTGCCATCTACAGCCAGGTATATCAGGCCAAACTTGTTGCAGGATAGACTGAATCTTCACGATA
ATTTTGAGTCCCTGTGGGATACCATCACAACATCCAACTACATTCTGGCCAGGTCCGTCGTTCCCGATTTGAAGGAGAAGGAGCTG
GTCTCCACCGAAGCACAGATCCAGAAAATGAGCCAGGACCTGCAGCTGGAGGCCCTCACTATTCAGAGCGAGACACAGTTTTTAG
CCGGGATTAACAGTCAGGCTGCCAATGATTGTTTCAAGACCCTCATAGCCGCCATGCTGTCTCAAAGAACCATGTCTTTGGACTTT
GTGACCACGAACTATATGAGCCTAATCTCCGGAATGTGGCTACTTACAGTGATTCCCAACGATATGTTCCTCCGGGAGTCACTAGT
GGCCTGTGAGCTGGCGATCATCAACACCATCGTGTATCCAGCATTCGGAATGCAGAGAATGCATTACCGGAATGGCGACCCTCAG
ACACCCTTCCAGATCGCAGAACAGCAGATCCAGAATTTCCAGGTGGCGAACTGGCTCCATTTTATTAACAATAACAGATTCAGGCA
AGTTGTGATTGATGGAGTTCTGAATCAGACTCTGAACGACAATATACGGAATGGACAGGTCATCAACCAGCTGATGGAAGCATTG
ATGCAACTCAGCAGACAGCAGTTCCCCACGATGCCTGTGGATTACAAACGGAGCATCCAACGGGGCATTCTGCTTCTCTCCAATAG
GCTGGGGCAGCTTGTCGACTTAACCCGACTGGTCTCCTATAACTACGAGACGCTAATGGCTTGTGTGACCATGAACATGCAGCAC
GTGCAAACCCTGACAACTGAGAAGTTGCAGCTCACTTCTGTGACTTCGCTTTGTATGTTAATTGGTAACACAACCGTGATTCCGTCC
CCACAGACACTGTTCCACTACTACAACATCAACGTGAATTTCCACTCCAATTATAATGAGCGGATCAACGACGCCGTCGCCATAATT
ACCGCAGCAAATAGGCTGAATCTTTATCAGAAAAAAATGAAGTCCATAGTGGAAGACTTTCTGAAACGGCTCCAGATTTTCGACG
TACCACGAGTGCCTGACGACCAAATGTACAGGCTGAGGGATCGCCTTCGGCTCTTACCCGTTGAACGGAGACGGCTTGACATATT
CAACTTGATCCTGATGAATATGGAGCAGATCGAACGCGCTTCTGATAAGATTGCTCAGGGGGTTATCATCGCATACCGAGATATG
CAGCTGGAACGCGACGAGATGTACGGATATGTTAATATTGCACGGAATCTTGATGGCTACCAGCAAATTAACTTGGAGGAACTCA
TGCGCACCGGTGATTACGGACAAATTACGAACATGCTTCTCAACAATCAACCCGTTGCCCTTGTGGGTGCATTGCCCTTCGTTACG
GACTCATCCGTGATCAGTCTAATCGCCAAGCTCGACGCAACCGTCTTCGCTCAGATAGTGAAGCTCAGGAAAGTTGACACACTGA
AGCCCATACTGTACAAAATAAACTCGGATTCCAATGACTTTTACCTTGTGGCCAACTACGACTGGATCCCCACAAGTACAACTAAG</u>

Figure 7F continued

GTCTACAAACAGGTGCCACAACCATTCGACTTTAGAGCCAGCATGCACATGCTGACTTCTAACCTTACGTTTACCGTCTACTCTGAC
CTACTGTCATTTGTTTCAGCGGACACGGTAGAGCCCATTAACGCAGTCGCATTCGACAATATGCGAATAATGAACGAGCTTTAAAG
GCCTATTTTCTTTAGTTTGAATTTACTGTTATTCGGTGTGCATTTCTATGTTTGGTGAGCGGTTTTCTGTGCTCAGAGTGTGTTTATTT
TATGTAATTTAATTTCTTTGTGAGCTCCTGTTTAGCAGGTCGTCCCTTCAGCAAGGACACAAAAAGATTTTAATTTTATTAAAAAAA
AAAAAAAAAAAGACCGGGAATTCGATATCAAGCTTATCGACCTGCAGATCGTTCAAACATTTGGCAATAAAGTTTCTTAAGATTGA
ATCCTGTTGCCGGTCTTGCGATGATTATCATATAATTTCTGTTGAATTACGTTAAGCATGTAATAATTAACATGTAATGCATGACGT
TATTTATGAGATGGGTTTTTATGATTAGAGTCCCGCAATTATACATTTAATACGCGATAGAAAACAAAATATAGCGCGCAAACTAG
GATAAATTATCGCGCGCGGTGTCATCTATGTTACTAGAT

Figure 7G, SEQ ID NO: 24

Amino acid sequence of VP2 from Rotavirus A WA strain

MAYRKRGAKRENLPQQNERLQEKEIEKDVDVTMENKNNNRKQQLSDKVLSQKEEIITDAQDDIKIAGEIKKSSKEESKQLLEILKTKEDH
QKEIQYEILQKTIPTFESKESILKKLEDIRPEQAKKQMKLFRIFEPKQLPIYRANGEKELRNRWYWKLKKDTLPDGDYDVREYFLNLYDQILIE
MPDYLLLKDMAVENKNSRDAGKVVDSETANICDAIFQDEETEGVVRRFIADMRQQVQADRNIVNYPSILHPIDHAFNEYFLNHQLVEP
LNNEIIFNYIPERIRNDVNYILNMDMNLPSTARYIRPNLLQDRLNLHDNFESLWDTITTSNYILARSVVPDLKEKELVSTEAQIQKMSQDL
QLEALTIQSETQFLAGINSQAANDCFKTLIAAMLSQRTMSLDFVTTNYMSLISGMWLLTVIPNDMFLRESLVACELAIINTIVYPAFGMQ
RMHYRNGDPQTPFQIAEQQIQNFQVANWLHFINNNRFRQVVIDGVLNQTLNDNIRNGQVINQLMEALMQLSRQQFPTMPVDYKRS
IQRGILLLSNRLGQLVDLTRLVSYNYETLMACVTMNMQHVQTLTTEKLQLTSVTSLCMLIGNTTVIPSPQTLFHYYNINVNFHSNYNERIN
DAVAIITAANRLNLYQKKMKSIVEDFLKRLQIFDVPRVPDDQMYRLRDRLRLLPVERRRLDIFNLILMNMEQIERASDKIAQGVIIAYRDM
QLERDEMYGYVNIARNLDGYQQINLEELMRTGDYGQITNMLLNNQPVALVGALPFVTDSSVISLIAKLDATVFAQIVKLRKVDTLKPILY
KINSDSNDFYLVANYDWIPTSTTKVYKQVPQPFDFRASMHMLTSNLTFTVYSDLLSFVSADTVEPINAVAFDNMRIMNEL

Figure 7H Schematic representation of construct number 1710

2. 2X35S/CPMV-HT/RVA(WA) VP6(opt)/NOS (Construct number 1713)

Figure 8A, SEQ ID NO: 25

IF-WA_VP6(opt).s1+3c

AAATTTGTCGGGCCCATGGAGGTCCTTTATAGTCTCTCCAAAACGCTGA

Figure 8B, SEQ ID NO: 26

IF-WA_VP6(opt).s1-4r

ACTAAAGAAAATAGGCCTCTACTTGATCAACATACTCCGGATAGAGGCCACA

Figure 8C, SEQ ID NO :27

Optimized coding sequence of Rotavirus A VP6 from strain WA

ATGGAGGTCCTTTATAGTCTCTCCAAAACGCTGAAGGACGCTAGGGACAAGATCGTGGAGGGTACACTTTATAGCAATGTCAGCG
ACCTAATACAGCAGTTTAATCAAATGATCGTTACAATGAATGGGAATGATTTCCAAACTGGCGGTATTGGTAATCTGCCCGTGAGG
AACTGGACATTCGATTTCGGCCTGCTGGGCACGACTCTCCTTAATCTCGATGCAAATTATGTAGAAAACGCCAGAACGATTATCGA
GTACTTTATCGATTTCATTGATAACGTTTGTATGGATGAGATGGCCCGCGAGTCACAACGGAACGGAGTTGCTCCACAGTCCGAG
GCCCTTCGGAAACTCGCCGGCATTAAGTTCAAGCGTATTAATTTCGACAACTCCTCCGAATATATAGAGAACTGGAACTTGCAGAA
TCGTCGACAGAGAACCGGCTTCGTGTTCCATAAACCTAATATCTTTCCGTATAGCGCCTCATTCACCCTGAATAGGAGTCAGCCCAT
GCACGACAACCTCATGGGTACAATGTGGCTGAATGCGGGGAGTGAAATACAGGTCGCCGGGTTCGATTACTCCTGTGCCATTAAT
GCACCCGCAAACATCCAGCAGTTCGAACATATCGTGCAACTAAGACGGGCTCTCACGACCGCGACAATTACACTCCTGCCCGACG
CCGAGCGCTTCTCCTTTCCCCGCGTAATCAACTCAGCTGATGGCGCCACCACTTGGTTCTTCAACCCTGTTATATTGCGCCCTAACA
ACGTAGAGGTGGAGTTTCTCTTAAACGGACAGATCATCAATACCTACCAAGCCAGGTTCGGCACGATTATTGCAAGAAATTTCGAC
GCTATCAGGCTGCTCTTCCAACTGATGAGGCCCCCCAATATGACTCCCGCTGTGAACGCTTTGTTTCCGCAGGCTCAGCCTTTCCAG
CACCACGCCACCGTCGGCTTGACTCTTCGAATAGAGAGCGCGGTCTGCGAATCAGTGCTGGCAGACGCCAACGAGACGCTGCTG
GCAAACGTTACCGCCGTGCGGCAAGAGTATGCCATCCCAGTAGGGCCTGTGTTTCCACCCGGCATGAACTGGACTGAACTAATTA
CTAACTATAGCCCATCCAGAGAAGACAACTTGCAGCGGGTCTTCACTGTGGCCTCTATCCGGAGTATGTTGATCAAGTAG

Figure 8D, SEQ ID NO: 28

Expression cassette number 1713 from 2X35S promoter to NOS terminator. VP6(opt) from Rotavirus A WA strain is underlined.

GTCAACATGGTGGAGCACGACACACTTGTCTACTCCAAAAATATCAAAGATACAGTCTCAGAAGACCAAAGGGCAATTGAGACTT
TTCAACAAAGGGTAATATCCGGAAACCTCCTCGGATTCCATTGCCCAGCTATCTGTCACTTTATTGTGAAGATAGTGGAAAAGGAA
GGTGGCTCCTACAAATGCCATCATTGCGATAAAGGAAAGGCCATCGTTGAAGATGCCTCTGCCGACAGTGGTCCCAAAGATGGAC
CCCCACCCACGAGGAGCATCGTGGAAAAAGAAGACGTTCCAACCACGTCTTCAAAGCAAGTGGATTGATGTGATAACATGGTGG
AGCACGACACACTTGTCTACTCCAAAAATATCAAAGATACAGTCTCAGAAGACCAAAGGGCAATTGAGACTTTTCAACAAAGGGT
AATATCCGGAAACCTCCTCGGATTCCATTGCCCAGCTATCTGTCACTTTATTGTGAAGATAGTGGAAAAGGAAGGTGGCTCCTACA
AATGCCATCATTGCGATAAAGGAAAGGCCATCGTTGAAGATGCCTCTGCCGACAGTGGTCCCAAAGATGGACCCCCACCCACGAG
GAGCATCGTGGAAAAAGAAGACGTTCCAACCACGTCTTCAAAGCAAGTGGATTGATGTGATATCTCCACTGACGTAAGGGATGAC
GCACAATCCCACTATCCTTCGCAAGACCCTTCCTCTATATAAGGAAGTTCATTTCATTTGGAGAGGTATTAAAATCTTAATAGGTTTT
GATAAAAGCGAACGTGGGGAAACCCGAACCAAACCTTCTTCTAAACTCTCTCTCATCTCTCTTAAAGCAAACTTCTCTCTTGTCTTTC
TTGCGTGAGCGATCTTCAACGTTGTCAGATCGTGCTTCGGCACCAGTACAACGTTTTCTTTCACTGAAGCGAAATCAAAGATCTCTT
TGTGGACACGTAGTGCGGCGCCATTAAATAACGTGTACTTGTCCTATTCTTGTCGGTGTGGTCTTGGGAAAAGAAAGCTTGCTGG
AGGCTGCTGTTCAGCCCCATACATTACTTGTTACGATTCTGCTGACTTTCGGCGGGTGCAATATCTCTACTTCTGCTTGACGAGGTA

Figure 8D continued

```
TTGTTGCCTGTACTTCTTTCTTCTTCTTGCTGATTGGTTCTATAAGAAATCTAGTATTTTCTTTGAAACAGAGTTTTCCCGTGGTT
TTCGAACTTGGAGAAAGATTGTTAAGCTTCTGTATATTCTGCCCAAATTTGTCGGGCCCATGGAGGTCCTTTATAGTCTCTCCAAAA
CGCTGAAGGACGCTAGGGACAAGATCGTGGAGGGTACACTTTATAGCAATGTCAGCGACCTAATACAGCAGTTTAATCAAATGAT
CGTTACAATGAATGGGAATGATTTCCAAACTGGCGGTATTGGTAATCTGCCCGTGAGGAACTGGACATTCGATTTCGGCCTGCTG
GGCACGACTCTCCTTAATCTCGATGCAAATTATGTAGAAAACGCCAGAACGATTATCGAGTACTTTATCGATTTCATTGATAACGTT
TGTATGGATGAGATGGCCCGCGAGTCACAACGGAACGGAGTTGCTCCACAGTCCGAGGCCCTTCGGAAACTCGCCGGCATTAAG
TTCAAGCGTATTAATTTCGACAACTCCTCCGAATATATAGAGAACTGGAACTTGCAGAATCGTCGACAGAGAACCGGCTTCGTGTT
CCATAAACCTAATATCTTTCCGTATAGCGCCTCATTCACCCTGAATAGGAGTCAGCCCATGCACGACAACCTCATGGGTACAATGT
GGCTGAATGCGGGGAGTGAAATACAGGTCGCCGGGTTCGATTACTCCTGTGCCATTAATGCACCCGCAAACATCCAGCAGTTCGA
ACATATCGTGCAACTAAGACGGGCTCTCACGACCGCGACAATTACACTCCTGCCCGACGCCGAGCGCTTCTCCTTTCCCCGCGTAA
TCAACTCAGCTGATGGCGCCACCACTTGGTTCTTCAACCCTGTTATATTGCGCCCTAACAACGTAGAGGTGGAGTTTCTCTTAAACG
GACAGATCATCAATACCTACCAAGCCAGGTTCGGCACGATTATTGCAAGAAATTTCGACGCTATCAGGCTGCTCTTCCAACTGATG
AGGCCCCCCAATATGACTCCCGCTGTGAACGCTTTGTTTCCGCAGGCTCAGCCTTTCCAGCACCACGCCACCGTCGGCTTGACTCTT
CGAATAGAGAGCGCGGTCTGCGAATCAGTGCTGGCAGACGCCAACGAGACGCTGCTGGCAAACGTTACCGCCGTGCGGCAAGA
GTATGCCATCCCAGTAGGGCCTGTGTTCCACCCGGCATGAACTGGACTGAACTAATTACTAACTATAGCCCATCCAGAGAAGACA
ACTTGCAGCGGGTCTTCACTGTGGCCTCTATCCGGAGTATGTTGATCAAGTAGAGGCCTATTTTCTTTAGTTTGAATTTACTGTTAT
TCGGTGTGCATTTCTATGTTTGGTGAGCGGTTTTCTGTGCTCAGAGTGTGTTTATTTTATGTAATTTAATTTCTTTGTGAGCTCCTGT
TTAGCAGGTCGTCCCTTCAGCAAGGACACAAAAAGATTTTAATTTTATTAAAAAAAAAAAAAAAAAAGACCGGGAATTCGATATC
AAGCTTATCGACCTGCAGATCGTTCAAACATTTGGCAATAAAGTTTCTTAAGATTGAATCCTGTTGCCGGTCTTGCGATGATTATCA
TATAATTTCTGTTGAATTACGTTAAGCATGTAATAATTAACATGTAATGCATGACGTTATTTATGAGATGGGTTTTTATGATTAGAG
TCCCGCAATTATACATTTAATACGCGATAGAAAACAAAATATAGCGCGCAAACTAGGATAAATTATCGCGCGCGGTGTCATCTATG
TTACTAGAT
```

Figure 8E, SEQ ID NO: 29

Amino acid sequence of VP6 from Rotavirus A WA strain

```
MEVLYSLSKTLKDARDKIVEGTLYSNVSDLIQQFNQMIVTMNGNDFQTGGIGNLPVRNWTFDFGLLGTTLLNLDANYVENARTIIEYFID
FIDNVCMDEMARESQRNGVAPQSEALRKLAGIKFKRINFDNSSEYIENWNLQNRRQRTGFVFHKPNIFPYSASFTLNRSQPMHDNLM
GTMWLNAGSEIQVAGFDYSCAINAPANIQQFEHIVQLRRALTTATITLLPDAERFSFPRVINSADGATTWFFNPVILRPNNVEVEFLLNG
QIINTYQARFGTIIARNFDAIRLLFQLMRPPNMTPAVNALFPQAQPFQHHATVGLTLRIESAVCESVLADANETLLANVTAVRQEYAIPV
GPVFPPGMNWTELITNYSPSREDNLQRVFTVASIRSMLIK
```

Figure 8F

Schematic representation of construct number 1713

3. 2X35S/CPMV-HT/ RVA(Rtx) VP4(opt)/ NOS (Construct number 1730)

Figure 9A, SEQ ID NO: 30

IF-Rtx_VP4(opt).s1+3c

AAATTTGTCGGGCCCATGGCTAGCCTGATCTACAGACAACTCTTGACCAATTC

Figure 9B, SEQ ID NO: 31

IF-Rtx_VP4(opt).s1-4r

ACTAAAGAAAATAGGCCTTCAGAGTTTACATTGCAGGATTAATTGCTCAATCCTA

Figure 9C, SEQ ID NO: 32

Optimized coding sequence of Rotavirus A VP4 from strain RVA/Vaccine/USA/Rotarix-A41CB052A/1988/G1P1A[8]

ATGGCTAGCCTGATCTACAGACAACTCTTGACCAATTCATATTCTGTGGATCTTCATGACGAAATCGAGCAGATTGGGTCCGAGAA
GACCCAGAACGTGACCATCAACCCTGGACCTTTTGCTCAGACCCGCTATGCCCCTGTGAATTGGGATCACGGAGAAATCAACGAC

Figure 9C continued

```
AGTACGACCGTCGAACCCATTCTGGACGGGCCATACCAACCCACCACCTTCACCCCACCTAATGATTATTGGATTTTAATCAACTCC
AACACAAACGGAGTGGTCTACGAGTCCACTAATAACTCCGATTTTTGGACCGCCGTTGTAGCCATCGAGCCACACGTCAATCCTGT
CGATCGCCAGTATATGATATTCGGCGAGTCCAAACAGTTTAACGTTTCCAATGACAGCAACAAATGGAAGTTTCTGGAGATGTTTC
GCAGCTCCTCTCAGAACGAATTCTATAATAGACGGACCCTTACCTCCGATACACGACTCGTGGGTATTTTTAAGTACGGCGGCAGG
GTGTGGACATTTCACGGTGAAACCCCTCGAGCAACCACTGACTCCAGTAGCACTGCAAACCTGAACAATATATCTATTACCATCCA
CAGCGAATTCTACATAATCCCAAGATCTCAGGAAAGTAAGTGTAACGAATATATCAACAACGGACTCCCCCCAATTCAGAATACAC
GGAACGTGGTGCCTCTCCCACTCAGTTCTCGGTCTATCCAGTATAAGAGAGCACAAGTGAATGAGGACATTATTGTGAGCAAGAC
TAGCCTTTGGAAAGAAATGCAGTACAACAGAGACATTATCATCCGGTTTAAGTTTGGGAACTCTATCGTGAAGATGGGCGGCCTG
GGGTACAAATGGTCAGAAATCTCATATAAAGCCGCCAACTATCAGTATAACTACTTGAGAGACGGCGAGCAGGTAACCGCCCACA
CAACATGCTCTGTCAACGGCGTTAATAACTTTAGCTACAACGGAGGCTTCCTTCCCACCGACTTCGGTATCAGCCGGTATGAAGTC
ATCAAGGAAAATTCTTATGTGTACGTAGATTACTGGGATGATAGCAAAGCGTTCCGCAACATGGTGTATGTTAGGAGCCTGGCTG
CTAATCTCAATTCTGTGAAGTGTACTGGTGGATCATATTATTTCTCAATTCCCGTGGGGGCTTGGCCAGTCATGAATGGCGGGGCA
GTCTCCCTCCATTTTGCTGGCGTGACGTTGAGCACTCAGTTTACCGATTTCGTGTCTCTGAACTCCCTGAGGTTCCGGTTTTCCCTTA
CTGTCGACGAGCCCCCATTCAGCATTCTGCGTACAAGAACTGTCAACCTCTACGGGTTACCTGCCGCGAATCCAAACAACGGCAAT
GAATACTATGAAATTTCGGGCCGCTTCTCTTTGATAAGTCTGGTACCAACTAATGACGACTATCAGACACCCATCATGAACAGCGT
GACTGTCAGACAGGACCTGGAAAGACAACTTACAGATCTGCGGGAAGAATTCAATTCTCTCAGTCAGGAGATTGCAATGGCCCAA
TTGATAGATCTTGCCCTACTGCCTCTCGATATGTTTAGTATGTTCTCCGGCATCAAATCAACTATAGATCTGACAAAGAGCATGGCT
ACTTCTGTGATGAAGAAGTTCAGGAAATCAAAACTTGCCACGAGCATATCAGAAATGACGAACTCTCTGAGTGATGCAGCATCAT
CAGCGTCACGCAACGTTTCCATTCGGTCGAATCTCAGCGCCATCAGCAACTGGACAAACGTGTCCAACGACGTCAGCAACGTGAC
CAACTCCTTGAACGATATTTCTACCCAGACGTCAACGATCAGTAAGAAACTCCGCTTGAAAGAAATGATCACCCAGACTGAGGGA
ATGTCTTTCGACGACATTTCCGCCGCCGTGCTAAAAACCAAAATCGATATGTCTACTCAGATCGGCAAGAACACTCTGCCGGATAT
CGTAACCGAAGCCTCCGAAAAGTTTATCCCTAAGCGCAGCTACAGAATATTGAAAGATGACGAGGTCATGGAGATCAACACAGAA
GGGAAGTTCTTCGCTTATAAGATCAACACCTTTGACGAGGTTCCGTTTGACGTCAATAAGTTTGCAGAGCTCGTGACAGATAGTCC
AGTGATTTCTGCCATCATTGACTTTAAGACTTTGAAGAACCTGAACGACAACTATGGAATAACACGGACCGAAGCGTTGAACCTCA
TTAAGTCCAATCCCAATATGTTGCGCAATTTCATTAACCAGAACAATCCAATCATAAGAAATAGGATTGAGCAATTAATCCTGCAAT
GTAAACTCTGA
```

Figure 9D, SEQ ID NO: 33

Expression cassette number 1730 from 2X35S promoter to NOS terminator. VP4(opt) from Rotavirus A Rotarix strain is underlined.

```
GTCAACATGGTGGAGCACGACACACTTGTCTACTCCAAAAATATCAAAGATACAGTCTCAGAAGACCAAAGGGCAATTGAGACTT
TTCAACAAAGGGTAATATCCGGAAACCTCCTCGGATTCCATTGCCCAGCTATCTGTCACTTTATTGTGAAGATAGTGGAAAAGGAA
GGTGGCTCCTACAAATGCCATCATTGCGATAAAGGAAAGGCCATCGTTGAAGATGCCTCTGCCGACAGTGGTCCCAAAGATGGAC
CCCCACCCACGAGGAGCATCGTGGAAAAAGAAGACGTTCCAACCACGTCTTCAAAGCAAGTGGATTGATGTGATAACATGGTGG
AGCACGACACACTTGTCTACTCCAAAAATATCAAAGATACAGTCTCAGAAGACCAAAGGGCAATTGAGACTTTTCAACAAAGGGT
AATATCCGGAAACCTCCTCGGATTCCATTGCCCAGCTATCTGTCACTTTATTGTGAAGATAGTGGAAAAGGAAGGTGGCTCCTACA
AATGCCATCATTGCGATAAAGGAAAGGCCATCGTTGAAGATGCCTCTGCCGACAGTGGTCCCAAAGATGGACCCCCACCCACGAG
GAGCATCGTGGAAAAAGAAGACGTTCCAACCACGTCTTCAAAGCAAGTGGATTGATGTGATATCTCCACTGACGTAAGGGATGAC
GCACAATCCCACTATCCTTCGCAAGACCCTTCCTCTATATAAGGAAGTTCATTTCATTTGGAGAGGTATTAAAATCTTAATAGGTTTT
GATAAAAGCGAACGTGGGGAAACCCGAACCAAACCTTCTTCTAAACTCTCTCATCTCTCTTAAAGCAAACTTCTCTCTTGTCTTTC
TTGCGTGAGCGATCTTCAACGTTGTCAGATCGTGCTTCGGCACCAGTACAACGTTTTCTTTCACTGAAGCGAAATCAAAGATCTCTT
TGTGGACACGTAGTGCGGCGCCATTAAATAACGTGTACTTGTCCTATTCTTGTCGGTGTGGTCTTGGGAAAAGAAAGCTTGCTGG
AGGCTGCTGTTCAGCCCCATACATTACTTGTTACGATTCTGCTGACTTTCGGCGGGTGCAATATCTCTACTTCTGCTTGACGAGGTA
TTGTTGCCTGTACTTCTTTCTTCTTCTTGCTGATTGGTTCTATAAGAAATCTAGTATTTTCTTTGAAACAGAGTTTTCCCGTGGTT
TTCGAACTTGGAGAAAGATTGTTAAGCTTCTGTATATTCTGCCCAAATTTGTCGGGCCCATGGCTAGCCTGATCTACAGACAACTCT
TGACCAATTCATATTCTGTGGATCTTCATGACGAAATCGAGCAGATTGGGTCCGAGAAGACCCAGAACGTGACCATCAACCCTGG
ACCTTTTGCTCAGACCCGCTATGCCCCTGTGAATTGGGATCACGGAGAAATCAACGACAGTACGACCGTCGAACCCATTCTGGACG
GGCCATACCAACCCACCACCTTCACCCCACCTAATGATTATTGGATTTTAATCAACTCCAACACAAACGGAGTGGTCTACGAGTCCA
CTAATAACTCCGATTTTTGGACCGCCGTTGTAGCCATCGAGCCACACGTCAATCCTGTCGATCGCCAGTATATGATATTCGGCGAG
```

Figure 9D continued

TCCAAACAGTTTAACGTTTCCAATGACAGCAACAAATGGAAGTTTCTGGAGATGTTTCGCAGCTCCTCTCAGAACGAATTCTATAAT
AGACGGACCCTTACCTCCGATACACGACTCGTGGGTATTTTTAAGTACGGCGGCAGGGTGTGGACATTTCACGGTGAAACCCCTC
GAGCAACCACTGACTCCAGTAGCACTGCAAACCTGAACAATATATCTATTACCATCCACAGCGAATTCTACATAATCCCAAGATCTC
AGGAAAGTAAGTGTAACGAATATATCAACAACGGACTCCCCCCAATTCAGAATACACGGAACGTGGTGCCTCTCCCACTCAGTTCT
CGGTCTATCCAGTATAAGAGAGCACAAGTGAATGAGGACATTATTGTGAGCAAGACTAGCCTTTGGAAAGAAATGCAGTACAACA
GAGACATTATCATCCGGTTTAAGTTTGGGAACTCTATCGTGAAGATGGGCGGCCTGGGGTACAAATGGTCAGAAATCTCATATAA
AGCCGCCAACTATCAGTATAACTACTTGAGAGACGGCGAGCAGGTAACCGCCCACACAACATGCTCTGTCAACGGCGTTAATAAC
TTTAGCTACAACGGAGGCTTCCTTCCCACCGACTTCGGTATCAGCCGGTATGAAGTCATCAAGGAAAATTCTTATGTGTACGTAGA
TTACTGGGATGATAGCAAAGCGTTCCGCAACATGGTGTATGTTAGGAGCCTGGCTGCTAATCTCAATTCTGTGAAGTGTACTGGT
GGATCATATTATTTCTCAATTCCCGTGGGGGCTTGGCCAGTCATGAATGGCGGGGCAGTCTCCCTCCATTTTGCTGGCGTGACGTT
GAGCACTCAGTTTACCGATTTCGTGTCTCTGAACTCCCTGAGGTTCCGGTTTTCCCTTACTGTCGACGAGCCCCCATTCAGCATTCT
GCGTACAAGAACTGTCAACCTCTACGGGTTACCTGCCGCGAATCCAAACAACGGCAATGAATACTATGAAATTTCGGGCCGCTTCT
CTTTGATAAGTCTGGTACCAACTAATGACGACTATCAGACACCCATCATGAACAGCGTGACTGTCAGACAGGACCTGGAAAGACA
ACTTACAGATCTGCGGGAAGAATTCAATTCTCTCAGTCAGGAGATTGCAATGGCCCAATTGATAGATCTTGCCCTACTGCCTCTCG
ATATGTTTAGTATGTTCTCCGGCATCAAATCAACTATAGATCTGACAAAGAGCATGGCTACTTCTGTGATGAAGAAGTTCAGGAAA
TCAAAACTTGCCACGAGCATATCAGAAATGACGAACTCTCTGAGTGATGCAGCATCATCAGCGTCACGCAACGTTTCCATTCGGTC
GAATCTCAGCGCCATCAGCAACTGGACAAACGTGTCCAACGACGTCAGCAACGTGACCAACTCCTTGAACGATATTTCTACCCAGA
CGTCAACGATCAGTAAGAAACTCCGCTTGAAAGAAATGATCACCCAGACTGAGGGAATGTCTTTCGACGACATTTCCGCCGCCGT
GCTAAAAACCAAAATCGATATGTCTACTCAGATCGGCAAGAACACTCTGCCGGATATCGTAACCGAAGCCTCCGAAAAGTTTATCC
CTAAGCGCAGCTACAGAATATTGAAAGATGACGAGGTCATGGAGATCAACACAGAAGGGAAGTTCTTCGCTTATAAGATCAACAC
CTTTGACGAGGTTCCGTTTGACGTCAATAAGTTTGCAGAGCTCGTGACAGATAGTCCAGTGATTTCTGCCATCATTGACTTTAAGA
CTTTGAAGAACCTGAACGACAACTATGGAATAACACGGACCGAAGCGTTGAACCTCATTAAGTCCAATCCCAATATGTTGCGCAAT
TTCATTAACCAGAACAATCCAATCATAAGAAATAGGATTGAGCAATTAATCCTGCAATGTAAACTCTGAAGGCCTATTTTCTTTAGT
TTGAATTTACTGTTATTCGGTGTGCATTTCTATGTTTGGTGAGCGGTTTTCTGTGCTCAGAGTGTGTTTATTTTATGTAATTTAATTT
CTTTGTGAGCTCCTGTTTAGCAGGTCGTCCCTTCAGCAAGGACACAAAAAGATTTTAATTTTATTAAAAAAAAAAAAAAAAAAGAC
CGGGAATTCGATATCAAGCTTATCGACCTGCAGATCGTTCAAACATTTGGCAATAAAGTTTCTTAAGATTGAATCCTGTTGCCGGTC
TTGCGATGATTATCATATAATTTCTGTTGAATTACGTTAAGCATGTAATAATTAACATGTAATGCATGACGTTATTTATGAGATGGG
TTTTTATGATTAGAGTCCCGCAATTATACATTTAATACGCGATAGAAAACAAAATATAGCGCGCAAACTAGGATAAATTATCGCGC
GCGGTGTCATCTATGTTACTAGAT

Figure 9E, SEQ ID NO: 34

Amino acid sequence of VP4 from Rotavirus A Rotarix strain

MASLIYRQLLTNSYSVDLHDEIEQIGSEKTQNVTINPGPFAQTRYAPVNWDHGEINDSTTVEPILDGPYQPTTFTPPNDYWILINSNTNG
VVYESTNNSDFWTAVVAIEPHVNPVDRQYMIFGESKQFNVSNDSNKWKFLEMFRSSSQNEFYNRRTLTSDTRLVGIFKYGGRVWTFH
GETPRATTDSSSTANLNNISITIHSEFYIIPRSQESKCNEYINNGLPPIQNTRNVVPLPLSSRSIQYKRAQVNEDIIVSKTSLWKEMQYNRDIII
RFKFGNSIVKMGGLGYKWSEISYKAANYQYNYLRDGEQVTAHTTCSVNGVNNFSYNGGFLPTDFGISRYEVIKENSYVYVDYWDDSKA
FRNMVYVRSLAANLNSVKCTGGSYYFSIPVGAWPVMNGGAVSLHFAGVTLSTQFTDFVSLNSLRFRFSLTVDEPPFSILRTRTVNLYGLP
AANPNNGNEYYEISGRFSLISLVPTNDDYQTPIMNSVTVRQDLERQLTDLREEFNSLSQEIAMAQLIDLALLPLDMFSMFSGIKSTIDLTKS
MATSVMKKFRKSKLATSISEMTNSLSDAASSASRNVSIRSNLSAISNWTNVSNDVSNVTNSLNDISTQTSTISKKLRLKEMITQTEGMSF
DDISAAVLKTKIDMSTQIGKNTLPDIVTEASEKFIPKRSYRILKDDEVMEINTEGKFFAYKINTFDEVPFDVNKFAELVTDSPVISAIIDFKTLK
NLNDNYGITRTEALNLIKSNPNMLRNFINQNNPIIRNRIEQLILQCKL

Schematic representation of construct number 1730

4. 2X35S/CPMV-HT/RVA(Rtx) VP7(Opt)/NOS (Construct number 1734)

Figure 10A, SEQ ID NO: 35

IF-TrSP+Rtx_VP7(opt).s1+3c

AAATTTGTCGGGCCCATGGATTATATTATCTATCGTAGCCTCCTCATCTA

Figure 10B, SEQ ID NO: 36

IF-Rtx_VP7(opt).s1-4r

ACTAAAGAAAATAGGCCTCTAAACGCGATAATAGAAGGCTGCTGAGTTCAGGGA

Figure 10C, SEQ ID NO: 37

Optimized coding sequence of Rotavirus A VP7 from strain RVA/Vaccine/USA/Rotarix-A41CB052A/1988/G1P1A[8]

Figure 10C continued

ATGTACGGCATCGAGTATACAACAATTTTAATTTTCCTGATTTCCATCATTCTGTTAAACTACATCCTTAAGTCCGTGACCAGAATTA
TGGATTATATTATCTATCGTAGCCTCCTCATCTACGTGGCCCTTTTTGCCCTGACCAGGGCCCAGAACTATGGCCTGAACTTACCAA
TCACCGGTTCAATGGATACCGTTTACGCTAATTCCACTCAAGAGGGGATATTTCTGACAAGTACCCTGTGCCTGTATTATCCAACAG
AAGCCTCTACCCAGATCAATGATGGGGAGTGGAAGGATAGTCTCTCACAGATGTTCCTAACCAAGGGCTGGCCCACCGGTTCCGT
CTACTTCAAGGAATACTCTAGTATTGTCGACTTCTCAGTTGACCCCCAGCTTTATTGCGACTACAACCTGGTACTTATGAAATACGA
CCAGAACCTGGAGCTGGATATGTCCGAGCTGGCTGACCTGATCCTCAATGAGTGGCTGTGCAACCCCATGGACATCACATTATATT
ACTACCAGCAGTCTGGAGAATCCAACAAGTGGATCAGTATGGGCTCAAGTTGCACCGTGAAGGTGTGTCCCTTGAACACCCAAAT
GCTGGGCATTGGTTGTCAGACAACTAATGTGGATTCGTTTGAAATGGTAGCCGAAAACGAGAAGCTGGCTATAGTGGACGTAGTC
GATGGGATTAACCACAAGATCAATCTGACTACCACCACTTGTACCATCAGAAACTGTAAAAAGCTCGGCCCCCGGGAGAACGTCG
CCGTGATCCAGGTGGGGGGGAGCAATGTGCTCGACATTACTGCCGACCCTACCACCAATCCACAGACGGAACGGATGATGAGAG
TCAACTGGAAGAAATGGTGGCAGGTCTTTTATACCATTGTGGACTACATTAACCAGATTGTGCAAGTCATGAGTAAACGGTCCAG
ATCCCTGAACTCAGCAGCCTTCTATTATCGCGTTTAG

Figure 10D, SEQ ID NO: 38

Expression cassette number 1734 from 2X35S promoter to NOS terminator. VP7 from Rotavirus A vaccine USA/Rotarix-A41CB052A/1988/G1P1A[8] strain is underlined.

GTCAACATGGTGGAGCACGACACACTTGTCTACTCCAAAAATATCAAAGATACAGTCTCAGAAGACCAAAGGGCAATTGAGACTT
TTCAACAAAGGGTAATATCCGGAAACCTCCTCGGATTCCATTGCCCAGCTATCTGTCACTTTATTGTGAAGATAGTGGAAAAGGAA
GGTGGCTCCTACAAATGCCATCATTGCGATAAAGGAAAGGCCATCGTTGAAGATGCCTCTGCCGACAGTGGTCCCAAAGATGGAC
CCCCACCCACGAGGAGCATCGTGGAAAAAGAAGACGTTCCAACCACGTCTTCAAAGCAAGTGGATTGATGTGATAACATGGTGG
AGCACGACACACTTGTCTACTCCAAAAATATCAAAGATACAGTCTCAGAAGACCAAAGGGCAATTGAGACTTTTCAACAAAGGGT
AATATCCGGAAACCTCCTCGGATTCCATTGCCCAGCTATCTGTCACTTTATTGTGAAGATAGTGGAAAAGGAAGGTGGCTCCTACA
AATGCCATCATTGCGATAAAGGAAAGGCCATCGTTGAAGATGCCTCTGCCGACAGTGGTCCCAAAGATGGACCCCCACCCACGAG
GAGCATCGTGGAAAAAGAAGACGTTCCAACCACGTCTTCAAAGCAAGTGGATTGATGTGATATCTCCACTGACGTAAGGGATGAC
GCACAATCCCACTATCCTTCGCAAGACCCTTCCTCTATATAAGGAAGTTCATTTCATTTGGAGAGGTATTAAAATCTTAATAGGTTTT
GATAAAAGCGAACGTGGGGAAACCCGAACCAAACCTTCTTCTAAACTCTCTCTCATCTCTCTTAAAGCAAACTTCTCTCTTGTCTTTC
TTGCGTGAGCGATCTTCAACGTTGTCAGATCGTGCTTCGGCACCAGTACAACGTTTTCTTTCACTGAAGCGAAATCAAAGATCTCTT
TGTGGACACGTAGTGCGGCGCCATTAAATAACGTGTACTTGTCCTATTCTTGTCGGTGTGGTCTTGGGAAAAGAAAGCTTGCTGG
AGGCTGCTGTTCAGCCCCATACATTACTTGTTACGATTCTGCTGACTTTCGGCGGGTGCAATATCTCTACTTCTGCTTGACGAGGTA
TTGTTGCCTGTACTTCTTTCTTCTTCTTCTTGCTGATTGGTTCTATAAGAAATCTAGTATTTTCTTTGAAACAGAGTTTTCCCGTGGTT
TTCGAACTTGGAGAAAGATTGTTAAGCTTCTGTATATTCTGCCCAAATTTGTCGGGCCCATGGATTATATTATCTATCGTAGCCTCC
TCATCTACGTGGCCCTTTTTGCCCTGACCAGGGCCCAGAACTATGGCCTGAACTTACCAATCACCGGTTCAATGGATACCGTTTACG
CTAATTCCACTCAAGAGGGGATATTTCTGACAAGTACCCTGTGCCTGTATTATCCAACAGAAGCCTCTACCCAGATCAATGATGGG
GAGTGGAAGGATAGTCTCTCACAGATGTTCCTAACCAAGGGCTGGCCCACCGGTTCCGTCTACTTCAAGGAATACTCTAGTATTGT
CGACTTCTCAGTTGACCCCCAGCTTTATTGCGACTACAACCTGGTACTTATGAAATACGACCAGAACCTGGAGCTGGATATGTCCG
AGCTGGCTGACCTGATCCTCAATGAGTGGCTGTGCAACCCCATGGACATCACATTATATTACTACCAGCAGTCTGGAGAATCCAAC
AAGTGGATCAGTATGGGCTCAAGTTGCACCGTGAAGGTGTGTCCCTTGAACACCCAAATGCTGGGCATTGGTTGTCAGACAACTA
ATGTGGATTCGTTTGAAATGGTAGCCGAAAACGAGAAGCTGGCTATAGTGGACGTAGTCGATGGGATTAACCACAAGATCAATCT
GACTACCACCACTTGTACCATCAGAAACTGTAAAAAGCTCGGCCCCCGGGAGAACGTCGCCGTGATCCAGGTGGGGGGGAGCAA
TGTGCTCGACATTACTGCCGACCCTACCACCAATCCACAGACGGAACGGATGATGAGAGTCAACTGGAAGAAATGGTGGCAGGT
CTTTTATACCATTGTGGACTACATTAACCAGATTGTGCAAGTCATGAGTAAACGGTCCAGATCCCTGAACTCAGCAGCCTTCTATTA
TCGCGTTTAGAGGCCTATTTTCTTTAGTTTGAATTTACTGTTATTCGGTGTGCATTTCTATGTTTGGTGAGCGGTTTTCTGTGCTCAG
AGTGTGTTTATTTTATGTAATTTAATTTCTTTGTGAGCTCCTGTTTAGCAGGTCGTCCCTTCAGCAAGGACACAAAAAGATTTTAATT
TTATTAAAAAAAAAAAAAAAAAAGACCGGGAATTCGATATCAAGCTTATCGACCTGCAGATCGTTCAAACATTTGGCAATAAAGTT
TCTTAAGATTGAATCCTGTTGCCGGTCTTGCGATGATTATCATATAATTTCTGTTGAATTACGTTAAGCATGTAATAATTAACATGTA
ATGCATGACGTTATTTATGAGATGGGTTTTTATGATTAGAGTCCCGCAATTATACATTTAATACGCGATAGAAAACAAAATATAGC
GCGCAAACTAGGATAAATTATCGCGCGCGGTGTCATCTATGTTACTAGAT

Figure 10E, SEQ ID NO: 39

Amino acid sequence of TrSp-VP7 from Rotavirus A vaccine USA/Rotarix-A41CB052A/1988/G1P1A[8] strain MDYIIYRSLLIYVALFALTRAQNYGLNLPITGSMDTVYANSTQEGIFLTSTLCLYYPTEASTQINDGEWKDSLSQMFLTKGWPTGSVYFKE
YSSIVDFSVDPQLYCDYNLVLMKYDQNLELDMSELADLILNEWLCNPMDITLYYYQQSGESNKWISMGSSCTVKVCPLNTQMLGIGCQ
TTNVDSFEMVAENEKLAIVDVVDGINHKINLTTTTCTIRNCKKLGPRENVAVIQVGGSNVLDITADPTTNPQTERMMRVNWKKWWQ
VFYTIVDYINQIVQVMSKRSRSLNSAAFYYRV

Figure 10F

Schematic representation of construct number 1734

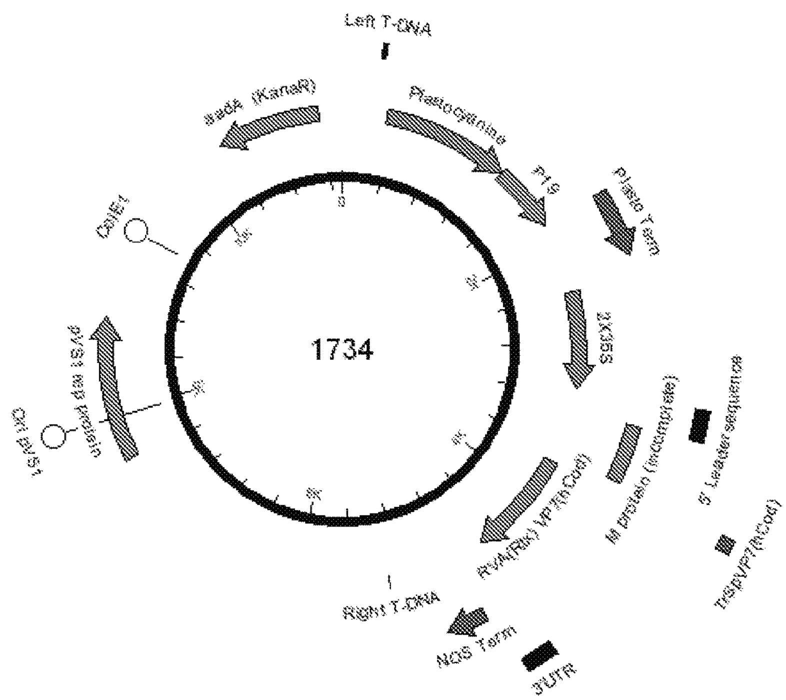

<u>5. 2X35S/CPMV-HT/RVA(WA) NSP4/NOS (Construct number 1706)</u>

Figure 11A, SEQ ID NO: 40

IF-WA_NSP4.s1+3c

AAATTTGTCGGGCCCATGGATAAGCTTGCCGACCTCAACTACACATTGAGTG

Figure 11B, SEQ ID NO: 41

IF-WA_NSP4.s1-4r

ACTAAAGAAAATAGGCCTTCACATGGATGCAGTCACTTCTGACGGTTCATATGGA

Figure 11C, SEQ ID NO : 42

Coding sequence of Rotavirus A NSP4 from strain WA

ATGGATAAGCTTGCCGACCTCAACTACACATTGAGTGTAATCACTTCAATGAATGACACATTGCATTCTATAATTCAAGATCCTGGA
ATGGCGTATTTTCTATATATTGCATCTGTTCTAACAGTTTTGTTCACATTACATAAAGCTTCAATTCCAACCATGAAAATAGCATTGA
AAACATCAAAATGTTCATATAAAGTGATTAAATATTGTATAGTCACGATCATTAATACTCTTTTAAAATTGGCTGGATATAAAGAGC
AGGTTACTACAAAAGACGAAATTGAGCAACAGATGGACAGAATTGTGAAAGAGATGAGACGTCAGCTGGAGATGATTGATAAAC
TAACTACTCGTGAAATTGAACAGGTTGAATTGCTTAAACGTATACATGACAACCTGATAACTAGACCAGTTGACGTTATAGATATG
TCGAAGGAATTCAATCAGAAAAACATCAAAACGCTAGATGAATGGGAGAGTGGAAAAAATCCATATGAACCGTCAGAAGTGACT
GCATCCATGTGA

Figure 11D, SEQ ID NO: 43

Expression cassette number 1706 from 2X35S promoter to NOS terminator. NSP4 from Rotavirus A WA strain is underlined.

GTCAACATGGTGGAGCACGACACACTTGTCTACTCCAAAAATATCAAAGATACAGTCTCAGAAGACCAAAGGGCAATTGAGACTT
TTCAACAAAGGGTAATATCCGGAAACCTCCTCGGATTCCATTGCCCAGCTATCTGTCACTTTATTGTGAAGATAGTGGAAAAGGAA
GGTGGCTCCTACAAATGCCATCATTGCGATAAAGGAAAGGCCATCGTTGAAGATGCCTCTGCCGACAGTGGTCCCAAAGATGGAC
CCCCACCCACGAGGAGCATCGTGGAAAAAGAAGACGTTCCAACCACGTCTTCAAAGCAAGTGGATTGATGTGATAACATGGTGG
AGCACGACACACTTGTCTACTCCAAAAATATCAAAGATACAGTCTCAGAAGACCAAAGGGCAATTGAGACTTTTCAACAAAGGGT
AATATCCGGAAACCTCCTCGGATTCCATTGCCCAGCTATCTGTCACTTTATTGTGAAGATAGTGGAAAAGGAAGGTGGCTCCTACA
AATGCCATCATTGCGATAAAGGAAAGGCCATCGTTGAAGATGCCTCTGCCGACAGTGGTCCCAAAGATGGACCCCCACCCACGAG
GAGCATCGTGGAAAAAGAAGACGTTCCAACCACGTCTTCAAAGCAAGTGGATTGATGTGATATCTCCACTGACGTAAGGGATGAC
GCACAATCCCACTATCCTTCGCAAGACCCTTCCTCTATATAAGGAAGTTCATTTCATTTGGAGAGGTATTAAAATCTTAATAGGTTTT
GATAAAAGCGAACGTGGGGAAACCCGAACCAAACCTTCTTCTAAACTCTCTCTCATCTCTCTTAAAGCAAACTTCTCTCTTGTCTTTC
TTGCGTGAGCGATCTTCAACGTTGTCAGATCGTGCTTCGGCACCAGTACAACGTTTTCTTTCACTGAAGCGAAATCAAAGATCTCTT
TGTGGACACGTAGTGCGGCGCCATTAAATAACGTGTACTTGTCCTATTCTTGTCGGTGTGGTCTTGGGAAAAGAAAGCTTGCTGG
AGGCTGCTGTTCAGCCCCATACATTACTTGTTACGATTCTGCTGACTTTCGGCGGGTGCAATATCTCTACTTCTGCTTGACGAGGTA
TTGTTGCCTGTACTTCTTTCTTCTTCTTCTTGCTGATTGGTTCTATAAGAAATCTAGTATTTTCTTTGAAACAGAGTTTTCCCGTGGTT
TTCGAACTTGGAGAAAGATTGTTAAGCTTCTGTATATTCTGCCCAAATTTGTCGGGCCCATGGATAAGCTTGCCGACCTCAACTACA
CATTGAGTGTAATCACTTCAATGAATGACACATTGCATTCTATAATTCAAGATCCTGGAATGGCGTATTTTCTATATATTGCATCTGT
TCTAACAGTTTTGTTCACATTACATAAAGCTTCAATTCCAACCATGAAAATAGCATTGAAAACATCAAAATGTTCATATAAAGTGAT
TAAATATTGTATAGTCACGATCATTAATACTCTTTTAAAATTGGCTGGATATAAAGAGCAGGTTACTACAAAAGACGAAATTGAGC
AACAGATGGACAGAATTGTGAAAGAGATGAGACGTCAGCTGGAGATGATTGATAAACTAACTACTCGTGAAATTGAACAGGTTG
AATTGCTTAAACGTATACATGACAACCTGATAACTAGACCAGTTGACGTTATAGATATGTCGAAGGAATTCAATCAGAAAAACATC
AAAACGCTAGATGAATGGGAGAGTGGAAAAAATCCATATGAACCGTCAGAAGTGACTGCATCCATGTGAAGGCCTATTTTCTTTA
GTTTGAATTTACTGTTATTCGGTGTGCATTTCTATGTTTGGTGAGCGGTTTTCTGTGCTCAGAGTGTGTTTATTTTATGTAATTTAAT
TTCTTTGTGAGCTCCTGTTTAGCAGGTCGTCCCTTCAGCAAGGACACAAAAAGATTTTAATTTTATTAAAAAAAAAAAAAAAAAAG
ACCGGGAATTCGATATCAAGCTTATCGACCTGCAGATCGTTCAAACATTTGGCAATAAAGTTTCTTAAGATTGAATCCTGTTGCCG
GTCTTGCGATGATTATCATATAATTTCTGTTGAATTACGTTAAGCATGTAATAATTAACATGTAATGCATGACGTTATTTATGAGAT
GGGTTTTTATGATTAGAGTCCCGCAATTATACATTTAATACGCGATAGAAAACAAAATATAGCGCGCAAACTAGGATAAATTATCG
CGCGCGGTGTCATCTATGTTACTAGAT

Figure11E, SEQ ID NO: 44

Amino acid sequence of NSP4 from Rotavirus A WA strain

MDKLADLNYTLSVITSMNDTLHSIIQDPGMAYFLYIASVLTVLFTLHKASIPTMKIALKTSKCSYKVIKYCIVTIINTLLKLAGYKEQVTTKDEI
EQQMDRIVKEMRRQLEMIDKLTTREIEQVELLKRIHDNLITRPVDVIDMSKEFNQKNIKTLDEWESGKNPYEPSEVTASM

Figure 11F

Schematic representation of construct number 1706

<u>6. 2X35S/CPMV-160/ RVA(WA) VP2(opt)/ NOS (Construct number 1108)</u>

Figure 12A, SEQ ID NO: 45

IF(C160)-WA_VP2(opt).c

TCGTGCTTCGGCACCAGTACAATGGCATACCGGAAGAGAGGAGCAAAGCGCGAA

Figure 12B

Schematic representation of construct 1190. SacII and StuI restriction enzyme sites used for plasmid linearization are annotated on the representation.

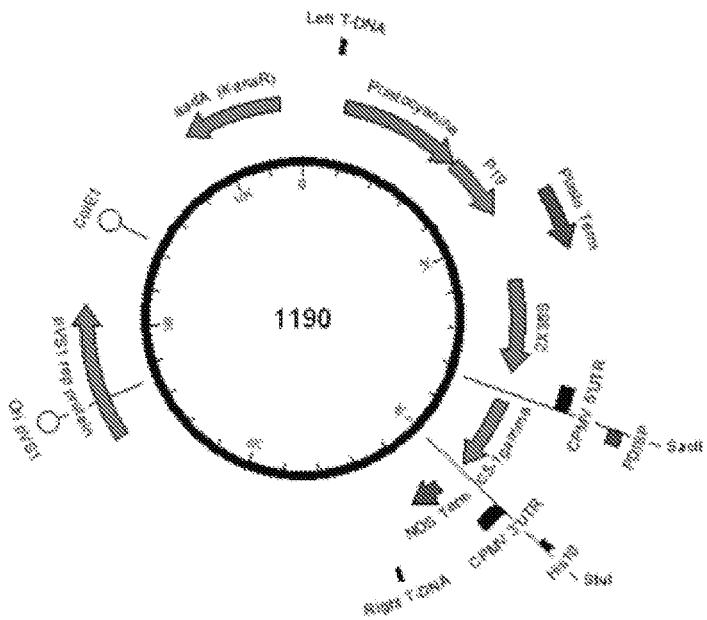

Figure 12C, SEQ ID NO: 46

Construct 1190 from left to right t-DNA borders (underlined). 2X35S/CPMV-160/NOS with Plastocyanine-P19-Plastocyanine silencing inhibitor expression cassette TGGCAGGATATATTGTGGTGTAAACAAATTGACGCTTAGACAACTTAATAACACATTGCGGACGTTTTTAATGTACTGAATTAACG
CCGAATCCCGGGCTGGTATATTTATATGTTGTCAAATAACTCAAAAACCATAAAAGTTTAAGTTAGCAAGTGTGTACATTTTTACTT
GAACAAAAATATTCACCTACTACTGTTATAAATCATTATTAAACATTAGAGTAAAGAAATATGGATGATAAGAACAAGAGTAGTGA
TATTTTGACAACAATTTTGTTGCAACATTTGAGAAAATTTTGTTGTTCTCTCTTTTCATTGGTCAAAAACAATAGAGAGAGAAAAAG
GAAGAGGGAGAATAAAAACATAATGTGAGTATGAGAGAGAAAGTTGTACAAAAGTTGTACCAAAATAGTTGTACAAATATCATT
GAGGAATTTGACAAAAGCTACACAAATAAGGGTTAATTGCTGTAAATAAATAAGGATGACGCATTAGAGAGATGTACCATTAGAG
AATTTTTGGCAAGTCATTAAAAAGAAAGAATAAATTATTTTTAAAATTAAAAGTTGAGTCATTTGATTAAACATGTGATTATTTAAT
GAATTGATGAAAGAGTTGGATTAAAGTTGTATTAGTAATTAGAATTTGGTGTCAAATTTAATTTGACATTTGATCTTTTCCTATATA
TTGCCCCATAGAGTCAGTTAACTCATTTTTATATTTCATAGATCAAATAAGAGAAATAACGGTATATTAATCCCTCCAAAAAAAAAA
AACGGTATATTTACTAAAAAATCTAAGCCACGTAGGAGGATAACAGGATCCCCGTAGGAGGATAACATCCAATCCAACCAATCAC
AACAATCCTGATGAGATAACCCACTTTAAGCCCACGCATCTGTGGCACATCTACATTATCTAAATCACACATTCTTCCACACATCTG
AGCCACACAAAAACCAATCCACATCTTTATCACCCATTCTATAAAAAATCACACTTTGTGAGTCTACACTTTGATTCCCTTCAAACAC
ATACAAAGAGAAGAGACTAATTAATTAATTAATCATCTTGAGAGAAAATGGAACGAGCTATACAAGGAAACGACGCTAGGGAAC
AAGCTAACAGTGAACGTTGGGATGGAGGATCAGGAGGTACCACTTCTCCCTTCAAACTTCCTGACGAAAGTCCGAGTTGGACTGA
GTGGCGGCTACATAACGATGAGACGAATTCGAATCAAGATAATCCCCTTGGTTTCAAGGAAAGCTGGGGTTTCGGGAAAGTTGTA
TTTAAGAGATATCTCAGATACGACAGGACGGAAGCTTCACTGCACAGAGTCCTTGGATCTTGGACGGGAGATTCGGTTAACTATG

Figure 12C continued

CAGCATCTCGATTTTTCGGTTTCGACCAGATCGGATGTACCTATAGTATTCGGTTTCGAGGAGTTAGTATCACCGTTTCTGGAGGG
TCGCGAACTCTTCAGCATCTCTGTGAGATGGCAATTCGGTCTAAGCAAGAACTGCTACAGCTTGCCCCAATCGAAGTGGAAAGTA
ATGTATCAAGAGGATGCCCTGAAGGTACTCAAACCTTCGAAAAAGAAAGCGAGTAAGTTAAAATGCTTCTTCGTCTCCTATTTATA
ATATGGTTTGTTATTGTTAATTTTGTTCTTGTAGAAGAGCTTAATTAATCGTTGTTGTTATGAAATACTATTTGTATGAGATGAACTG
GTGTAATGTAATTCATTTACATAAGTGGAGTCAGAATCAGAATGTTTCCTCCATAACTAACTAGACATGAAGACCTGCCGCGTACA
ATTGTCTTATATTTGAACAACTAAAATTGAACATCTTTTGCCACAACTTTATAAGTGGTTAATATAGCTCAAATATATGGTCAAGTTC
AATAGATTAATAATGGAAATATCAGTTATCGAAATTCATTAACAATCAACTTAACGTTATTAACTACTAATTTTATATCATCCCCTTT
GATAAATGATAGTACACCAATTAGGAAGGAGCATGCTCGCCTAGGAGATTGTCGTTTCCCGCCTTCAGTTTGCAAGCTGCTCTAGC
CGTGTAGCCAATACGCAAACCGCCTCTCCCCGCGCGTTGGGAATTACTAGCGCGTGTCGACAAGCTTGCATGCCGGTCAACATGG
TGGAGCACGACACACTTGTCTACTCCAAAAATATCAAAGATACAGTCTCAGAAGACCAAAGGGCAATTGAGACTTTTCAACAAAG
GGTAATATCCGGAAACCTCCTCGGATTCCATTGCCCAGCTATCTGTCACTTTATTGTGAAGATAGTGGAAAAGGAAGGTGGCTCCT
ACAAATGCCATCATTGCGATAAAGGAAAGGCCATCGTTGAAGATGCCTCTGCCGACAGTGGTCCCAAAGATGGACCCCCACCCAC
GAGGAGCATCGTGGAAAAAGAAGACGTTCCAACCACGTCTTCAAAGCAAGTGGATTGATGTGATAACATGGTGGAGCACGACAC
ACTTGTCTACTCCAAAAATATCAAAGATACAGTCTCAGAAGACCAAAGGGCAATTGAGACTTTTCAACAAAGGGTAATATCCGGA
AACCTCCTCGGATTCCATTGCCCAGCTATCTGTCACTTTATTGTGAAGATAGTGGAAAAGGAAGGTGGCTCCTACAAATGCCATCA
TTGCGATAAAGGAAAGGCCATCGTTGAAGATGCCTCTGCCGACAGTGGTCCCAAAGATGGACCCCCACCCACGAGGAGCATCGT
GGAAAAAGAAGACGTTCCAACCACGTCTTCAAAGCAAGTGGATTGATGTGATATCTCCACTGACGTAAGGGATGACGCACAATCC
CACTATCCTTCGCAAGACCCTTCCTCTATATAAGGAAGTTCATTTCATTTGGAGAGGTATTAAAATCTTAATAGGTTTTGATAAAAG
CGAACGTGGGGAAACCCGAACCAAACCTTCTTCTAAACTCTCTCTCATCTCTCTTAAAGCAAACTTCTCTCTTGTCTTTCTTGCGTGA
GCGATCTTCAACGTTGTCAGATCGTGCTTCGGCACCGCGGATGGCGAAAAACGTTGCGATTTTCGGCTTATTGTTTTCTCTTCTTGT
GTTGGTTCCTTCTCAGATCTTCGCCTGCAGGCTCCTCAGCCAAAACGACACCCCCATCTGTCTATCCACTGGCCCCTGGATCTGCTG
CCCAAACTAACTCCATGGTGACCCTGGGATGCCTGGTCAAGGGCTATTTCCCTGAGCCAGTGACAGTGACCTGGAACTCTGGATCC
CTGTCCAGCGGTGTGCACACCTTCCCAGCTGTCCTGCAGTCTGACCTCTACACTCTGAGCAGCTCAGTGACTGTCCCCTCCAGCACC
TGGCCCAGCGAGACCGTCACCTGCAACGTTGCCCACCCGGCCAGCAGCACCAAGGTGGACAAGAAATTGTGCCCAGGGATTGT
GGTTGTAAGCCTTGCATATGTACAGTCCCAGAAGTATCATCTGTCTTCATCTTCCCCCCAAAGCCCAAGGATGTGCTCACCATTACT
CTGACTCCTAAGGTCACGTGTGTTGTGGTAGACATCAGCAAGGATGATCCCGAGGTCCAGTTCAGCTGGTTTGTAGATGATGTGG
AGGTGCACACAGCTCAGACGCAACCCCGGGAGGAGCAGTTCAACAGCACTTTCCGCTCAGTCAGTGAACTTCCCATCATGCACCA
GGACTGGCTCAATGGCAAGGAGCGATCGCTCACCATCACCATCACCATCACCATTAAAGGCCTATTTTCTTTAGTTTGAAT
TTACTGTTATTCGGTGTGCATTTCTATGTTTGGTGAGCGGTTTTCTGTGCTCAGAGTGTGTTTATTTTATGTAATTTAATTTCTTTGTG
AGCTCCTGTTTAGCAGGTCGTCCCTTCAGCAAGGACACAAAAAGATTTTAATTTTATTAAAAAAAAAAAAAAAAAAGACCGGGAA
TTCGATATCAAGCTTATCGACCTGCAGATCGTTCAAACATTTGGCAATAAAGTTTCTTAAGATTGAATCCTGTTGCCGGTCTTGCGA
TGATTATCATATAATTTCTGTTGAATTACGTTAAGCATGTAATAATTAACATGTAATGCATGACGTTATTTATGAGATGGGTTTTTAT
GATTAGAGTCCCGCAATTATACATTTAATACGCGATAGAAAACAAAATATAGCGCGCAAACTAGGATAAATTATCGCGCGCGGTG
TCATCTATGTTACTAGATCTCTAGAGTCTCAAGCTTGGCGCGCCCACGTGACTAGTGGCACTGGCCGTCGTTTTACAACGTCGTGA
CTGGGAAAACCCTG

Figure 12D continued

```
GCACAATCCCACTATCCTTCGCAAGACCCTTCCTCTATATAAGGAAGTTCATTTCATTTGGAGAGGTATTAAAATCTTAATAGGTTTT
GATAAAAGCGAACGTGGGGAAACCCGAACCAAACCTTCTTCTAAACTCTCTCTCATCTCTCTTAAAGCAAACTTCTCTCTTGTCTTTC
TTGCGTGAGCGATCTTCAACGTTGTCAGATCGTGCTTCGGCACCAGTACAATGGCATACCGGAAGAGAGGAGCAAAGCGCGAAA
ACCTGCCGCAACAGAACGAGAGACTGCAAGAAAAAGAGATAGAGAAAGATGTCGACGTAACAATGGAAAACAAGAATAACAAT
AGGAAACAACAGCTGTCCGACAAAGTTCTGTCCCAGAAGGAGGAAATTATCACTGACGCCCAGGACGATATTAAAATTGCCGGA
GAAATAAAGAAGAGCTCGAAAGAAGAATCTAAACAGCTGCTCGAAATTCTGAAAACAAAAGAAGACCATCAGAAAGAGATTCAA
TATGAAATTTTGCAAAAAACAATACCTACATTTGAGTCCAAAGAAAGTATCCTCAAGAAGCTTGAAGACATAAGACCGGAGCAGG
CAAAAAAACAGATGAAACTCTTTCGCATTTTCGAGCCAAAACAGCTCCCTATATATCGCGCCAATGGCGAGAAGGAGCTACGCAA
CCGGTGGTACTGGAAGTTGAAAAAAGACACCCTGCCAGATGGAGATTATGACGTCCGGGAGTATTTCCTCAATCTCTATGATCAG
ATCCTCATCGAAATGCCGGACTATCTGCTCCTCAAGGACATGGCCGTGGAGAACAAAAATAGCAGAGACGCCGGCAAAGTTGTCG
ACTCTGAGACTGCCAATATTTGTGATGCCATCTTCCAGGATGAGGAGACCGAGGGAGTCGTCCGTAGATTCATCGCTGATATGCG
GCAACAGGTCCAGGCTGATCGTAACATTGTCAATTACCCTTCCATCCTTCACCCTATTGATCATGCATTCAATGAGTATTTTCTTAAC
CACCAGTTGGTGGAGCCGCTGAACAATGAGATAATCTTCAATTACATACCAGAGAGGATAAGGAATGACGTGAATTACATCCTGA
ACATGGATATGAATCTGCCATCTACAGCCAGGTATATCAGGCCAAACTTGTTGCAGGATAGACTGAATCTTCACGATAATTTTGAG
TCCCTGTGGGATACCATCACAACATCCAACTACATTCTGGCCAGGTCCGTCGTTCCCGATTTGAAGGAGAAGGAGCTGGTCTCCAC
CGAAGCACAGATCCAGAAAATGAGCCAGGACCTGCAGCTGGAGGCCCTCACTATTCAGAGCGAGACACAGTTTTTAGCCGGGAT
TAACAGTCAGGCTGCCAATGATTGTTTCAAGACCCTCATAGCCGCCATGCTGTCTCAAAGAACCATGTCTTTGGACTTTGTGACCAC
GAACTATATGAGCCTAATCTCCGGAATGTGGCTACTTACAGTGATTCCCAACGATATGTTCCTCCGGGAGTCACTAGTGGCCTGTG
AGCTGGCGATCATCAACACCATCGTGTATCCAGCATTCGGAATGCAGAGAATGCATTACCGGAATGGCGACCCTCAGACACCCTT
CCAGATCGCAGAACAGCAGATCCAGAATTTCCAGGTGGCGAACTGGCTCCATTTTATTAACAATAACAGATTCAGGCAAGTTGTG
ATTGATGGAGTTCTGAATCAGACTCTGAACGACAATATACGGAATGGACAGGTCATCAACCAGCTGATGGAAGCATTGATGCAAC
TCAGCAGACAGCAGTTCCCCACGATGCCTGTGGATTACAAACGGAGCATCCAACGGGGCATTCTGCTTCTCTCCAATAGGCTGGG
GCAGCTTGTCGACTTAACCCGACTGGTCTCCTATAACTACGAGACGCTAATGGCTTGTGTGACCATGAACATGCAGCACGTGCAAA
CCCTGACAACTGAGAAGTTGCAGCTCACTTCTGTGACTTCGCTTTGTATGTTAATTGGTAACACAACCGTGATTCCGTCCCCACAGA
CACTGTTCCACTACTACAACATCAACGTGAATTTCCACTCCAATTATAATGAGCGGATCAACGACGCCGTCGCCATAATTACCGCAG
CAAATAGGCTGAATCTTTATCAGAAAAAAATGAAGTCCATAGTGGAAGACTTTCTGAAACGGCTCCAGATTTTCGACGTACCACGA
GTGCCTGACGACCAAATGTACAGGCTGAGGGATCGCCTTCGGCTCTTACCCGTTGAACGGAGACGGCTTGACATATTCAACTTGA
TCCTGATGAATATGGAGCAGATCGAACGCGCTTCTGATAAGATTGCTCAGGGGGTTATCATCGCATACCGAGATATGCAGCTGGA
ACGCGACGAGATGTACGGATATGTTAATATTGCACGGAATCTTGATGGCTACCAGCAAATTAACTTGGAGGAACTCATGCGCACC
GGTGATTACGGACAAATTACGAACATGCTTCTCAACAATCAACCCGTTGCCCTTGTGGGTGCATTGCCCTTCGTTACGGACTCATCC
GTGATCAGTCTAATCGCCAAGCTCGACGCAACCGTCTTCGCTCAGATAGTGAAGCTCAGGAAAGTTGACACACTGAAGCCCATAC
TGTACAAAATAAACTCGGATTCCAATGACTTTTACCTTGTGGCCAACTACGACTGGATCCCCACAAGTACAACTAAGGTCTACAAA
CAGGTGCCACAACCATTCGACTTTAGAGCCAGCATGCACATGCTGACTTCTAACCTTACGTTTACCGTCTACTCTGACCTACTGTCA
TTTGTTTCAGCGGACACGGTAGAGCCCATTAACGCAGTCGCATTCGACAATATGCGAATAATGAACGAGCTTTAAAGGCCTATTTT
CTTTAGTTTGAATTTACTGTTATTCGGTGTGCATTTCTATGTTTGGTGAGCGGTTTTCTGTGCTCAGAGTGTGTTTATTTTATGTAAT
TTAATTTCTTTGTGAGCTCCTGTTTAGCAGGTCGTCCCTTCAGCAAGGACACAAAAAGATTTTAATTTTATTAAAAAAAAAAAAAAA
AAAGACCGGGAATTCGATATCAAGCTTATCGACCTGCAGATCGTTCAAACATTTGGCAATAAAGTTTCTTAAGATTGAATCCTGTT
GCCGGTCTTGCGATGATTATCATATAATTTCTGTTGAATTACGTTAAGCATGTAATAATTAACATGTAATGCATGACGTTATTTATG
AGATGGGTTTTTATGATTAGAGTCCCGCAATTATACATTTAATACGCGATAGAAAACAAAATATAGCGCGCAAACTAGGATAAATT
ATCGCGCGCGGTGTCATCTATGTTACTAGAT
```

Figure 12E

Schematic representation of construct number 1108

7. 2X35S/CPMV-160/RVA(WA) VP6(opt)/NOS (Construct number 1128)

Figure 13A, SEQ ID NO: 48

IF(C160)-WA_VP6(opt).c

TCGTGCTTCGGCACCAGTACAATGGAGGTCCTTTATAGTCTCTCCAAAACGCTGA

Figure 13B, SEQ ID NO: 49

Expression cassette number 1128 from 2X35S promoter to NOS terminator. VP6(opt) from Rotavirus A WA strain is underlined.

GTCAACATGGTGGAGCACGACACACTTGTCTACTCCAAAAATATCAAAGATACAGTCTCAGAAGACCAAAGGGCAATTGAGACTT
TTCAACAAAGGGTAATATCCGGAAACCTCCTCGGATTCCATTGCCCAGCTATCTGTCACTTTATTGTGAAGATAGTGGAAAAGGAA
GGTGGCTCCTACAAATGCCATCATTGCGATAAAGGAAAGGCCATCGTTGAAGATGCCTCTGCCGACAGTGGTCCCAAAGATGGAC
CCCCACCCACGAGGAGCATCGTGGAAAAAGAAGACGTTCCAACCACGTCTTCAAAGCAAGTGGATTGATGTGATAACATGGTGG
AGCACGACACACTTGTCTACTCCAAAAATATCAAAGATACAGTCTCAGAAGACCAAAGGGCAATTGAGACTTTTCAACAAAGGGT
AATATCCGGAAACCTCCTCGGATTCCATTGCCCAGCTATCTGTCACTTTATTGTGAAGATAGTGGAAAAGGAAGGTGGCTCCTACA
AATGCCATCATTGCGATAAAGGAAAGGCCATCGTTGAAGATGCCTCTGCCGACAGTGGTCCCAAAGATGGACCCCCACCCACGAG
GAGCATCGTGGAAAAAGAAGACGTTCCAACCACGTCTTCAAAGCAAGTGGATTGATGTGATATCTCCACTGACGTAAGGGATGAC
GCACAATCCCACTATCCTTCGCAAGACCCTTCCTCTATATAAGGAAGTTCATTTCATTTGGAGAGGTATTAAAATCTTAATAGGTTTT
GATAAAAGCGAACGTGGGGAAACCCGAACCAAACCTTCTTCTAAACTCTCTCTCATCTCTCTTAAAGCAAACTTCTCTCTTGTCTTTC

Figure 13B continued

TTGCGTGAGCGATCTTCAACGTTGTCAGATCGTGCTTCGGCACCAGTACAATGGAGGTCCTTTATAGTCTCTCCAAAACGCTGAAG
GACGCTAGGGACAAGATCGTGGAGGGTACACTTTATAGCAATGTCAGCGACCTAATACAGCAGTTTAATCAAATGATCGTTACAA
TGAATGGGAATGATTTCCAAACTGGCGGTATTGGTAATCTGCCCGTGAGGAACTGGACATTCGATTTCGGCCTGCTGGGCACGAC
TCTCCTTAATCTCGATGCAAATTATGTAGAAAACGCCAGAACGATTATCGAGTACTTTATCGATTTCATTGATAACGTTTGTATGGA
TGAGATGGCCCGCGAGTCACAACGGAACGGAGTTGCTCCACAGTCCGAGGCCCTTCGGAAACTCGCCGGCATTAAGTTCAAGCGT
ATTAATTTCGACAACTCCTCCGAATATATAGAGAACTGGAACTTGCAGAATCGTCGACAGAGAACCGGCTTCGTGTTCCATAAACC
TAATATCTTTCCGTATAGCGCCTCATTCACCCTGAATAGGAGTCAGCCCATGCACGACAACCTCATGGGTACAATGTGGCTGAATG
CGGGGAGTGAAATACAGGTCGCCGGGTTCGATTACTCCTGTGCCATTAATGCACCCGCAAACATCCAGCAGTTCGAACATATCGT
GCAACTAAGACGGGCTCTCACGACCGCGACAATTACACTCCTGCCCGACGCCGAGCGCTTCTCCTTTCCCCGCGTAATCAACTCAG
CTGATGGCGCCACCACTTGGTTCTTCAACCCTGTTATATTGCGCCCTAACAACGTAGAGGTGGAGTTTCTCTTAAACGGACAGATC
ATCAATACCTACCAAGCCAGGTTCGGCACGATTATTGCAAGAAATTTCGACGCTATCAGGCTGCTCTTCCAACTGATGAGGCCCCC
CAATATGACTCCCGCTGTGAACGCTTTGTTTCCGCAGGCTCAGCCTTTCCAGCACCACGCCACCGTCGGCTTGACTCTTCGAATAGA
GAGCGCGGTCTGCGAATCAGTGCTGGCAGACGCCAACGAGACGCTGCTGGCAAACGTTACCGCCGTGCGGCAAGAGTATGCCAT
CCCAGTAGGGCCTGTGTTTCCACCCGGCATGAACTGGACTGAACTAATTACTAACTATAGCCCATCCAGAGAAGACAACTTGCAGC
GGGTCTTCACTGTGGCCTCTATCCGGAGTATGTTGATCAAGTAGAGGCCTATTTTCTTTAGTTTGAATTTACTGTTATTCGGTGTGC
ATTTCTATGTTTGGTGAGCGGTTTTCTGTGCTCAGAGTGTGTTTATTTTATGTAATTTAATTTCTTTGTGAGCTCCTGTTTAGCAGGT
CGTCCCTTCAGCAAGGACACAAAAAGATTTTAATTTTATTAAAAAAAAAAAAAAAAAAGACCGGGAATTCGATATCAAGCTTATCG
ACCTGCAGATCGTTCAAACATTTGGCAATAAAGTTTCTTAAGATTGAATCCTGTTGCCGGTCTTGCGATGATTATCATATAATTTCT
GTTGAATTACGTTAAGCATGTAATAATTAACATGTAATGCATGACGTTATTTATGAGATGGGTTTTATGATTAGAGTCCCGCAATT
ATACATTTAATACGCGATAGAAAACAAAATATAGCGCGCAAACTAGGATAAATTATCGCGCGCGGTGTCATCTATGTTACTAGAT

Figure 13C

Schematic representation of construct number 1128

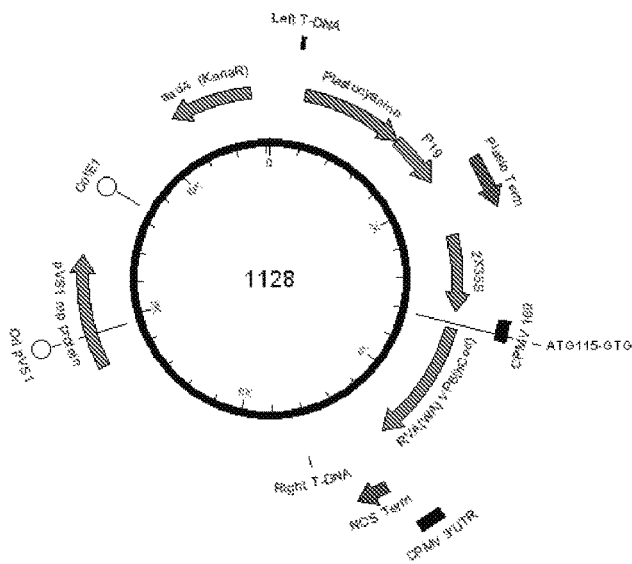

8. 2X35S/CPMV-160/ RVA(Rtx) VP4(opt)/ NOS (Construct number 1178)

Figure 14A, SEQ ID NO: 50

IF(C160)-Rtx_VP4(opt).c

TCGTGCTTCGGCACCAGTACAATGGCTAGCCTGATCTACAGACAACTCTTGACCAATTC

Figure 14B, SEQ ID NO: 51

Expression cassette number 1178 from 2X35S promoter to NOS terminator. VP4(opt) from Rotavirus A Rotarix strain is underlined.

GTCAACATGGTGGAGCACGACACACTTGTCTACTCCAAAAATATCAAAGATACAGTCTCAGAAGACCAAAGGGCAATTGAGACTT
TTCAACAAAGGGTAATATCCGGAAACCTCCTCGGATTCCATTGCCCAGCTATCTGTCACTTTATTGTGAAGATAGTGGAAAAGGAA
GGTGGCTCCTACAAATGCCATCATTGCGATAAAGGAAAGGCCATCGTTGAAGATGCCTCTGCCGACAGTGGTCCCAAAGATGGAC
CCCCACCCACGAGGAGCATCGTGGAAAAAGAAGACGTTCCAACCACGTCTTCAAAGCAAGTGGATTGATGTGATAACATGGTGG
AGCACGACACACTTGTCTACTCCAAAAATATCAAAGATACAGTCTCAGAAGACCAAAGGGCAATTGAGACTTTTCAACAAAGGGT
AATATCCGGAAACCTCCTCGGATTCCATTGCCCAGCTATCTGTCACTTTATTGTGAAGATAGTGGAAAAGGAAGGTGGCTCCTACA
AATGCCATCATTGCGATAAAGGAAAGGCCATCGTTGAAGATGCCTCTGCCGACAGTGGTCCCAAAGATGGACCCCCACCCACGAG
GAGCATCGTGGAAAAAGAAGACGTTCCAACCACGTCTTCAAAGCAAGTGGATTGATGTGATATCTCCACTGACGTAAGGGATGAC
GCACAATCCCACTATCCTTCGCAAGACCCTTCCTCTATATAAGGAAGTTCATTTCATTTGGAGAGGTATTAAAATCTTAATAGGTTTT
GATAAAAGCGAACGTGGGGAAACCCGAACCAAACCTTCTTCTAAACTCTCTCTCATCTCTCTTAAAGCAAACTTCTCTCTTGTCTTTC
TTGCGTGAGCGATCTTCAACGTTGTCAGATCGTGCTTCGGCACCAGTACA<u>ATGGCTAGCCTGATCTACAGACAACTCTTGACCAAT
TCATATTCTGTGGATCTTCATGACGAAATCGAGCAGATTGGGTCCGAGAAGACCCAGAACGTGACCATCAACCCTGGACCTTTTGC
TCAGACCCGCTATGCCCCTGTGAATTGGGATCACGGAGAAATCAACGACAGTACGACCGTCGAACCCATTCTGGACGGGCCATAC
CAACCCACCACCTTCACCCCACCTAATGATTATTGGATTTTAATCAACTCCAACACAAACGGAGTGGTCTACGAGTCCACTAATAAC
TCCGATTTTTGGACCGCCGTTGTAGCCATCGAGCCACACGTCAATCCTGTCGATCGCCAGTATATGATATTCGGCGAGTCCAAACA
GTTTAACGTTTCCAATGACAGCAACAAATGGAAGTTTCTGGAGATGTTTCGCAGCTCCTCTCAGAACGAATTCTATAATAGACGGA
CCCTTACCTCCGATACACGACTCGTGGGTATTTTTAAGTACGGCGGCAGGGTGTGGACATTTCACGGTGAAACCCCTCGAGCAACC
ACTGACTCCAGTAGCACTGCAAACCTGAACAATATATCTATTACCATCCACAGCGAATTCTACATAATCCCAAGATCTCAGGAAAGT
AAGTGTAACGAATATATCAACAACGGACTCCCCCCAATTCAGAATACACGGAACGTGGTGCCTCTCCCACTCAGTTCTCGGTCTAT
CCAGTATAAGAGAGCACAAGTGAATGAGGACATTATTGTGAGCAAGACTAGCCTTTGGAAAGAAATGCAGTACAACAGAGACAT
TATCATCCGGTTTAAGTTTGGGAACTCTATCGTGAAGATGGGCGGCCTGGGGTACAAATGGTCAGAAATCTCATATAAAGCCGCC
AACTATCAGTATAACTACTTGAGAGACGGCGAGCAGGTAACCGCCCACACAACATGCTCTGTCAACGGCGTTAATAACTTTAGCTA
CAACGGAGGCTTCCTTCCCACCGACTTCGGTATCAGCCGGTATGAAGTCATCAAGGAAAATTCTTATGTGTACGTAGATTACTGGG
ATGATAGCAAAGCGTTCCGCAACATGGTGTATGTTAGGAGCCTGGCTGCTAATCTCAATTCTGTGAAGTGTACTGGTGGATCATAT
TATTTCTCAATTCCCGTGGGGGCTTGGCCAGTCATGAATGGCGGGGCAGTCTCCCTCCATTTTGCTGGCGTGACGTTGAGCACTCA
GTTTACCGATTTCGTGTCTCTGAACTCCCTGAGGTTCCGGTTTTCCCTTACTGTCGACGAGCCCCCATTCAGCATTCTGCGTACAAG
AACTGTCAACCTCTACGGGTTACCTGCCGCGAATCCAAACAACGGCAATGAATACTATGAAATTTCGGGCCGCTTCTCTTTGATAA
GTCTGGTACCAACTAATGACGACTATCAGACACCCATCATGAACAGCGTGACTGTCAGACAGGACCTGGAAAGACAACTTACAGA
TCTGCGGGAAGAATTCAATTCTCTCAGTCAGGAGATTGCAATGGCCCAATTGATAGATCTTGCCCTACTGCCTCTCGATATGTTTAG
TATGTTCTCCGGCATCAAATCAACTATAGATCTGACAAGAGCATGGCTACTTCTGTGATGAAGAAGTTCAGGAAATCAAAACTTG
CCACGAGCATATCAGAAATGACGAACTCTCTGAGTGATGCAGCATCATCAGCGTCACGCAACGTTTCCATTCGGTCGAATCTCAGC
GCCATCAGCAACTGGACAAACGTGTCCAACGACGTCAGCAACGTGACCAACTCCTTGAACGATATTTCTACCCAGACGTCAACGAT
CAGTAAGAAACTCCGCTTGAAAGAAATGATCACCCAGACTGAGGGAATGTCTTTCGACGACATTTCCGCCGCCGTGCTAAAAACC
AAAATCGATATGTCTACTCAGATCGGCAAGAACACTCTGCCGGATATCGTAACCGAAGCCTCCGAAAAGTTTATCCCTAAGCGCAG
CTACAGAATATTGAAAGATGACGAGGTCATGGAGATCAACACAGAAGGGAAGTTCTTCGCTTATAAGATCAACACCTTTGACGAG
GTTCCGTTTGACGTCAATAAGTTTGCAGAGCTCGTGACAGATAGTCCAGTGATTTCTGCCATCATTGACTTTAAGACTTTGAAGAA
CCTGAACGACAACTATGGAATAACACGGACCGAAGCGTTGAACCTCATTAAGTCCAATCCAATATGTTGCGCAATTTCATTAACC
AGAACAATCCAATCATAAGAAATAGGATTGAGCAATTAATCCTGCAATGTAAACTCTGA</u>AGGCCTATTTTCTTTAGTTTGAATTTAC

Figure 14B continued

```
TGTTATTCGGTGTGCATTTCTATGTTTGGTGAGCGGTTTTCTGTGCTCAGAGTGTGTTTATTTTATGTAATTTAATTTCTTTGTGAGC
TCCTGTTTAGCAGGTCGTCCCTTCAGCAAGGACACAAAAAGATTTTAATTTTATTAAAAAAAAAAAAAAAAAAAGACCGGGAATTCG
ATATCAAGCTTATCGACCTGCAGATCGTTCAAACATTTGGCAATAAAGTTTCTTAAGATTGAATCCTGTTGCCGGTCTTGCGATGAT
TATCATATAATTTCTGTTGAATTACGTTAAGCATGTAATAATTAACATGTAATGCATGACGTTATTTATGAGATGGGTTTTTATGATT
AGAGTCCCGCAATTATACATTTAATACGCGATAGAAAACAAAATATAGCGCGCAAACTAGGATAAATTATCGCGCGCGGTGTCAT
CTATGTTACTAGAT
```

Figure 14C

Schematic representation of construct number 1178

9. 2X35S/CPMV-160/TrSp-RVA(Rtx) VP7(Opt)/NOS (Construct number 1199)

Figure 15A, SEQ ID NO: 52

IF(C160)-TrSP+Rtx_VP7(opt).c

TCGTGCTTCGGCACCAGTACAATGGATTATATTATCTATCGTAGCCTCCTCATCTA

Figure 15B, SEQ ID NO: 53

Expression cassette number 1199 from 2X35S promoter to NOS terminator. VP7 from Rotavirus A vaccine USA/Rotarix-A41CB052A/1988/G1P1A[8] strain is underlined.

```
GTCAACATGGTGGAGCACGACACACTTGTCTACTCCAAAAATATCAAAGATACAGTCTCAGAAGACCAAAGGGCAATTGAGACTT
TTCAACAAAGGGTAATATCCGGAAACCTCCTCGGATTCCATTGCCCAGCTATCTGTCACTTTATTGTGAAGATAGTGGAAAAGGAA
GGTGGCTCCTACAAATGCCATCATTGCGATAAAGGAAAGGCCATCGTTGAAGATGCCTCTGCCGACAGTGGTCCCAAAGATGGAC
CCCCACCCACGAGGAGCATCGTGGAAAAAGAAGACGTTCCAACCACGTCTTCAAAGCAAGTGGATTGATGTGATAACATGGTGG
```

Figure 15B continued

AGCACGACACACTTGTCTACTCCAAAAATATCAAAGATACAGTCTCAGAAGACCAAAGGGCAATTGAGACTTTTCAACAAAGGGT
AATATCCGGAAACCTCCTCGGATTCCATTGCCCAGCTATCTGTCACTTTATTGTGAAGATAGTGGAAAAGGAAGGTGGCTCCTACA
AATGCCATCATTGCGATAAAGGAAAGGCCATCGTTGAAGATGCCTCTGCCGACAGTGGTCCCAAAGATGGACCCCCACCCACGAG
GAGCATCGTGGAAAAAGAAGACGTTCCAACCACGTCTTCAAAGCAAGTGGATTGATGTGATATCTCCACTGACGTAAGGGATGAC
GCACAATCCCACTATCCTTCGCAAGACCCTTCCTCTATATAAGGAAGTTCATTTCATTTGGAGAGGTATTAAAATCTTAATAGGTTTT
GATAAAAGCGAACGTGGGGAAACCCGAACCAAACCTTCTTCTAAACTCTCTCTCATCTCTCTTAAAGCAAACTTCTCTCTTGTCTTTC
TTGCGTGAGCGATCTTCAACGTTGTCAGATCGTGCTTCGGCACCAGTACAATGGATTATATTATCTATCGTAGCCTCCTCATCTACG
TGGCCCTTTTTGCCCTGACCAGGGCCCAGAACTATGGCCTGAACTTACCAATCACCGGTTCAATGGATACCGTTTACGCTAATTCCA
CTCAAGAGGGGATATTTCTGACAAGTACCCTGTGCCTGTATTATCCAACAGAAGCCTCTACCCAGATCAATGATGGGGAGTGGAA
GGATAGTCTCTCACAGATGTTCCTAACCAAGGGCTGGCCCACCGGTTCCGTCTACTTCAAGGAATACTCTAGTATTGTCGACTTCTC
AGTTGACCCCCAGCTTTATTGCGACTACAACCTGGTACTTATGAAATACGACCAGAACCTGGAGCTGGATATGTCCGAGCTGGCTG
ACCTGATCCTCAATGAGTGGCTGTGCAACCCCATGGACATCACATTATATTACTACCAGCAGTCTGGAGAATCCAACAAGTGGATC
AGTATGGGCTCAAGTTGCACCGTGAAGGTGTGTCCCTTGAACACCCAAATGCTGGGCATTGGTTGTCAGACAACTAATGTGGATT
CGTTTGAAATGGTAGCCGAAAACGAGAAGCTGGCTATAGTGGACGTAGTCGATGGGATTAACCACAAGATCAATCTGACTACCAC
CACTTGTACCATCAGAAACTGTAAAAAGCTCGGCCCCCGGGAGAACGTCGCCGTGATCCAGGTGGGGGGGAGCAATGTGCTCGA
CATTACTGCCGACCCTACCACCAATCCACAGACGGAACGGATGATGAGAGTCAACTGGAAGAAATGGTGGCAGGTCTTTTATACC
ATTGTGGACTACATTAACCAGATTGTGCAAGTCATGAGTAAACGGTCCAGATCCCTGAACTCAGCAGCCTTCTATTATCGCGTTTA
GAGGCCTATTTTCTTTAGTTTGAATTTACTGTTATTCGGTGTGCATTTCTATGTTTGGTGAGCGGTTTTCTGTGCTCAGAGTGTGTTT
ATTTTATGTAATTTAATTTCTTTGTGAGCTCCTGTTTAGCAGGTCGTCCCTTCAGCAAGGACACAAAAAGATTTTAATTTTATTAAAA
AAAAAAAAAAAAAGACCGGGAATTCGATATCAAGCTTATCGACCTGCAGATCGTTCAAACATTTGGCAATAAAGTTTCTTAAGAT
TGAATCCTGTTGCCGGTCTTGCGATGATTATCATATAATTTCTGTTGAATTACGTTAAGCATGTAATAATTAACATGTAATGCATGA
CGTTATTTATGAGATGGGTTTTTATGATTAGAGTCCCGCAATTATACATTTAATACGCGATAGAAAACAAAATATAGCGCGCAAAC
TAGGATAAATTATCGCGCGCGGTGTCATCTATGTTACTAGAT

Figure 15C

Schematic representation of construct number 1199

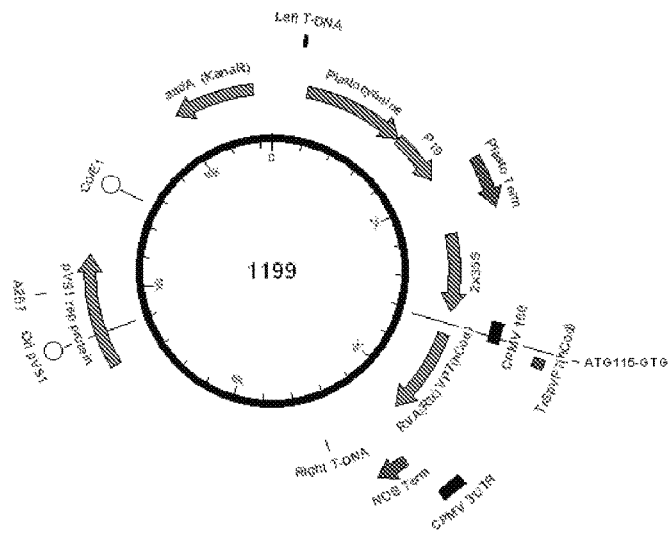

10. Double gene construct for the expression of VP6 and VP2 under CPMV-HT expression cassette (construct number 1708)

Figure 16 Schematic representation of construct number 1708

11. Double gene construct for the expression of VP7 and VP4 under CPMV-HT expression cassette (construct number 1719)

Figure 17 Schematic representation of construct number 1719

12. Double gene construct for the expression of VP6 and VP2 under CPMV-160 expression cassette (construct number 2400)

Figure 18 Schematic representation of construct number 2400

13. Double gene construct for the expression of VP7 and VP4 under CPMV-160 expression cassette (construct number 2408)

Figure 19 Schematic representation of construct number 2408

14. Quadruple gene construct for the expression of VP7, VP4, VP6 and VP2 under CPMV-HT expression cassette (construct number 1769)

**Figure

ROTAVIRUS-LIKE PARTICLE PRODUCTION IN PLANTS

FIELD OF INVENTION

This invention relates to producing rotavirus-like particles in plants.

BACKGROUND OF THE INVENTION

Rotavirus infection is a global problem mainly affecting children under the age of five. It results in severe gastroenteritis and in worst cases death.

Rotaviruses are members of the Reoviridae family of viruses (genus Rotavirus) that affect the gastrointestinal system and respiratory tract. The name is derived from the wheel like appearance of virions when viewed by negative contrast electron microscopy. The rotavirus is usually globular shape and is named after the outer and inner shells or double-shelled capsid structure of the same. The outer capsid is about 70 nm, and inner capsid is about 55 nm in diameter, respectively. The double-shelled capsid of the rotavirus surrounds the core including the inner protein shell and genome. The genome of the rotavirus consists of double stranded RNA segments encoding at least 11 rotavirus proteins—either structural viral proteins (VP) or nonstructural proteins (NSP; Desselberger, Virus Res 190: 75-96 (2014)).

The dsRNA codes for six structural proteins (VP) and six non-structural proteins (NSP). The structural proteins comprise VP1, VP2, VP3, VP4, VP6 and VP7. Three concentric layers are formed by the assembly of VP2, VP6 and VP7 respectively, with VP4 forming "spikes" on the surface of the virus structure. VP4 is cleaved by trypsin to VP8* and VP5*. VP8* and VP5* are proteolytic products of VP4.

VP2 is a 102 kDa protein and is the most abundant protein of the viral core. It forms the inner-most structural protein layer and provides a scaffold for the correct assembly of the components and transcription enzymes of the viral core (Lawton, 2000). VP1, the largest viral protein at 125 kDa, acts as an RNA-dependent polymerase for rotavirus, creating a core replication intermediate, and associates with VP2 at its icosahedral vertices (Varani and Allain, 2002; Vende et al., 2002). VP3, a 98 kDa protein, is also directly associated with the viral genome, acting as an mRNA capping enzyme that adds a 5' cap structure to viral mRNAs. Together, VP1 and VP3 form a complex that is attached to the outer 5-fold vertices of the VP2 capsid layer (Angel, 2007). VP6 is a 42 kDa protein which forms the middle shell of the viral core, is the major capsid protein and accounts for more than 50% of the total protein mass of the virion (González et al., 2004; Estes, 1996). It is required for gene transcription and may have a role in encapsulation of the rotavirus RNA by anchoring VP1 to VP2 in the core, as seen in bluetongue virus, another member of the Reoviridae family. It also determines the classification of rotaviruses into five groups (A to E) with group A most commonly affecting humans (Palombo, 1999). VP6 in rotavirus group A has at least four subgroups (SG), which depend on the presence or absence of SG specific epitopes: SG I, SG II, SG (I+II) and SG non-(I+II). Groups B and C lack a common group A antigen but are also known to infect humans, while group D only affects animals e.g. chickens and cows (Thongprachum, 2010).

The two outer capsid proteins VP7, a 37 kDa glycoprotein (G) and the 87 kDa protease sensitive VP4 (P), define the virus' serotypes. These two proteins induce neutralizing antibody responses and are thus used to classify rotavirus serotypes into a dual nomenclature system, depending on the G-P antigen combination (e.g. G1 P[8] or G2 P[4]) (Sanchez-Padilla et al., 2009, Rahman et al., J Clin Microbiol 41: 2088-2095 (2003)). The VP4 protein dimerizes to form 60 spikes on the outer shell of the virus, which are directly involved in the initial stages of host cell entry. The spike protein contains a cleavage site at amino acid (aa) position 248. Upon infection, it is cleaved by the protease trypsin to produce VP5 (529 aa, 60 kDa) and VP8 (246 aa, 28 kDa) (Denisova et al., 1999). This process enhances virus infectivity (cell attachment and invasion of host cell) and stabilizes the spike structure (Glass, 2006). The VP7 glycoprotein forms the third or outside layer of the virus. At present, 27 G and 35 P genotypes are known (Greenberg and Estes, 2009). VP4 and VP7 are the major antigens involved in virus neutralization and are important targets for vaccine development (Dennehy, 2007).

The non-structural proteins (NSPs) are synthesized in infected cells and function in various parts of the replication cycle or interact with some of the host proteins to influence pathogenesis or the immune response to infection (Greenberg and Estes, 2009). The rotavirus nonstructural protein, NSP4, has been shown to have multiple functions including the release of calcium from the endoplasmic reticulum (ER; Tian et al, 1995); the disruption of the ER membranes and may play an important role in the removal of the transient envelope from budding particles during viral morphogenesis (see FIG. 1); affecting membrane trafficking from the ER to the Golgi complex with its ability to bind to micro tubules (Xu et al 2000); and function as an intracellular receptor to aid in the budding of subviral particles into the ER (Tian et al 1996).

In infected mammalian cells, rotaviruses undergo a unique mode of morphogenesis to form the complete triple-layered VP2/6/4/7 viral particles (Lopez et al., 2005). The triple-layer capsid is a very stable complex which enables faecal-oral transmission and delivery of the virus into the small intestine where it infects non-dividing differentiated enterocytes near the tips of the villi (Greenberg and Estes, 2009). Firstly, the intact virus attaches to sialic acid-independent receptors via 60 VP4 dimer spikes on the surface of the virus (Lundgren and Svensson, 2001). The 60 VP4 dimer spikes on the surface of the virus allow the virus to attach to these cell receptors. VP4 is susceptible to proteolytic cleavage by trypsin which results in a conformational change that exposes additional attachment sites on the surface of the glycoprotein for interaction with a series of co-receptors.

The multi-step attachment and entry process is, however, not clearly understood but the virus is delivered across the host's plasma membrane. The VP7 outer capsid shell which is also involved in the entry process, is removed in the process and double-layered particles (DLP) are delivered into the cell cytoplasm in vesicles (FIG. 1; prior art). The DLP escapes from the vesicle and goes into non-membrane bound cytoplasmic inclusions. Early transcription of the genome by VP1 begins in particles so that dsRNA is never exposed to the cytoplasm. RNA replication and core formation takes place in these non-membrane-bound cytoplasmic inclusions. The nascent (+) RNAs are then transported into the cytoplasm and serve as templates for viral protein synthesis. VP4 is produced in the cytosol and transported to the rough endoplasmic reticulum (RER), and VP7 is secreted into the RER. VP2 and VP6 are produced and assemble in the cytosol in virosomes and subsequently bud into the RER compartments, receiving a transient membrane envelope in the process (Lopez et al., 2005; Tian et al., 1996). In the RER, the transient envelopes of the viral particles are removed and replaced by VP4 and VP7 protein monomers, with critical involvement of rotaviral glycoprotein NSP4 (Tian et al., 1996; Lopez et al., 2005; Gonzalez et al., 2000). NSP4 functions as an intracellular receptor in the ER membrane and binds newly made subviral particles and probably also the spike protein VP4 (Tian et al., 1996). NSP4 is also toxic to humans and is the causative agent of the diarrhea. The complete, mature particles are subsequently transferred from the RER through the Golgi apparatus to the plasma membrane for secretion (Lopez et al., 2005).

A variety of different approaches have been taken to generate a rotavirus vaccine suitable to protect human populations from the various serotypes of rotavirus. These approaches include various Jennerian approaches, use of live attenuated viruses, use of virus-like particles, nucleic acid vaccines and viral sub-units as immunogens. At present there are two oral vaccines available on the market, however, these have low efficacy in due to strain variation.

U.S. Pat. Nos. 4,624,850, 4,636,385, 4,704,275, 4,751,080, 4,927,628, 5,474,773, and 5,695,767, each describe a variety of rotavirus vaccines and/or methods of preparing these vaccines, where the whole viral particles is used to create each of the rotavirus vaccines.

Production of rotavirus-like particles is a challenging task, as both the synthesis and assembly of one or more recombinant proteins are required. Rotavirus comprises a capsid formed by 1860 monomers of four different proteins. For RLP production the simultaneous expression and assembly of two to three recombinant proteins may be required. For example, an inner layer comprising 120 molecules of VP2, 780 molecules of VP6 (middle layer) and an outer layer of 780 molecules of the glycoprotein VP7 and 60 VP4 dimers, to form a double or triple-layered particle (Libersou et al. J. of Virology, March 2008).

Crawford et al. (J Virol. 1994 September; 68(9): 5945-5952) describe the expression of VP2, VP4, VP6, and VP7 in a baculovirus expression system. Co-expression of different combinations of the rotavirus major structural proteins resulted in the formation of stable virus-like particles (VLPs). The co-expression of VP2 and VP6 alone or with VP4 resulted in the production of VP2/6 or VP2/4/6 VLPs, which were similar to double-layered rotavirus particles. Co-expression of VP2, VP6, and VP7, with or without VP4, produced triple-layered VP2/6/7 or VP2/4/6/7 VLPs, which were similar to native infectious rotavirus particles. The VLPs maintained the structural and functional characteristics of native particles, as determined by electron microscopic examination of the particles, the presence of non-neutralizing and neutralizing epitopes on VP4 and VP7, and hemagglutination activity of the VP2/4/6/7 VLPs.

Vaccine candidates generated from rotavirus-like particles of different protein compositions have shown potential as subunit vaccines. O'Neal et al. (J. Virology, 1997, 71(11): 8707-8717) show that VLPs containing VP 2 and VP6, or VP2, VP6, and VP7, and administered to mice with and without the addition of cholera toxin induced protective immunity in immunized mice. Core-like particles (CLP) and VLPs have also been used to immunize cows with VLPs more effective than CLPs in inducing passive immunity Fernandez, et al., (Vaccine, 1998, 16(5):507-516).

Plants are increasingly being used for large-scale production of recombinant proteins. For example US 2003/0175303 discloses the expression of recombinant rotavirus structural protein VP6, VP2, VP4 or VP7 in stably transformed tomato plants.

Saldana et al. (Viral Immunol. 19: 42-53 (2006)) expressed VP2 and VP6 in the cytoplasm of tomato plants. Electron microscopy studies showed that a small proportion of the proteins had assembled into 2/6 VLPs. A protective immune response was detected in mice and this may have to some extent been contributed by the non-assembled VPs. Individual proteins have been shown to elicit immune responses in mice, as in the case of VP8 and VP6 (Rodriguez-Diaz et al. Biotechnol Lett. 2011, 33(6):1169-75, Zhou et al., Vaccine 28: 6021-6027 (2010)).

Matsumura et al., (Archives of Virology 147: 1263-1270 (2002)) report bovine rotavirus A VP6 expression in transgenic potato plants. The VP6 was expressed, purified and immunogenic studies performed Immune-response in adult mice showed presence of VP6 antibodies in the sera. However, no evidence of assembled VP6 proteins was provided. It may have been that monomers or trimers of VP6 were responsible for eliciting the immune response. O'Brien et al. (2000, Virol. 270: 10444-10453) show VP6 assembly in *Nicotiana benthamiana* using a potato virus X (PVX) vector. Assembly of VP6 protein into icosahedral VLPs was only observed when the VP6 was fused to the PVX protein rods. Following cleavage the VP6 assembled into the icosahedral VLPs.

Codon-optimized human rotavirus VP6 has been successfully expressed in *Chenopodium amaranticolor* using a Beet black scorch virus (BBSV) mediated expression system. The protein was engineered as a replacement to the coat protein of BBSV. Oral immunization of female BALB/c mice with the plant based VP6 protein induced high titers of anti-VP6 mucosal IgA and serum IgG (Zhou et al., Vaccine 28: 6021-6027 (2010)). However, there was no teaching that the VP6 proteins assembled into VLPs or particles.

Rotavirus VP7 has been expressed in potato plants and was shown to produce a neutralizing immune response in mice (Yu and Langridge, 2001 Nature Biotechnol 19: 548-552). In transgenic potato plants, the VP7 gene was stable over 50 generations, with the VP7 protein from the 50th generation induced both protective and neutralizing antibodies in adult mice (Li et al., 2006, Virol 356:171-178).

Yang et al. (Yang Y M, Li X, Yang H, et al. Science China Life Science 54: 82-89 (2011)) co-expressed three rotavirus capsid proteins VP2, VP6 and VP7 of group A RV (P[8]G1) in tobacco plants and expression levels of these proteins, as well as formation of rotavirus-like particles and immunogenicity were studied. VLPs were purified from transgenic tobacco plants and analyzed by electron microscopy and Western blot. These results indicate that the plant derived VP2, VP6 and VP7 protein self-assembled into 2/6 or 2/6/7 rotavirus like particle with a diameter of 60-80 nm.

WO 2013/166609 described the production of rotavirus-like particle (RLPs) in plants, by co-expressing rotavirus structural proteins VP2, VP4, VP6 and VP7 in plants and purifying the resulting RLPs in the presence of calcium.

Rotavirus NSP4 has been expressed and purified from insect cells (Tian et al. 1996, Arch Virol. 1996; Rodriguez-Diaz et al. Protein Expr. Purif. 2003) and in *E. coli* (Sharif et al. Medical Journal of the Islamic Republic of Iran 2003). NSP4 has also been expressed as a fusion protein with the cholera toxin B (CTB) subunit in potato (Arakawa et al., Plant Cell Report 20: 343-348 (2001)).

SUMMARY OF THE INVENTION

The present invention relates to producing rotavirus-like particles in plants.

It is an object of the invention to produce rotavirus-like particles in plants.

Several methods to produce a rotavirus like particle (RLP) in a plant, portion of a plant or plant cell are described.

For example, a method (A) for producing a rotavirus like particle (RLP) in a host or host cell may comprise:
a) providing a host or host cell comprising one or more nucleic acid comprising a first nucleotide sequence encoding a first rotavirus protein, a second nucleotide sequence encoding a second rotavirus protein and a third nucleotide sequence encoding a third rotavirus protein, the first, second and third nucleotide sequence being operatively linked to one or more regulatory region active in the host or host cell; and
the first nucleotide sequence encoding rotavirus protein NSP4, the second nucleotide sequence encoding rotavirus protein VP6, and the third nucleotide sequence encoding one of rotavirus protein VP7 or VP4;
b) incubating the host or host cell under conditions that permit the expression of the one or more nucleic acid, so that each of NSP4, VP6 and VP7 or VP4 are expressed, thereby producing the RLP.

In the method (A) as described above the one or more nucleic acid may further comprises a fourth nucleotide sequence encoding a fourth rotavirus protein, the first, second, third, and fourth nucleotide sequence being operatively linked to one or more regulatory region active in the host or host cell; and
the first nucleotide sequence encoding rotavirus protein NSP4, the second nucleotide sequence encoding rotavirus protein VP6, and the third and fourth nucleotide sequence encoding rotavirus protein VP2, VP4 or VP7 and wherein each of NSP4, VP6 and two of VP2, VP4 and VP7 are expressed from the one or more nucleic acid.

A method (B) to produce a rotavirus like particle (RLP) in a host or host cell is further described, the method may comprise:
a) providing a host or host cell comprising one or more nucleic acid comprising
a first nucleotide sequence encoding a first rotavirus protein, a second nucleotide sequence encoding a second rotavirus protein and a third nucleotide sequence encoding a third rotavirus protein, the first, second and third nucleotide sequence being operatively linked to one or more regulatory region active in the host or host cell; and
the first, second and third nucleotide sequence encoding one of rotavirus protein NSP4, VP6 and one of rotavirus protein VP7 or VP4;
b) incubating the host or host cell under conditions that permit the expression of the one or more nucleic acid, so that each of NSP4, VP6 and VP7 or VP4 are expressed, thereby producing the RLP.

In the method (B) as described above the one or more nucleic acid may further comprises a fourth nucleotide sequence encoding a fourth rotavirus protein, the first, second, third, and fourth nucleotide sequence being operatively linked to one or more regulatory region active in the host or host cell; and
the first, second, third and fourth nucleotide sequence encoding one of rotavirus protein NSP4, VP6 and two of rotavirus protein VP2, VP7 or VP4 and wherein each of NSP4, VP6 and two of VP2, VP7 or VP4 are expressed from the one or more nucleic acid.

In the method (A) and (B) as described above the one or more nucleic acid may further comprises a fourth nucleotide sequence encoding a fourth rotavirus protein and a fifth nucleotide sequence encoding a fifth rotavirus protein, the first, second, third, fourth and fifth nucleotide sequence being operatively linked to one or more regulatory region active in the host or host cell; and
the first, second, third, fourth and fifth nucleotide sequence encoding one of rotavirus protein VP2, VP4, VP6, VP7 or NSP4 and wherein each of VP2, VP4, VP6, VP7 and NSP4 are expressed from the one or more nucleic acid.

In the method (A) or (B) as described above, if a host or host cell is provided where the one or more nucleic acid comprising a first nucleotide sequence encoding a first rotavirus protein, a second nucleotide sequence encoding a second rotavirus protein, a third nucleotide sequence encoding a third rotavirus protein, fourth nucleotide sequence encoding a fourth rotavirus protein and a fifth nucleotide sequence encoding a fifth rotavirus protein, the first, second, third, fourth and fifth nucleotide sequence being operatively linked to one or more regulatory region active in the host or host cell, then the one or more nucleic acid may comprise the first, second, third, fourth and fifth nucleotide sequence encoding the first, second, third, fourth and fifth rotavirus protein, or the one or more nucleic acid may comprise for example two nucleic acids, a first nucleic acid comprising the first nucleotide sequence encoding the first rotavirus protein, and a second nucleic acid comprising the second, third, fourth and fifth nucleotide sequence encoding the second, third, fourth and fifth rotavirus protein, or the one or more nucleic acid may comprise for example two nucleic acids, a first nucleic acid comprising the first and second nucleotide sequence encoding the first and second rotavirus protein, and a second nucleic acid comprising the third, fourth and fifth nucleotide sequence encoding the third, fourth and fifth rotavirus protein or the one or more nucleic acid may comprise for example three nucleic acids, a first nucleic acid comprising the first and second nucleotide sequence encoding the first and second rotavirus protein, a second nucleic acid comprising the third and fourth nucleotide sequence encoding the third and fourth rotavirus protein, and a third nucleic acid comprising the fifth nucleotide sequence encoding the fifth rotavirus protein or the one or more nucleic acid may comprise for example three nucleic acids, a first nucleic acid comprising the first nucleotide sequence encoding the first rotavirus protein, a second nucleic acid comprising the second nucleotide sequence encoding the second rotavirus protein, and a third nucleic acid comprising the third, fourth and fifth nucleotide sequence encoding the third, fourth and fifth rotavirus protein or the one or more nucleic acid may comprise for example four nucleic acids, a first nucleic acid comprising the first nucleotide sequence encoding the first rotavirus protein, a second nucleic acid comprising the second nucleotide sequence encoding the second rotavirus protein, a third nucleic acid comprising the third nucleotide sequence encoding the third rotavirus protein, and a fourth nucleic acid comprising the fourth and fifth nucleotide sequence encoding the fourth and fifth rotavirus protein or the one or more nucleic acid may comprise for example five nucleic acids, a first nucleic acid comprising the first nucleotide sequence encoding the first rotavirus protein, a second nucleic acid comprising the second nucleotide sequence encoding the second rotavirus protein, a third nucleic acid comprising the third nucleotide sequence encoding the third rotavirus protein, a fourth nucleic acid comprising the fourth nucleotide sequence encoding the fourth rotavirus protein, and a fifth nucleic acid comprising the fifth nucleotide sequence encoding the fifth rotavirus protein.

The methods (A) or (B) as described above may further comprise the steps of:

c) harvesting the host or host cell, and d) purifying the RLPs from the host or host cell, wherein the RLPs range in size from 70-100 nm.

The one or more nucleotide sequence of the method (A) or (B) as described above may be operatively linked to one or more expression enhancer. Furthermore, the expression enhancer may be selected from the group consisting of CPMV HT, CPMV 160, CPMV 160+ and CPMV HT+.

Also described herein is a method (C) of producing a rotavirus like particle (RLP) in host or host cell comprising:

a) introducing into the host or host cell one or more nucleic acid comprising a first nucleotide sequence encoding a first rotavirus protein, a second nucleotide sequence encoding a second rotavirus protein and a third nucleotide sequence encoding a third rotavirus protein, the first, second and third nucleotide sequence being operatively linked to one or more regulatory region active in the host or host cell; and the first nucleotide sequence encoding rotavirus protein NSP4, the second nucleotide sequence encoding rotavirus protein VP6, and the third nucleotide sequence encoding one of rotavirus protein VP7 or VP4;

b) incubating the host or host cell under conditions that permit the expression of the one or more nucleic acid so that each of NSP4, VP6 and VP7 or VP4 are expressed, thereby producing the RLP.

In the method (C) as described above the one or more nucleic acid may further comprises a fourth nucleotide sequence encoding a fourth rotavirus protein, the first, second, third, and fourth nucleotide sequence being operatively linked to one or more regulatory region active in the host or host cell; and the first nucleotide sequence encoding rotavirus protein NSP4, the second nucleotide sequence encoding rotavirus protein VP6, and the third and fourth nucleotide sequence encoding rotavirus protein VP2, VP4 or VP7 and wherein each of NSP4, VP6 and two of VP2, VP4 and VP7 are expressed from the one or more nucleic acid.

Also described herein is a method (D) of producing a rotavirus like particle (RLP) in host or host cell comprising:

a) introducing into the host or host cell one or more nucleic acid comprising a first nucleotide sequence encoding a first rotavirus protein, a second nucleotide sequence encoding a second rotavirus protein and a third nucleotide sequence encoding a third rotavirus protein, the first, second and third nucleotide sequence being operatively linked to one or more regulatory region active in the host or host cell; and the first, second and third nucleotide sequence encoding one of rotavirus protein NSP4, VP6 and one of rotavirus protein VP7 or VP4;

b) incubating the host or host cell under conditions that permit the expression of the one or more nucleic acid so that each of NSP4, VP6 and VP7 or VP4 are expressed, thereby producing the RLP.

In the method (D) as described above the one or more nucleic acid may further comprises a fourth nucleotide sequence encoding a fourth rotavirus protein, the first, second, third, and fourth nucleotide sequence being operatively linked to one or more regulatory region active in the host or host cell; and the first, second, third and fourth nucleotide sequence encoding one of rotavirus protein NSP4, VP6 and two of rotavirus protein VP2, VP7 or VP4 and wherein each of NSP4, VP6 and two of VP2, VP7 or VP4 are expressed from the one or more nucleic acid.

In the method (C) and (D) as described above the one or more nucleic acid may further comprises a fourth nucleotide sequence encoding a fourth rotavirus protein and a fifth nucleotide sequence encoding a fifth rotavirus protein, the first, second, third, fourth and fifth nucleotide sequence being operatively linked to one or more regulatory region active in the host or host cell; and the first, second, third, fourth and fifth nucleotide sequence encoding one of rotavirus protein VP2, VP4, VP6, VP7 or NSP4 and wherein each of VP2, VP4, VP6, VP7 and NSP4 are expressed from the one or more nucleic acid.

The methods (C) or (D) as described above may further comprise the steps of:

c) harvesting the host or host cell, and d) purifying the RLPs from the host or host cell, wherein the RLPs range in size from 70-100 nm.

In the method (C) or (D) as described above, if a host or host cell is provided where the one or more nucleic acid comprising a first nucleotide sequence encoding a first rotavirus protein, a second nucleotide sequence encoding a second rotavirus protein, a third nucleotide sequence encoding a third rotavirus protein, fourth nucleotide sequence encoding a fourth rotavirus protein and a fifth nucleotide sequence encoding a fifth rotavirus protein, the first, second, third, fourth and fifth nucleotide sequence being operatively linked to one or more regulatory region active in the host or host cell, then in the step of introducing (step a), the one or more nucleic acid may comprise two nucleic acids, with a first nucleic acid comprising encoding the NSP4, and a second nucleic acid encoding VP2, VP4, VP6 and VP7, the ratio of an amount of the first nucleic acid relative to the second nucleic acid that is introduced into the plant, portion of a plant or plant cell is between 1:0.8 and 1:2. The ratio may also be 1:1. Alternatively, the one or more nucleic acid may comprise two nucleic acids, with a first nucleic acid comprising the first nucleotide sequence encoding the first rotavirus protein and the second nucleotide sequence encoding the second rotavirus protein, and a second nucleic acid comprising the third to fifth nucleotide sequence encoding the third to fifth rotavirus protein.

In the method (C) or (D) as described above, in the step of introducing (step a), the one or more nucleic acid may comprise three nucleic acids, with a first nucleic acid comprising the first and the second nucleotide sequence encoding the first and the second rotavirus protein, a second nucleic acid comprising the third and fourth nucleotide sequence encoding the third and the fourth rotavirus protein, and a third nucleic acid comprising the fifth nucleotide sequence encoding the fifth rotavirus protein, and wherein the ratio of an amount of the first nucleic acid relative to the second nucleic acid and to the third nucleic that is introduced into the plant, the portion of the plant, or the plant cell, is 1:1:1.

Alternatively, in the method (C) or (D) as described above, in the step of introducing (step a), the one or more nucleic acid may comprise three nucleic acids, with the first nucleic acid comprising the first nucleotide sequence encoding the first rotavirus protein, the second nucleic acid comprising the second nucleotide sequence encoding the second rotavirus protein, and the third nucleic acid comprising the third to fifth nucleotide sequence encoding the third to fifth rotavirus protein, and wherein the ratio of an amount of the first nucleic acid relative to the second nucleic acid and to the third nucleic that is introduced into the plant, the portion of the plant, or the plant cell, is 1:1:1.

Furthermore, in method (C) or (D) described above, in the step of introducing (step a), the one or more nucleic acid may comprise four nucleic acids, a first nucleic acid comprising the first nucleic acid encoding the first rotavirus protein, a second nucleic acid comprising the second nucleotide sequence encoding the second rotavirus protein, a third nucleic acid comprising the third nucleotide sequence encoding the third rotavirus protein, and a fourth nucleic acid comprising the fourth and the fifth nucleotide sequence encoding the fourth and fifth rotavirus protein, wherein the ratio of an amount of the first nucleic acid relative to the second nucleic acid, to the third nucleic and to the fourth nucleic acid that is introduced into the plant, the portion of the plant, or the plant cell, is 1:1:1:1.

In the method (C) or (D) as described above, in the step of introducing (step a), the one or more nucleic acid may comprise five nucleic acids, a first nucleic acid comprising the first nucleotide sequence encoding the first rotavirus protein, a second nucleic acid comprising the second nucleotide sequence encoding the second rotavirus protein, a third nucleic acid comprising the third nucleotide sequence encoding the third rotavirus protein, a fourth nucleic acid comprising the fourth nucleotide sequence encoding the fourth rotavirus protein, and a fifth nucleic acid comprising the fifth nucleotide sequence encoding the fifth rotavirus protein, and the ratio of an amount of the first nucleic acid relative to the second nucleic acid, to the third nucleic acid, to the fourth nucleic acid and to the fifth nucleic acid that is introduced into the plant, the portion of the plant, or the plant cell, is 1:1:1:1:1.

The one or more nucleotide sequence of the method (C) or (D) as described above may be operatively linked to one or more expression enhancer. Furthermore, the expression enhancer may be selected from the group consisting of CPMV HT, CPMV 160, CPMV 160+ and CPMV HT+.

A method (E) of increasing incorporation of VP4, VP7, or both VP4 and VP7 in a rotavirus like particle (RLP) is also described, the method comprising:

a) providing a host or host cell comprising one or more nucleic acid comprising
   a first nucleotide sequence encoding a first rotavirus protein, a second nucleotide sequence encoding a second rotavirus protein and a third nucleotide sequence encoding a third rotavirus protein, the first, second and third nucleotide sequence being operatively linked to one or more regulatory region active in the host or host cell; and
   the first nucleotide sequence encoding rotavirus protein NSP4, the second nucleotide sequence encoding rotavirus protein VP6, and the third nucleotide sequence encoding one of rotavirus protein VP7 or VP4;
b) incubating the host or host cell under conditions that permit the expression of the one or more nucleic acid, so that each of NSP4, VP6 and VP7 or VP4 are expressed, thereby producing the RLP with enhanced levels of VP4, VP7, or both VP4 and VP7 when compared to the level of VP4 or VP7 produced by a second host or host cell that expresses the one or more nucleic acid that does not comprise NSP4, under the same conditions.

In the method (E) as described above the one or more nucleic acid may further comprises a fourth nucleotide sequence encoding a fourth rotavirus protein, the first, second, third, and fourth nucleotide sequence being operatively linked to one or more regulatory region active in the host or host cell; and
the first nucleotide sequence encoding rotavirus protein NSP4, the second nucleotide sequence encoding rotavirus protein VP6, and the third and fourth nucleotide sequence encoding rotavirus protein VP2, VP4 or VP7 and wherein each of NSP4, VP6 and two of VP2, VP4 and VP7 are expressed from the one or more nucleic acid.

A method (F) of increasing incorporation of VP4, VP7, or both VP4 and VP7 in a rotavirus like particle (RLP) is also described, the method comprising:

a) providing a host or host cell comprising one or more nucleic acid comprising
a first nucleotide sequence encoding a first rotavirus protein, a second nucleotide sequence encoding a second rotavirus protein and a third nucleotide sequence encoding a third rotavirus protein, the first, second and third nucleotide sequence being operatively linked to one or more regulatory region active in the host or host cell; and
the first, second and third nucleotide sequence encoding one of rotavirus protein NSP4, VP6 and one of rotavirus protein VP7 or VP4;
b) incubating the host or host cell under conditions that permit the expression of the one or more nucleic acid, so that each of NSP4, VP6 and VP7 or VP4 are expressed, thereby producing the RLP with enhanced levels of VP4, VP7, or both VP4 and VP7 when compared to the level of VP4 or VP7 produced by a second host or host cell that expresses the one or more nucleic acid that does not comprise NSP4, under the same conditions.

In the method (F) as described above the one or more nucleic acid may further comprises a fourth nucleotide sequence encoding a fourth rotavirus protein, the first, second, third, and fourth nucleotide sequence being operatively linked to one or more regulatory region active in the host or host cell; and
the first, second, third and fourth nucleotide sequence encoding one of rotavirus protein NSP4, VP6 and two of rotavirus protein VP2, VP7 or VP4 and wherein each of NSP4, VP6 and two of VP2, VP7 or VP4 are expressed from the one or more nucleic acid.

In the method (E) and (F) as described above the one or more nucleic acid may further comprises a fourth nucleotide sequence encoding a fourth rotavirus protein and a fifth nucleotide sequence encoding a fifth rotavirus protein, the first, second, third, fourth and fifth nucleotide sequence being operatively linked to one or more regulatory region active in the host or host cell; and
the first, second, third, fourth and fifth nucleotide sequence encoding one of rotavirus protein VP2, VP4, VP6, VP7 or NSP4 and wherein each of VP2, VP4, VP6, VP7 and NSP4 are expressed from the one or more nucleic acid.

The one or more nucleotide sequence of the method (E) or (F) as described above may be operatively linked to one or more expression enhancer. Furthermore, the expression enhancer may be selected from the group consisting of CPMV HT, CPMV 160, CPMV 160+ and CPMV HT+.

A method (G) of increasing incorporation of VP4, VP7, or both VP4 and VP7 in a rotavirus like particle (RLP) is also described, the method comprising:

a) introducing into a host or host cell one or more nucleic acid comprising
   a first nucleotide sequence encoding a first rotavirus protein, a second nucleotide sequence encoding a second rotavirus protein and a third nucleotide sequence encoding a third rotavirus protein, the first, second and third nucleotide sequence being operatively linked to one or more regulatory region active in the host or host cell; and
   the first nucleotide sequence encoding rotavirus protein NSP4, the second nucleotide sequence encoding rotavirus protein VP6, and the third nucleotide sequence encoding one of rotavirus protein VP7 or VP4;
b) incubating the host or host cell under conditions that permit the expression of the one or more nucleic acid, so that each of NSP4, VP6 and VP7 or VP4 are expressed, thereby producing the RLP with enhanced levels of VP4, VP7, or both VP4 and VP7 when compared to the level of VP4 or VP7 produced by a second host or host cell that expresses the one or more nucleic acid that does not comprise NSP4, under the same conditions.

In the method (G) as described above the one or more nucleic acid may further comprises a fourth nucleotide sequence encoding a fourth rotavirus protein, the first, second, third, and fourth nucleotide sequence being operatively linked to one or more regulatory region active in the host or host cell; and
the first nucleotide sequence encoding rotavirus protein NSP4, the second nucleotide sequence encoding rotavirus protein VP6, and the third and fourth nucleotide sequence encoding rotavirus protein VP2, VP4 or VP7 and wherein each of NSP4, VP6 and two of VP2, VP4 and VP7 are expressed from the one or more nucleic acid.

A method (H) of increasing incorporation of VP4, VP7, or both VP4 and VP7 in a rotavirus like particle (RLP) is also described, the method comprising:

a) introducing in a host or host cell comprising one or more nucleic acid comprising a first nucleotide sequence encoding a first rotavirus protein, a second nucleotide sequence encoding a second rotavirus protein and a third nucleotide sequence encoding a third rotavirus protein, the first, second and third nucleotide sequence being operatively linked to one or more regulatory region active in the host or host cell; and the first, second and third nucleotide sequence encoding one of rotavirus protein NSP4, VP6 and one of rotavirus protein VP7 or VP4;

b) incubating the host or host cell under conditions that permit the expression of the one or more nucleic acid, so that each of NSP4, VP6 and VP7 or VP4 are expressed, thereby producing the RLP with enhanced levels of VP4, VP7, or both VP4 and VP7 when compared to the level of VP4 or VP7 produced by a second host or host cell that expresses the one or more nucleic acid that does not comprise NSP4, under the same conditions.

In the method (H) as described above the one or more nucleic acid may further comprises a fourth nucleotide sequence encoding a fourth rotavirus protein, the first, second, third, and fourth nucleotide sequence being operatively linked to one or more regulatory region active in the host or host cell; and the first, second, third and fourth nucleotide sequence encoding one of rotavirus protein NSP4, VP6 and two of rotavirus protein VP2, VP7 or VP4 and wherein each of NSP4, VP6 and two of VP2, VP7 or VP4 are expressed from the one or more nucleic acid.

In the method (G) and (H) as described above the one or more nucleic acid may further comprises a fourth nucleotide sequence encoding a fourth rotavirus protein and a fifth nucleotide sequence encoding a fifth rotavirus protein, the first, second, third, fourth and fifth nucleotide sequence being operatively linked to one or more regulatory region active in the host or host cell; and the first, second, third, fourth and fifth nucleotide sequence encoding one of rotavirus protein VP2, VP4, VP6, VP7 or NSP4 and wherein each of VP2, VP4, VP6, VP7 and NSP4 are expressed from the one or more nucleic acid.

In the method (G) and (H) as described above the one or more nucleic acid may further comprises a fourth nucleotide sequence encoding a fourth rotavirus protein and a fifth nucleotide sequence encoding a fifth rotavirus protein, the first, second, third, fourth and fifth nucleotide sequence being operatively linked to one or more regulatory region active in the host or host cell; and the first, second, third, fourth and fifth nucleotide sequence encoding one of rotavirus protein VP2, VP4, VP6, VP7 or NSP4 and wherein each of VP2, VP4, VP6, VP7 and NSP4 are expressed from the one or more nucleic acid.

In the method (G) or (H) as described above, in the step of introducing (step a), the one or more nucleic acid may comprise two nucleic acids, with a first nucleic acid comprising encoding the NSP4, and a second nucleic acid encoding VP2, VP4, VP6 and VP7, the ratio of an amount of the first nucleic acid relative to the second nucleic acid that is introduced into the plant, portion of a plant or plant cell is between 1:0.8 and 1:2. The ratio may also be 1:1. Alternatively, the one or more nucleic acid may comprise two nucleic acids, with a first nucleic acid comprising the first nucleotide sequence encoding the first rotavirus protein and the second nucleotide sequence encoding the second rotavirus protein, and a second nucleic acid comprising the third to fifth nucleotide sequence encoding the third to fifth rotavirus protein.

In the method (G) or (H) as described above, in the step of introducing (step a), the one or more nucleic acid may comprise three nucleic acids, with a first nucleic acid comprising the first and the second nucleotide sequence encoding the first and the second rotavirus protein, a second nucleic acid comprising the third and fourth nucleotide sequence encoding the third and the fourth rotavirus protein, and a third nucleic acid comprising the fifth nucleotide sequence encoding the fifth rotavirus protein, and wherein the ratio of an amount of the first nucleic acid relative to the second nucleic acid and to the third nucleic that is introduced into the plant, the portion of the plant, or the plant cell, is 1:1:1.

Alternatively, in the method (G) or (H) as described above, in the step of introducing (step a), the one or more nucleic acid may comprise three nucleic acids, with the first nucleic acid comprising the first nucleotide sequence encoding the first rotavirus protein, the second nucleic acid comprising the second nucleotide sequence encoding the second rotavirus protein, and the third nucleic acid comprising the third to fifth nucleotide sequence encoding the third to fifth rotavirus protein, and wherein the ratio of an amount of the first nucleic acid relative to the second nucleic acid and to the third nucleic that is introduced into the plant, the portion of the plant, or the plant cell, is 1:1:1.

Furthermore, in the method (G) or (H) described above, in the step of introducing (step a), the one or more nucleic acid may comprise four nucleic acids, a first nucleic acid comprising the first nucleic acid encoding the first rotavirus protein, a second nucleic acid comprising the second nucleotide sequence encoding the second rotavirus protein, a third nucleic acid comprising the third nucleotide sequence encoding the third rotavirus protein, and a fourth nucleic acid comprising the fourth and the fifth nucleotide sequence encoding the fourth and fifth rotavirus protein, wherein the ratio of an amount of the first nucleic acid relative to the second nucleic acid, to the third nucleic and to the fourth nucleic acid that is introduced into the plant, the portion of the plant, or the plant cell, is 1:1:1:1.

In the method in the method (G) or (H) as described above, in the step of introducing (step a), the one or more nucleic acid may comprise five nucleic acids, a first nucleic acid comprising the first nucleotide sequence encoding the first rotavirus protein, a second nucleic acid comprising the second nucleotide sequence encoding the second rotavirus protein, a third nucleic acid comprising the third nucleotide sequence encoding the third rotavirus protein, a fourth nucleic acid comprising the fourth nucleotide sequence encoding the fourth rotavirus protein, and a fifth nucleic acid comprising the fifth nucleotide sequence encoding the fifth rotavirus protein, and the ratio of an amount of the first nucleic acid relative to the second nucleic acid, to the third nucleic acid, to the fourth nucleic acid and to the fifth nucleic acid that is introduced into the plant, the portion of the plant, or the plant cell, is 1:1:1:1:1.

The one or more nucleotide sequence of the method (G) or (H) as described above may be operatively linked to one or more expression enhancer. Furthermore, the expression enhancer may be selected from the group consisting of CPMV HT, CPM 160, CPMV 160+ and CPMV HT+.

The methods (G) or (H) as described above may further comprise the steps of:
c) harvesting the host or host cell, and
d) purifying the RLPs from the host or host cell, wherein the RLPs range in size from 70-100 nm.

In the method (A), the method (B), the method (C), the method (D), the method (E), the method (F), the method (G) or the method (H) as described above, the one or more nucleic acid may comprise one nucleic acid comprising the first, second, third, fourth and fifth nucleotide sequence encoding the first, second, third, fourth, and fifth rotavirus protein.

In the method (A), the method (B), the method (C), the method (D), the method (E), the method (F), the method (G) or the method (H) as described above, the one or more nucleic acid may comprise two nucleic acids, for example, a first nucleic acid comprising the first nucleotide sequence encoding the first rotavirus protein, and a second nucleic acid comprising the second to fifth nucleotide sequence encoding the second to fifth rotavirus protein. Alternatively, the one or more nucleic acid may comprise two nucleic acids, with a first nucleic acid comprising the first nucleotide sequence encoding the first rotavirus protein and the second nucleotide sequence encoding the second rotavirus protein, and a second nucleic acid comprising the third to fifth nucleotide sequence encoding the third to fifth rotavirus protein.

In the method (A), the method (B), the method (C), the method (D), the method (E), the method (F), the method (G) or the method (H) as described above, the one or more nucleic acid may also comprise three nucleic acids, a first nucleic acid comprising the first nucleotide sequence encoding the first rotavirus protein, the second nucleotide sequence encoding the second rotavirus protein, a second nucleic acid comprising the third nucleotide sequence encoding the third rotavirus protein and fourth nucleotide sequence encoding the fourth rotavirus protein, and a third nucleic acid comprising the fifth nucleotide sequence encoding the fifth rotavirus protein. Alternatively, the one or more nucleic acid may comprise three nucleic acids, with a first nucleic acid comprising the first nucleotide sequence encoding the first rotavirus protein, a second nucleic acid comprising the second nucleotide sequence encoding the second rotavirus protein, and a third nucleic acid comprising the third to fifth nucleotide sequence encoding the third to fifth rotavirus protein.

In the method (A), the method (B), the method (C), the method (D), the method (E), the method (F), the method (G) or the method (H) as described above the one or more nucleic acid comprises four nucleic acids, a first nucleic acid comprising the first nucleotide sequence encoding the first rotavirus protein, a second nucleic acid comprising the second nucleotide sequence encoding the second rotavirus protein, a third nucleic acid comprising the third nucleotide sequence encoding the third rotavirus protein, and a fourth nucleic acid comprising the fourth and fifth nucleotide sequence encoding the fourth and fifth rotavirus protein.

Furthermore, in the method (A), the method (B), the method (C), the method (D), the method (E), the method (F), the method (G) or the method (H) as described above the one or more nucleic acid may comprise five nucleic acids, with a first nucleic acid comprising the first nucleotide sequence encoding the first rotavirus protein, a second nucleic acid comprising the second nucleotide sequence encoding the second rotavirus protein, a third nucleic acid comprising the third nucleotide sequence encoding the third rotavirus protein, a fourth nucleic acid comprising the fourth nucleotide sequence encoding the fourth rotavirus protein, and a fifth nucleic acid comprising the fifth nucleotide sequence encoding the fifth rotavirus protein.

The one or more nucleotide sequence of the method (A), the method (B), the method (C), the method (D), the method (E), the method (F), the method (G) or the method (H) as described above may be operatively linked to one or more expression enhancer. Furthermore, the expression enhancer may be selected from the group consisting of CPMV HT, CPM 160, CPMV 160+ and CPMV HT+.

In the method (A), the method (B), the method (C), the method (D), the method (E), the method (F), the method (G) or the method (H) as described above the host or host cell may comprise insect cells, mammalian cells, plant, portion of a plant or plant cells. The plant may be *Nicotiana benthamiana*.

Also described herein is an RLP produced by the method (A), the method (B), the method (C), the method (D), the method (E), the method (F), the method (G) or the method (H) described above, wherein the RLP is a triple layered RLP comprising rotavirus protein, the rotavirus protein consists of VP2, VP4, VP6 and VP7. The RLP may not comprise NSP4.

A composition comprising an effective dose of the RLP for inducing an immune response in a subject, and a pharmaceutically acceptable carrier, and a method of inducing immunity to a rotavirus infection in a subject, that comprises administering the composition, are also described. In the method of inducing immunity, the composition may be administered to a subject orally, intradermally, intranasally, intramuscularly, intraperitoneally, intravenously, or subcutaneously.

Also described herein is plant matter comprising an RLP produced by the method (A), the method (B), the method (C), the method (D), the method (E), the method (F), the method (G) or the method (H) as described above.

In the method (A), the method (B), the method (C), the method (D), the method (E), the method (F), the method (G) or the method (H) as described above, the one or more nucleic acid may comprise one nucleic acid comprising the first, second and third nucleotide sequence encoding the first, second and third, rotavirus protein. Furthermore, in the method (A), the method (B), the method (C), the method (D), the method (E), the method (F), the method (G) or the method (H) as described above the one or more nucleic acid may comprise two nucleic acids, a first nucleic acid comprising the first nucleotide sequence encoding the first rotavirus protein, and a second nucleic acid comprising the second and third nucleotide sequence encoding the second and third rotavirus protein. Furthermore, in the method (A), the method (B), the method (C), the method (D), the method (E), the method (F), the method (G) or the method (H) as described above the one or more nucleic acid may comprise two nucleic acids, a first nucleic acid comprising the first and second nucleotide sequence encoding the first and second rotavirus protein, and a second nucleic acid comprising the third nucleotide sequence encoding the third rotavirus protein. Alternatively, in the method (A), the method (B), the method (C), the method (D), the method (E), the method (F), the method (G) or the method (H) as described above the one or more nucleic acid may comprise three nucleic acids, a first nucleic acid comprising the first nucleotide sequence encoding the first rotavirus protein, a second nucleic acid comprising the second nucleotide sequence encoding the second rotavirus protein and a third nucleic acid comprising the third nucleotide sequence encoding the third rotavirus protein.

As described herein, by co-expressing NSP4 along with VP6 and VP4 or VP7, in a host or host cell, for example a plant, portion of the plant, or a plant cell, RLPs comprising increased levels of VP4, VP7, or both VP4 and VP7 are observed, when compared to the level of VP4 and VP7 in RLPs produced by a second host or host cell for example a plant, portion of a second plant, or second plant cell, that expresses the one or more nucleic acid that encodes VP6 and VP4 or VP7, and does not encode NSP4, the second host or second host cell for example a second plant, the second portion of plant, or the second plant cell, incubated or grown, under the same conditions as the host or host cell for example a plant, portion of the plant, or plant cell.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 1 shows rotavirus cell entry and replication. When rotavirus enters a cell, VP4 and VP7 are lost, forming a double layered particle (DLP). Transcription of the dsRNA commences resulting in translation of VP2, VP4, VP6 and VP7. Progeny cores with replicase activity are produced in virus factories (also called viroplasms). Late transcription occurs in these progeny cores. At the periphery of virus factories, these core are coated with VP6, forming immature DLPs that bud across the membrane of the endoplasmic reticulum, acquiring a transient lipid membrane which is modified with the ER resident viral glycoproteins NSP4 and VP7; these enveloped particles also contain VP4. As the particles move towards the interior of the ER cisternae, the transient lipid membrane and the nonstructural protein NSP4 are lost, while the virus surface proteins VP4 and VP7 rearrange to form the outermost virus protein layer, yielding mature infectious triple-layered particles (see Swiss Institute of Bioinformatics (ViralZone): viralzone.expasy.org/viralzone/all_by_species/107.html)

FIG. 2 shows rotavirus-like particle purification by ultracentrifugation on iodixanol density gradient. FIG. 2A presents the percentage of iodixanol and volume for each layer of the gradient used for the purification of rotavirus-like particles. After centrifugation, the gradient was fractionated into 1 ml fractions starting from the bottom of the tube. The approximate localization of fractions 1 to 13 are indicated by arrows. FIG. 2B shown a Coomassie-stained SDS-PAGE analysis of the protein content of fractions 1 to 10 from an iodixanol density gradient separation applied to a crude protein extract from leaves expressing rotavirus VP2, VP4, VP6 and VP7 antigens.

FIG. 3 shows rotavirus protein expression. FIG. 3A shows a Coomassie-stained SDS-PAGE analysis of fractions 2 and 3 from an iodixanol density gradient separation applied to crude protein extracts from leaves expressing VP2, VP4, VP6, VP7 in the presence or absence of NSP4. Rotavirus structural proteins VP2, VP6, VP7, VP4 were expressed, left panel, using individual constructs for each structural antigen ("single gene constructs"), with NSP4 on a separate construct; middle panel, two constructs, each having the genes of two structural antigens ("dual gene constructs"), with NSP4 on a separate construct; or right panel, a single construct for the co-expression of the four structural antigens (Quadruple gene constructs), with a separate construct for the expression of NSP4. Position of the rotavirus VP2 and VP6 antigen are shown by arrows. FIG. 3B shows a Western blot analysis of fraction F2 from the same treatments as in FIG. 3A using an anti-rotavirus VP4 or VP7 antibody as specified.

FIG. 4 shows rotavirus protein expression in the presence of an expression enhancer. FIG. 4A shows a Coomassie-stained SDS-PAGE analysis of fractions F2 and F3 from an iodixanol density gradient applied to crude protein extracts from leaves co-expressing VP2, VP4, VP6, VP7 and NSP4. Rotavirus structural proteins VP2, VP6, VP7, VP4 were expressed from single gene constructs, and one construct expressing NSP4 (left panel), or from two dual gene constructs and one construct expressing NSP4 (middle and right panel)). Each construct comprised an expression enhancer, either CPMV HT (left and middle panels) or CMPV 160 (right panel), except for NSP4 which always comprised the CPMV-HT enhancer. The ratios indicate the proportion of the *Agrobacterium* strains in the bacterial suspension used for transformation: left panel—five single gene constructs (VP2, VP6, VP4, VP7 and NSP4; ratio of 1:1:1:1:1); middle and right panels—dual gene constructs encoding structural proteins (VP6/2 and VP7/4) and the construct encoding non-structural protein (NSP4; ratio of 1:1:1). FIG. 4B shows a Western blot analysis of F2 from the same treatments as in FIG. 4A using an anti-rotavirus VP4 or VP7 antibody as specified. The ratios indicate the proportion of the *Agrobacterium* strains in the bacterial suspension used for transformation: left panel—five single gene constructs (VP2, VP6, VP4, VP7 and NSP4; ratio of 1:1:1:1:1); middle and right panels—dual gene constructs encoding structural proteins (VP6/2 and VP7/4) and the construct encoding non-structural protein (NSP4; ratio of 1:1:1).

FIG. 5 shows rotavirus protein expression. Upper panel shows a Coomassie-stained SDS-PAGE analysis of fractions F2 and F3 an iodixanol density gradient applied to crude protein extracts from leaves co-expressing VP2, VP4, VP6, VP7 and NSP4, and the lower panel shows a Western blot analysis of the corresponding F2 fraction from the upper panel. Rotavirus structural proteins VP2, VP6, VP7 and VP4 were expressed within a quadruple gene construct, and the non-structural protein NSP4 was co-expressed from a distinct single gene construct (lanes 1 and 2), or structural proteins VP2, VP6, VP7, VP4 and the non-structural protein NSP4 were expressed within a quintuple gene construct (lane 3). The ratio of agroinfiltration of the constructs is indicated. An OD of 0.4 of *Agrobacterium* strains in the bacterial suspension is indicated as 1. An OD of 0.6 of *Agrobacterium* strains in the bacterial suspension is indicated as 1.5.

FIG. 6 shows a general schematic of an example of several enhancer sequences that may be used in the constructs of the present invention. FIG. 6A and FIG. 6B show a general schematic of the CPMV HT and CPMV HT+ enhancer sequences fused to a nucleotide sequence of interest (for example encoding a rotavirus structural protein VP2, VP4, VP6, VP7, or a non-structural protein NSP4). Not all of the elements shown in FIG. 5A or 5B may be required within the enhancer sequence. Additional elements may be included at the 3' end of the nucleotide sequence of interest including a sequence encoding a comovirus 3' untranslated region (CPMV 3' UTR), or a plastocyanin 3' UTR (3'UTR). FIGS. 6C and 6D show a general schematic of the enhancer sequence of CPMVX, and CPMVX+ (comprising CPMVX, and a stuffer fragment, which in this non-limiting example, comprises a multiple cloning site and a plant kozak sequence), as described herein. CPMVX and CPMVX+ are each shown as operatively linked to plant regulatory region at their 5' ends, and at their 3' ends, in series, a nucleotide sequence of interest (including an ATG initiation site and STOP site), a 3'UTR, and a terminator sequence. An example of construct CPMVX as described herein, is CPMV160. An example of construct CPMVX+ as described herein, is CPMV160+.

FIG. 7 shows sequence components used to prepare construct number 1710 (2X35S/CPMV-HT/RVA(WA) VP2 (opt)/NOS. FIG. 7A shows the nucleotide sequence of IF-WA_VP2(opt).s1+3c (SEQ ID NO: 19). FIG. 7B shows the nucleotide sequence of IF-WA_VP2(opt).s1−4r (SEQ ID NO: 20). FIG. 7C shows the optimized coding sequence of Rotavirus A VP2 from strain WA (SEQ ID NO: 21). FIG. 7D shows the schematic representation of construct 1191. FIG. 7E shows the nucleotide sequence of construct 1191 (SEQ ID NO: 22). FIG. 7F shows the nucleotide sequence of expression cassette number 1710 (SEQ ID NO: 23). FIG. 7G shows the amino acid sequence of VP2 from Rotavirus A WA strain (SEQ ID NO: 24). FIG. 7H shows the schematic representation of construct number 1710.

FIG. 8 shows sequence components used to prepare construct number 1713 (2X35S/CPMV-HT/RVA(WA) VP6 (opt)/NOS). FIG. 8A shows the nucleotide sequence of IF-WA_VP6(opt).s1+3c (SEQ ID NO: 25). FIG. 8B shows the nucleotide sequence of IF-WA_VP6(opt).s1−4r (SEQ ID NO: 26). FIG. 8C shows the optimized coding sequence of Rotavirus A VP6 from strain WA (SEQ ID NO: 217. FIG. 8D shows the nucleotide sequence of expression cassette number 1713 (SEQ ID NO: 28). FIG. 8E shows the amino acid sequence of VP6 from Rotavirus A WA strain (SEQ ID NO: 29). FIG. 8F shows the schematic representation of construct number 1713.

FIG. 9 shows sequence components used to prepare construct number 1730 (2X35S/CPMV-HT/RVA(Rtx) VP4 (opt)/NOS). FIG. 9A shows the nucleotide sequence of IF-Rtx_VP4(opt).s1+3c (SEQ ID NO: 30). FIG. 9B shows the nucleotide sequence of IF-Rtx_VP4(opt).s1−4r (SEQ ID NO: 31). FIG. 9C shows the optimized coding sequence of Rotavirus A VP4 from strain RVA/Vaccine/USA/Rotarix-A41CB052A/1988/G1P1A[8] (SEQ ID NO:32). FIG. 9D shows the nucleotide sequence of expression cassette number 1730 (SEQ ID NO: 33). FIG. 9E shows the amino acid sequence of VP4 from Rotavirus A Rotarix strain (SEQ ID NO: 34). FIG. 9F shows the schematic representation of construct number 1730.

FIG. 10 shows sequence components used to prepare construct number 1734 (2X35S/CPMV-HT/RVA(Rtx) VP7 (Opt)/NOS). FIG. 10A shows the nucleotide sequence of IF-TrSP+Rtx_VP7(opt).s1+3c (SEQ ID NO: 35). FIG. 10B shows the nucleotide sequence of IF-Rtx_VP7(opt).s1−4r (SEQ ID NO: 36). FIG. 10C shows the optimized coding sequence of Rotavirus A VP7 from strain RVA/Vaccine/USA/Rotarix-A41CB052A/1988/G1P1A[8] (SEQ ID NO: 37). FIG. 10D shows the nucleotide sequence of expression cassette number 1734 (SEQ ID NO: 38). FIG. 10E shows the amino acid sequence of TrSp-VP7 from Rotavirus A vaccine USA/Rotarix-A41CB052A/1988/G1P1A[8] strain (SEQ ID NO: 39). FIG. 10F shows the schematic representation of construct number 1734.

FIG. 11 shows sequence components used to prepare construct number 1706 (2X35S/CPMV-HT/RVA(WA) NSP4/NOS). FIG. 11A shows the nucleotide sequence of IF-WA_NSP4.s1+3c (SEQ ID NO: 40). FIG. 11B shows the nucleotide sequence of IF-WA_NSP4.s1−4r (SEQ ID NO: 41). FIG. 11C shows the coding sequence of Rotavirus A VP6 from strain WA (SEQ ID NO: 42). FIG. 11D shows the nucleotide sequence of expression cassette number 1706 (SEQ ID NO: 43). FIG. 11E shows the amino acid sequence of NSP4 from Rotavirus A WA strain (SEQ ID NO: 44). FIG. 11F shows the schematic representation of construct number 1706.

FIG. 12 shows sequence components used to prepare construct number 1108 (2X35S/CPMV-160/RVA(WA) VP2 (opt)/NOS). FIG. 12A shows the nucleotide sequence of IF(C160)-WA_VP2(opt).c (SEQ ID NO: 45). FIG. 12B shows a schematic representation of construct 1190. FIG. 12C shows the nucleotide sequence of construct 1190 (SEQ ID NO: 46). FIG. 12D shows the nucleotide sequence of expression cassette number 1108 (SEQ ID NO: 47). FIG. 12E shows a schematic representation of construct number 1108.

FIG. 13 shows sequence components used to prepare construct number 1128 (2X35S/CPMV-160/RVA(WA) VP6 (opt)/NOS). FIG. 13A shows the nucleotide sequence of IF(C160)-WA_VP6(opt).c (SEQ ID NO: 48). FIG. 13B shows the nucleotide sequence of expression cassette number 1128 (SEQ ID NO: 49). FIG. 13C shows a schematic representation of construct number 1128.

FIG. 14 shows sequence components used to prepare construct number 1178 (2X35S/CPMV-160/RVA(Rtx) VP4 (opt)/NOS). FIG. 14A shows the nucleotide sequence of IF(C160)-Rtx_VP4(opt).c (SEQ ID NO: 50). FIG. 14B shows the nucleotide sequence of expression cassette number 1178 (SEQ ID NO: 51). FIG. 14C shows the schematic representation of construct number 1178.

FIG. 15 shows sequence components used to prepare construct number 1199 (2X35S/CPMV-160/TrSp-RVA(Rtx) VP7(Opt)/NOS). FIG. 15A shows the nucleotide sequence of IF(C160)-TrSP+Rtx_VP7(opt).c (SEQ ID NO: 52). FIG. 15B shows the nucleotide sequence of Expression cassette number 1199 (SEQ ID NO: 53). FIG. 15C shows the schematic representation of construct number 1199.

FIG. 16 shows the schematic representation of construct number 1708 (double gene construct for the expression of VP6 and VP2 under CPMV-HT expression cassette).

FIG. 17 shows the schematic representation of construct number 1719 (double gene construct for the expression of VP7 and VP4 under CPMV-HT expression cassette).

FIG. 18 shows the schematic representation of construct number 2400 (double gene construct for the expression of VP6 and VP2 under CPMV-160 expression cassette).

FIG. 19 shows the schematic representation of construct number 2408 (double gene construct for the expression of VP7 and VP4 under CPMV-160 expression cassette).

FIG. 20 shows the schematic representation of construct number 1769 (quadruple gene construct for the expression of VP7, VP4, VP6 and VP2 under CPMV-HT expression cassette).

FIG. 21 shows the schematic representation of construct number 2441 (quintuple gene construct for the expression of VP4, VP7, NSP4, VP6 and VP2 under CPMV-HT expression cassette).

DETAILED DESCRIPTION

Figure 1:
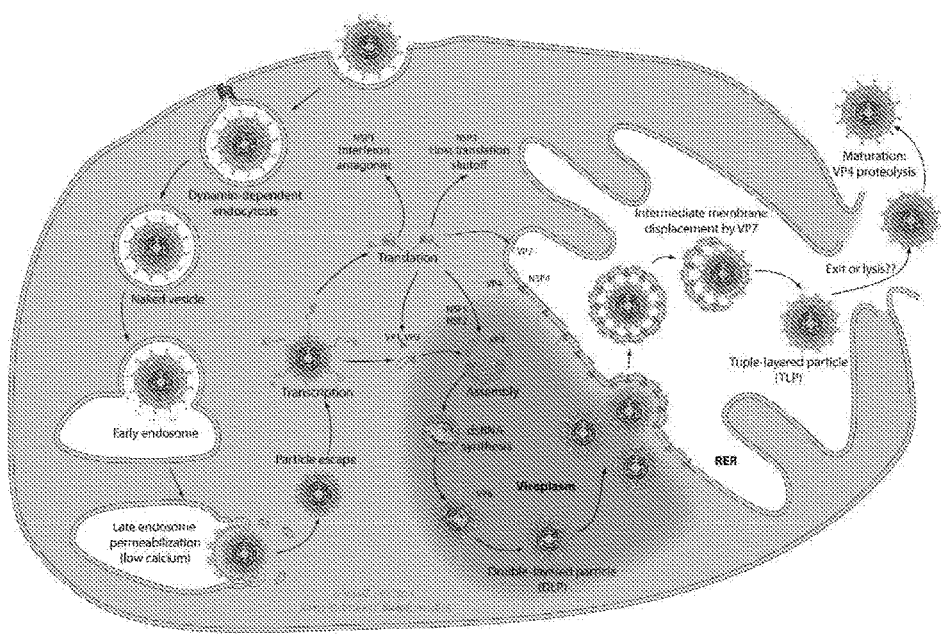

The following description is of a preferred embodiment.

The present invention relates to virus-like particles (VLPs) comprising one or more rotavirus structural protein (i.e. a rotavirus like particle, rotavirus VLP or RLP), and methods of producing rotavirus-like particle (RLPs) in any host, particularly in plants, a portion of a plant, or a plant cell. Other hosts might comprise, for example, insect cells and mammalian cells. The rotavirus like particle (RLP) may comprise one or more rotavirus structural protein. The RLP may triple layered. The RLP may be produced by co-expressing rotavirus structural and nonstructural proteins in plant, however, the RLP does not comprise any rotavirus nonstructural proteins.

The host or host cell may be from any source including plants, fungi, bacteria, insect and animals. In a preferred embodiment the host or host cell is a plant or plant cell.

The present invention in part provides further a method of producing a rotavirus-like particle (RLP) in a host, such as a plant, a portion of a plant, or a plant cell. The method may comprise introducing one or more nucleic acid comprising a regulatory region active in the host, such as a plant, a portion of a plant, or a plant cell, the regulatory region operatively linked to a nucleotide sequence encoding one or more rotavirus structural protein and one or more rotavirus non-structural protein into the host, such as into a plant, portion of the plant, or plant cell. Followed by incubating the host, such as a plant, portion of the plant, or plant cell under conditions that permit the expression of the nucleic acids, thereby producing the RLP comprising one or more rotavirus structural protein. The one or more rotavirus structural protein may be rotavirus protein VP2, VP4, VP6 or VP7. The rotavirus nonstructural protein may be NSP4. The RLP may be triple layered. The RLP may comprise rotavirus structural protein VP2, VP4, VP6 and VP7, and does not comprise the nonstructural protein NSP4.

The present invention in part provides further a method of producing a rotavirus like particle (RLP) in a host or host cell, the method may comprise:
providing a host or host cell comprising one or more nucleic acid comprising a first nucleotide sequence encoding a first rotavirus protein, a second nucleotide sequence encoding a second rotavirus protein and a third nucleotide sequence encoding a third rotavirus protein, the first, second and third nucleotide sequence being operatively linked to one or more regulatory region active in the host or host cell; and
the first, second and third nucleotide sequence encoding NSP4 and one or two of rotavirus protein VP2 or VP6 and one or two of rotavirus protein VP7 or VP4;
incubating the host or host cell under conditions that permit the expression of the one or more nucleic acid, so that NSP4 and either VP2, VP4 and VP7, or VP2, VP6 and VP7, or VP2, VP6 and VP4, or VP6, VP4 and VP7, are expressed, thereby producing the RLP.

Furthermore, the one or more nucleic acid may comprise a fourth nucleotide sequence encoding a fourth rotavirus protein. The first, second, third, and fourth nucleotide sequence being operatively linked to one or more regulatory region active in the host or host cell; and the first nucleotide sequence, the second nucleotide sequence, the third and fourth nucleotide sequence encoding rotavirus protein VP2, or VP6, VP4 or VP7 and NSP4, wherein NSP4 and wherein either VP2 or VP6 and VP4 or VP7 are expressed from the one or more nucleic acid.

Furthermore, the present invention in part provides a method of producing a rotavirus-like particle (RLP) vaccine candidate in a host, such as a plant, a portion of the plant, or a plant cell. The method may comprise expressing in a host, such as in a plant or portion of a plant, one or more nucleic acid ($R_1$-$R_5$) comprising one or more regulatory region active in the host, such as in the plant, portion of a plant, or plant cell, the regulatory region operatively linked to nucleotide sequences $R_1$-$R_5$, wherein nucleotide sequence $R_1$ encodes rotavirus protein $X_1$, nucleotide sequence $R_2$ encodes rotavirus protein $X_2$, nucleotide sequence $R_3$ encodes rotavirus protein $X_3$, nucleotide sequence $R_4$ encodes rotavirus protein $X_4$ and nucleotide sequence $R_5$ encodes rotavirus protein $X_5$ and each of $X_1$-$X_5$ are selected from the group of rotavirus protein VP2, VP4, VP6, VP7 and NSP4, so that each of VP2, VP4, VP6, VP7 and NSP4 are expressed in the host, such as in the plant, portion of the plant, or plant cell (see Table 1). The RLP may comprise rotavirus structural protein VP2, VP4, VP6 and VP7. The RLP does not comprise nonstructural protein NSP4.

It has been found that by introducing and co-expressing rotavirus structural protein and a rotavirus non-structural protein in the host, such as a plant or portion of the plant that the yield of the RLP produced may be modulated. In particular, it has been found that by co-expressing rotavirus structural proteins along with a rotavirus non-structural protein NSP4 in the host, such as a plant, portion of the plant, or plant cell, that the incorporation of structural protein VP4, VP7 or both VP4 and VP7 into the RLP may be increased, when compared to the level of VP4 and VP7 produced by a second host, such as a second plant, portion of a second plant, or second plant cell that expresses the same rotavirus structural proteins but that does not express the rotavirus non-structural protein, under the same conditions.

For example a method of increasing incorporation of VP4, VP7, or both VP4 and VP7 in a rotavirus like particle (RLP) is provided. The method comprises:
a) providing a host or host cell comprising one or more nucleic acid comprising
a first nucleotide sequence encoding a first rotavirus protein, a second nucleotide sequence encoding a second rotavirus protein, a third nucleotide sequence encoding a third rotavirus protein and a fourth nucleotide sequence encoding a fourth rotavirus protein; the first, second, third and fourth nucleotide sequence being operatively linked to one or more regulatory region active in the host or host cell; and
the first, second, third and fourth nucleotide sequence encoding one of rotavirus protein VP7, VP4, NSP4 and VP2 or VP6;
b) incubating the host or host cell under conditions that permit the expression of the one or more nucleic acid, so that each of the VP7, VP4, NSP4 and VP2 or VP6 and are expressed, thereby producing the RLP with enhanced levels of VP4, VP7, or both VP4 and VP7 when compared to the level of VP4 or VP7 produced by a second host or host cell that expresses the one or more nucleic acid that does not comprise NSP4, under the same conditions.

Furthermore, an alternative method of increasing production of VP4, VP7 or both VP4 and VP7 in a rotavirus like particle (RLP) may comprises:

a) introducing into a plant, portion of a plant or plant cell one or more nucleic acid comprising one or more regulatory operatively linked to a first, second, third, fourth and fifth nucleotide sequence, the one or more regulatory region active in the plant, portion of the plant or the plant cell, the first nucleotide sequence encoding a first rotavirus protein, the second nucleotide sequence encoding a second rotavirus protein, the third nucleotide sequence encoding a third rotavirus protein, the fourth nucleotide sequence encoding a fourth rotavirus protein and the fifth nucleotide sequence encoding a fifth rotavirus protein, each of the first, second, third, fourth or fifth nucleotide sequence encoding one of VP2, VP4, VP6, VP7 or NSP4, and b) incubating the plant, portion of a plant or plant cell under conditions that permit the transient expression of the one or more nucleic acid so that each of VP2, VP4, VP6, VP7 and NSP4 are transiently expressed, thereby producing the RLP with enhanced levels of VP4 and VP7 when compared to the level of VP4 and VP7 produced by a second plant, portion of a second plant, or second plant cell that expresses the one or more nucleic acid that does not comprise NSP4, under the same conditions.

If desired, the method may further comprises the steps of:

c) harvesting the plant, portion of a plant or plant cell, and d) purifying the RLPs from the plant, portion of a plant or plant cell, wherein the RLPs range in size from 70-100 nm.

An alternate method of increasing production of VP4, VP7 or both VP4 and VP7 in a rotavirus like particle (RLP) is also provided, the method comprising:

a) providing a plant, portion of a plant or plant cell comprising one or more nucleic acid comprising one or more regulatory region operatively linked to a first, second, third, fourth and fifth nucleotide sequence, the one or more regulatory region active in the plant, portion of the plant or the plant cell, the first nucleotide sequence encoding a first rotavirus protein, the second nucleotide sequence encoding a second rotavirus protein, the third nucleotide sequence encoding a third rotavirus protein, the fourth nucleotide sequence encoding a fourth rotavirus protein and the fifth nucleotide sequence encoding a fifth rotavirus protein, each of the first, second, third, fourth and fifth nucleotide sequence encoding one of VP2, VP4, VP6, VP7 or NSP4, and b) incubating the plant, portion of a plant or plant cell under conditions that permit the expression of the one or more nucleic acid, so that each of the VP2, VP4, VP6, VP7 and NSP4 are expressed, thereby producing the RLP with enhanced levels of VP4 and VP7 when compared to the level of VP4 and VP7 produced by a second plant, portion of a second plant, or second plant cell that expresses the one or more nucleic acid that does not comprise NSP4, under the same conditions.

It has been further found that by modulating the ratio between constructs comprising nucleic acids encoding rotavirus structural proteins and the non-structural protein NSP4 during transient expression in the host, such as a plant, portion of the plant, or plant cell, the yield of RLP production and the incorporation of structural proteins VP4 and VP7 into the RLP may be improved.

Without wishing to be bound by theory, the co-expression of a rotavirus non-structural protein for example NSP4 together with one or more rotavirus structural protein for example VP2, VP4, VP6 and/or VP7 may lead to an increase in incorporation of VP4 and/or VP7 into RLPs. This increase of incorporation of VP4 and/or VP7 into RLPs may occur via an increase of expression or production of the rotavirus proteins and/or because of an increase of the efficacy of the assembly of RLPs and/or an increase of recruiting of the rotavirus proteins at the RLP assembly site.

As shown in FIGS. 3A and 3B, the co-expression of rotavirus non-structural protein NSP4 together with rotavirus structural protein VP2, VP6, VP4 and VP7 in plants lead to an increase in incorporation of VP4 and VP7 into RLPs, when compared to the expression of structural protein VP2, VP6, VP4 and VP7 without the presence of NSP4 (see FIG. 3B).

The ratios of the constructs encoding the various structural and non-structural proteins that are transiently expressed in the host, such as a plant, portion of the plant, or plant cell, may be altered by providing constructs comprising nucleic acid sequences encoding rotavirus structural proteins and the non-structural protein NSP4 on two, three, four or five constructs and varying the amount of each construct during the step of introducing the construct in the host (using *Agrobacterium* to the plant, plant portion or plant cell). For example, five separate constructs, each encoding one structural protein and the non-structural protein, may be co-introduced at various ratios resulting co-expression of the nucleic acids at various ratios within a plant, plant portion, or plant cell. Alternatively, the nucleic acid sequences may be provided in various combinations on two, three or four constructs and the constructs co-introduced in the plant, portion of the plant, or plant cell, at various ratios, as described below.

Additionally, the nucleic acid sequences may be provided on the same construct.

"Rotavirus protein" may refer to rotavirus structural protein or rotavirus nonstructural proteins. A "rotavirus structural protein" may refer to all or a portion of a rotavirus structural protein isolated from rotavirus, present in any naturally occurring, or a variant of any naturally occurring, rotavirus strain or isolate. Thus, the term rotavirus structural protein includes a naturally occurring rotavirus structural protein, or a variant of a rotavirus structural protein that may be produced by mutation during the virus life-cycle or produced in response to selective pressure (e.g., drug therapy, expansion of host cell tropism, or infectivity, etc.). As one of skill in the art appreciates, such rotavirus structural proteins and variants thereof may be also produced using recombinant techniques. Rotavirus structural proteins may include capsid proteins such for example VP2 and VP6, surface proteins, for example VP4, or a combination of capsid and surface proteins. The structural protein may further include for example VP7.

By rotavirus "non structural protein", "nonstructural protein", "non-structural protein", "NSP" or "nonstructural rotavirus protein" it is meant a protein that is encoded by the rotavirus genome, but not packaged into the viral particle. Non-limiting examples of rotavirus nonstructural proteins are rotavirus NSP4.

By "co-expressed" it is meant that two, or more than two, nucleotide sequences are expressed at about the same time within the plant, within the same tissue of the plant and within the same cells in the plant. The nucleotide sequences need not be expressed at exactly the same time. Rather, the two or more nucleotide sequences are expressed in a manner such that the encoded products have a chance to interact within a desired cellular compartment. For example, the non-structural protein may be preferably expressed either before or during the period when the structural proteins are expressed. The two or more than two nucleotide sequences can be co-expressed using a transient expression system, where the two or more sequences are introduced within the plant at about the same time, under conditions that the two or more sequences are expressed. The two or more than two sequences may be present on different constructs, and co-expression requires introduction of each of the constructs into the plant, portion of plant or plant cell, or the two or more than two sequences may be present on one construct and the construct introduced into the plant, portion of plant or plant cell.

The term "virus-like particle" (VLP), or "virus-like particles" or "VLPs" refers to structures that self-assemble and comprise one or more structural proteins such as for example rotavirus structural protein, for example but not limited to VP2, VP4, VP6, VP7, or a combination of VP2, VP4, VP6, VP7, structural protein. VLPs comprising rotavirus structural protein maybe also be referred to "rotavirus VLP", "rotavirus-like particle (RVLP)", "rotavirus-like particle (RLP)", "rotavirus-like particle", "RVLP" or "RLP". VLPs or RLPs are generally morphologically and antigenically similar to virions produced in an infection, but lack genetic information sufficient to replicate and thus are non-infectious. VLPs may be produced in suitable eukaryotic host cells including plant host cells. Following extraction from the host cell and upon isolation and further purification under suitable conditions, VLPs may be recovered as intact structures. The RLP may be a single, double, or triple-layered RLP. Triple-layered RLPs may be obtained by the simultaneous expression of three or more rotavirus structural proteins, and as described herein, co-expression with one or more non-structural protein. For example, the co-expression of structural proteins VP2, VP6, VP7, VP4 and nonstructural protein NSP4 results in producing triple-layered RLPs.

Co-expression of VP4, along with VP2, VP6, VP7, and one or more non-structural protein as required, results in a particle with spikes that resembles native rotavirus. VP4 may be processed or cleaved to produce VP5 and VP8. This processing may take place within the host using endogenous proteases, or by co-expressing a suitable protease, for example, trypsin, a trypsin-like protease, a serine protease, a chymotrypsin-like protease, subtilisin. Alternatively, VP4 may be processed to produce VP5 and VP8 by adding a suitable protease, for example, trypsin, a trypsin-like protease, a serine protease, a chymotrypsin-like protease, subtilisin during any step of the RLP extraction procedure, or after RLP purification.

Each of the rotavirus structural proteins has different characteristics and size, and is required in different amounts for assembly into RLP. The term "rotavirus VLP", "rotavirus virus-like particle (RVLP)", "rotavirus virus-like particle (RLP)", "rotavirus virus-like particle", "RVLP" or "RLP" refers to a virus-like particle (VLP) comprising one or more rotavirus structural proteins. Example of rotavirus structural proteins may include, but are not limited to VP2, VP4 (or VP5 and VP8) VP6 and VP7 structural protein. The RLP may not comprise rotavirus nonstructural proteins.

The present invention provides for a method of producing RLPs in a plant, wherein one or more nucleic acid ($N_1$-$N_5$) comprising one or more regulatory region active in the plant are operatively linked to nucleotide sequences $R_1$-$R_5$, wherein nucleotide sequence $R_1$ encodes rotavirus protein $X_1$, nucleotide sequence $R_2$ encodes rotavirus protein $X_2$, nucleotide sequence $R_3$ encodes rotavirus protein $X_3$, nucleotide sequence $R_4$ encodes rotavirus protein $X_4$ and nucleotide sequence $R_5$ encodes rotavirus protein $X_5$ and wherein $X_1$-$X_5$ are selected from the group of rotavirus protein VP2, VP4, VP6, VP7 and NSP4, wherein VP2, VP4, VP6, VP7 and NSP4 are each selected once (see Table 1). The final set, or combination, of nucleic acids used to transform the host results in the expression of each rotavirus protein within the host resulting in expression of VP2, VP4, VP6, VP7 and NSP4 and formation of an RLP.

For example, with reference to Table 1, 2 nucleic acids ($N_1$ and $N_2$), may be used to transform a host, (see example #2.1). In this case $N_1$ comprises the $R_1$ nucleotide sequence and $R_1$ may encode one of VP2, VP4, VP6, VP7, or NSP4. The nucleic acid $N_2$ comprises four sequences $R_2$ to $R_5$, each of $R_2$ to $R_5$ encoding one of VP2, VP4, VP6, VP7, or NSP4, but not the protein encoded by $R_1$, so that each of the VP2, VP4, VP6, VP7 and NSP4 are expressed within the host, thereby producing the RLP. As a non-limiting example, $N_1$ may comprise $R_1$ which may encode VP2, and $N_2$ may comprise $R_2$ to $R_5$ which may encode VP4, VP6, VP7 and NSP4 respectively.

Table 1, provides an overview of combinations, which is not to be considered limiting, of nucleic acids (N), and nucleotide sequences (R) that may be expressed or co-expressed within a host to produce an RLP comprising VP2, VP4, VP6, and VP7.

TABLE 1

| Combination # | | | | | | Total # Nucleic Acids |
|---|---|---|---|---|---|---|
| 1.1 | Nucleic | $N_1$ | | | | 1 |
| 1.2 | Acids | | $N_1$ | | | 1 |
| 1.3 | | | | $N_1$ | | 1 |
| 2.1 | | $N_1$ | | $N_2$ | | 2 |
| 2.2 | | $N_1$ | | | $N_2$ | 2 |
| 2.3 | | | $N_1$ | | $N_2$ | 2 |
| 2.4 | | | $N_1$ | $N_2$ | | 2 |
| 2.5 | | | $N_1$ | $N_2$ | | 2 |
| 3.1 | | $N_1$ | | $N_2$ | $N_3$ | 3 |
| 3.2 | | $N_1$ | $N_2$ | | $N_3$ | 3 |
| 3.3 | | $N_1$ | $N_2$ | $N_3$ | | 3 |
| 3.4 | | $N_1$ | $N_2$ | $N_3$ | | 3 |
| 4.1 | | $N_1$ | $N_2$ | $N_3$ | $N_4$ | 4 |
| 4.2 | | $N_1$ | $N_2$ | $N_3$ | $N_4$ | 4 |
| 5 | | $N_1$ | $N_2$ | $N_3$ | $N_4$ $N_5$ | 5 |

| Nucleotide Sequence | $R_1$ | $R_2$ | $R_3$ | $R_4$ | $R_5$ | |
|---|---|---|---|---|---|---|
| Rotavirus Protein | $X_1$ | $X_2$ | $X_3$ | $X_4$ | $X_5$ | Protein type |
| $X_{(1-5)}$ may be* | VP2 | VP2 | VP2 | VP2 | VP2 | Structural |
| | VP4 | VP4 | VP4 | VP4 | VP4 | Structural |
| | VP6 | VP6 | VP6 | VP6 | VP6 | Structural |
| | VP7 | VP7 | VP7 | VP7 | VP7 | Structural |
| | NSP4 | NSP4 | NSP4 | NSP4 | NSP4 | Non-structural |

*For combinations 1.1, 2.1, 2.2, 3.1, 3.2, 4.1 and 5: $X_1$, $X_2$, $X_3$, $X_4$ and $X_5$ each have to be a different rotavirus protein selected from the group of VP2, VP4, VP6, VP7 and NSP4.
For combination 1.3, 2.5 and 3.4: $X_1$, $X_2$ and $X_3$ each have to be a different rotavirus protein selected from either VP4, VP6 and NSP4 or VP7, VP6 and NSP4.
For combination 1.2, 2.3, 2.4, 3.3 and 4.2: $X_1$, $X_2$, $X_3$ and $X_4$ each have to be a different rotavirus protein selected from the group of VP2, VP4, VP6 and NSP4, VP2, VP7, VP6 and NSP4 or VP4, VP7, VP6 and NSP4.

1. One Construct
1.1 Quintuple Gene Construct

As described herein, a method of producing RLPs in a plant is provided, wherein a nucleic acid ($N_1$; a first nucleic acid) comprising a first, second, third, fourth and fifth nucleotide sequences ($R_1$, $R_2$, $R_3$, $R_4$, $R_5$) encoding a first, second, third, fourth and fifth rotavirus protein ($X_1$, $X_2$, $X_3$, $X_4$, $X_5$) is expressed in a plant or portion of a plant (See Table 1, Combination #1.1).

Accordingly, nucleic acid $N_1$ comprises nucleotide sequences $R_1$, $R_2$, $R_3$, $R_4$ and $R_5$, wherein $R_1$ encodes rotavirus protein $X_1$, where $X_1$ may be any rotavirus protein selected from the group of VP2, VP4, VP6, VP7 and NSP4, and wherein $R_2$-$R_5$ encode a rotavirus protein that is not $X_1$, where $X_2$ may be any rotavirus protein selected from the group of VP2, VP4, VP6, VP7 and NSP4, and wherein $R_1$ and $R_3$-$R_5$ encode a rotavirus protein that is not $X_2$, where $X_3$ may be any rotavirus protein selected from the group of VP2, VP4, VP6, VP7 and NSP4, and wherein $R_1$ $R_2$, $R_4$, and $R_5$ encode a rotavirus protein that is not $X_3$, where $X_4$ may be any rotavirus protein selected from the group of VP2, VP4, VP6, VP7 and NSP4, and wherein $R_1$-$R_3$ and $R_5$ encode a rotavirus protein that is not $X_4$, where $X_5$ may be any rotavirus protein selected from the group of VP2, VP4, VP6, VP7 and NSP4, and wherein $R_1$-$R_4$ encode a rotavirus protein that is not $X_5$, with the result that a nucleotide sequence encoding for each rotavirus protein VP2, VP4, VP6, VP7 and NSP4 is comprised on nucleic acid $N_1$, thereby allowing for the expression of each rotavirus protein VP2, VP4, VP6, VP7 and NSP4 in the transformed host.

The nucleic acid may comprise a nucleotide sequence $R_1$, wherein $R_1$ may encode rotavirus protein VP2, VP4, VP6, VP7 or NSP4 and nucleotide sequences $R_2$-$R_5$, wherein $R_2$-$R_5$ encode a rotavirus protein selected from VP2, VP4, VP6, VP7 or NSP4, and wherein the rotavirus protein is not encoded by $R_1$. For example which is not to be considered limiting, nucleotide sequence $R_1$ may encode rotavirus protein VP2 and nucleotide sequence $R_2$-$R_5$ may encode in any order rotavirus protein VP4, VP6, VP7 and NSP4, but $R_2$-$R_5$ may not encode VP2. In another example which is not to be considered limiting, nucleotide sequence $R_1$ may encode rotavirus protein VP4 and nucleotide sequence $R_2$-$R_5$ may encode in any order rotavirus protein VP2, VP6, VP7 and NSP4, but $R_2$-$R_5$ may not encode VP4. In yet another non-limiting example, nucleotide sequence $R_1$ may encode rotavirus protein VP6 and nucleotide sequence $R_2$-$R_5$ may encode in any order rotavirus protein VP2, VP4, VP7 and NSP4, but $R_2$-$R_5$ may not encode VP6. In yet another example which is not to be considered limiting, nucleotide sequence $R_1$ may encode rotavirus protein VP7 and nucleotide sequence $R_2$-$R_5$ may encode in any order rotavirus protein VP2, VP4, VP6 and NSP4, but $R_2$-$R_5$ may not encode VP7. In yet another example which is not to be considered limiting, nucleotide sequence $R_1$ may encode rotavirus protein NSP4 and nucleotide sequence $R_2$-$R_5$ may encode in any order rotavirus protein VP2, VP4, VP6 and VP7, but $R_2$-$R_5$ may not encode NSP4.

For example, which is not to be considered limiting, the nucleotide sequence ($N_1$) comprises a first nucleotide sequences ($R_1$) encoding a first rotavirus protein, for example rotavirus protein VP7, a second nucleotide sequences ($R_2$) encoding a second rotavirus protein, for example rotavirus protein VP4, a third nucleotide sequences ($R_3$) encoding a third rotavirus protein, for example rotavirus protein NSP4, a fourth nucleotide sequences ($R_4$) encoding a fourth rotavirus protein, for example rotavirus protein VP6 and a fifth nucleotide sequences ($R_5$) encoding a fifth rotavirus protein, for example rotavirus protein VP2.

In a further non-limiting example the nucleotide sequence ($N_1$) comprises a first nucleotide sequences ($R_1$) encoding a first rotavirus protein, for example rotavirus protein VP4, a second nucleotide sequences ($R_2$) encoding a second rotavirus protein, for example rotavirus protein VP7, a third nucleotide sequences ($R_3$) encoding a third rotavirus protein, for example rotavirus protein NSP4, a fourth nucleotide sequences ($R_4$) encoding a fourth rotavirus protein, for example rotavirus protein VP6 and a fifth nucleotide sequences ($R_5$) encoding a fifth rotavirus protein, for example rotavirus protein VP2.

In a further non-limiting example the nucleotide sequence ($N_1$) comprises a first nucleotide sequences ($R_1$) encoding a first rotavirus protein, for example rotavirus protein VP4, a second nucleotide sequences ($R_2$) encoding a second rotavirus protein, for example rotavirus protein VP7, a third nucleotide sequences ($R_3$) encoding a third rotavirus protein, for example rotavirus protein VP6, a fourth nucleotide sequences ($R_4$) encoding a fourth rotavirus protein, for example rotavirus protein VP2 and a fifth nucleotide sequences ($R_5$) encoding a fifth rotavirus protein, for example rotavirus protein NSP4.

In another non-limiting example the nucleotide sequence ($N_1$) comprises a first nucleotide sequences ($R_1$) encoding a first rotavirus protein, for example rotavirus protein VP7, a second nucleotide sequences ($R_2$) encoding a second rotavirus protein, for example rotavirus protein VP4, a third nucleotide sequences ($R_3$) encoding a third rotavirus protein, for example rotavirus protein VP6, a fourth nucleotide sequences ($R_4$) encoding a fourth rotavirus protein, for example rotavirus protein VP2 and a fifth nucleotide sequences ($R_5$) encoding a fifth rotavirus protein, for example rotavirus protein NSP4. (see FIG. 5) A plant may be transformed with a single nucleic acid ($N_1$) comprising a first, second, third, fourth and fifth nucleotide sequences ($R_1$, $R_2$, $R_3$, $R_4$, $R_5$) encoding a first, second, third, fourth and fifth rotavirus protein, so that each of the first, second, third, fourth and fifth protein are expressed in the plant. The rotavirus proteins are selected from the group of rotavirus protein VP2, VP4, VP6, VP7 and NSP4, so that each of VP2, VP4, VP6, VP7 and NSP4 are expressed in the plant. The single nucleic acid may be introduced in the plant in a transient manner, or in a stable manner.

The VP4 may be processed or cleaved to produce VP5 and VP8 within the host by co-expressing a nucleic acid encoding a suitable protease, for example, trypsin, a trypsin-like protease, a serine protease, a chymotrypsin-like protease, subtilisin. Alternatively, VP4 may be processed during any step of RLP extraction, or after RLP purification by adding a sutible protease, for example, trypsin, a trypsin-like protease, a serine protease, a chymotrypsin-like protease, subtilisin.

1.2. Quadruple Gene Construct

As described herein, a method of producing RLPs in a plant is provided, wherein a nucleic acid ($N_1$; a first nucleic acid) comprising a first, second, third and fourth nucleotide sequences ($R_1$, $R_2$, $R_3$, $R_4$) encoding a first, second, third and fourth rotavirus protein ($X_1$, $X_2$, $X_3$, $X_4$) is expressed in a plant or portion of a plant (See Table 1, Combination #1.2).

Accordingly, nucleic acid $N_1$ may comprises nucleotide sequences ($R_1$, $R_2$, $R_3$, $R_4$), wherein $R_1$ encodes rotavirus protein $X_1$, where $X_1$ may be any rotavirus protein selected from the group of VP2, VP4, VP6 and NSP4, and wherein $R_2$-$R_4$ encode a rotavirus protein that is not $X_1$, where $X_2$ may be any rotavirus protein selected from the group of VP2, VP4, VP6 and NSP4, and wherein $R_1$ and $R_3$-$R_4$ encode a rotavirus protein that is not $X_2$, where $X_3$ may be any rotavirus protein selected from the group of VP2, VP4, VP6 and NSP4, and wherein $R_1$ $R_2$, and $R_4$ encode a rotavirus protein that is not $X_3$, where $X_4$ may be any rotavirus protein selected from the group of VP2, VP4, VP6 and NSP4, and wherein $R_1$-$R_3$ encode a rotavirus protein that is not $X_4$, with the result that a nucleotide sequence encoding for each rotavirus protein VP2, VP4, VP6 and NSP4 is comprised on nucleic acid $N_1$, thereby allowing for the expression of each rotavirus protein VP2, VP4, VP6 and NSP4 in the transformed host.

For example, which is not to be considered limiting, the nucleotide sequence ($N_1$) comprises a first nucleotide sequences ($R_1$) encoding a first rotavirus protein, for example rotavirus protein VP6, a second nucleotide sequences ($R_2$) encoding a second rotavirus protein, for example rotavirus protein VP4, a third nucleotide sequences ($R_3$) encoding a third rotavirus protein, for example rotavirus proteinVP2, and a fourth nucleotide sequences ($R_4$) encoding a fourth rotavirus protein, for example rotavirus protein NSP4.

Further accordingly, nucleic acid $N_1$ may comprises nucleotide sequences ($R_1$, $R_2$, $R_3$, $R_4$), wherein $R_1$ encodes rotavirus protein $X_1$, where $X_1$ may be any rotavirus protein selected from the group of VP2, VP7, VP6 and NSP4, and wherein $R_2$-$R_4$ encode a rotavirus protein that is not $X_1$, where $X_2$ may be any rotavirus protein selected from the group of VP2, VP7, VP6 and NSP4, and wherein $R_1$ and $R_3$-$R_4$ encode a rotavirus protein that is not $X_2$, where $X_3$ may be any rotavirus protein selected from the group of VP2, VP7, VP6 and NSP4, and wherein $R_1$ $R_2$, and $R_4$ encode a rotavirus protein that is not $X_3$, where $X_4$ may be any rotavirus protein selected from the group of VP2, VP7, VP6 and NSP4, and wherein $R_1$-$R_3$ encode a rotavirus protein that is not $X_4$, with the result that a nucleotide sequence encoding for each rotavirus protein VP2, VP7, VP6 and NSP4 is comprised on nucleic acid $N_1$, thereby allowing for the expression of each rotavirus protein VP2, VP7, VP6 and NSP4 in the transformed host.

For example, which is not to be considered limiting, the nucleotide sequence ($N_1$) comprises a first nucleotide sequences ($R_1$) encoding a first rotavirus protein, for example rotavirus protein VP6, a second nucleotide sequences ($R_2$) encoding a second rotavirus protein, for example rotavirus protein VP7, a third nucleotide sequences ($R_3$) encoding a third rotavirus protein, for example rotavirus proteinVP2, and a fourth nucleotide sequences ($R_4$) encoding a fourth rotavirus protein, for example rotavirus protein NSP4.

Further accordingly, nucleic acid $N_1$ may comprises nucleotide sequences ($R_1$, $R_2$, $R_3$, $R_4$), wherein $R_1$ encodes rotavirus protein $X_1$, where $X_1$ may be any rotavirus protein selected from the group of VP7, VP4, VP6 and NSP4, and wherein $R_2$-$R_4$ encode a rotavirus protein that is not $X_1$, where $X_2$ may be any rotavirus protein selected from the group of VP7, VP4, VP6 and NSP4, and wherein $R_1$ and $R_3$-$R_4$ encode a rotavirus protein that is not $X_2$, where $X_3$ may be any rotavirus protein selected from the group of VP7, VP4, VP6 and NSP4, and wherein $R_1$ $R_2$, and $R_4$ encode a rotavirus protein that is not $X_3$, where $X_4$ may be any rotavirus protein selected from the group of VP7, VP4, VP6 and NSP4, and wherein $R_1$-$R_3$ encode a rotavirus protein that is not $X_4$, with the result that a nucleotide sequence encoding for each rotavirus protein VP7, VP4, VP6 and NSP4 is comprised on nucleic acid $N_1$, thereby allowing for the expression of each rotavirus protein VP7, VP4, VP6 and NSP4 in the transformed host.

For example, which is not to be considered limiting, the nucleotide sequence ($N_1$) comprises a first nucleotide sequences ($R_1$) encoding a first rotavirus protein, for example rotavirus protein VP6, a second nucleotide sequences ($R_2$) encoding a second rotavirus protein, for example rotavirus protein VP4, a third nucleotide sequences ($R_3$) encoding a third rotavirus protein, for example rotavirus proteinVP7, and a fourth nucleotide sequences ($R_4$) encoding a fourth rotavirus protein, for example rotavirus protein NSP4.

1.3 Triple Gene Construct

As described herein, a method of producing RLPs in a plant is provided, wherein a nucleic acid ($N_1$; a first nucleic acid) comprising a first, second and third nucleotide sequences ($R_1$, $R_2$, $R_3$) encoding a first, second and third rotavirus protein ($X_1$, $X_2$, $X_3$) is expressed in a plant or portion of a plant (See Table 1, Combination #1.3).

Accordingly, nucleic acid $N_1$ may comprises nucleotide sequences ($R_1$, $R_2$, $R_3$), wherein $R_1$ encodes rotavirus protein $X_1$, where $X_1$ may be any rotavirus protein selected from the group of VP4, VP6 and NSP4, and wherein $R_2$-$R_3$ encode a rotavirus protein that is not $X_1$, where $X_2$ may be any rotavirus protein selected from the group of VP4, VP6 and NSP4, and wherein $R_1$ and $R_3$ encode a rotavirus protein that is not $X_2$, where $X_3$ may be any rotavirus protein selected from the group of VP4, VP6 and NSP4, and wherein $R_1$ $R_2$ encode a rotavirus protein that is not $X_3$, with the result that a nucleotide sequence encoding for each rotavirus protein VP4, VP6 and NSP4 is comprised on nucleic acid $N_1$, thereby allowing for the expression of each rotavirus protein VP4, VP6 and NSP4 in the transformed host.

For example, which is not to be considered limiting, the nucleotide sequence ($N_1$) comprises a first nucleotide sequences ($R_1$) encoding a first rotavirus protein, for example rotavirus protein VP6, a second nucleotide sequences ($R_2$) encoding a second rotavirus protein, for example rotavirus protein VP4, a third nucleotide sequences ($R_3$) encoding a third rotavirus protein, for example rotavirus protein.

Further accordingly, nucleic acid $N_1$ may comprises nucleotide sequences ($R_1$, $R_2$, $R_3$), wherein $R_1$ encodes rotavirus protein $X_1$, where $X_1$ may be any rotavirus protein selected from the group of VP7, VP6 and NSP4, and wherein $R_2$-$R_3$ encode a rotavirus protein that is not $X_1$, where $X_2$ may be any rotavirus protein selected from the group of VP7, VP6 and NSP4, and wherein $R_1$ and $R_3$ encode a rotavirus protein that is not $X_2$, where $X_3$ may be any rotavirus protein selected from the group of VP7, VP6 and NSP4, and wherein $R_1$ $R_2$ encode a rotavirus protein that is not $X_3$, with the result that a nucleotide sequence encoding for each rotavirus protein VP7, VP6 and NSP4 is comprised on nucleic acid $N_1$, thereby allowing for the expression of each rotavirus protein VP7, VP6 and NSP4 in the transformed host.

For example, which is not to be considered limiting, the nucleotide sequence ($N_1$) comprises a first nucleotide sequences ($R_1$) encoding a first rotavirus protein, for example rotavirus protein VP6, a second nucleotide sequences ($R_2$) encoding a second rotavirus protein, for example rotavirus protein VP7, a third nucleotide sequences ($R_3$) encoding a third rotavirus protein, for example rotavirus protein.

2. Two Constructs
2.1. Quadruple Gene Construct+Single Gene Construct

The present invention also provides for a method of producing RLPs in a plant, wherein a first nucleic acid ($N_1$) comprising a nucleotide sequence ($R_1$) encoding a first rotavirus protein ($X_1$), is co-expressed with a second nucleic acid ($N_2$) comprising four nucleotide sequences ($R_2$-$R_5$) encoding a second, third, fourth and fifth rotavirus protein ($X_2$-$X_5$) (see Table 1, Combination #2.1), so that the first, second, third, fourth and fifth nucleotide sequence ($R_1$-$R_5$) are co-expressed in the plant.

In this non-limiting example, $N_1$ comprises nucleotide sequence ($R_1$) and $N_2$ comprises nucleotide sequences ($R_2$, $R_3$, $R_4$, $R_5$), wherein each rotavirus protein selected from the group of VP2, VP4, VP6, VP7 and NSP4 is encoded in the combination of both constructs $N_1$ and $N_2$, and wherein $R_1$ encodes rotavirus protein $X_1$, wherein $X_1$ may be any rotavirus protein selected from the group of VP2, VP4, VP6, VP7 and NSP4, and wherein $R_2$-$R_5$ encode a rotavirus protein that is not $X_1$, where $X_2$ may be any rotavirus protein selected from the group of VP2, VP4, VP6, VP7 and NSP4, and wherein $R_1$ and $R_3$-$R_5$ encode a rotavirus protein that is not $X_2$, where $X_3$ may be any rotavirus protein selected from the group of VP2, VP4, VP6, VP7 and NSP4, and wherein $R_1$ $R_2$, $R_4$, and $R_5$ encode a rotavirus protein that is not $X_3$, where $X_4$ may be any rotavirus protein selected from the group of VP2, VP4, VP6, VP7 and NSP4, and wherein $R_1$-$R_3$ and $R_5$ encode a rotavirus protein that is not $X_4$, where $X_5$ may be any rotavirus protein selected from the group of VP2, VP4, VP6, VP7 and NSP4, and wherein $R_1$-$R_4$ encode a rotavirus protein that is not $X_5$, with the result that each rotavirus protein VP2, VP4, VP6, VP7 and NSP4 is expressed in the host.

For example, which is not to be considered limiting, nucleotide sequence $R_1$ may encode rotavirus protein VP2 and nucleotide sequence $R_2$-$R_5$ may encode in any order rotavirus protein VP4, VP6, VP7 and NSP4, but $R_2$-$R_5$ may not encode VP2. In another non-limiting example nucleotide sequence $R_1$ may encode rotavirus protein VP4 and nucleotide sequence $R_2$-$R_5$ may encode in any order rotavirus protein VP2, VP6, VP7 and NSP4, but $R_2$-$R_5$ may not encode VP4. In yet another non-limiting example nucleotide sequence $R_1$ may encode rotavirus protein VP6 and nucleotide sequence $R_2$-$R_5$ may encode in any order rotavirus protein VP2, VP4, VP7 and NSP4, but $R_2$-$R_5$ may not encode VP6. In yet another example which is not to be considered limiting, nucleotide sequence $R_1$ may encode rotavirus protein VP7 and nucleotide sequence $R_2$-$R_5$ may encode in any order rotavirus protein VP2, VP4, VP6 and NSP4, but $R_2$-$R_5$ may not encode VP7. In yet another non-limiting example nucleotide sequence $R_1$ may encode rotavirus protein NSP4 and nucleotide sequence $R_2$-$R_5$ may encode in any order rotavirus protein VP2, VP4, VP6 and VP7, but $R_2$-$R_5$ may not encode NSP4.

The first nucleic acid ($N_1$) and second nucleic acid ($N_2$) may be introduced into the plant in the same step, or may be introduced to the plant sequentially.

Figure 5:
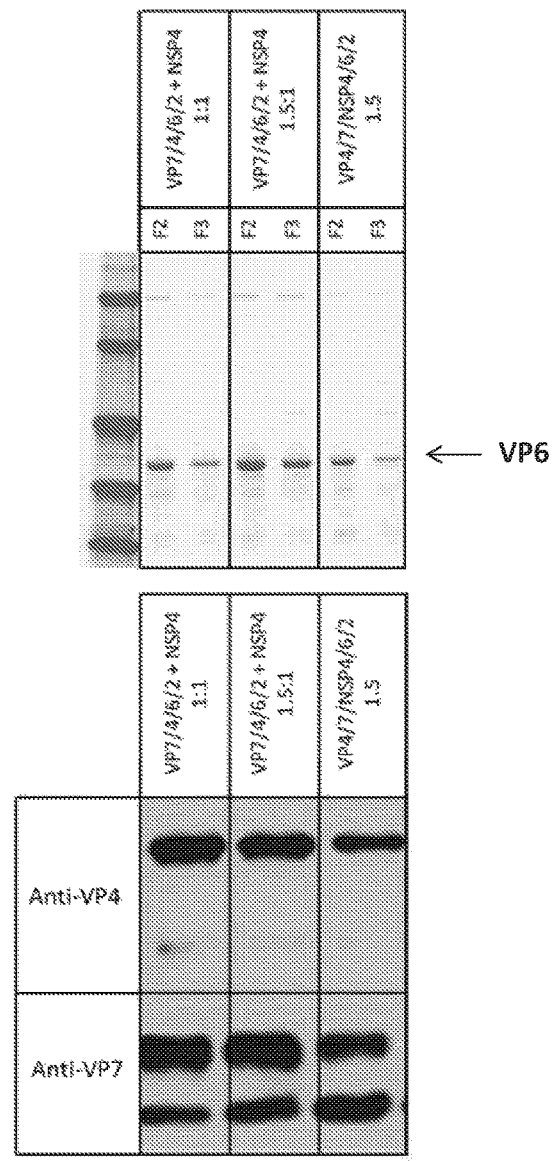

For example, which is not to be considered limiting, a first nucleotide sequence ($N_1$) comprising a nucleotide sequence ($R_1$) encoding a first rotavirus protein, for example NSP4, is co-expressed with a second nucleic acid ($N_2$) comprising four nucleotide sequences ($R_2$-$R_5$) encoding a second, third, fourth and fifth rotavirus protein, for example VP7, VP4, VP6 and VP2, respectively (see FIG. 5).

In another non-limiting example, a first nucleotide sequence ($N_1$) comprising a nucleotide sequence ($R_1$) encoding a first rotavirus protein, for example NSP4, is co-expressed with a second nucleic acid ($N_2$) comprising four sequential nucleotide sequences ($R_2$-$R_5$) encoding a second, third, fourth and fifth rotavirus protein, for example VP4, VP7, VP6 and VP2, respectively. In yet another non-limiting example, a first nucleotide sequence ($N_1$) comprising a nucleotide sequence ($R_1$) encoding a first rotavirus protein, for example NSP4, is co-expressed with a second nucleic acid ($N_2$) comprising four sequential nucleotide sequences ($R_2$-$R_5$) encoding a second, third, fourth and fifth rotavirus protein, for example VP7, VP4, VP2 and VP6, respectively. In yet another non-limiting example, a first nucleotide sequence ($N_1$) comprising a nucleotide sequence ($R_1$) encoding a first rotavirus protein, for example NSP4, is co-expressed with a second nucleic acid ($N_2$) comprising four sequential nucleotide sequences ($R_2$-$R_5$) encoding a second, third, fourth and fifth rotavirus protein, for example VP4, VP7, VP2 and VP6, respectively. In yet another non-limiting example, a first nucleotide sequence ($N_1$) comprising a nucleotide sequence ($R_1$) encoding a first rotavirus protein, for example NSP4, is co-expressed with a second nucleic acid ($N_2$) comprising four sequential nucleotide sequences ($R_2$-$R_5$) encoding a second, third, fourth and fifth rotavirus protein, for example VP6, VP2, VP4 and VP7, respectively. In yet another non-limiting example, a first nucleotide sequence ($N_1$) comprising a nucleotide sequence ($R_1$) encoding a first rotavirus protein, for example NSP4, is co-expressed with a second nucleic acid ($N_2$) comprising four sequential nucleotide sequences ($R_2$-$R_5$) encoding a second, third, fourth and fifth rotavirus protein, for example VP6, VP2, VP7 and VP4, respectively. In yet another non-limiting example, a first nucleotide sequence ($N_1$) comprising a nucleotide sequence ($R_1$) encoding a first rotavirus protein, for example NSP4, is co-expressed with a second nucleic acid ($N_2$) comprising four sequential nucleotide sequences ($R_2$-$R_5$) encoding a second, third, fourth and fifth rotavirus protein, for example VP2, VP4, VP6 and VP7, respectively. In yet another non-limiting example, a first nucleotide sequence ($N_1$) comprising a nucleotide sequence ($R_1$) encoding a first rotavirus protein, for example NSP4, is co-expressed with a second nucleic acid ($N_2$) comprising four sequential nucleotide sequences ($R_2$-$R_5$) encoding a second, third, fourth and fifth rotavirus protein, for example VP7, VP6, VP4 and VP2, respectively. In yet another non-limiting example, a first nucleotide sequence ($N_1$) comprising a nucleotide sequence ($R_1$) encoding a first rotavirus protein, for example VP7, is co-expressed with a second nucleic acid ($N_2$) comprising four sequential nucleotide sequences ($R_2$-$R_5$) encoding a second, third, fourth and fifth rotavirus protein, for example NSP4, VP2, VP6 and VP4, respectively. In yet another non-limiting example, a first nucleotide sequence ($N_1$) comprising a nucleotide sequence ($R_1$) encoding a first rotavirus protein, for example VP4, is co-expressed with a second nucleic acid ($N_2$) comprising four sequential nucleotide sequences ($R_2$-$R_5$) encoding a second, third, fourth and fifth rotavirus protein, for example NSP4, VP2, VP6 and VP7, respectively.

A plant that expresses a first nucleic acid ($N_1$) comprising a first nucleotide sequence ($R_1$) encoding a first rotavirus protein ($X_1$), may be transformed with a second nucleic acid ($N_2$) comprising four nucleotide sequences ($R_2$-$R_5$) encoding a second, third, fourth and fifth rotavirus protein ($X_2$-$X_5$), so that the first, second, third, fourth and fifth nucleotide sequence are co-expressed in the plant. Furthermore, a plant that expresses a first nucleic acid ($N_2$) comprising four nucleotide sequences ($R_2$-$R_5$) encoding a rotavirus protein $X_2$-$X_5$ may be transformed with a second nucleic acid ($N_1$) comprising a nucleotide sequence ($R_1$) encoding a rotavirus protein ($X_1$), so that the first and second nucleotide sequences $R_1$-$R_5$ are co-expressed in the plant. The rotavirus protein $X_1$ may be any rotavirus protein selected from the group of VP2, VP4, VP6, VP7 and NSP4, and rotavirus proteins $X_2$-$X_5$ may be any rotavirus protein selected from the group of VP2, VP4, VP6, VP7 and NSP4, but not $X_1$, so that each rotavirus protein VP2, VP4, VP6, VP7 and NSP4 is expressed. Furthermore, a plant may be simultaneously co-transformed with a first nucleic acid ($N_2$) comprising four nucleotide sequences ($R_2$-$_{R5}$) encoding a rotavirus protein $X_2$-$X_5$, and with a second nucleic acid ($N_1$) comprising a nucleotide sequence ($R_1$) encoding a rotavirus protein ($X_1$), so that the first and second nucleotide sequences $R_1$-$R_5$ are co-expressed in the plant. The rotavirus protein $X_1$ may be any rotavirus protein selected from the group of VP2, VP4, VP6, VP7 and NSP4, and rotavirus proteins $X_2$-$X_5$ may be any rotavirus protein selected from the group of VP2, VP4, VP6, VP7 and NSP4, but not the protein selected for $X_1$, so that each rotavirus protein VP2, VP4, VP6, VP7 and NSP4 is expressed. The first nucleic acid ($N_1$) and second nucleic acid ($N_2$) may be introduced in the plant in a transient manner, or in a stable manner.

For example, which is not to be considered limiting, a plant that expresses a first nucleic acid ($N_1$) comprising a first nucleotide sequence ($R_1$) encoding a first rotavirus protein ($X_1$) for example NSP4, may be transformed with a second nucleic acid encoding ($N_2$) comprising four nucleotide sequences ($R_2$-$R_5$) encoding a second, third, fourth and fifth rotavirus protein ($X_2$-$X_5$), for example VP7, VP4, VP6 and VP2, so that NSP4, VP7, VP4, VP6 and VP2 are co-expressed in the plant.

A first plant expressing a first nucleic acid ($N_1$) comprising a first nucleotide sequence ($R_1$) encoding a first rotavirus protein ($X_1$), may be crossed with a second plant expressing the second nucleic acid ($N_2$) comprising four nucleotide sequences ($R_2$-$R_5$) encoding a second, third, fourth and fifth rotavirus protein ($X_2$-$X_5$) to produce a progeny plant (third plant) that co-expresses the first, second, third, fourth and fifth rotavirus protein ($X_1$-$X_5$). Furthermore, a first plant expressing a first nucleic acid ($N_2$) comprising four nucleotide sequences ($R_2$-$R_5$) encoding a rotavirus protein $X_2$-$X_5$ may be crossed with a second plant expressing a second nucleic acid ($N_1$) comprising a nucleotide sequence ($R_1$) encoding a rotavirus protein ($X_1$), so that nucleotide sequences $R_1$-$R_5$ are co-expressed in the progeny plant. The rotavirus protein may be any rotavirus protein selected from the group of rotavirus protein VP2, VP4, VP6, VP7 and NSP4, wherein VP2, VP4, VP6, VP7 and NSP4 are selected once, so that each rotavirus protein VP2, VP4, VP6, VP7 and NSP4 is expressed in the progeny plant.

The VP4 may be processed or cleaved to produce VP5 and VP8 within the host by co-expressing a nucleic acid encoding a suitable protease, for example, trypsin, a trypsin-like protease, a serine protease, a chymotrypsin-like protease, subtilisin. Alternatively, VP4 may be processed during any step of RLP extraction, or after RLP purification by adding a suitable protease, for example, trypsin, a trypsin-like protease, a serine protease, a chymotrypsin-like protease, subtilisin.

2.2 Triple Gene Construct+Dual Gene Construct

The present invention also provides for a method of producing RLPs in a plant, wherein a first nucleic acid ($N_1$) comprising two nucleotide sequences ($R_1$ and $R_2$) encoding a first rotavirus protein ($X_1$) and second rotavirus protein ($X_2$) respectively, is co-expressed with a second nucleic acid ($N_2$) comprising three nucleotide sequences ($R_3$-$R_5$) encoding a third, fourth and fifth rotavirus proteins ($X_3$-$X_5$) (see Table 1, Combination #2.2), so that the first, second, third, fourth and fifth nucleotide sequence are co-expressed in the plant.

In a non-limiting example, $N_1$ comprises nucleotide sequences ($R_1$, $R_2$) and $N_2$ comprises nucleotide sequences ($R_3$, $R_4$, $R_5$), wherein each rotavirus protein selected from the group of VP2, VP4, VP6, $V_{P7}$ and NSP4 is encoded and wherein $R_1$ encodes rotavirus protein $X_1$, wherein $X_1$ may be any rotavirus protein selected from the group of VP2, VP4, VP6, VP7 and NSP4, and wherein $R_2$-$R_5$ encode a rotavirus protein that is not $X_1$, where $X_2$ may be any rotavirus protein selected from the group of VP2, VP4, VP6, VP7 and NSP4, and wherein $R_1$ and $R_3$-$R_5$ encode a rotavirus protein that is not $X_2$, where $X_3$ may be any rotavirus protein selected from the group of VP2, VP4, VP6, VP7 and NSP4, and wherein $R_1$ $R_2$, $R_4$, and $R_5$ encode a rotavirus protein that is not $X_3$, where $X_4$ may be any rotavirus protein selected from the group of VP2, VP4, VP6, VP7 and NSP4, and wherein $R_1$-$R_3$ and $R_5$ encode a rotavirus protein that is not $X_4$, where $X_5$ may be any rotavirus protein selected from the group of VP2, VP4, VP6, VP7 and NSP4, and wherein $R_1$-$R_4$ encode a rotavirus protein that is not $X_5$, with the result that each rotavirus protein VP2, VP4, VP6, VP7 and NSP4 is expressed in the host.

Therefore, the first nucleic acid ($N_1$) may comprise a nucleotide sequence $R_1$, wherein $R_1$ may encode rotavirus protein VP2, VP4, VP6, VP7 or NSP4 and a second nucleotide sequence $R_2$ which may encode any rotavirus protein selected from the group of VP2, VP4, VP6, VP7 and NSP4, that is not encoded by $R_1$. The second nucleic acid ($N_2$) may comprise nucleotide sequences $R_3$-$R_5$, wherein $R_3$-$R_5$ encode rotavirus protein VP2, VP4, VP6, VP7 or NSP4, but not rotavirus protein that are encoded by $R_1$ or $R_2$. For example, which is not to be considered limiting, nucleotide sequence $R_1$ may encode rotavirus protein VP2 and nucleotide sequence $R_2$-$R_5$ may encode in any order rotavirus protein VP4, VP6, VP7 and NSP4, but $R_2$-$R_5$ may not encode VP2. In another non-limiting example nucleotide sequence $R_1$ may encode rotavirus protein VP4 and nucleotide sequences $R_2$-$R_5$ may encode in any order rotavirus protein VP2, VP6, VP7 and NSP4. In yet another example nucleotide sequence $R_1$ may encode rotavirus protein VP6 and nucleotide sequences $R_2$-$R_5$ may encode in any order rotavirus protein VP2, VP4, VP7 and NSP4. In yet another non-limiting example nucleotide sequence $R_1$ may encode rotavirus protein VP7 and nucleotide sequences $R_2$-$R_5$ may encode in any order rotavirus protein VP2, VP4, VP6 and NSP4. In yet another non-limiting example nucleotide sequence $R_1$ may encode rotavirus protein NSP4 and nucleotide sequences $R_2$-$R_5$ may encode in any order rotavirus protein VP2, VP4, VP6 and VP7.

A plant that expresses a first nucleic acid ($N_1$) comprising a first and second nucleotide sequence ($R_1$+$R_2$) encoding a first and second rotavirus protein ($X_1$+$X_2$), may be transformed with a second nucleic acid ($N_2$) comprising three nucleotide sequences ($R_3$-$R_5$) encoding a third, fourth and fifth rotavirus protein ($X_3$-$X_5$), so that the first, second, third, fourth and fifth nucleotide sequence are co-expressed in the plant. The first nucleic acid ($N_1$) and second nucleic acid ($N_2$) may be introduced in the plant in a transient manner, or in a stable manner.

Furthermore, a plant that expresses a first nucleic acid ($N_2$) comprising three nucleotide sequences ($R_3$-$R_5$) encoding a first, second and third rotavirus protein ($X_3$-$X_5$) may be transformed with a second nucleic acid ($N_1$) comprising a fourth nucleotide sequence ($R_1$) encoding a fourth rotavirus protein ($X_1$) and a fifth rotavirus protein ($X_2$) so that the first and second nucleic acids $R_1$-$R_5$ are co-expressed in the plant. The rotavirus protein $X_1$ may be any rotavirus protein selected from the group of VP2, VP4, VP6, VP7 and NSP4, and rotavirus proteins $X_2$-$X_5$ may be any rotavirus protein selected from the group of VP2, VP4, VP6, VP7 and NSP4, but not $X_1$, so that each rotavirus protein VP2, VP4, VP6, VP7 and NSP4 is expressed. For example, which is not to be considered limiting, a plant that expresses a first nucleic acid ($N_2$) comprising three nucleotide sequences ($R_3$-$R_5$) encoding a first, second and third rotavirus proteins ($X_3$-$X_5$), for example VP7, VP4 and VP6 may be transformed with a second nucleic acid encoding ($N_1$) comprising a fourth and a fifth nucleotide sequences ($R_1$-$R_2$) encoding a fourth and a fifth rotavirus protein ($X_1$-$X_2$) for example VP2 and NSP4, so that NSP4, VP7, VP4, VP6 and VP2 are co-expressed in the plant. Furthermore, a plant may be simultaneously co-transformed with a first nucleic acid ($N_1$) comprising a first and second nucleotide sequence ($R_1$+$R_2$) encoding a first and second rotavirus protein ($X_1$+$X_2$), and a second nucleic acid ($N_2$) comprising three nucleotide sequences ($R_3$-$R_5$) encoding a third, fourth and fifth rotavirus protein ($X_3$-$X_5$), so that the first, second, third, fourth and fifth nucleotide sequence are co-expressed in the plant. The first nucleic acid ($N_1$) and second nucleic acid ($N_2$) may be introduced in the plant in a transient manner, or in a stable manner.

A first plant expressing a first nucleic acid ($N_1$) comprising a first nucleotide sequence ($R_1$) encoding a first rotavirus protein ($X_1$) and a second nucleotide sequence ($R_2$) encoding a second rotavirus protein ($X_2$), may be crossed with a second plant expressing the second nucleic acid ($N_2$) comprising three nucleotide sequences ($R_3$-$R_5$) encoding a third, fourth and fifth rotavirus protein ($X_3$-$X_5$) to produce a progeny plant (third plant) that co-expresses the first, second, third, fourth and fifth rotavirus protein ($X_1$-$X_5$). Furthermore, a first plant expressing a first nucleic acid ($N_2$) comprising three nucleotide sequences ($R_3$-$R_5$) encoding a rotavirus protein $X_3$-$X_5$ may be crossed with a second plant expressing a second nucleic acid ($N_1$) comprising a nucleotide sequence ($R_1$) encoding a rotavirus protein ($X_1$) and a second nucleotide sequence ($R_2$) encoding a second rotavirus protein ($X_2$), so that nucleotide sequences $R_1$-$R_5$ are co-expressed in the progeny plant. The rotavirus protein may be any rotavirus protein selected from the group of rotavirus protein VP2, VP4, VP6, VP7 and NSP4, wherein VP2, VP4, VP6, VP7 and NSP4 are selected once, so that each rotavirus protein VP2, VP4, VP6, VP7 and NSP4 is expressed in the progeny plant.

2.3. Triple Gene Construct+Single Gene Construct

The present invention also provides for a method of producing RLPs in a plant, wherein a first nucleic acid ($N_1$) comprising one nucleotide sequence ($R_1$) encoding a first rotavirus protein ($X_1$), is co-expressed with a second nucleic acid ($N_2$) comprising three nucleotide sequences ($R_2$-$R_4$) encoding a second, third and fourth rotavirus proteins ($X_2$-$X_4$), so that the first, second, third and fourth nucleotide sequence are co-expressed in the plant (See Table 1, Combination #2.3).

In a non-limiting example, $N_1$ comprises nucleotide sequence ($R_1$) and $N_2$ comprises nucleotide sequences ($R_2$, $R_3$, $R_4$), wherein each rotavirus protein selected from the group of VP2, VP4, VP6 and NSP4 is encoded and wherein $R_1$ encodes rotavirus protein $X_1$, wherein $X_1$ may be any rotavirus protein selected from the group of VP2, VP4, VP6 and NSP4, and wherein $R_2$-$R_4$ encode a rotavirus protein that is not $X_1$, where $X_2$ may be any rotavirus protein selected from the group of VP2, VP4, VP6 and NSP4, and wherein $R_1$ and $R_3$-$R_4$ encode a rotavirus protein that is not $X_2$, where $X_3$ may be any rotavirus protein selected from the group of VP2, VP4, VP6 and NSP4, and wherein $R_1$ $R_2$, and $R_4$ encode a rotavirus protein that is not $X_3$, where $X_4$ may be any rotavirus protein selected from the group of VP2, VP4, VP6 and NSP4, and wherein $R_1$-$R_3$ encode a rotavirus protein that is not $X_4$, with the result that each rotavirus protein VP2, VP4, VP6 and NSP4 is expressed in the host.

In a further non-limiting example, $N_1$ comprises nucleotide sequence ($R_1$) and $N_2$ comprises nucleotide sequences ($R_2$, $R_3$, $R_4$), wherein each rotavirus protein selected from the group of VP2, VP7, VP6 and NSP4 is encoded and wherein $R_1$ encodes rotavirus protein $X_1$, wherein $X_1$ may be any rotavirus protein selected from the group of VP2, VP7, VP6 and NSP4, and wherein $R_2$-$R_4$ encode a rotavirus protein that is not $X_1$, where $X_2$ may be any rotavirus protein selected from the group of VP2, VP7, VP6 and NSP4, and wherein $R_1$ and $R_3$-$R_4$ encode a rotavirus protein that is not $X_2$, where $X_3$ may be any rotavirus protein selected from the group of VP2, VP7, VP6 and NSP4, and wherein $R_1$ $R_2$, and $R_4$ encode a rotavirus protein that is not $X_3$, where $X_4$ may be any rotavirus protein selected from the group of VP2, VP7, VP6 and NSP4, and wherein $R_1$-$R_3$ encode a rotavirus protein that is not $X_4$, with the result that each rotavirus protein VP2, VP7, VP6 and NSP4 is expressed in the host.

In yet a further non-limiting example, $N_1$ comprises nucleotide sequence ($R_1$) and $N_2$ comprises nucleotide sequences ($R_2$, $R_3$, $R_4$), wherein each rotavirus protein selected from the group of VP4, VP7, VP6 and NSP4 is encoded and wherein $R_1$ encodes rotavirus protein $X_1$, wherein $X_1$ may be any rotavirus protein selected from the group of VP4, VP7, VP6 and NSP4, and wherein $R_2$-$R_4$ encode a rotavirus protein that is not $X_1$, where $X_2$ may be any rotavirus protein selected from the group of VP4, VP7, VP6 and NSP4, and wherein $R_1$ and $R_3$-$R_4$ encode a rotavirus protein that is not $X_2$, where $X_3$ may be any rotavirus protein selected from the group of VP4, VP7, VP6 and NSP4, and wherein $R_1$ $R_2$, and $R_4$ encode a rotavirus protein that is not $X_3$, where $X_4$ may be any rotavirus protein selected from the group of VP4, VP7, VP6 and NSP4, and wherein $R_1$-$R_3$ encode a rotavirus protein that is not $X_4$, with the result that each rotavirus protein VP4, VP7, VP6 and NSP4 is expressed in the host.

2.4 Two Double Gene Constructs

The present invention also provides for a method of producing RLPs in a plant, wherein a first nucleic acid ($N_1$) comprising nucleotide sequences ($R_1$-$R_2$) encoding a first and a second rotavirus proteins ($X_1$-$X_2$), is co-expressed with a second nucleic acid ($N_2$) comprising two nucleotide sequences ($R_3$-$R_4$) encoding a third and fourth rotavirus proteins ($X_3$-$X_4$), so that the first, second, third and fourth nucleotide sequences are co-expressed in the plant (See Table 1, Combination #2.4).

In a non-limiting example, $N_1$ comprises nucleotide sequences ($R_1$, $R_2$) and $N_2$ comprises nucleotide sequences ($R_3$, $R_4$), wherein each rotavirus protein selected from the group of VP2, VP4, VP6 and NSP4 is encoded and wherein $R_1$ encodes rotavirus protein $X_1$, wherein $X_1$ may be any rotavirus protein selected from the group of VP2, VP4, VP6 and NSP4, and wherein $R_2$-$R_4$ encode a rotavirus protein that is not $X_1$, where $X_2$ may be any rotavirus protein selected from the group of VP2, VP4, VP6 and NSP4, and wherein $R_1$ and $R_3$-$R_4$ encode a rotavirus protein that is not $X_2$, where $X_3$ may be any rotavirus protein selected from the group of VP2, VP4, VP6 and NSP4, and wherein $R_1$ $R_2$, and $R_4$ encode a rotavirus protein that is not $X_3$, where $X_4$ may be any rotavirus protein selected from the group of VP2, VP4, VP6 and NSP4, and wherein $R_1$-$R_3$ encode a rotavirus protein that is not $X_4$, with the result that each rotavirus protein VP2, VP4, VP6 and NSP4 is expressed in the host.

In a further non-limiting example, $N_1$ comprises nucleotide sequences ($R_1$, $R_2$) and $N_2$ comprises nucleotide sequences ($R_3$, $R_4$), wherein each rotavirus protein selected from the group of VP2, VP7, VP6 and NSP4 is encoded and wherein $R_1$ encodes rotavirus protein $X_1$, wherein $X_1$ may be any rotavirus protein selected from the group of VP2, VP7, VP6 and NSP4, and wherein $R_2$-$R_4$ encode a rotavirus protein that is not $X_1$, where $X_2$ may be any rotavirus protein selected from the group of VP2, VP7, VP6 and NSP4, and wherein $R_1$ and $R_3$-$R_4$ encode a rotavirus protein that is not $X_2$, where $X_3$ may be any rotavirus protein selected from the group of VP2, VP7, VP6 and NSP4, and wherein $R_1$ $R_2$, and $R_4$ encode a rotavirus protein that is not $X_3$, where $X_4$ may be any rotavirus protein selected from the group of VP2, VP7, VP6 and NSP4, and wherein $R_1$-$R_3$ encode a rotavirus protein that is not $X_4$, with the result that each rotavirus protein VP2, VP7, VP6 and NSP4 is expressed in the host.

In yet a further non-limiting example, $N_1$ comprises nucleotide sequences ($R_1$, $R_2$) and $N_2$ comprises nucleotide sequences ($R_3$, $R_4$), wherein each rotavirus protein selected from the group of VP4, VP7, VP6 and NSP4 is encoded and wherein $R_1$ encodes rotavirus protein $X_1$, wherein $X_1$ may be any rotavirus protein selected from the group of VP4, VP7, VP6 and NSP4, and wherein $R_2$-$R_4$ encode a rotavirus protein that is not $X_1$, where $X_2$ may be any rotavirus protein selected from the group of VP4, VP7, VP6 and NSP4, and wherein $R_1$ and $R_3$-$R_4$ encode a rotavirus protein that is not $X_2$, where $X_3$ may be any rotavirus protein selected from the group of VP4, VP7, VP6 and NSP4, and wherein $R_1$ $R_2$, and $R_4$ encode a rotavirus protein that is not $X_3$, where $X_4$ may be any rotavirus protein selected from the group of VP4, VP7, VP6 and NSP4, and wherein $R_1$-$R_3$ encode a rotavirus protein that is not $X_4$, with the result that each rotavirus protein VP4, VP7, VP6 and NSP4 is expressed in the host.

2.5 Double Gene Construct+Single Gene Construct

The present invention also provides for a method of producing RLPs in a plant, wherein a first nucleic acid ($N_1$) comprising nucleotide sequences ($R_1$-$R_2$) encoding a first and a second rotavirus proteins ($X_1$-$X_2$), is co-expressed with a second nucleic acid ($N_2$) comprising a nucleotide sequence ($R_3$) encoding a third rotavirus proteins ($X_3$), so that the first, second and third nucleotide sequences are co-expressed in the plant (See Table 1, Combination #2.5).

In a non-limiting example, $N_1$ comprises nucleotide sequences ($R_1$, $R_2$) and $N_2$ comprises nucleotide sequence ($R_3$), wherein each rotavirus protein selected from the group of VP4, VP6 and NSP4 is encoded and wherein $R_1$ encodes rotavirus protein $X_1$, wherein $X_1$ may be any rotavirus protein selected from the group of VP4, VP6 and NSP4, and wherein $R_2$-$R_3$ encode a rotavirus protein that is not $X_1$, where $X_2$ may be any rotavirus protein selected from the group of VP4, VP6 and NSP4, and wherein $R_1$ and $R_3$ encode a rotavirus protein that is not $X_2$, where $X_3$ may be any rotavirus protein selected from the group of VP4, VP6 and NSP4, and wherein $R_1$ and $R_2$ encode a rotavirus protein that is not $X_3$, with the result that each rotavirus protein VP4, VP6 and NSP4 is expressed in the host.

In a further non-limiting example, $N_1$ comprises nucleotide sequences ($R_1$, $R_2$) and $N_2$ comprises nucleotide sequence ($R_3$), wherein each rotavirus protein selected from the group of VP7, VP6 and NSP4 is encoded and wherein $R_1$ encodes rotavirus protein $X_1$, wherein $X_1$ may be any rotavirus protein selected from the group of VP7, VP6 and NSP4, and wherein $R_2$-$R_3$ encode a rotavirus protein that is not $X_1$, where $X_2$ may be any rotavirus protein selected from the group of VP7, VP6 and NSP4, and wherein $R_1$ and $R_3$ encode a rotavirus protein that is not $X_2$, where $X_3$ may be any rotavirus protein selected from the group of VP7, VP6 and NSP4, and wherein $R_1$ and $R_2$ encode a rotavirus protein that is not $X_3$, with the result that each rotavirus protein VP7, VP6 and NSP4 is expressed in the host.

3. Three Constructs 3.1 Two Dual Gene Constructs+One Single Gene Construct

The present invention also provides for a method of producing RLPs in a plant, wherein a first nucleic acid ($N_1$) comprising a nucleotide sequence ($R_1$) encoding a first rotavirus protein ($X_1$) and a second nucleotide sequence ($R_2$) encoding a second rotavirus protein ($X_2$), is co-expressed with a second nucleic acid ($N_2$) comprising a third nucleotide sequence ($R_3$) encoding a third rotavirus protein ($X_3$) and a fourth nucleotide sequences ($R_4$) encoding a fourth rotavirus protein ($X_4$) and a third nucleic acid ($N_3$) comprising a fifth nucleotide sequence ($R_5$) encoding a fifth rotavirus protein ($X_5$) (see Table 1, Combination #3.1) so that the first, second, third, fourth and fifth nucleotide sequence are co-expressed in the plant.

In this non-limiting example, $N_1$ comprises ($R_1$, $R_2$), $N_2$ comprises ($R_3$, $R_4$) and $N_3$ comprises ($R_5$), wherein each rotavirus protein selected from the group of VP2, VP4, VP6, VP7 and NSP4 is encoded once and wherein $R_1$ encodes rotavirus protein $X_1$, wherein $X_1$ may be any rotavirus protein selected from the group of VP2, VP4, VP6, VP7 and NSP4, and wherein $R_2$-$R_5$ encode a rotavirus protein that is not $X_1$, where $X_2$ may be any rotavirus protein selected from the group of VP2, VP4, VP6, VP7 and NSP4, and wherein $R_1$ and $R_3$-$R_5$ encode a rotavirus protein that is not $X_2$, where $X_3$ may be any rotavirus protein selected from the group of VP2, VP4, VP6, VP7 and NSP4, and wherein $R_1$ $R_2$, $R_4$, and $R_5$ encode a rotavirus protein that is not $X_3$, where $X_4$ may be any rotavirus protein selected from the group of VP2, VP4, VP6, VP7 and NSP4, and wherein $R_1$-$R_3$ and $R_5$ encode a rotavirus protein that is not $X_4$, where $X_5$ may be any rotavirus protein selected from the group of VP2, VP4, VP6, VP7 and NSP4, and wherein $R_1$-$R_4$ encode a rotavirus protein that is not $X_5$, with the result that each rotavirus protein VP2, VP4, VP6, VP7 and NSP4 is expressed in the host.

For example, the first nucleic acid ($N_1$) may comprise a nucleotide sequence $R_1$, wherein $R_1$ may encode rotavirus protein VP2, VP4, VP6, VP7 or NSP4 and a second nucleotide sequence $R_2$ which may encode any rotavirus protein selected from the group of VP2, VP4, VP6, VP7 and NSP4 that is not encoded by $R_1$. The second nucleotide sequence may comprise nucleotide sequences $R_3$ and $R_4$, wherein $R_3$ encode rotavirus protein VP2, VP4, VP6, VP7 or NSP4, but not a rotavirus protein that are encoded by $R_1$ or $R_2$, and $R_4$ encodes rotavirus protein VP2, VP4, VP6, VP7 or NSP4, but not a rotavirus protein that are encoded by $R_1$, $R_2$ or $R_3$. The third nucleotide sequence may comprise nucleotide sequences $R_5$, wherein $R_5$ encode rotavirus protein VP2, VP4, VP6, VP7 or NSP4, but not a rotavirus protein that are encoded by $R_1$, $R_2$, $R_2$ or $R_4$, so that each of VP2, VP4, VP6, VP7 or NSP4 are expressed in a host.

For example which is not to be considered limiting, nucleotide sequence $R_1$ may encode rotavirus protein VP2 and nucleotide sequence $R_2$-$R_5$ may encode in any order rotavirus protein VP4, VP6, VP7 and NSP4, but $R_2$-$R_5$ may not encode VP2. In another example nucleotide sequence $R_1$ may encode rotavirus protein VP4 and nucleotide sequences $R_2$-$R_5$ may encode in any order rotavirus protein VP2, VP6, VP7 and NSP4. In yet another example nucleotide sequence $R_1$ may encode rotavirus protein VP6 and nucleotide sequences $R_2$-$R_5$ may encode in any order rotavirus protein VP2, VP4, VP7 and NSP4. In yet another non-limiting example nucleotide sequence $R_1$ may encode rotavirus protein VP7 and nucleotide sequences $R_2$-$R_5$ may encode in any order rotavirus protein VP2, VP4, VP6 and NSP4. In yet another non-limiting example nucleotide sequence $R_1$ may encode rotavirus protein NSP4 and nucleotide sequences $R_2$-$R_5$ may encode in any order rotavirus protein VP2, VP4, VP6 and VP7.

Figure 2A:
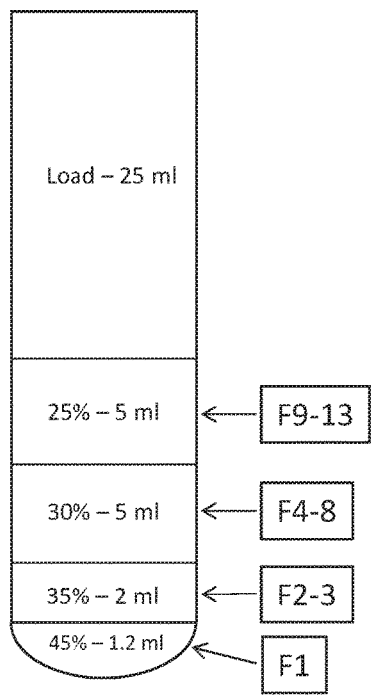

For example, which is not to be considered limiting, a first nucleic acid ($N_1$) comprising a first nucleotide sequence ($R_1$) encoding a first rotavirus protein, for example VP6 and a second nucleotide sequence ($R_2$) encoding a second rotavirus protein, for example VP2, is co-expressed with a second nucleic acid ($N_2$) comprising a third nucleotide sequence ($R_3$) encoding a third rotavirus protein for example VP7 and a fourth nucleotide sequence ($R_4$) encoding a fourth rotavirus protein, for example VP4 and a third nucleic acid ($N_3$) comprising a fifth nucleotide sequence ($R_5$) encoding a fifth rotavirus protein for example NSP4. (see FIGS. 2 and 3).

A plant that expresses a first nucleic acid ($N_1$) comprising a first nucleotide sequence ($R_1$) encoding a first rotavirus protein ($X_1$) and a second rotavirus protein ($X_2$), may be transformed with a second nucleic acid ($N_2$) comprising a third nucleotide sequence ($R_3$) encoding a third rotavirus protein ($X_3$) and a fourth nucleotide sequences ($R_4$) encoding a fourth rotavirus protein ($X_4$). The plant may be further transformed with a third nucleic acid ($R_3$) comprising a fifth nucleotide sequence ($R_5$) encoding a fifth rotavirus protein ($X_5$), so that the first, second, third, fourth and fifth nucleotide sequence are co-expressed in the plant. Rotavirus protein $X_1$-$X_5$ may be selected from the group of VP2, VP4, VP6, VP7 and NSP4, wherein VP2, VP4, VP6, VP7 and NSP4 are selected once, so that each rotavirus protein VP2, VP4, VP6, VP7 and NSP4 is expressed in the plant. Furthermore, a plant may be simultaneously co-transformed with a first nucleic acid ($N_1$) comprising a first and second nucleotide sequence ($R_1$+$R_2$) encoding a first and second rotavirus protein ($X_1$+$X_2$), a second nucleic acid ($N_2$) comprising a third and a fourth nucleotide sequences ($R_3$+$R_4$) encoding a third and a fourth rotavirus protein ($X_3$+$X_4$), and a third nucleic acid ($N_3$) comprising a fifth nucleotide sequences ($R_5$) encoding a fifth rotavirus protein ($X_5$), so that the first, second, third, fourth and fifth nucleotide sequence are co-expressed in the plant. The first nucleic acid ($N_1$), second nucleic acid ($N_2$) and third nucleic acid ($N_3$) may be introduced in the plant in a transient manner, or in a stable manner.

3.2 Two Single Gene Constructs+One Triple Gene Construct

An alternated method of producing RLPs in a plant is also provided, wherein a first nucleic acid ($N_1$) comprising a nucleotide sequence ($R_1$) encoding a first rotavirus protein ($X_1$) is co-expressed with a second nucleic acid ($N_2$) comprising a second nucleotide sequence ($R_2$) encoding a second rotavirus protein ($X_2$) and a third nucleic acid ($N_3$) comprising a third nucleotide sequence ($R_3$) encoding a third rotavirus protein ($X_3$), a fourth nucleotide sequences ($R_4$) encoding a fourth rotavirus protein ($X_4$) and a fifth nucleotide sequence ($R_5$) encoding a fifth rotavirus protein ($X_5$) (see Table 1, Combination #3.2) so that the first, second, third, fourth and fifth nucleotide sequence are co-expressed in the plant.

In an alternate example, $N_1$ comprises ($R_1$), $N_2$ comprises ($R_2$) and $N_3$ comprises ($R_3$, $R_4$, $R_5$), wherein each rotavirus protein selected from the group of VP2, VP4, VP6, VP7 and NSP4 is encoded once and wherein $R_1$ encodes rotavirus protein $X_1$, wherein $X_1$ may be any rotavirus protein selected from the group of VP2, VP4, VP6, VP7 and NSP4, and wherein $R_2$-$R_5$ encode a rotavirus protein that is not $X_1$, where $X_2$ may be any rotavirus protein selected from the group of VP2, VP4, VP6, VP7 and NSP4, and wherein $R_1$ and $R_3$-$R_5$ encode a rotavirus protein that is not $X_2$, where $X_3$ may be any rotavirus protein selected from the group of VP2, VP4, VP6, VP7 and NSP4, and wherein $R_1$ $R_2$, $R_4$, and $R_5$ encode a rotavirus protein that is not $X_3$, where $X_4$ may be any rotavirus protein selected from the group of VP2, VP4, VP6, VP7 and NSP4, and wherein $R_1$-$R_3$ and $R_5$ encode a rotavirus protein that is not $X_4$, where $X_5$ may be any rotavirus protein selected from the group of VP2, VP4, VP6, VP7 and NSP4, and wherein $R_1$-$R_4$ encode a rotavirus protein that is not $X_5$, with the result that each rotavirus protein VP2, VP4, VP6, VP7 and NSP4 is expressed in the host.

For example which is not to be considered limiting, the first nucleic acid ($N_1$) may comprise a nucleotide sequence $R_1$, wherein $R_1$ may encode rotavirus protein VP2, VP4, VP6, VP7 or NSP4 and a second nucleotide sequence $R_2$ which may encode any rotavirus protein selected from the group of VP2, VP4, VP6, VP7 and NSP4 that is not encoded by $R_1$. The second nucleotide sequence may comprise nucleotide sequences $R_3$ and $R_4$, wherein $R_3$ encode rotavirus protein VP2, VP4, VP6, VP7 or NSP4, but not a rotavirus protein that are encoded by $R_1$ or $R_2$ and $R_4$ encodes rotavirus protein VP2, VP4, VP6, VP7 or NSP4, but not a rotavirus protein that are encoded by $R_1$, $R_2$ or $R_3$. The third nucleotide sequence may comprise nucleotide sequences $R_5$, wherein $R_5$ encode rotavirus protein VP2, VP4, VP6, VP7 or NSP4, but not a rotavirus protein that are encoded by $R_1$, $R_2$, $R_3$ or $R_4$, and wherein VP2, VP4, VP6, VP7 or NSP4 are encoded once. For example nucleotide sequence $R_1$ may encode rotavirus protein VP2 and nucleotide sequence $R_2$-$R_5$ may encode in any order rotavirus protein VP4, VP6, VP7 and NSP4, but $R_2$-$R_5$ may not encode VP2. In another example nucleotide sequence $R_1$ may encode rotavirus protein VP4 and nucleotide sequences $R_2$-$R_5$ may encode in any order rotavirus protein VP2, VP6, VP7 and NSP4. In yet another example nucleotide sequence $R_1$ may encode rotavirus protein VP6 and nucleotide sequences $R_2$-$R_5$ may encode in any order rotavirus protein VP2, VP4, VP7 and NSP4. In yet another example nucleotide sequence $R_1$ may encode rotavirus protein VP7 and nucleotide sequences $R_2$-$R_5$ may encode in any order rotavirus protein VP2, VP4, VP6 and NSP4. In yet another example nucleotide sequence $R_1$ may encode rotavirus protein NSP4 and nucleotide sequences $R_2$-$R_5$ may encode in any order rotavirus protein VP2, VP4, VP6 and VP7.

A plant that expresses a first nucleic acid ($N_1$) comprising a first nucleotide sequence ($R_1$) encoding a first rotavirus protein ($X_1$) may be transformed with a second nucleic acid ($N_2$) comprising a second nucleotide sequence ($R_2$) encoding a second rotavirus protein ($X_2$). The plant may be further transformed with a third nucleic acid ($N_3$) comprising a third nucleotide sequence ($R_3$) encoding a third rotavirus protein ($X_3$), a fourth nucleotide sequences ($R_4$) encoding a fourth rotavirus protein ($X_4$) and a fifth nucleotide sequence ($R_5$) encoding a fifth rotavirus protein ($X_5$), so that the first, second, third, fourth and fifth nucleotide sequence are co-expressed in the plant. Rotavirus protein $X_1$-$X_5$ may be selected from the group of VP2, VP4, VP6, VP7 and NSP4, wherein VP2, VP4, VP6, VP7 and NSP4 are selected once, so that each rotavirus protein VP2, VP4, VP6, VP7 and NSP4 is expressed in the plant. Furthermore, a plant may be simultaneously co-transformed with a first nucleic acid ($N_1$) comprising a first nucleotide sequence ($R_1$) encoding a first rotavirus protein ($X_1$), a second nucleic acid ($N_2$) comprising a second nucleotide sequence ($R_2$) encoding a second rotavirus protein ($X_2$), and a third nucleic acid ($N_3$) comprising a third, a fourth and a five nucleotide sequences ($R_3$-$R_5$) encoding a third, a fourth and a fifth rotavirus protein ($X_3$-$X_5$), so that the first, second, third, fourth and fifth nucleotide sequence are co-expressed in the plant. The first nucleic acid ($N_1$), second nucleic acid ($N_2$) and third nucleic acid ($N_3$) may be introduced in the plant in a transient manner, or in a stable manner.

For example, a first plant expressing a first nucleic acid ($N_1$) comprising a first, second and third nucleotide sequence ($R_1$, $R_2$, and $R_3$) encoding a first, second and third rotavirus protein ($X_1$, $X_2$, and $X_3$) may be crossed with a second plant expressing a second nucleic acid ($N_2$) comprising a fourth nucleotide sequence ($R_4$) encoding a fourth rotavirus protein ($X_4$) to produce a progeny plant (third plant). The third plant may be crossed with a fourth plant expressing a third nucleic acid ($N_3$) comprising a fifth nucleotide sequence ($R_5$) encoding a fifth rotavirus protein ($X_5$) to produces a progeny plant that co-expresses the first, second, third, fourth and fifth rotavirus protein ($X_1$-$X_5$). Furthermore, a first plant expressing a first nucleic acid ($N_1$) comprising a first nucleotide sequence ($R_1$) encoding a first rotavirus protein ($X_1$) may be crossed with a second plant expressing a second nucleic acid ($N_2$) comprising a second nucleotide sequence ($R_2$) encoding a rotavirus protein ($X_2$) to produce a progeny plan (third plant). The third plant may be crossed with a fourth plant expressing a third nucleic acid ($N_3$) comprising a third, fourth and fifth nucleotide sequence ($R_3$, $R_4$ and $R_5$) encoding a third, fourth and fifth rotavirus protein ($X_3$, $X_4$, and $X_5$) to produce a progeny plant that co-expresses the first, second, third, fourth and fifth rotavirus protein ($X_1$-$X_5$). Rotavirus protein $X_1$-$X_5$ may be selected from the group of VP2, VP4, VP6, VP7 and NSP4, so that each rotavirus protein VP2, VP4, VP6, VP7 and NSP4 is expressed in the plant.

3.3 Two Single Gene Constructs+One Dual Gene Construct

An alternated method of producing RLPs in a plant is also provided, wherein a first nucleic acid ($N_1$) comprising a nucleotide sequence ($R_1$) encoding a first rotavirus protein ($X_1$) is co-expressed with a second nucleic acid ($N_2$) comprising a second nucleotide sequence ($R_2$) encoding a second rotavirus protein ($X_2$) and a third nucleic acid ($N_3$) comprising a third nucleotide sequence ($R_3$) encoding a third rotavirus protein ($X_3$), and a fourth nucleotide sequence ($R_4$) encoding a fourth rotavirus protein ($X_4$), so that the first, second, third and fourth nucleotide sequence are co-expressed in the plant (See Table 1, Combination #3.3).

As a non-limiting example, $N_1$ comprises ($R_1$), $N_2$ comprises ($R_2$) and $N_3$ comprises ($R_3$, $R_4$), wherein each rotavirus protein selected from the group of VP2, VP4, VP6, and NSP4 is encoded once and wherein $R_1$ encodes rotavirus protein $X_1$, wherein $X_1$ may be any rotavirus protein selected from the group of VP2, VP4, VP6, and NSP4, and wherein $R_2$-$R_4$ encode a rotavirus protein that is not $X_1$, where $X_2$ may be any rotavirus protein selected from the group of VP2, VP4, VP6, and NSP4, and wherein $R_1$ and $R_3$-$R_4$ encode a rotavirus protein that is not $X_2$, where $X_3$ may be any rotavirus protein selected from the group of VP2, VP4, VP6, and NSP4, and wherein $R_1$ $R_2$, and $R_4$ encode a rotavirus protein that is not $X_3$, where $X_4$ may be any rotavirus protein selected from the group of VP2, VP4, VP6, and NSP4, and wherein $R_1$-$R_3$ encode a rotavirus protein that is not $X_4$, with the result that each rotavirus protein VP2, VP4, VP6, and NSP4 is expressed in the host.

As another non-limiting example, $N_1$ comprises ($R_1$), $N_2$ comprises ($R_2$) and $N_3$ comprises ($R_3$, $R_4$), wherein each rotavirus protein selected from the group of VP2, VP7, VP6, and NSP4 is encoded once and wherein $R_1$ encodes rotavirus protein $X_1$, wherein $X_1$ may be any rotavirus protein selected from the group of VP2, VP7, VP6, and NSP4, and wherein $R_2$-$R_4$ encode a rotavirus protein that is not $X_1$, where $X_2$ may be any rotavirus protein selected from the group of VP2, VP7, VP6, and NSP4, and wherein $R_1$ and $R_3$-$R_4$ encode a rotavirus protein that is not $X_2$, where $X_3$ may be any rotavirus protein selected from the group of VP2, VP7, VP6, and NSP4, and wherein $R_1$ $R_2$, and $R_4$ encode a rotavirus protein that is not $X_3$, where $X_4$ may be any rotavirus protein selected from the group of VP2, VP7, VP6, and NSP4, and wherein $R_1$-$R_3$ encode a rotavirus protein that is not $X_4$, with the result that each rotavirus protein VP2, VP6, VP7 and NSP4 is expressed in the host.

As a further non-limiting example, $N_1$ comprises ($R_1$), $N_2$ comprises ($R_2$) and $N_3$ comprises ($R_3$, $R_4$), wherein each rotavirus protein selected from the group of VP4, VP7, VP6, and NSP4 is encoded once and wherein $R_1$ encodes rotavirus protein $X_1$, wherein $X_1$ may be any rotavirus protein selected from the group of VP4, VP7, VP6, and NSP4, and wherein $R_2$-$R_4$ encode a rotavirus protein that is not $X_1$, where $X_2$ may be any rotavirus protein selected from the group of VP4, VP7, VP6, and NSP4, and wherein $R_1$ and $R_3$-$R_4$ encode a rotavirus protein that is not $X_2$, where $X_3$ may be any rotavirus protein selected from the group of VP4, VP7, VP6, and NSP4, and wherein $R_1$ $R_2$, and $R_4$ encode a rotavirus protein that is not $X_3$, where $X_4$ may be any rotavirus protein selected from the group of VP4, VP7, VP6, and NSP4, and wherein $R_1$-$R_3$ encode a rotavirus protein that is not $X_4$, with the result that each rotavirus protein VP4, VP7, VP6, and NSP4 is expressed in the host.

3.4 Three Single Gene Constructs

An alternated method of producing RLPs in a plant is also provided, wherein a first nucleic acid ($N_1$) comprising a nucleotide sequence ($R_1$) encoding a first rotavirus protein ($X_1$) is co-expressed with a second nucleic acid ($N_2$) comprising a second nucleotide sequence ($R_2$) encoding a second rotavirus protein ($X_2$) and a third nucleic acid ($N_3$) comprising a third nucleotide sequence ($R_3$) encoding a third rotavirus protein ($X_3$), so that the first, second and third nucleotide sequence are co-expressed in the plant (See Table 1, Combination #3.4).

As a non-limiting example, $N_1$ comprises ($R_1$), $N_2$ comprises ($R_2$) and $N_3$ comprises ($R_3$), wherein each rotavirus protein selected from the group of VP4, VP6, and NSP4 is encoded once and wherein $R_1$ encodes rotavirus protein $X_1$, wherein $X_1$ may be any rotavirus protein selected from the group of VP4, VP6, and NSP4, and wherein $R_2$-$R_3$ encode a rotavirus protein that is not $X_1$, where $X_2$ may be any rotavirus protein selected from the group of VP4, VP6, and NSP4, and wherein $R_1$ and $R_3$ encode a rotavirus protein that is not $X_2$, where $X_3$ may be any rotavirus protein selected from the group of VP4, VP6, and NSP4, and wherein $R_1$ and $R_2$ encode a rotavirus protein that is not $X_3$, with the result that each rotavirus protein VP4, VP6, and NSP4 is expressed in the host.

As a further non-limiting example, $N_1$ comprises ($R_1$), $N_2$ comprises ($R_2$) and $N_3$ comprises ($R_3$), wherein each rotavirus protein selected from the group of VP7, VP6, and NSP4 is encoded once and wherein $R_1$ encodes rotavirus protein $X_1$, wherein $X_1$ may be any rotavirus protein selected from the group of VP7, VP6, and NSP4, and wherein $R_2$-$R_3$ encode a rotavirus protein that is not $X_1$, where $X_2$ may be any rotavirus protein selected from the group of VP7, VP6, and NSP4, and wherein $R_1$ and $R_3$ encode a rotavirus protein that is not $X_2$, where $X_3$ may be any rotavirus protein selected from the group of VP7, VP6, and NSP4, and wherein $R_1$ and $R_2$ encode a rotavirus protein that is not $X_3$, with the result that each rotavirus protein VP7, VP6, and NSP4 is expressed in the host.

4. Four Constructs 4.1. Three Single Gene Constructs+One Dual Gene Construct

Also provided herein is a method of producing RLPs in a plant, wherein a first nucleic acid ($N_1$) comprising a first nucleotide sequence ($R_1$) encoding a first rotavirus protein ($X_1$) is co-expressed with a second nucleic acid ($N_2$) comprising a second nucleotide sequence ($R_2$) encoding a second rotavirus protein ($X_2$), a third nucleic acid ($N_3$) comprising a third nucleotide sequence ($R_3$) encoding a third rotavirus protein ($X_3$), and fourth nucleic acid ($N_4$) comprising a fourth nucleotide sequences ($R_4$) encoding a fourth rotavirus protein ($X_4$) and a fifth nucleotide sequence ($R_5$) encoding a fifth rotavirus protein ($X_5$) (see Table 1, Combination #4.1) so that the first, second, third, fourth and fifth nucleotide sequence are co-expressed in the plant.

In this example, $N_1$ comprises ($R_1$), $N_2$ comprises ($R_2$), $N_3$ comprises ($R_3$), and $N_4$ comprises ($R_4$, and $R_5$), wherein each rotavirus protein selected from the group of VP2, VP4, VP6, VP7 and NSP4 is encoded, and wherein $R_1$ encodes rotavirus protein $X_1$, wherein $X_1$ may be any rotavirus protein selected from the group of VP2, VP4, VP6, VP7 and NSP4, and wherein $R_2$-$R_5$ encode a rotavirus protein that is not $X_1$, where $X_2$ may be any rotavirus protein selected from the group of VP2, VP4, VP6, VP7 and NSP4, and wherein $R_1$ and $R_3$-$R_5$ encode a rotavirus protein that is not $X_2$, where $X_3$ may be any rotavirus protein selected from the group of VP2, VP4, VP6, VP7 and NSP4, and wherein $R_1$ $R_2$, $R_4$, and $R_5$ encode a rotavirus protein that is not $X_3$, where $X_4$ may be any rotavirus protein selected from the group of VP2, VP4, VP6, VP7 and NSP4, and wherein $R_1$-$R_3$ and $R_5$ encode a rotavirus protein that is not $X_4$, where $X_5$ may be any rotavirus protein selected from the group of VP2, VP4, VP6, VP7 and NSP4, and wherein $R_1$-$R_4$ encode a rotavirus protein that is not $X_5$, with the result that each rotavirus protein VP2, VP4, VP6, VP7 and NSP4 is expressed in the host.

The four nucleic acids may be introduced into a plant in any order. For example, which is not be considered limiting, a plant that expresses a first nucleic acid ($N_1$) comprising a first nucleotide sequence ($R_1$) encoding a first rotavirus protein ($X_1$) may be transformed with a second nucleic acid ($N_2$) comprising a second nucleotide sequence ($R_2$) encoding a second rotavirus protein ($X_2$). The plant may be further transformed with a third nucleic acid ($N_3$) comprising a third nucleotide sequence ($R_3$) encoding a third rotavirus protein ($X_3$). The plant then may be further be transformed with a fourth nucleic acid ($N_4$) comprising a fourth nucleotide sequences ($R_4$) encoding a fourth rotavirus protein ($X_4$) and a fifth nucleotide sequence ($R_5$) encoding a fifth rotavirus protein ($X_5$), so that the first, second, third, fourth and fifth nucleotide sequence are co-expressed in the plant. Furthermore, a plant may be simultaneously co-transformed with a first nucleic acid ($N_1$) comprising a first nucleotide sequence ($R_1$) encoding a first rotavirus protein ($X_1$), a second nucleic acid ($N_2$) comprising a second nucleotide sequence ($R_2$) encoding a second rotavirus protein ($X_2$), a third nucleic acid ($N_3$) comprising a third nucleotide sequence ($R_3$) encoding a third rotavirus protein ($X_3$), and a fourth nucleic acid ($N_4$) comprising a fourth and a fifth nucleotide sequences ($R_4$-$R_5$) encoding a fourth and a fifth rotavirus protein ($X_4$-$X_5$) so that the first, second, third, fourth and fifth nucleotide sequence are co-expressed in the plant. The first nucleic acid ($N_1$), second nucleic acid ($N_2$), third nucleic acid ($N_3$) and fourth nucleic acid ($N_4$) may be introduced in the plant in a transient manner, or in a stable manner.

Furthermore, a plant that expresses a first nucleic acid ($N_4$) comprising a first nucleotide sequence ($R_4$) encoding a first rotavirus protein ($X_4$) and a second nucleotide sequence ($R_5$) encoding a second rotavirus protein ($X_5$) may be transformed with a second nucleic acid ($N_1$) comprising a third nucleotide sequence ($R_1$) encoding a third rotavirus protein ($X_1$). The plant may be further transformed with a third nucleic acid ($N_2$) comprising a third nucleotide sequence ($R_2$) encoding a fourth rotavirus protein ($X_3$). The plant then may be further be transformed with a fourth nucleic acid ($N_3$) comprising a fifth nucleotide sequences ($R_3$) encoding a fifth rotavirus protein and a fifth nucleotide sequence ($R_3$) encoding a fifth rotavirus protein ($X_3$), so that the first, second, third, fourth and fifth nucleotide sequence are co-expressed in the plant. Rotavirus protein $X_1$-$X_5$ may be selected from the group of VP2, VP4, VP6, VP7 and NSP4, wherein VP2, VP4, VP6, VP7 and NSP4 are selected once, so that each rotavirus protein VP2, VP4, VP6, VP7 and NSP4 is expressed in the plant. The first nucleic acid ($N_4$), second nucleic acid ($N_1$), third nucleic acid ($N_2$) and fourth nucleic acid ($N_3$) may be introduced in the plant in a transient manner, or in a stable manner.

A first plant expressing a first nucleic acid ($N_1$) comprising a first nucleotide sequence ($R_1$) encoding a first rotavirus protein ($X_1$), may be crossed with a second plant expressing a second nucleic acid ($N_2$) comprising a second nucleotide sequence ($R_2$) encoding a second rotavirus protein ($X_2$) to produce a progeny plant (third plant).

The third plant may be crossed with a fourth plant expressing a third nucleic acid ($N_3$) comprising a third nucleotide sequence ($R_3$) encoding a third rotavirus protein ($X_3$) to produces a progeny plant (fifth plant). The fifth plant may be crossed with a sixth plant expressing a fourth nucleic acid ($N_4$) comprising a fourth nucleotide sequences ($R_4$) encoding a fourth rotavirus protein ($X_4$) and a fifth nucleotide sequences ($R_5$) encoding a fifth rotavirus protein ($X_5$) to produce a progeny plant that co-expresses the first, second, third, fourth and fifth rotavirus protein ($X_1$-$X_5$).

Furthermore, a first plant expressing a first nucleic acid ($N_4$) comprising a first nucleotide sequence ($R_4$) encoding a first rotavirus protein ($X_4$) and a second nucleotide sequence ($R_5$) encoding a second rotavirus protein ($X_5$) may be crossed with a second plant expressing a second nucleic acid ($N_2$) comprising a third nucleotide sequence ($R_1$) encoding a third rotavirus protein ($X_1$) to produce a progeny plan (third plant). The third plant may be crossed with a fourth plant expressing a third nucleic acid ($N_2$) comprising a fourth nucleotide sequence ($R_2$) encoding a fourth rotavirus protein ($X_2$) to produce a progeny plant (fifth plant). The fifth plant may be crossed with a sixth plant expressing a fifth nucleotide sequence ($R_3$) encoding a fifth rotavirus protein ($X_3$) to produce a progeny plant that co-expresses the first, second, third, fourth and fifth rotavirus protein ($X_1$-$X_5$). Rotavirus protein $X_1$-$X_5$ may be selected from the group of VP2, VP4, VP6, VP7 and NSP4, wherein VP2, VP4, VP6, VP7 and NSP4 are selected once, so that each rotavirus protein VP2, VP4, VP6, VP7 and NSP4 is expressed in the plant.

4.2 Four Single Gene Constructs

Also provided herein is a method of producing RLPs in a plant, wherein a first nucleic acid ($N_1$) comprising a first nucleotide sequence ($R_1$) encoding a first rotavirus protein ($X_1$) is co-expressed with a second nucleic acid ($N_2$) comprising a second nucleotide sequence ($R_2$) encoding a second rotavirus protein ($X_2$), a third nucleic acid ($N_3$) comprising a third nucleotide sequence ($R_3$) encoding a third rotavirus protein ($X_3$), and a fourth nucleic acid ($N_4$) comprising a fourth nucleotide sequences ($R_4$) encoding a fourth rotavirus protein ($X_4$), so that the first, second, third, fourth and fifth nucleotide sequence are co-expressed in the plant (See Table 1, Combination #4.2).

In a non-limiting example, $N_1$ comprises ($R_1$), $N_2$ comprises ($R_2$), $N_3$ comprises ($R_3$), and $N_4$ comprises ($R_4$), wherein each rotavirus protein selected from the group of VP2, VP4, VP6 and NSP4 is encoded, and wherein $R_1$ encodes rotavirus protein $X_1$, wherein $X_1$ may be any rotavirus protein selected from the group of VP2, VP4, VP6 and NSP4, and wherein $R_2$-$R_4$ encode a rotavirus protein that is not $X_1$, where $X_2$ may be any rotavirus protein selected from the group of VP2, VP4, VP6 and NSP4, and wherein $R_1$ and $R_3$-$R_4$ encode a rotavirus protein that is not $X_2$, where $X_3$ may be any rotavirus protein selected from the group of VP2, VP4, VP6 and NSP4, and wherein $R_1$ $R_2$, and $R_4$ encode a rotavirus protein that is not $X_3$, where $X_4$ may be any rotavirus protein selected from the group of VP2, VP4, VP6 and NSP4, and wherein $R_1$-$R_3$ encode a rotavirus protein that is not $X_4$, with the result that each rotavirus protein VP2, VP4, VP6 and NSP4 is expressed in the host.

In another non-limiting example, $N_1$ comprises ($R_1$), $N_2$ comprises ($R_2$), $N_3$ comprises ($R_3$), and $N_4$ comprises ($R_4$), wherein each rotavirus protein selected from the group of VP2, VP7, VP6 and NSP4 is encoded, and wherein $R_1$ encodes rotavirus protein $X_1$, wherein $X_1$ may be any rotavirus protein selected from the group of VP2, VP7, VP6 and NSP4, and wherein $R_2$-$R_4$ encode a rotavirus protein that is not $X_1$, where $X_2$ may be any rotavirus protein selected from the group of VP2, VP7, VP6 and NSP4, and wherein $R_1$ and $R_3$-$R_4$ encode a rotavirus protein that is not $X_2$, where $X_3$ may be any rotavirus protein selected from the group of VP2, VP7, VP6 and NSP4, and wherein $R_1$ $R_2$, and $R_4$ encode a rotavirus protein that is not $X_3$, where $X_4$ may be any rotavirus protein selected from the group of VP2, VP7, VP6 and NSP4, and wherein $R_1$-$R_3$ encode a rotavirus protein that is not $X_4$, with the result that each rotavirus protein VP2, VP7, VP6 and NSP4 is expressed in the host.

In a further non-limiting example, $N_1$ comprises ($R_1$), $N_2$ comprises ($R_2$), $N_3$ comprises ($R_3$), and $N_4$ comprises ($R_4$), wherein each rotavirus protein selected from the group of VP4, VP7, VP6 and NSP4 is encoded, and wherein $R_1$ encodes rotavirus protein $X_1$, wherein $X_1$ may be any rotavirus protein selected from the group of VP4, VP7, VP6 and NSP4, and wherein $R_2$-$R_4$ encode a rotavirus protein that is not $X_1$, where $X_2$ may be any rotavirus protein selected from the group of VP4, VP7, VP6 and NSP4, and wherein $R_1$ and $R_3$-$R_4$ encode a rotavirus protein that is not $X_2$, where $X_3$ may be any rotavirus protein selected from the group of VP4, VP7, VP6 and NSP4, and wherein $R_1$ $R_2$, and $R_4$ encode a rotavirus protein that is not $X_3$, where $X_4$ may be any rotavirus protein selected from the group of VP4, VP7, VP6 and NSP4, and wherein $R_1$-$R_3$ encode a rotavirus protein that is not $X_4$, with the result that each rotavirus protein VP4, VP7, VP6 and NSP4 is expressed in the host.

5. Five Constructs
5. Five Single Gene Constructs

The present invention also provides for a method of producing RLPs in a plant, wherein a first nucleic acid ($N_1$) comprising a first nucleotide sequence ($R_1$) encoding a first rotavirus protein ($X_1$) is co-expressed with a second nucleic acid ($N_2$) comprising a second nucleotide sequence ($R_2$) encoding a second rotavirus protein ($X_2$) and a third nucleic acid ($N_3$) comprising a third nucleotide sequence ($R_3$) encoding a third rotavirus protein ($X_3$) and fourth nucleic acid ($N_4$) comprising a fourth nucleotide sequences ($R_4$) encoding a fourth rotavirus protein ($X_4$) and a fifth nucleic acid ($R_5$) comprising a fifth nucleotide sequence ($R_5$) encoding a fifth rotavirus protein ($X_5$) (see Table 1, Combination #5) so that the first, second, third, fourth and fifth nucleotide sequence are co-expressed in the plant.

In this non-limiting example, $N_1$ comprises ($R_1$), $N_2$ comprises ($R_2$), $N_3$ comprises ($R_3$), $N_4$ comprises ($R_4$) and $N_5$ comprises ($R_5$), wherein each rotavirus protein selected from the group of VP2, VP4, VP6, VP7 and NSP4, and wherein $R_1$ encodes rotavirus protein $X_1$, wherein $X_1$ may be any rotavirus protein selected from the group of VP2, VP4, VP6, VP7 and NSP4, and wherein $R_2$-$R_5$ encode a rotavirus protein that is not $X_1$, where $X_2$ may be any rotavirus protein selected from the group of VP2, VP4, VP6, VP7 and NSP4, and wherein $R_1$ and $R_3$-$R_5$ encode a rotavirus protein that is not $X_2$, where $X_3$ may be any rotavirus protein selected from the group of VP2, VP4, VP6, VP7 and NSP4, and wherein $R_1$ $R_2$, $R_4$, and $R_5$ encode a rotavirus protein that is not $X_3$, where $X_4$ may be any rotavirus protein selected from the group of VP2, VP4, VP6, VP7 and NSP4, and wherein $R_1$-$R_3$ and $R_5$ encode a rotavirus protein that is not $X_4$, where $X_5$ may be any rotavirus protein selected from the group of VP2, VP4, VP6, VP7 and NSP4, and wherein $R_1$-$R_4$ encode a rotavirus protein that is not $X_5$, with the result that each rotavirus protein VP2, VP4, VP6, VP7 and NSP4 is expressed in the host.

For example, which is not to be considered limiting, nucleotide sequence $R_1$ may encode rotavirus protein VP2 and nucleotide sequence $R_2$-$R_5$ may encode in any order rotavirus protein VP4, VP6, VP7 and NSP4, but $R_2$-$R_5$ may not encode VP2. In another non-limiting example nucleotide sequence $R_1$ may encode rotavirus protein VP4 and nucleotide sequences $R_2$-$R_5$ may encode in any order rotavirus protein VP2, VP6, VP7 and NSP4. In yet another non-limiting example nucleotide sequence $R_1$ may encode rotavirus protein VP6 and nucleotide sequences $R_2$-$R_5$ may encode in any order rotavirus protein VP2, VP4, VP7 and NSP4. In yet another example which is not to be considered limiting, nucleotide sequence $R_1$ may encode rotavirus protein VP7 and nucleotide sequences $R_2$-$R_5$ may encode in any order rotavirus protein VP2, VP4, VP6 and NSP4. In yet another non-limiting example nucleotide sequence $R_1$ may encode rotavirus protein NSP4 and nucleotide sequences $R_2$-$R_5$ may encode in any order rotavirus protein VP2, VP4, VP6 and VP7.

For example, which is not to be considered limiting, a first nucleic acid ($N_1$) comprising a first nucleotide sequence ($R_1$) encoding a first rotavirus protein, for example VP2 is co-expressed with a second nucleic acid ($N_2$) comprising a second nucleotide sequence ($R_2$) encoding a second rotavirus protein, for example VP6, a third nucleic acid ($N_3$) comprising a third nucleotide sequence ($R_3$) encoding a third rotavirus protein for example VP4, a fourth nucleic acid ($N_4$) comprising a fourth nucleotide sequence ($R_4$) encoding a fourth rotavirus protein, for example VP7 and a fifth nucleic acid (N5) comprising a fifth nucleotide sequence ($R_5$) encoding a fifth rotavirus protein for example NSP4 (see FIG. 3).

The five nucleic acids may be introduced into a plant in any order. For example, which is not to be considered limiting, a plant that expresses a first nucleic acid ($N_1$) comprising a first nucleotide sequence ($R_1$) encoding a first rotavirus protein ($X_1$) may be transformed with a second nucleic acid ($N_2$) comprising a second nucleotide sequence ($R_2$) encoding a second rotavirus protein ($X_2$). The plant may be further transformed with a third nucleic acid ($N_3$) comprising a third nucleotide sequence ($R_3$) encoding a third rotavirus protein ($X_3$). The plant then may be further transformed with a fourth nucleic acid ($N_4$) comprising a fourth nucleotide sequences ($R_4$) encoding a fourth rotavirus protein ($X_4$). The plant then may be further transformed with a fifth nucleic acid ($N_5$) comprising a fourth nucleotide sequences ($R_5$) encoding a fourth rotavirus protein ($X_5$), so that the first, second, third, fourth and fifth nucleotide sequence are co-expressed in the plant. Rotavirus protein $X_1$-$X_5$ may be selected from the group of VP2, VP4, VP6, VP7 and NSP4, wherein VP2, VP4, VP6, VP7 and NSP4 are selected once, so that each rotavirus protein VP2, VP4, VP6, VP7 and NSP4 is expressed in the plant. Furthermore, a plant may be co-transformed simultaneously with a first nucleic acid ($N_1$) comprising a first nucleotide sequence ($R_1$) encoding a first rotavirus protein ($X_1$), a second nucleic acid ($N_2$) comprising a second nucleotide sequence ($R_2$) encoding a second rotavirus protein ($X_2$), a third nucleic acid ($N_3$) comprising a third nucleotide sequence ($R_3$) encoding a third rotavirus protein ($X_3$), a fourth nucleic acid ($N_4$) comprising a fourth nucleotide sequences ($R_4$) encoding a fourth and a fifth rotavirus protein ($X_4$), and a fifth nucleic acid ($N_5$) comprising a fifth nucleotide sequences ($R_5$) encoding a fifth rotavirus protein ($X_5$) so that the first, second, third, fourth and fifth nucleotide sequence are co-expressed in the plant. The first nucleic acid ($N_1$), second nucleic acid ($N_2$), third nucleic acid ($N_3$), fourth nucleic acid ($N_4$) and fifth nucleic acid ($N_5$) may be introduced in the plant in a transient manner, or in a stable manner.

A first plant expressing a first nucleic acid ($N_1$) comprising a first nucleotide sequence ($R_1$) encoding a first rotavirus protein ($X_1$), may be crossed with a second plant expressing a second nucleic acid ($N_2$) comprising a second nucleotide sequence ($R_2$) encoding a second rotavirus protein ($X_2$) to produce a progeny plant (third plant). The third plant may be crossed with a fourth plant expressing a third nucleic acid ($N_3$) comprising a third nucleotide sequence ($R_3$) encoding a third rotavirus protein ($X_3$) to produces a progeny plant (fifth plant). The fifth plant may be crossed with a sixth plant expressing a fourth nucleic acid ($N_4$) comprising a fourth nucleotide sequences ($R_4$) encoding a fourth rotavirus protein ($X_4$) to produce a progeny plant (seventh plant). The seventh plant may be crossed with an eight plant expressing a fifth nucleic acid ($N_5$) comprising a fifth nucleotide sequences ($R_5$) encoding a fifth rotavirus protein ($X_5$) to produce a progeny plant that co-expresses the first, second, third, fourth and fifth rotavirus protein ($X_1$-$X_5$). Rotavirus protein $X_1$-$X_5$ may be selected from the group of VP2, VP4, VP6, VP7 and NSP4, wherein VP2, VP4, VP6, VP7 and NSP4 are selected once, so that each rotavirus protein VP2, VP4, VP6, VP7 and NSP4 is expressed in the plant.

Ratio of Nucleic Acids (N) used to Transform a Host

As may be seen in FIG. 5, the level of RLP accumulation in the plant, portion of the plant or plant cell, may be influenced by the ratio of the nucleic acids encoding rotavirus structural and nonstructural proteins that are expressed in a plant. For example, which is not to be considered limiting, the ratio of nucleic acids (N) that are introduced into a plant may be modified by providing different amounts of *Agrobacterium*, that are used to infiltrate the plant, portion of the plant or plant cell, where each *Agrobacterium* comprises a construct comprising a nucleic acid (N) as set out in Table 1 (and accompanying text) above. For example which is not to be considered limiting, the ratio of the structural protein-containing to nonstructural protein-containing *Agrobacterium* may range for example from about 0.8:1 to about 2.5:1.5 (structural protein:nonstructural protein), or any amount therebetween, for example from about 0.8:1, 0.9:1, 1:1, 1.1:1, 1.2:1, 1.3:1, 1.4:1, 1.5:1, 1.6:1, 1.7:1, 1.8:1, 1.9:1, 2:0.5, 2:1, 2.2:1, 2.3:1, 2.4:1, 2.5:1, 2.5:1.1, 2.5:1.2, 2.5:1.3, 2.5:1.4, 2.5:1.5 (structural protein:nonstructural protein), or any amount therebetween. For example, as described below, the ratio of structural rotavirus protein to nonstructural protein may be varied for example by introducing different ratios of *Agrobacterium* containing the one or more nucleic acid (N) comprising one or more nucleotide sequence (R) encoding the rotavirus structural and non-structural proteins (X) into a host, for example a plant, portion of the plant or plant cell. For example the absorbance or optical density (OD) of *Agrobacterium* strains in the bacterial suspension may be used as measure to establish a ratio between *Agrobacterium* strains that containing the structural protein to *Agrobacterium* strains that contain the nonstructural protein. For example, which is not considered limiting, the OD may range for example from about 0.2:0.4 to about 1:0.6 (*Agrobacterium* strains containing structural protein:*Agrobacterium* strains containing nonstructural protein in the bacterial suspension) or any amount therebetween, for example from about 0.2:0.4, 0.3:0.4, 0.4:0.4, 0.5:0.4, 0.6:0.4, 0.7:0.4, 0.8:0.4, 0.9:0.4, 1:0.4, 0.2:0.5, 0.3:0.5, 0.4:0.5, 0.5:0.5, 0.6:0.5, 0.7:0.5, 0.8:0.5, 0.9:0.5, 1:05, 0.2:0.6, 0.3:0.6, 0.4:0.6, 0.5:0.6, 0.6:0.6, 0.7:0.6, 0.8:0.6, 0.9:0.6, 1:06, 0.3:0.4, 0.3:0.5, 0.3:0.6, 0.4:0.4, 0.4:0.5, 0.4:0.6, 0.5:0.4, 0.5:0.5, 0.5:0.6, 0.6:0.4, 0.6:0.5, 0.6:0.6, 0.7:0.4, 0.7:0.5, 0.7:0.6, 0.8:0.4, 0.8:0.5, 0.8:0.6, 0.9:0.4, 0.9:0.5, 0.9:0.6, 1:0.4, 1:0.5, 1:0.6 (*Agrobacterium* strains containing structural protein:*Agrobacterium* strains containing nonstructural protein in the bacterial suspension) or any amount therebetween. For example, which is not considered limiting, an OD of 0.4 of *Agrobacterium* strains in bacterial suspension may be designated as a reference of 1. Therefore a ratio of 1.5:1 of structural to non structural protein may be achieved by using an OD of 0.6 of *Agrobacterium* strain containing structural protein to an OD of 0.4 of *Agrobacterium* strain containing nonstructural protein in bacterial suspension.

The ratio of rotavirus structural protein to nonstructural protein may be varied for example by introducing different ratios of *Agrobacterium* containing the one or more nucleic acid (N) comprising one or more nucleotide sequence (R) encoding the rotavirus structural and non-structural proteins (X) into the plant, portion of the plant or plant cell. Alternatively, if the rotavirus structural proteins and nonstructural proteins are present on the same construct, and therefore are introduced into the plant, plant portion or plant cell, using one *Agrobacterium*, they may be differentially expressed within the plant, portion of the plant or plant cell using suitable promoters so that the desired ratio of rotavirus structural proteins and nonstructural proteins is obtained.

Therefore as described herein, a method is provided for increasing RLP production yield, increasing VP4 and VP7 yield, or increasing both RLPS and VP4 and VP7 yield, by modulating the ratio between the one or more nucleic acid (N) comprising one or more nucleotide sequence (R) encoding the rotavirus structural proteins (X) and the one or more nucleic acid (N) comprising one or more nucleotide sequence (R) encoding the rotavirus nonstructural proteins (X).

For example, the percentage of the *Agrobacterium* containing rotavirus nonstructural protein may be between 20% to 60% or any amount therebetween, of total amount of *Agrobacterium* use to infiltrate the plant, plant portion or plant cell. For example the percent ratio of *Agrobacterium* containing rotavirus nonstructural protein may be 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49% 50%, 51%, 52%, 53%, 54%, 55%, 56%, 57%, 58%, 59%, 60%, or any amount therebetween of the total *Agrobacterium* use to infiltrate the plant, plant portion or plant cell. Similarly, the percentage of *Agrobacterium* containing structural protein within the total amount of *Agrobacterium* infiltrated may be 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41% or 40% or any amount therebetween, of the total *Agrobacterium* use to infiltrate the plant, plant portion or plant cell.

For example, the percentage ratio of *Agrobacterium* containing rotavirus structural protein to *Agrobacterium* containing nonstructural protein may be 70%:30%, 60%:40%, 50%:50%, 40%:60% or any percentage ratio amount therebetween. For example, the percentage ratio between *Agrobacterium* containing structural protein and *Agrobacterium* containing nonstructural protein may be 50%:50%, 51%:49%, 52%:48%, 53%:47%, 54%:46%, 55%:45%, 56%:44%, 57%:43%, 58%:42%, 59%: 41%, 60%:40%, or any percentage ratio in between.

As described below, the ratio of rotavirus structural protein to rotavirus nonstructural protein may further be varied for example by differentially expressing the rotavirus structural protein and the rotavirus nonstructural protein. Expression may be varied by modulating for example replication, transcription, translation, or a combination thereof, of the rotavirus structural protein, the rotavirus nonstructural protein, or both the rotavirus structural protein and the rotavirus nonstructural protein. For example different regulatory elements, including promoters, amplification elements, enhancers or a combination thereof, may be used in addition to varying the ratio of the rotavirus structural protein-containing *Agrobacterium* to rotavirus nonstructural protein-containing *Agrobacterium* infiltrated as described above. A first set or combination of regulatory elements may be used to regulate the replication, transcription or a combination thereof, of the one or more nucleic acid comprising one or more nucleotide sequence encoding rotavirus structural protein and a second set or combination of regulatory elements may be used to regulate the replication, transcription or a combination thereof, of the one or more nucleotide sequence encoding rotavirus nonstructural protein. The first set or combination of regulatory elements is different from the second set or combination of regulatory elements and permits differential expression of the one or more nucleic acid comprising one or more nucleotide sequence encoding rotavirus structural protein and the one or more nucleic acid comprising one or more nucleotide sequence encoding rotavirus nonstructural protein to permit modulating the ratio of rotavirus structural protein:rotavirus nonstructural protein in vivo.

For example, which is not to be considered limiting, one set or combination of regulatory elements, for example the first set, may include an enhancer element for example elements obtained from CPMV, such as CPMV HT, or CPMV 160 (see FIG. 6). CMPV HT is described in U.S. 61/971,274 (which is incorporated herein by reference) and CPMV 160 is described in U.S. 61/925,852 (which is incorporated herein by reference). The enhancer element, for example those obtained from CPMV, for example CPMV HT or CPMV 160 (see FIG. 6; U.S. 61/971,274, and U.S. 61/925,852, respectively) may be absent in the other set or combination of regulatory elements, for example the second set. Alternatively, the second set may include an enhancer element (for example elements obtained from CPMV, (for example CPMV HT or CPMV 160), while the amplification element (for example elements obtained from CPMV, (for example CPMV HT or CPMV 160) may be absent in the first set or combination of regulatory elements. In a similar manner, the strength of a promoters may differ between the first and second set or combination of regulatory elements, or one of the promoters may be inducible, and the other constitutive, so that differential expression between the rotavirus structural protein relative to the rotavirus nonstructural protein is achieved in vivo.

For example, the ratio of rotavirus structural protein to nonstructural protein may be varied for example by introducing different ratios of *Agrobacterium* containing a first nucleic acid ($N_1$) comprising a nucleotide sequence ($R_1$) encoding first rotavirus protein for example rotavirus nonstructural protein NSP4 to *Agrobacterium* containing a second nucleic acid ($N_2$) comprising four nucleotide sequences ($R_2$-$R_5$) encoding a second, third, fourth and fifth rotavirus protein, for example in any order rotavirus structural proteins VP2, VP4, VP6 and VP7. For example the ratio of the *Agrobacterium* containing a first nucleic acid ($N_1$) comprising a nucleotide sequence ($R_1$) encoding rotavirus nonstructural protein NSP4 to the *Agrobacterium* containing a second nucleic acid ($N_2$) comprising four nucleotide sequences ($R_2$-$R_5$) encoding rotavirus structural proteins VP2, VP4, VP6 and VP7 may be 0.8:1 and 1:2 (*Agrobacterium* containing $N_1$ to $N_2$) or any amount there between for example 1:1.5 (*Agrobacterium* containing $N_1$ to $N_2$).

Furthermore, the ratio of rotavirus structural protein to nonstructural protein may be varied by differentially expressing within the plant, portion of the plant or plant cell the rotavirus structural protein to nonstructural protein using enhancer elements. For example, the ratio of rotavirus structural protein to nonstructural protein may be varied for example by co-expressing within the plant, portion of the plant or plant cell a first nucleic acid ($N_1$) comprising a nucleotide sequence ($R_1$) encoding a first rotavirus protein for example a nonstructural protein NSP4 with a second nucleic acid ($N_2$) comprising four nucleotide sequences ($R_2$-$R_5$) encoding a second, third, fourth and fifth rotavirus protein for example in any order rotavirus structural proteins VP2, VP4, VP6 and VP7, wherein the second, third, fourth and fifth nucleotide sequence are operatively linked to an enhancer sequence for example CPMV HT, CPM 160, CPMV 160+ and CPMV HT+ (described in U.S. 61/971, 274, and U.S. 61/925,852, respectively which are incorporated herein by reference), as described below. In another example, the ratio of rotavirus structural protein to nonstructural protein may be varied for example by co-expressing within the plant, portion of the plant or plant cell a first nucleic acid ($N_1$) comprising first nucleotide sequence ($R_1$) encoding a first rotavirus protein for example structural protein VP6 or VP7 and second nucleotide sequence ($R_2$) encoding a second rotavirus protein for example structural protein VP2 or VP4, second nucleic acid ($N_2$) comprising a third nucleotide sequence ($R_3$) encoding a third rotavirus protein for example structural protein VP7 or VP6 and a fourth nucleotide sequence ($R_4$) encoding a fourth rotavirus protein for example structural protein VP4 or VP2 and a third nucleic acid ($N_3$) comprising fifth nucleotide sequences ($R_5$) encoding a fifth rotavirus protein for example nonstructural protein NSP4, wherein the first, second, third and fourth nucleotide sequence are operatively linked to an enhancer sequence for example CPMV HT, CPMV 160, CPMV 160+ and CPMV HT+, as described below.

In another example, the ratio of rotavirus structural protein to nonstructural protein may be varied for example by co-expressing within the plant, portion of the plant or plant cell one or more nucleic acids comprising a first nucleotide sequence ($R_1$) encoding a first rotavirus protein for example structural protein VP6 or VP7 and second nucleotide sequence ($R_2$) encoding a second rotavirus protein for example structural protein VP2 or VP4, a third nucleotide sequence ($R_3$) encoding a third rotavirus protein for example structural protein VP7 or VP6 and a fourth nucleotide sequence ($R_4$) encoding fourth rotavirus protein for example structural protein VP4 or VP2, and a fifth nucleotide sequences ($R_5$) encoding a fifth rotavirus protein for example nonstructural protein NSP4, wherein the first, second, third and fourth nucleotide sequence are operatively linked to an enhancer sequence for example CPM 160, CPMV 160+ and CPMV HT+, as described below and the fifth nucleotide sequence is operatively linked to CPMV HT as described below.

In another example, the ratio of rotavirus structural protein to nonstructural protein may be varied for example by co-expressing within the plant, portion of the plant or plant cell a first nucleic acid ($N_1$) comprising first nucleotide sequence ($R_1$) encoding a first rotavirus protein for example structural protein VP6 or VP7, a second nucleic acid ($N_2$) comprising second nucleotide sequence ($R_2$) encoding a second rotavirus protein for example structural protein VP2 or VP4, a third nucleic acid ($N_3$) comprising a third nucleotide sequence ($R_3$) encoding a third rotavirus protein for example structural protein VP7 or VP6, a fourth nucleic acid ($N_4$) comprising a fourth nucleotide sequence ($R_4$) encoding a fourth rotavirus protein for example structural protein VP4 or VP2 and a fifth nucleic acid ($N_5$) comprising fifth nucleotide sequences ($R_5$) encoding a fifth rotavirus protein for example nonstructural protein NSP4, wherein the first, second, third and fourth nucleotide sequence are operatively linked to an enhancer sequence for example CPMV HT, CPMV 160, CPMV 160+ and CPMV HT+, as described below.

Amplification Elements and Enhancer Elements/Regulatory Elements

The rotavirus protein or polypeptide may be expressed in an expression system comprising a viral based, DNA or RNA, expression system, for example but not limited to, a comovirus-based expression cassette and geminivirus-based amplification element.

Enhancer elements may be used to achieve high level of transient expression of rotavirus structural and nonstructural proteins. Enhancer elements may be based on RNA plant viruses, including comoviruses, such as Cowpea mosaic virus (CPMV; see, for example, WO2007/135480; WO2009/087391; US 2010/0287670, Sainsbury F. et al., 2008, *Plant Physiology;* 148: 121-1218; Sainsbury F. et al., 2008, *Plant Biotechnology Journal;* 6: 82-92; Sainsbury F. et al., 2009, *Plant Biotechnology Journal;* 7: 682-693; Sainsbury F. et al. 2009, *Methods in Molecular Biology, Recombinant Proteins From Plants*, vol. 483: 25-39).

CPMV 160 (CPMVX) and CPMV 160+ (CPMVX+)

In an embodiment the enhancer Elements are "CPMVX" (also referred as "CPMV 160") and/or "CPMVX+" (also referred to as "CPMV 160+") and are described in U.S. 61/925,852 (which is incorporated herein by reference).

Expression enhancer "CPMVX" comprises a comovirus cowpea mosaic virus (CPMV) 5' untranslated region (UTR). The 5'UTR from nucleotides 1-160 of the CPMV RNA-2 sequence (SEQ ID NO: 1), starts at the transcription start site to the first in frame initiation start codon (at position 161), which serve as the initiation site for the production of the longer of two carboxy coterminal proteins encoded by a wild-type comovirus genome segment. Furthermore a 'third' initiation site at (or corresponding to) position 115 in the CPMV RNA-2 genomic sequence may also be mutated, deleted or otherwise altered. It has been shown that removal of AUG 115 in addition to the removal of AUG 161 enhances expression when combined with an incomplete M protein (Sainsbury and Lomonossoff, 2008, *Plant Physiology;* 148: 1212-1218; WO 2009/087391; which are incorporated herein by reference).

CPMVX comprises X nucleotides of SEQ ID NO:1, where X=160, 155, 150, or 114 of SEQ ID NO:1, or a sequence that comprises between 80% to 100% sequence similarity with CPMVX, where X=160, 155, 150, or 114 of SEQ ID NO:93. This expression enhancer is generally referred to as CPMVX (see FIG. 6*c*).

The expression enhancer CPMVX, where X=160, consists of nucleotides 1-160 of SEQ ID NO: 1:

```
                                                        (SEQ ID NO: 1)
  1  tattaaaatc ttaataggtt ttgataaaag cgaacgtggg gaaacccgaa ccaaaccttc 61  ttctaaactc tctctcatct ctcttaaagc aaacttctct cttgtctttc ttgcgtgagc 121  gatcttcaac gttgtcagat cgtgcttcgg caccagtaca
```

The CPMVX enhancer sequence may further be fused to a stuffer sequence, wherein the CMPVX comprises X nucleotides of SEQ ID NO:1, where X=160, 155, 150, or 114 of SEQ ID NO:1, or a sequence that comprises between 80 to 100% sequence similarity with CPMVX, where X=160, 155, 150, or 114 of SEQ ID NO:1, and the stuffer sequence comprises from 1-100 nucleotides fused to the 3' end of the CMPVX sequence. For example, the stuffer sequence may comprise from about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 nucleotides, or any number of nucleotides therebetween.

If the CMPVX sequence comprises a stuffer fragment, then this expression enhancer may be referred to as CPMVX+ (see FIG. 6*d*), where X=160, 155, 150, 114 of SEQ ID NO:1, it may also be referred to as CMPVX comprising a stuffer sequence, or it may be referred to as CPMV160+; CPMV155+; CPMV150+; CPMV114+, when X-160, 155, 150, or 114, respectively. Constructs comprising CPMVX that do not comprise a stuffer sequence may be termed CPMVX+, where X=160, 155, 150, 114 of SEQ ID NO:1, and where the stuffer sequence is of 0 nucleotides in length.

The stuffer sequence may be modified by truncation, deletion, or replacement of the native CMPV 5'UTR sequence that is located 3' to nucleotide 160. The modified stuffer sequence may be removed, replaced, truncated or shortened when compared to the initial or unmodified (i.e. native) stuffer sequence associated with the 5'UTR (as described in Sainsbury F., and Lomonossoff G. P., 2008, Plant Physiol. 148: pp. 1212-1218). The stuffer sequence may comprise a one or more restriction sites (polylinker, multiple cloning site, one or more cloning sites), one or more plant kozak sequences, one or more linker sequences, one or more recombination sites, or a combination thereof. For example, which is not to be considered limiting, a stuffer sequence may comprise in series, a multiple cloning site of a desired length fused to a plant kozak sequence. The stuffer sequence does not comprise a nucleotide sequence from the native 5'UTR sequence that is positioned 3' to nucleotide 160 of the native CPMV 5'UTR, for example nucleotides 161 to 512 as shown in FIG. 1 of Sainsbury F., and Lomonossoff G. P. (2008, Plant Physiol. 148: pp. 1212-1218; which is incorporated herein by reference), or nucleotides 161-509 of prior art CPMV HT sequence. That is, the incomplete M protein present in the prior art CPMV HT sequence (FIG. 1; of Sainsbury F., and Lomonossoff G. P., 2008) is removed from the 5'UTR in the present invention.

Plant Kozak consensus sequences are known in the art (see for example Rangan et al. Mol. Biotechnol., 2008, July 39(3), pp. 207-213). Both naturally occurring and synthetic Kozak sequences may be used in the expression enhancer or may be fused to the nucleotide sequence of interest as described herein.

The plant kozak sequence may be any known plant kozak sequences (see for example L. Rangan et. al. Mol. Biotechnol. 2008), including, but not limited to the following plant consensus sequences:

```
                    (SEQ ID NO: 2; plant kingdom)
caA(A/C)a (SEQ ID NO: 3; dicots)
aaA(A/C)a (SEQ ID NO: 4; arabidopsis)
aa(A/G) (A/C)a
```

The plant kozak sequence may also be selected from the group of:

```
                                    (SEQ ID NO: 5)
AGAAA (SEQ ID NO: 6)
AGACA (SEQ ID NO: 7)
AGGAA (SEQ ID NO: 8)
AAAAA (SEQ ID NO: 9)
AAACA (SEQ ID NO: 10)
AAGCA
```

-continued

```
                                   (SEQ ID NO: 11)
AAGAA (SEQ ID NO: 12)
AAAGAA (SEQ ID NO: 13)
AAAGAA (SEQ ID NO: 14; Consensus sequence)
(A/-)A(A/G) (A/G) (A/C)A.
```

The expression enhancer CPMVX, or CPMVX+, may be operatively linked at the 5' end of the enhancer sequence with a regulatory region that is active in a plant, and operatively linked to a nucleotide sequence of interest at the 3' end of the expression enhancer (FIG. 6*c*), in order to drive expression of the nucleotide sequence of interest within a plant host.

CPMV HT+, CPMV HT+[WT115], CPMV HT+[511]

In another embodiment the enhancer elements is "CPMV HT+" which is described in U.S. 61/971,274 (which is incorporated herein by reference). Expression enhancer "CPMV HT+" (see FIG. 6*b*) comprises a comovirus 5' untranslated region (UTR) and a modified, lengthened, or truncated stuffer sequence.

A plant expression system comprising a first nucleic acid sequence comprising a regulatory region, operatively linked with one or more than one expression enhancer as described herein (e.g. CPMV HT+, CPMV HT+[WT115], CPMV HT+[511]), and a nucleotide sequence encoding a rotavirus structural or nonstructural proteins is also provided. Furthermore, a nucleic acid comprising a promoter (regulatory region) sequence, an expression enhancer (e.g. CPMV HT+ or CPMV HT+[WT115]) comprising a comovirus 5'UTR and a stuffer sequence with a plant kozak sequence fused to one or more nucleic acid sequences encoding a rotavirus structural or nonstructural proteins are described. The nucleic acid may further comprise a sequence comprising a comovirus 3' untranslated region (UTR), for example, a plastocyanin 3' UTR, or other 3'UTR active in a plant, and a terminator sequence, for example a NOS terminator, operatively linked to the 3' end of the nucleotide sequence encoding a rotavirus structural or nonstructural proteins (referred to as nucleotide of interest in FIG. 6*a*), so that the nucleotide sequence encoding the rotavirus structural or nonstructural proteins is inserted upstream from the comovirus 3' untranslated region (UTR), plastocyanin 3' UTR, or other 3'UTR sequence.

SEQ ID NO:15 comprises a "CPMV HT" expression enhancer as known in the prior art (e.g. FIG. 1 of Sainsbury and Lomonossoff 2008, Plant Physiol. 148: pp. 1212-1218; which is incorporated herein by reference). CPMV HT includes the 5'UTR sequence from nucleotides 1-160 of SEQ ID NO:15 with modified nucleotides at position 115 (cgt), and an incomplete M protein with a modified nucleotide at position 162 (acg), and lacks a plant kozak sequence (5'UTR: nucleotides 1-160; incomplete M protein underlined, nucleotides 161-509). SEQ ID NO:15 also includes a multiple cloning site (italics, nucleotides 510-528) which is not present in the prior art CPMV HT sequence:

```
                                                                SEQ ID NO: 15
  1  tattaaaatc ttaataggtt ttgataaaag cgaacgtggg gaaacccgaa ccaaaccttc 61  ttctaaactc tctctcatct ctcttaaagc aaacttctct cttgtctttc ttgcgtgagc 121  gatcttcaac gttgtcagat cgtgcttcgg caccagtaca acgttttctt tcactgaagc 181  gaaatcaaag atctctttgt ggacacgtag tgcggcgcca ttaaataacg tgtacttgtc 241  ctattcttgt cggtgtggtc ttgggaaaag aaagcttgct ggaggctgct gttcagcccc 301  atacattact tgttacgatt ctgctgactt tcggcgggtg caatatctct acttctgctt 361  gacgaggtat tgttgcctgt acttctttct tcttcttctt gctgattggt tctataagaa 421  atctagtatt ttctttgaaa cagagttttc ccgtggtttt cgaacttgga gaaagattgt 481  taagcttctg tatattctgc ccaaatttgt cgggccc
```

CPMV HT+ with a plant kozak consensus sequence is provided in SEQ ID NO:16 (nucleotide 1-160, 5'UTR, including modified ATG at positions 115 (GTG) lower case bold and italics; stuffer fragment comprising: an incomplete M protein underlined, nucleotides 161-509, with modified nucleotide at 162 (ACG); a multiple cloning site, italics, nucleotides 510-528; and a consensus plant kozak sequence, caps and bold, nucleotides 529-534).

(SEQ ID NO: 16)

1 tattaaaatc ttaataggtt ttgataaaag cgaacgtggg gaaacccgaa ccaaaccttc 61 ttctaaactc tctctcatct ctcttaaagc aaacttctct cttgtctttc ttgcgtgagc 121 gatcttcaac gttgtcagat cgtgcttcgg caccagtaca *acg*ttttctt tcactgaagc 181 gaaatcaaag atctctttgt ggacacgtag tgcggcgcca ttaaataacg tgtacttgtc 241 ctattcttgt cggtgtggtc ttgggaaaag aaagcttgct ggaggctgct gttcagcccc 301 atacattact tgttacgatt ctgctgactt tcggcgggtg caatatctct acttctgctt 361 gacgaggtat tgttgcctgt acttctttct tcttcttctt gctgattggt tctataagaa 421 atctagtatt ttctttgaaa cagagttttc ccgtggtttt cgaacttgga gaaagattgt 481 taagcttctg tatattctgc ccaaatttg*t tcgggcccaa taccgcgg* (A/-)A(A/G)(A/G)(A/C)A

SEQ ID NO:17 ("CPMV HT+511") comprises a segment of the native sequence of the CPMV RNA 2 genome from nucleotides 1-154. The 5'UTR sequence from nucleotides 1-511 of SEQ ID NO:17 comprises modified "atg" sequences at positions 115 ("g" in place of "a"; italics bold) and 162 ("c" in place of "t"; italics bold), and an incomplete M protein (underlined) from nucleotides 161-511. CPMV HT+511 comprises a native M protein kozak consensus sequence (nucleotides 508-511; bold):

SEQ ID NO: 17

1 tattaaaatc ttaataggtt ttgataaaag cgaacgtggg gaaacccgaa ccaaaccttc 61 ttctaaactc tctctcatct ctcttaaagc aaacttctct cttgtctttc ttgc*gtg*agc 121 gatcttcaac gttgtcagat cgtgcttcgg caccagtaca *acg*ttttctt tcactgaagc 181 gaaatcaaag atctctttgt ggacacgtag tgcggcgcca ttaaataacg tgtacttgtc 241 ctattcttgt cggtgtggtc ttgggaaaag aaagcttgct ggaggctgct gttcagcccc 301 atacattact tgttacgatt ctgctgactt tcggcgggtg caatatctct acttctgctt 361 gacgaggtat tgttgcctgt acttctttct tcttcttctt gctgattggt tctataagaa 421 atctagtatt ttctttgaaa cagagttttc ccgtggtttt cgaacttgga gaaagattgt 481 taagcttctg tatattctgc ccaaatttga a...

Another non-limiting example of a CPMV HT+ enhancer sequence is provided by the sequence of SEQ ID NO:18 (CPMV HT+[WT115]). Expression cassettes or vectors comprising CPMV HT+ and including a plant regulatory region in operative association with the expression enhancer sequence of SEQ ID NO: 18, and the transcriptional start site (ATG) at the 3' end fused to a nucleotide sequence encoding rotavirus structural or nonstructural protein are also part o the present invention.

SEQ ID NO: 18 (CPMV HT+[WT115]) nucleotide 1-160, 5'UTR, with an ATG at position 115-117, lower case bold; stuffer fragment comprising: an incomplete M protein underlined, nucleotides 161-509; with a modified ATG at position 161-153 lower case bold, and underlined, a multiple cloning site, italics, nucleotides 510-528; and a plant kozak sequence, caps and bold, nucleotides 529-534).

For size exclusion chromatography, total soluble proteins may be extracted from plant tissue by homogenizing (Polytron) sample of frozen-crushed plant material in extraction buffer, and insoluble material removed by centrifugation. Precipitation with ice cold acetone or PEG may also be of benefit. The soluble protein is quantified, and the extract passed through a Sephacryl™ column, for example a Sephacryl™ S500 column. Blue Dextran 2000 may be used as a calibration standard. Following chromatography, fractions may be further analyzed by immunoblot to determine the protein complement of the fraction.

The separated fraction may be for example a supernatant (if centrifuged, sedimented, or precipitated), or a filtrate (if filtered), and is enriched for proteins, or suprastructure proteins, and include higher molecular weight, particles such as single-layered (sl), double-layered (dl) or triple-layered (tl) RLPs.

(SEQ ID NO: 18)

```
1 tattaaaatc ttaataggtt ttgataaaag cgaacgtggg gaaacccgaa ccaaaccttc
61 ttctaaactc tctctcatct ctcttaaagc aaacttctct cttgtctttc ttgc***atg***agc
121 gatcttcaac gttgtcagat cgtgcttcgg caccagtaca *acg*ttttctt tcactgaagc
181 gaaatcaaag atctctttgt ggacacgtag tgcggcgcca ttaaataacg tgtacttgtc
241 ctattcttgt cggtgtggtc ttgggaaaag aaagcttgct ggaggctgct gttcagcccc
301 atacattact tgttacgatt ctgctgactt tcggcgggtg caatatctct acttctgctt
361 gacgaggtat tgttgcctgt acttctttct tcttcttctt gctgattggt tctataagaa
421 atctagtatt ttctttgaaa cagagttttc ccgtggtttt cgaacttgga gaaagattgt
481 taagcttctg tatattctgc ccaaatttg*t tcgggcccaa taccgcgg***AG AAAA**
```

The plant kozak sequence of SEQ ID NO:18 may be any plant kozak sequence, including but not limited, to one of the sequences of SEQ ID NO's: 2-14.

A plant expression system comprising a first nucleic acid sequence comprising a regulatory region, operatively linked with one or more than one expression enhancer as described herein (e.g. CPMV HT+, CPMV HT+[WT115], CPMV HT+[511]), and a nucleotide sequence encoding a rotavirus structural or nonstructural protein is also provided. Furthermore, a nucleic acid comprising a promoter (regulatory region) sequence, an expression enhancer (e.g. CPMV HT+ or CPMV HT+[WT115]) comprising a comovirus 5'UTR and a stuffer sequence with a plant kozak sequence fused to one or more nucleic acid sequences encoding rotavirus structural or nonstructural protein are described. The nucleic acid may further comprise a sequence comprising a comovirus 3' untranslated region (UTR), for example, a plastocyanin 3' UTR, or other 3'UTR active in a plant, and a terminator sequence, for example a NOS terminator, operatively linked to the 3' end of the nucleotide sequence encoding rotavirus structural or nonstructural protein (referred to as nucleotide of interest in FIG. **6*a***), so that the nucleotide sequence encoding rotavirus structural or nonstructural protein is inserted upstream from the comovirus 3' untranslated region (UTR), plastocyanin 3' UTR, or other 3'UTR sequence.

The occurrence of RLPs produced using the methods described herein may be detected using any suitable method for example density gradient centrifugation or size exclusion chromatography. RLPs may be assessed for structure and size, for example by electron microscopy, size exclusion chromatography, or other techniques that would be evident to one of skill in the art.

The separated fraction may be further processed to isolate, purify, concentrate or a combination thereof, the proteins, suprastructure proteins or higher-order particles by, for example, additional centrifugation steps, precipitation, chromatographic steps (e.g. size exclusion, ion exchange, affinity chromatography), tangential flow filtration, or a combination thereof. The presence of purified proteins, suprastructure proteins or higher-order particles such as RLPs, may be confirmed by, for example, native or SDS-PAGE, Western analysis using an appropriate detection antibody, capillary electrophoresis, electron microscopy, or any other method as would be evident to one of skill in the art.

The RLP's produced according to the present invention may be purified, partially purified from a plant, portion of a plant or plant matter, or may be administered as an oral vaccine, using methods as know to one of skill in the art.

RLP purification may involve gradient centrifugation, for example sucrose, iodixanol, OptiPrep™ or cesium chloride (CsCl) density gradients may be used to purify or partially purify the RLPs from transformed plant biomass. As shown for example in FIG. 4, an iodixanol step gradient or iodixanol continuous gradient might be used to purify the RLP and/or expressed rotavirus structural proteins.

Calcium (Ca2+) concentration has been shown to be important for the triple-layer particle (TLP) to double layer particle (DLP) transformation and is strain dependent (see for example Martin et al. Journal of Virology, January 2002, which is incorporated herein by reference). Complete loss of the outer-capsid proteins from TLPs (TLP decapsidation) takes place in the nanomolar range of [Ca2+]. Therefore the extraction and/or purification of RLP may be performed in the presence of calcium, and the step of gradient centrifugation may be performed in the presence of calcium, for example in the present of CaCl2. The concentration of CaCl2 maybe between for example, 1 mM and 1000 mM, or any amount there between, such as 2, 3, 4, 5, 6, 7, 8, 9, 10, 11, 12, 13, 14, 15, 20, 25, 30, 40, 50, 100, 150, 200, 250, 300, 350, 400, 450, 500, 50, 600, 650, 700, 750, 800, 850, 900, 950 mM or any amount therebetween.

The plants, or plant fragments may be minimally processed. By the term "minimal processing" it is meant plant matter, for example, a plant or portion thereof comprising a protein of interest and/or the RLP which is partially purified to yield a plant extract, homogenate, fraction of plant homogenate or the like (i.e. minimally processed). Partial purification may comprise, but is not limited to disrupting plant cellular structures thereby creating a composition comprising soluble plant components, and insoluble plant components which may be separated for example, but not limited to, by centrifugation, filtration or a combination thereof. In this regard, proteins secreted within the extracellular space of leaf or other tissues could be readily obtained using vacuum or centrifugal extraction, or tissues could be extracted under pressure by passage through rollers or grinding or the like to squeeze or liberate the protein free from within the extracellular space. Minimal processing could also involve preparation of crude extracts of soluble proteins, since these preparations would have negligible contamination from secondary plant products. Further, minimal processing may involve aqueous extraction of soluble protein from leaves, followed by precipitation with any suitable salt. Other methods may include large scale maceration and juice extraction in order to permit the direct use of the extract. The RLPs may be purified or extracted using any suitable method for example mechanical or biochemical extraction.

The one or more rotavirus structural protein may be synthesized at an amount up to 2 g per kilogram of plant fresh weight. For example, the amount of synthesized structural protein maybe between 1 and 2 g per kilogram of fresh weight, or any amount there between, such as 1.0, 1.1, 1.2, 1.3, 1.4, 1.5, 1.6, 1.7, 1.8, 1.9, 2 g per kilogram of fresh weight or any amount therebetween. For example, the structural protein may be synthesized at an amount up to 1.54 g per kilogram of plant fresh weight.

The size (i.e. the diameter) of the above-defined RLPs, maybe measures for example by dynamic light scattering (DLS) or electron microscope (EM) techniques, is usually between 50 to 110 nm, or any size therebetween. For example, the size of the intact RLP structure may range from about 70 nm to about 110 nm, or any size therebetween, such as 75 nm, 80 nm, 85 nm, 90 nm, 95 nm, 100 nm, 105 nm or any size therebetween.

Nucleotide Sequences

The present invention further provides a nucleic acid comprising a nucleotide sequence encoding one or more rotavirus structural protein operatively linked to a regulatory region active in a plant. The nucleotide sequence may be optimized for example for human codon usage or plant codon usage. Furthermore one or more rotavirus structural protein may be operatively linked to one or more than one amplification elements. In addition one or more rotavirus structural protein may be operatively linked to one or more than one compartment targeting sequence. The one or more rotavirus structural protein encoded by the nucleotide sequence may be for example VP2, VP4, VP6 or VP7. Furthermore the one or more rotavirus structural protein encoded by the nucleotide sequence may be for example from any rotavirus group A to G, but more preferably from rotavirus group A. Furthermore, the one or more rotavirus structural protein encoded by the nucleotide sequence maybe from any rotavirus strain having a genotype of any combinations of G- and P-types from G1 to G27 and from P1 to P34, and more preferably from G1 to G19 and from P1 to P27, including, but not limited to G1P[8], G2P[4], G2P[8], G3P[8], G4P[8], G9P[6], G9P[8], rotavirus A WA strain, rotavirus A vaccine USA/Rotarix-A41CB052A/1988/G1P1A[8] strain or rotavirus SA11 strain.

A nucleic acid sequence referred to in the present invention, may be "substantially homologous", "substantially similar" or "substantially identical" to a sequence, or a compliment of the sequence if the nucleic acid sequence hybridize to one or more than one nucleotide sequence or a compliment of the nucleic acid sequence as defined herein under stringent hybridization conditions. Sequences are "substantially homologous" "substantially similar" "substantially identical" when at least about 70%, or between 70 to 100%, or any amount therebetween, for example 70, 72, 74, 76, 78, 80, 82, 84, 86, 88, 90, 92, 94, 96, 98, 100%, or any amount therebetween, of the nucleotides match over a defined length of the nucleotide sequence providing that such homologous sequences exhibit one or more than one of the properties of the sequence, or the encoded product as described herein.

For example the present invention provides an isolated polynucleotide comprising a nucleotide sequence which encodes one or more rotavirus protein, for example a structural or nonstructural rotavirus protein, that is at least 60%, 65%, 70%, 75%, 80%, 85%, 86%, 87%, 88%, 89%, 90%, 91%, 92%, 93%, 94%, 95%, 96%, 97%, 98%, 99% 100% or any amount therebetween identical to sequences as defines for example in SEQ ID NOs: 21, 27, 32, 37 or 42. The polynucleotide may be human codon optimized by any of the methods known in the art. The nucleotide sequence may enclode for example a rotavirus protein that is at least 60%, 65%, 70%, 75%, 80%, 85%, 86%, 87%, 88%, 89%, 90%, 91%, 92%, 93%, 94%, 95%, 96%, 97%, 98%, 99% 100% or any amount therebetween identical the amino acid sequence of SEQ ID NOs: 24, 29, 34, 39 or 44.

Furthermore, the present invention provides RLPS that comprise rotavirus structural proteins that are for example encoded by nucleic acids that are at least 60%, 65%, 70%, 75%, 80%, 85%, 86%, 87%, 88%, 89%, 90%, 91%, 92%, 93%, 94%, 95%, 96%, 97%, 98%, 99% 100% or any amount therebetween identical to sequences as defines for example in SEQ ID NOs: 21, 27, 32, 37 or 42.

Such a sequence similarity or identity may be determined using a nucleotide sequence comparison program, such as that provided within DNASIS (using, for example but not limited to, the following parameters: GAP penalty 5, # of top diagonals 5, fixed GAP penalty 10, k tuple 2, floating gap 10, and window size 5). However, other methods of alignment of sequences for comparison are well-known in the art for example the algorithms of Smith & Waterman (1981, Adv. Appl. Math. 2:482), Needleman & Wunsch (J. Mol. Biol. 48:443, 1970), Pearson & Lipman (1988, Proc. Nat'l. Acad. Sci. USA 85:2444), and by computerized implementations of these algorithms (GAP, BESTFIT, FASTA, and BLAST, available through the NIH.), or by manual alignment and visual inspection (see, e.g., Current Protocols in Molecular Biology, Ausubel et al., eds. 1995 supplement), or using Southern or Northern hybridization under stringent conditions (see Maniatis et al., in Molecular Cloning (A Laboratory Manual), Cold Spring Harbor Laboratory, 1982). Preferably, sequences that are substantially homologous exhibit at least about 80% and most preferably at least about 90% sequence similarity over a defined length of the molecule.

An example of one such stringent hybridization conditions may be overnight (from about 16-20 hours) hybridization in 4×SSC at 65° C., followed by washing in 0.1×SSC at 65° C. for an hour, or 2 washes in 0.1×SSC at 65° C. each for 20 or 30 minutes. Alternatively an exemplary stringent hybridization condition could be overnight (16-20 hours) in 50% formamide, 4×SSC at 42° C., followed by washing in 0.1×SSC at 65° C. for an hour, or 2 washes in 0.1×SSC at 65° C. each for 20 or 30 minutes, or overnight (16-20 hours), or hybridization in Church aqueous phosphate buffer (7% SDS; 0.5M NaPO4 buffer pH 7.2; 10 mM EDTA) at 65° C., with 2 washes either at 50° C. in 0.1×SSC, 0.1% SDS for 20 or 30 minutes each, or 2 washes at 65° C. in 2×SSC, 0.1% SDS for 20 or 30 minutes each for unique sequence regions.

A nucleic acid encoding a rotavirus structural polypeptide may be described as a "rotavirus nucleic acid", a "rotavirus nucleotide sequence", a "rotavirus nucleic acid", or a "rotavirus nucleotide sequence". For example, which is not to be considered limiting, a virus-like particle comprising one or more rotavirus structural protein or rotavirus structural polypeptide, may be described as a "rotavirus VLP", "RVLP" or "RLP".

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. The process of optimizing the nucleotide sequence coding for a heterologously expressed protein can be an important step for improving expression yields. The optimization requirements may include steps to improve the ability of the host to produce the foreign protein.

"Codon optimization" is defined as modifying a nucleic acid sequence for enhanced expression in cells of interest by replacing at least one, more than one, or a significant number, of codons of the native sequence with codons that may be more frequently or most frequently used in the genes of another organism or species. Various species exhibit particular bias for certain codons of a particular amino acid.

The present invention includes synthetic polynucleotide sequences that have been codon optimized for example the sequences have been optimized for human codon usage or plant codon usage. The codon optimized polynucleotide sequences may then be expressed in plants. More specifically the sequences optimized for human codon usage or plant codon usage may be expressed in plants. Without wishing to be bound by theory, it is believed that the sequences optimized for human codon increases the guanine-cytosine content (GC content) of the sequence and improves expression yields in plants.

There are different codon-optimisation techniques known in the art for improving, the translational kinetics of translationally inefficient protein coding regions. These techniques mainly rely on identifying the codon usage for a certain host organism. If a certain gene or sequence should be expressed in this organism, the coding sequence of such genes and sequences will then be modified such that one will replace codons of the sequence of interest by more frequently used codons of the host organism.

Amino Acid Sequences

Non-limiting examples of rotavirus structural protein are rotavirus protein VP2, VP4, VP6 and VP7, and a fragment of VP2, VP4, VP6 and VP7. Non-limiting examples of VP2, VP4, VP6 and VP7, or fragments of VP2, VP4, VP6 and VP7 protein that may be used according to the present invention include those VP2, VP4 VP6 and VP7 protein from rotavirus strain G9 P[6], rotavirus A WA strain, rotavirus A vaccine USA/Rotarix-A41CB052A/1988/G1P1A[8] strain and rotavirus SA11 strain. For example, but not limited to Rotarix-A41CB052A: VP4 (accession #JN849113), VP7: (accession #JN849114), rotavirus A WA strain: VP2 (accession #X14942), VP4: (accession #L34161), VP6 (accession #K02086), VP7: (accession #GU723327), NSP4 (accession #K02032), rotavirus SA11 strain: VP2 (accession #NC_011506), VP4 (accession #NC_011510), VP6 (accession #NC_011509), VP7 (accession #NC_011503) and NSP4 (accession #NC_011504).

An example of a VP2 structural protein, which is not to be considered limiting, is set forth in the amino acid sequence of SEQ ID NO: 24. Furthermore, the VP2 structural protein may comprise the sequence set forth in SEQ ID NO: 24, or a sequence having at least about 90-100% sequence similarity thereto, including any percent similarity within these ranges, such as 91, 92, 93, 94, 95, 96, 97, 98, 99% sequence similarity thereto. In addition, a VP2 structural protein may be encoded by a nucleotide sequence as set forth in SEQ ID NO:21 or a sequence having at least about 80-100% sequence similarity thereto, including any percent similarity within these ranges, such as 81, 82, 83, 84, 85, 86, 87, 88, 89, 90, 91, 92, 93, 94, 95, 96, 97, 98, 99% sequence similarity thereto.

An example of a VP4 structural protein, which is not to be considered limiting, is set forth in the amino acid sequence of SEQ ID NO: 34. Furthermore, the VP4 structural protein may comprise the sequence set forth in SEQ ID NO: 34, or a sequence having at least about 90-100% sequence similarity thereto, including any percent similarity within these ranges, such as 91, 92, 93, 94, 95, 96, 97, 98, 99% sequence similarity thereto. In addition, a VP4 structural protein may be encoded by a nucleotide sequence as set forth in SEQ ID NO: 32 or a sequence having at least about 80-100% sequence similarity thereto, including any percent similarity within these ranges, such as 81, 82, 83, 84, 85, 86, 87, 88, 89, 90, 91, 92, 93, 94, 95, 96, 97, 98, 99% sequence similarity thereto.

An example of a VP6 structural protein, which is not to be considered limiting, is set forth in the amino acid sequence of SEQ ID NO: 29. Furthermore, the VP6 structural protein may comprise the sequence set forth in SEQ ID NO: 29, or a sequence having at least about 90-100% sequence similarity thereto, including any percent similarity within these ranges, such as 91, 92, 93, 94, 95, 96, 97, 98, 99% sequence similarity thereto. In addition, a VP6 structural protein may be encoded by a nucleotide sequence as set forth in SEQ ID NO:27 or a sequence having at least about 80-100% sequence similarity thereto, including any percent similarity within these ranges, such as 81, 82, 83, 84, 85, 86, 87, 88, 89, 90, 91, 92, 93, 94, 95, 96, 97, 98, 99% sequence similarity thereto.

An example of a VP7 structural protein, which is not to be considered limiting, is set forth in the amino acid sequence of SEQ ID NO: 39. Furthermore, the VP7 structural protein may comprise the sequence set forth in SEQ ID NO: 39, or a sequence having at least about 90-100% similarity thereto, including any percent similarity within these ranges, such as 91, 92, 93, 94, 95, 96, 97, 98, 99% sequence similarity thereto. In addition, a VP7 structural protein may be encoded by a nucleotide sequence as set forth in SEQ ID NO:37 or a sequence having at least about 80-100% sequence similarity thereto, including any percent similarity within these ranges, such as 81, 82, 83, 84, 85, 86, 87, 88, 89, 90, 91, 92, 93, 94, 95, 96, 97, 98, 99% sequence similarity thereto.

An example of a NSP4 structural protein, which is not to be considered limiting, is set forth in the amino acid sequence of SEQ ID NO: 44. Furthermore, the NSP4 nonstructural protein may comprise the sequence set forth in SEQ ID NO: 44, or a sequence having at least about 90-100% similarity thereto, including any percent similarity within these ranges, such as 91, 92, 93, 94, 95, 96, 97, 98, 99% sequence similarity thereto. In addition, a NSP4 nonstructural protein may be encoded by a nucleotide sequence as set forth in SEQ ID NO: 42 or a sequence having at least about 80-100% sequence similarity thereto, including any percent similarity within these ranges, such as 81, 82, 83, 84, 85, 86, 87, 88, 89, 90, 91, 92, 93, 94, 95, 96, 97, 98, 99% sequence similarity thereto.

Amino acid sequence similarity or identity may be computed by using the BLASTP and TBLASTN programs which employ the BLAST (basic local alignment search tool) 2.0 algorithm. Techniques for computing amino acid sequence similarity or identity are well known to those skilled in the art, and the use of the BLAST algorithm is described in ALTSCHUL et al. (1990, J Mol. Biol. 215: 403-410) and ALTSCHUL et al. (1997, Nucleic Acids Res. 25: 3389-3402).

Without wishing to be bound by theory, the protein concentration and ratio of the different rotavirus structural proteins may be important for the assembly efficiency of RLPs. Therefore multiplicity and time of infection, may be important to manipulate protein concentration and the overall assembly efficiency of RLPs in plants.

The construct of the present invention may be transiently expressed in a plants or portion of a plant. A transient expression system relying on the epichromosomal expression of recombinant *Agrobacterium tumefaciens* in a plant, portion of a plant or plant cell may be used to express the rotavirus structural protein, targeted to various cell compartments or sub-compartments. A transient expression system allows for a high production speed. Furthermore, large amounts of protein can be attained within a few days after infiltration of recombinant *Agrobacterium* in plants (Rybicki, 2010; Fischer et al., 1999). It is also possible to express long gene sequences and have more than one gene simultaneously expressed in the same cell, allowing for efficient assembly of multimeric proteins (Lombardi et al., 2009).

The nucleotide sequences encoding for the rotavirus structural proteins and nonstructural proteins may be transferred into the plant host using 1, 2, 3, 4 or 5 transformed *Agrobacterium tumefaciens* strains (as described in Table 1 and accompanying text During transient expression post-transcriptional gene silencing may limit the expression of the heterologous proteins in plants. The co-expression of a suppressor of silencing, for example, but not limited to Nss from Tomato spotted wilt virus may be used to counteract the specific degradation of transgene mRNAs (Brigneti et al., 1998). Alternate suppressors of silencing are well known in the art and may be used as described herein (Chiba et al., 2006, Virology 346:7-14; which is incorporated herein by reference), for example but not limited to HcPro, TEV-p1/HC-Pro (Tobacco etch virus-p1/HC-Pro), BYV-p21, p19 of Tomato bushy stunt virus (TBSV p19), capsid protein of Tomato crinkle virus (TCV-CP), 2b of Cucumber mosaic virus; CMV-2b), p25 of Potato virus X (PVX-p25), p11 of Potato virus M (PVM-p11), p11 of Potato virus S (PVS-p11), p16 of Blueberry scorch virus, (BScV-p16), p23 of Citrus tristexa virus (CTV-p23), p24 of Grapevine leafroll-associated virus-2, (GLRaV-2 p24), p10 of Grapevine virus A, (GVA-p10), p14 of Grapevine virus B (GVB-p14), p10 of Heracleum latent virus (HLV-p10), or p16 of Garlic common latent virus (GCLV-p16). Therefore, a suppressor of silencing, for example HcPro, TEV-p1/HC-Pro, BYV-p21, TBSV p19, TCV-CP, CMV-2b, PVX-p25, PVM-p11, PVS-p11, BScV-p16, CTV-p23, GLRaV-2 p24, GBV-p14, HLV-p10, GCLV-p16or GVA-p10, may be co-expressed along with one or more rotavirus structural or non structural protein for example VP2, VP4, VP6, VP7 and NSP4 or a combination thereof, to further ensure high levels of protein production within a plant or portion of a plant.

The present invention also provides a methods as described above, wherein an additional (second, third, fourth, fifth or sixth) nucleotide sequence is expressed within the plant, the additional (second, third, fourth, fifth or sixth) nucleotide sequence encoding a suppressor of silencing is operatively linked with an additional (second, third, fourth, fifth or sixth) regulatory region that is active in the plant. The nucleotide sequence encoding a suppressor of silencing may be, for example Nss, HcPro, TEV-p1/HC-Pro, BYV-p21, TBSV p19, TCV-CP, CMV-2b, PVX-p25, PVM-p11, PVS-p11, BScV-p16, CTV-p23, GLRaV-2 p24, GBV-p14, HLV-p10, GCLV-p16 or GVA-p10.

As described below, transient expression methods may be used to express the constructs of the present invention (see Liu and Lomonossoff, 2002, Journal of Virological Methods, 105:343-348; which is incorporated herein by reference). Alternatively, a vacuum-based transient expression method, as described by Kapila et al., 1997, which is incorporated herein by reference) may be used. These methods may include, for example, but are not limited to, a method of Agro-inoculation or Agro-infiltration, syringe infiltration, however, other transient methods may also be used as noted above. With Agro-inoculation, Agro-infiltration, or syringe infiltration, a mixture of Agrobacteria comprising the desired nucleic acid enter the intercellular spaces of a tissue, for example the leaves, aerial portion of the plant (including stem, leaves and flower), other portion of the plant (stem, root, flower), or the whole plant. After crossing the epidermis the Agrobacteria infect and transfer t-DNA copies into the cells. The t-DNA is episomally transcribed and the mRNA translated, leading to the production of the protein of interest in infected cells, however, the passage of t-DNA inside the nucleus is transient.

To aid in identification of transformed plant cells, the constructs of this invention may be further manipulated to include plant selectable markers. Useful selectable markers include enzymes that provide for resistance to chemicals such as an antibiotic for example, gentamycin, hygromycin, kanamycin, or herbicides such as phosphinothrycin, glyphosate, chlorosulfuron, and the like. Similarly, enzymes providing for production of a compound identifiable by colour change such as GUS (beta-glucuronidase), or luminescence, such as luciferase or GFP, may be used.

Also considered part of this invention are transgenic plants, plant cells or seeds containing the constructs as described herein. Methods of regenerating whole plants from plant cells are also known in the art. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques. Transgenic plants can also be generated without using tissue cultures.

The use of the terms "regulatory region", "regulatory element" or "promoter" in the present application is meant to reflect a portion of nucleic acid typically, but not always, upstream of the protein coding region of a gene, which may be comprised of either DNA or RNA, or both DNA and RNA. When a regulatory region is active, and in operative association, or operatively linked, with a gene of interest, this may result in expression of the gene of interest. A regulatory element may be capable of mediating organ specificity, or controlling developmental or temporal gene activation. A "regulatory region" may includes promoter elements, core promoter elements exhibiting a basal promoter activity, elements that are inducible in response to an external stimulus, elements that mediate promoter activity such as negative regulatory elements or transcriptional enhancers. "Regulatory region", as used herein, may also includes elements that are active following transcription, for example, regulatory elements that modulate gene expression such as translational and transcriptional enhancers, translational and transcriptional repressors, upstream activating sequences, and mRNA instability determinants. Several of these latter elements may be located proximal to the coding region.

In the context of this disclosure, the term "regulatory element" or "regulatory region" typically refers to a sequence of DNA, usually, but not always, upstream (5') to the coding sequence of a structural gene, which controls the expression of the coding region by providing the recognition for RNA polymerase and/or other factors required for transcription to start at a particular site. However, it is to be understood that other nucleotide sequences, located within introns, or 3' of the sequence may also contribute to the regulation of expression of a coding region of interest. An example of a regulatory element that provides for the recognition for RNA polymerase or other transcriptional factors to ensure initiation at a particular site is a promoter element. Most, but not all, eukaryotic promoter elements contain a TATA box, a conserved nucleic acid sequence comprised of adenosine and thymidine nucleotide base pairs usually situated approximately 25 base pairs upstream of a transcriptional start site. A promoter element comprises a basal promoter element, responsible for the initiation of transcription, as well as other regulatory elements (as listed above) that modify gene expression.

There are several types of regulatory regions, including those that are developmentally regulated, inducible or constitutive. A regulatory region that is developmentally regulated, or controls the differential expression of a gene under its control, is activated within certain organs or tissues of an organ at specific times during the development of that organ or tissue. However, some regulatory regions that are developmentally regulated may preferentially be active within certain organs or tissues at specific developmental stages, they may also be active in a developmentally regulated manner, or at a basal level in other organs or tissues within the plant as well. Examples of tissue-specific regulatory regions, for example see-specific a regulatory region, include the napin promoter, and the cruciferin promoter (Rask et al., 1998, J. Plant Physiol. 152: 595-599; Bilodeau et al., 1994, Plant Cell 14: 125-130). An example of a leaf-specific promoter includes the plastocyanin promoter (see U.S. Pat. No. 7,125,978, which is incorporated herein by reference).

An inducible regulatory region is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory region to activate transcription may be present in an inactive form, which is then directly or indirectly converted to the active form by the inducer. However, the protein factor may also be absent. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory region may be exposed to an inducer by externally applying the inducer to the cell or plant such as by spraying, watering, heating or similar methods. Inducible regulatory elements may be derived from either plant or non-plant genes (e.g. Gatz, C. and Lenk, L R. P., 1998, Trends Plant Sci. 3, 352-358; which is incorporated by reference). Examples, of potential inducible promoters include, but not limited to, tetracycline-inducible promoter (Gatz, C., 1997, Ann. Rev. Plant Physiol. Plant Mol. Biol. 48, 89-108; which is incorporated by reference), steroid inducible promoter (Aoyama. T. and Chua, N. H., 1997, Plant 1. 2, 397-404; which is incorporated by reference) and ethanol-inducible promoter (Salter, M. G., et al, 1998, Plant Journal 16, 127-132; Caddick, M. X., et al, 1998, Nature Biotech. 16, 177-180, which are incorporated by reference) cytokinin inducible IB6 and CKI 1 genes (Brandstatter, I. and Kieber, 1.1., 1998, Plant Cell 10, 1009-1019; Kakimoto, T., 1996, Science 274, 982-985; which are incorporated by reference) and the auxin inducible element, DR5 (Ulmasov, T., et al., 1997, Plant Cell 9, 1963-1971; which is incorporated by reference).

A constitutive regulatory region directs the expression of a gene throughout the various parts of a plant and continuously throughout plant development. Examples of known constitutive regulatory elements include promoters associated with the CaMV 35S transcript (Odell et al., 1985, Nature, 313: 810-812), the rice actin 1 (Zhang et al, 1991, Plant Cell, 3: 1155-1165), actin 2 (An et al., 1996, Plant J., 10: 107-121), or tms 2 (U.S. Pat. No. 5,428,147, which is incorporated herein by reference), and triosephosphate isomerase 1 (Xu et. al., 1994, Plant Physiol. 106: 459-467) genes, the maize ubiquitin 1 gene (Cornejo et al, 1993, Plant Mol. Biol. 29: 637-646), the *Arabidopsis* ubiquitin 1 and 6 genes (Holtorf et al, 1995, Plant Mol. Biol. 29: 637-646), and the tobacco translational initiation factor 4A gene (Mandel et al, 1995, Plant Mol. Biol. 29: 995-1004).

The term "constitutive" as used herein does not necessarily indicate that a gene under control of the constitutive regulatory region is expressed at the same level in all cell types, but that the gene is expressed in a wide range of cell types even though variation in abundance is often observed. Constitutive regulatory elements may be coupled with other sequences to further enhance the transcription and/or translation of the nucleotide sequence to which they are operatively linked. For example, the CPMV-HT system is derived from the untranslated regions of the Cowpea mosaic virus (CPMV) and demonstrates enhanced translation of the associated coding sequence. By "native" it is meant that the nucleic acid or amino acid sequence is naturally occurring, or "wild type". By "operatively linked" it is meant that the particular sequences, for example a regulatory element and a coding region of interest, interact either directly or indirectly to carry out an intended function, such as mediation or modulation of gene expression. The interaction of operatively linked sequences may, for example, be mediated by proteins that interact with the operatively linked sequences.

The RLP produced within a plant may produce a rotavirus VP7 structural protein comprising plant-specific N-glycans. Therefore, this invention also provides for a RLP comprising VP7 having plant specific N-glycans.

Furthermore, modification of N-glycan in plants is known (see for example U.S. 60/944,344; which is incorporated herein by reference) and VP7 having modified N-glycans may be produced. VP7 comprising a modified glycosylation pattern, for example with reduced fucosylated, xylosylated, or both, fucosylated and xylosylated, N-glycans may be obtained, or VP7 having a modified glycosylation pattern may be obtained, wherein the protein lacks fucosylation, xylosylation, or both, and comprises increased galactosylation. Furthermore, modulation of post-translational modifications, for example, the addition of terminal galactose may result in a reduction of fucosylation and xylosylation of the expressed VP7 when compared to a wild-type plant expressing VP7.

For example, which is not to be considered limiting, the synthesis of VP7 having a modified glycosylation pattern may be achieved by co-expressing VP7 along with a nucleotide sequence encoding beta-1.4 galactosyltransferase (GalT), for example, but not limited to mammalian GalT, or human GalT however GalT from another sources may also be used. The catalytic domain of GalT may also be fused to a CTS domain (i.e. the cytoplasmic tail, transmembrane domain, stem region) of N-acetylglucosaminyl transferase (GNT1), to produce a GNT1-GalT hybrid enzyme, and the hybrid enzyme may be co-expressed with VP7. The VP7 may also be co-expressed along with a nucleotide sequence encoding N-acetylglucosaminyl transferase III (GnT-III), for example but not limited to mammalian GnT-III or human GnT-III, GnT-III from other sources may also be used. Additionally, a GNT1-GnT-III hybrid enzyme, comprising the CTS of GNT1 fused to GnT-III may also be used.

Therefore the present invention also provides RLPs comprising VP7 having modified N-glycans.

Without wishing to be bound by theory, the presence of plant N-glycans on VP7 may stimulate the immune response by promoting the binding of VP7 by antigen presenting cells. Stimulation of the immune response using plant N glycan has been proposed by Saint-Jore-Dupas et al. (2007).

Table 2 lists sequences provided in various embodiments of the invention.

TABLE 2

| SEQ ID NO | Description | Page/FIG. |
|---|---|---|
| 1 | expression enhancer CPMVX | |
| 2 | plant kingdom kozak consensus sequence | |
| 3 | Dicots kozak consensus sequence | |
| 4 | *Arabidopsis* kozak consensus sequence | |
| 5-13 | plant kozak sequences | |
| 14 | Kozak consensus sequence | |
| 15 | CPMV HT | |
| 16 | CPMV HT+ | |

TABLE 2-continued

Figure 9F:
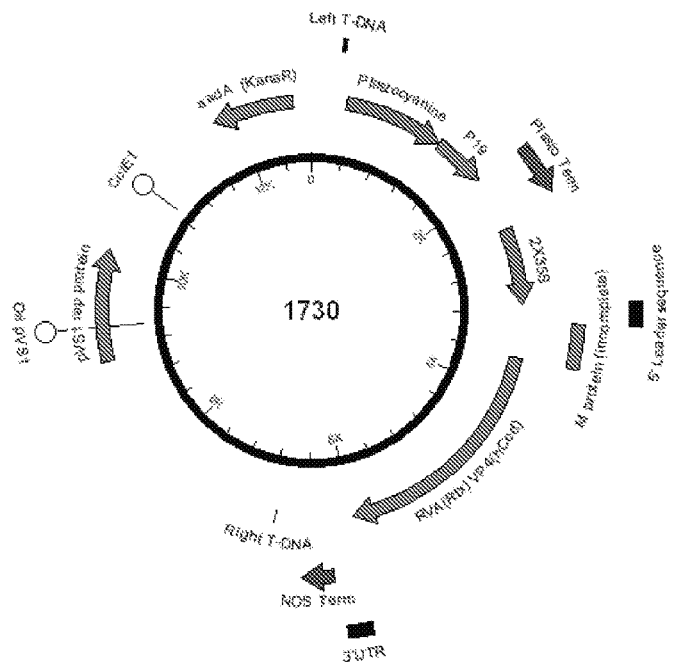

| SEQ ID NO | Description | Page/FIG. |
|---|---|---|
| 17 | CPMV HT+ 511 | |
| 18 | CPMV HT+ [WT115] | |
| 19 | IF-WA__VP2(opt).s1 + 3c | FIG. 7A |
| 20 | IF-WA__VP2(opt).s1 − 4r | FIG. 7B |
| 21 | Optimized coding sequence of Rotavirus A VP2 from strain WA | FIG. 7C |
| 22 | Construct 1191 | FIG. 7E |
| 23 | Expression cassette number 1710 | FIG. 7F |
| 24 | Amino acid sequence of VP2 from Rotavirus A WA strain | FIG. 7G |
| 25 | IF-WA__VP6(opt).s1 + 3c | FIG. 8A |
| 26 | IF-WA__VP6(opt).s1 − 4r | FIG. 8B |
| 27 | Optimized coding sequence of Rotavirus A VP6 from strain WA | FIG. 8C |
| 28 | Expression cassette number 1713 | FIG. 8D |
| 29 | Amino acid sequence of VP6 from Rotavirus A WA strain | FIG. 8E |
| 30 | IF-Rtx__VP4(opt).s1 + 3c | FIG. 9A |
| 31 | IF-Rtx__VP4(opt).s1 − 4r | FIG. 9B |
| 32 | Optimized coding sequence of Rotavirus A VP4 from strain RVA/Vaccine/USA/Rotarix-A41CB052A/1988/G1P1A[8] | FIG. 9C |
| 33 | Expression cassette number 1730 | FIG. 9D |
| 34 | Amino acid sequence of VP4 from Rotavirus A Rotarix strain | FIG. 9E |
| 35 | IF-TrSP + Rtx__VP7(opt).s1 + 3c | FIG. 10A |
| 36 | IF-Rtx__VP7(opt).s1 − 4r | FIG. 10B |
| 37 | Optimized coding sequence of Rotavirus A VP7 from strain RVA/Vaccine/USA/Rotarix-A41CB052A/1988/G1P1A[8] | FIG. 10C |
| 38 | Expression cassette number 1734 | FIG. 10D |
| 39 | Amino acid sequence of TrSp-VP7 from Rotavirus A vaccine USA/Rotarix-A41CB052A/1988/G1P1A[8] strain | FIG. 10E |
| 40 | IF-WA__NSP4.s1 + 3c | FIG. 11A |
| 41 | IF-WA__NSP4.s1 − 4r | FIG. 11B |
| 42 | Coding sequence of Rotavirus A NSV4 from strain WA | FIG. 11C |
| 43 | Expression cassette number 1706 | FIG. 11D |
| 44 | Amino acid sequence of NSP4 from Rotavirus A WA strain | FIG. 11E |
| 45 | IF(C160)-WA__VP2(opt).c | FIG. 12A |
| 46 | Construct 1190 | FIG. 12C |
| 47 | Expression cassette number 1108 | FIG. 12D |
| 48 | IF(C160)-WA__VP6(opt).c | FIG. 13A |
| 49 | Expression cassette number 1128 | FIG. 13B |
| 50 | IF(C160)-Rtx__VP4(opt).c | FIG. 14A |
| 51 | Expression cassette number 1178 | FIG. 14B |
| 52 | IF(C160)-TrSP + Rtx__VP7(opt).c | FIG. 15A |
| 53 | Expression cassette number 1199 | FIG. 15B |

The present invention will be further illustrated in the following examples.

EXAMPLES

Example 1

Materials and Methods

TABLE 3

Constructs

| Constr. # | Description | FIG. | Constr. # | Description | FIG. |
|---|---|---|---|---|---|
| 1108 | 160-VP2 | 3A/3B | 1706 | CPMV-HT NSP4 | 3A/3B 4A/4B |
| 1128 | 160-VP6 | 3A/3B | 1708 | CPMV-HT VP6/2 | 3A/3B 4A/4B |
| 1178 | 160-VP4 | 3A/3B | 2408 | 160-VP7/4 | 3A/3B 4A/4B |

TABLE 3-continued

Constructs

| Constr. # | Description | FIG. | Constr.# | Description | FIG. |
|---|---|---|---|---|---|
| 1199 | 160-VP7 | 3A/3B | 1769 | CPMV-HT VP7/4/6/2 | 3A/3B/5 |
| 1710 | CPMV-HT VP2 | 4A/4B | 2441 | CPMV-HT VP4/7/NSP4/6/2 | 5 |
| 1713 | CPMV-HT VP6 | 4A/4B | 2400 | 160-VP6/2 | 4A/4B |
| 1730 | CPMV-HT VP4 | 4A/4B | 1719 | CPMV-HT VP7/4 | 4A/4B |
| 1734 | CPMV-HT VP7 | 4A/4B | | | |

1. 2X35S/CPMV-HT/RVA(WA) VP2(opt)/NOS (Construct Number 1710)

An optimized sequence encoding VP2 from Rotavirus A WA strain was cloned into 2X35S-CPMV-HT-NOS expression system in a plasmid containing Plasto_pro/P19/Plasto_ter expression cassette using the following PCR-based method. A fragment containing the VP2 coding sequence was amplified using primers IF-WA_VP2(opt).s1+3c (FIG. 7*a*, SEQ ID NO: 19) and IF-WA_VP2(opt).s1-4r (FIG. 7B, SEQ ID NO: 20), using optimized VP2 gene sequence (FIG. 7C, SEQ ID NO:21) as template. For sequence optimization, VP2 protein sequence (Genbank accession number CAA33074) was backtranslated and optimized for human codon usage, GC content and mRNA structure. The PCR product was cloned in 2X35S/CPMV-HT/NOS expression system using In-Fusion cloning system (Clontech, Mountain View, Calif.). Construct number 1191 (FIG. 7D) was digested with SacII and StuI restriction enzyme and the linearized plasmid was used for the In-Fusion assembly reaction. Construct number 1191 is an acceptor plasmid intended for "In Fusion" cloning of genes of interest in a CPMV-HT-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 7E (SEQ ID NO: 22). The resulting construct was given number 1710 (FIG. 7F, SEQ ID NO: 23). The amino acid sequence of VP2 from Rotavirus A strain WA is presented in FIG. 7G (SEQ ID NO: 24). A representation of plasmid 1710 is presented in FIG. 7H.

2. 2X35S/CPMV-HT/RVA(WA) VP6(opt)/NOS (Construct Number 1713)

An optimized sequence encoding VP6 from Rotavirus A WA strain was cloned into 2X35S-CPMV-HT-NOS expression system in a plasmid containing Plasto_pro/P19/Plasto_ter expression cassette using the following PCR-based method. A fragment containing the VP6 coding sequence was amplified using primers IF-WA_VP6(opt).s1+3c (FIG. 8A, SEQ ID NO: 25) and IF-WA_VP6(opt).s1-4r (FIG. 8B, SEQ ID NO: 26), using optimized VP6 gene sequence (FIG. 8C, SEQ ID NO:27) as template. For sequence optimization, VP6 protein sequence (Genbank accession number AAA47311) was backtranslated and optimized for human codon usage, GC content and mRNA structure. The PCR product was cloned in 2X35S/CPMV-HT/NOS expression system using In-Fusion cloning system (Clontech, Mountain View, Calif.). Construct number 1191 (FIG. 7D) was digested with SacII and StuI restriction enzyme and the linearized plasmid was used for the In-Fusion assembly reaction. Construct number 1191 is an acceptor plasmid intended for "In Fusion" cloning of genes of interest in a CPMV-HT-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 7E (SEQ ID NO: 22). The resulting construct was given number 1713 (FIG. 8D, SEQ ID NO: 28). The amino acid sequence of VP6 from Rotavirus A strain WA is presented in FIG. 8E (SEQ ID NO: 29). A representation of plasmid 1713 is presented in FIG. 8F.

3. 2X35S/CPMV-HT/RVA(Rtx) VP4(opt)/NOS (Construct Number 1730)

An optimized sequence encoding VP4 from Rotavirus A vaccine USA/Rotarix-A41CB052A/1988/G1P1A[8] strain was cloned into 2X35S/CPMV-HT/NOS in a plasmid containing Plasto_pro/P19/Plasto_ter expression cassette using the following PCR-based method. A fragment containing the VP4 coding sequence was amplified using primers IF-Rtx_VP4(opt).s1+3c (FIG. 9A, SEQ ID NO: 30) and IF-Rtx_VP4(opt).s1-4r (FIG. 9B, SEQ ID NO: 31), using optimized VP4 gene sequence (FIG. 9C, SEQ ID NO: 32) as template. For sequence optimization, VP4 protein sequence (Genbank accession number AEX30660) was backtranslated and optimized for human codon usage, GC content and mRNA structure. The PCR product was cloned in 2X35S/CPMV-HT/NOS expression cassette using In-Fusion cloning system (Clontech, Mountain View, Calif.). Construct number 1191 (FIG. 7D) was digested with SacII and StuI restriction enzyme and the linearized plasmid was used for the In-Fusion assembly reaction. Construct number 1191 is an acceptor plasmid intended for "In Fusion" cloning of genes of interest in a CPMV-HT-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 7E (SEQ ID NO: 22). The resulting construct was given number 1730 (FIG. 9D, SEQ ID NO: 33). The amino acid sequence of VP4 from Rotavirus A vaccine USA/Rotarix-A41CB052A/1988/G1P1A[8] is presented in FIG. 9E (SEQ ID NO: 34). A representation of plasmid 1730 is presented in FIG. 9F.

4. 2X35S/CPMV-HT/TrSp-RVA(Rtx) VP7(opt)/NOS (Construct Number 1734)

An optimized sequence encoding VP7 with a truncated version of the native signal peptide from Rotavirus A vaccine USA/Rotarix-A41CB052A/1988/G1P1A[8] strain was cloned into 2X35S-CPMV-HT-NOS expression system in a plasmid containing Plasto_pro/P19/Plasto_ter expression cassette using the following PCR-based method. A fragment containing the VP7 coding sequence was amplified using primers IF-TrSP+Rtx_VP7(opt).s1+3c (FIG. 10A, SEQ ID NO: 35) and IF-Rtx_VP7(opt).s1-4r (FIG. 10B, SEQ ID NO: 36), using optimized VP7 gene sequence (corresponding to nt 88-891 from FIG. 10C, SEQ ID NO: 37) as template. For sequence optimization, VP7 protein sequence (Genbank accession number AEX30682) was backtranslated and optimized for human codon usage, GC content and mRNA structure. The PCR product was cloned in 2X35S/CPMV-HT/NOS expression system using In-Fusion cloning system (Clontech, Mountain View, Calif.). Construct number 1191 (FIG. 7D) was digested with SacII and StuI restriction enzyme and the linearized plasmid was used for the In-Fusion assembly reaction. Construct number 1191 is an acceptor plasmid intended for "In Fusion" cloning of genes of interest in a CPMV-HT-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 7E (SEQ ID NO: 22). The resulting construct was given number 1734 (FIG. 10D, SEQ ID NO: 38). The amino acid sequence of VP7 with truncated signal peptide from Rotavirus A vaccine USA/Rotarix-A41CB052A/1988/G1P1A[8] strain is presented in FIG. 10E (SEQ ID NO: 39). A representation of plasmid 1734 is presented in FIG. 10F.

5. 2X35S/CPMV-HT/RVA(WA) NSP4/NOS (Construct Number 1706)

A sequence encoding NSP4 from Rotavirus A WA strain was cloned into 2X35S-CPMV-HT-NOS expression system in a plasmid containing Plasto_pro/P19/Plasto_ter expression cassette using the following PCR-based method. A fragment containing the NSP4 coding sequence was amplified using primers IF-WA_NSP4.s1+3c (FIG. 11A, SEQ ID NO: 40) and IF-WA_NSP4.s1−4r (FIG. 11B, SEQ ID NO: 41), using synthesized NSP4 gene (corresponding to nt 42-569 from GenBank accession number K02032) (FIG. 11C, SEQ ID NO: 42) as template. The PCR product was cloned in 2X35S/CPMV-HT/NOS expression system using In-Fusion cloning system (Clontech, Mountain View, Calif.). Construct number 1191 (FIG. 7D) was digested with SacII and StuI restriction enzyme and the linearized plasmid was used for the In-Fusion assembly reaction. Construct number 1191 is an acceptor plasmid intended for "In Fusion" cloning of genes of interest in a CPMV-HT-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 7E (SEQ ID NO: 22). The resulting construct was given number 1706 (FIG. 11D, SEQ ID NO: 43). The amino acid sequence of NSP4 from Rotavirus A strain WA is presented in FIG. 11E (SEQ ID NO: 44). A representation of plasmid 1706 is presented in FIG. 11F.

6. 2X35S/CPMV-160/RVA(WA) VP2(opt)/NOS (Construct Number 1108)

An optimized sequence encoding VP2 from Rotavirus A WA strain was cloned into 2X35S/CPMV-160/NOS expression system in a plasmid containing Plasto_pro/P19/Plasto_ter expression cassette using the following PCR-based method. A fragment containing the VP2 coding sequence was amplified using primers IF(C160)-WA_VP2(opt).c (FIG. 12A, SEQ ID NO: 45) and IF-WA_VP2(opt).s1−4r (FIG. 7B, SEQ ID NO: 20), using optimized VP2 gene sequence (FIG. 7C, SEQ ID NO: 21) as template. For sequence optimization, VP2 protein sequence (Genbank accession number CAA33074) was backtranslated and optimized for human codon usage, GC content and mRNA structure. The PCR product was cloned in 2X35S/CPMV-160/NOS expression system using In-Fusion cloning system (Clontech, Mountain View, Calif.). Construct number 1190 (FIG. 12B) was digested with SacII and StuI restriction enzyme and the linearized plasmid was used for the In-Fusion assembly reaction. Construct number 1190 is an acceptor plasmid intended for "In Fusion" cloning of genes of interest in a CPMV-160-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 12C (SEQ ID NO: 46). The resulting construct was given number 1108 (FIG. 12D, SEQ ID NO: 47). The amino acid sequence of VP2 from Rotavirus A strain WA is presented in FIG. 7G (SEQ ID NO: 24). A representation of plasmid 1108 is presented in FIG. 12E.

7.—2X35S/CPMV-160/RVA(WA) VP6(opt)/NOS (Construct Number 1128)—

An optimized sequence encoding VP6 from Rotavirus A WA strain was cloned into 2X35S/CPMV-160/NOS expression system in a plasmid containing Plasto_pro/P19/Plasto_ter expression cassette using the following PCR-based method. A fragment containing the VP6 coding sequence was amplified using primers IF(C160)-WA_VP6(opt).c (FIG. 13A, SEQ ID NO: 48) and IF-WA_VP6(opt).s1−4r (FIG. 8B, SEQ ID NO: 26), using optimized VP6 gene sequence (FIG. 8C, SEQ ID NO: 27) as template. For sequence optimization, VP6 protein sequence (Genbank accession number AAA47311) was backtranslated and optimized for human codon usage, GC content and mRNA structure. The PCR product was cloned in 2X35S/CPMV-160/NOS expression system using In-Fusion cloning system (Clontech, Mountain View, Calif.). Construct number 1190 (FIG. 11B, SEQ ID NO:40) was digested with SacII and StuI restriction enzyme and the linearized plasmid was used for the In-Fusion assembly reaction. Construct number 1190 is an acceptor plasmid intended for "In Fusion" cloning of genes of interest in a CPMV-160-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 11C (SEQ ID NO: 41). The resulting construct was given number 1128 (FIG. 13B, SEQ ID NO: 49). The amino acid sequence of VP6 from Rotavirus A strain WA is presented in FIG. 8E (SEQ ID NO: 28). A representation of plasmid 1128 is presented in FIG. 13C.

8. X35S/CPMV-160/RVA(Rtx) VP4(opt)/NOS (Construct Number 1178)

An optimized sequence encoding VP4 from Rotavirus A vaccine USA/Rotarix-A41CB052A/1988/G1P1A[8] strain was cloned into 2X35S/CPMV-160/NOS in a plasmid containing Plasto_pro/P19/Plasto_ter expression cassette using the following PCR-based method. A fragment containing the VP4 coding sequence was amplified using primers IF(C160)-Rtx_VP4(opt).c (FIG. 14A, SEQ ID NO: 50) and IF-Rtx_VP4(opt).s1−4r (FIG. 9B, SEQ ID NO: 30), using optimized VP4 gene sequence (FIG. 9C, SEQ ID NO: 31) as template. For sequence optimization, VP4 protein sequence (Genbank accession number AEX30660) was backtranslated and optimized for human codon usage, GC content and mRNA structure. The PCR product was cloned in 2X35S/CPMV-160/NOS expression system using In-Fusion cloning system (Clontech, Mountain View, Calif.). Construct number 1190 (FIG. 11B, SEQ ID NO: 40) was digested with SacII and StuI restriction enzyme and the linearized plasmid was used for the In-Fusion assembly reaction. Construct number 1190 is an acceptor plasmid intended for "In Fusion" cloning of genes of interest in a CPMV-160-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 11C (SEQ ID NO: 41). The resulting construct was given number 1178 (FIG. H2, SEQ ID NO: H2). The amino acid sequence of VP4 from Rotavirus A vaccine USA/ Rotarix-A41CB052A/1988/G1P1A[8] is presented in FIG. 9E (SEQ ID NO: 33). A representation of plasmid 1178 is presented in FIG. 14C.

9. 2X35S/CPMV-160/TrSp-RVA(Rtx) VP7(opt)/NOS (Construct Number 1199)

An optimized sequence encoding VP7 with a truncated version of the native signal peptide from Rotavirus A vaccine USA/Rotarix-A41CB052A/1988/G1P1A[8] strain was cloned into 2X35S/CPMV-160/NOS expression system in a plasmid containing Plasto_pro/P19/Plasto_ter expression cassette using the following PCR-based method. A fragment containing the VP7 coding sequence was amplified using primers IF(C160)-TrSP+Rtx_VP7(opt).c (FIG. 15A, SEQ ID NO: 52) and IF-Rtx_VP7(opt).s1–4r (FIG. 10B, SEQ ID NO: 35), using optimized VP7 gene sequence (corresponding to nt 88-891 from FIG. 10C, SEQ ID NO: 36) as template. For sequence optimization, VP7 protein sequence (Genbank accession number AEX30682) was backtranslated and optimized for human codon usage, GC content and mRNA structure. The PCR product was cloned in 2X35S/CPMV-160/NOS expression system using InFusion cloning system (Clontech, Mountain View, Calif.). Construct number 1190 (FIG. 11B, SEQ ID NO: 40) was digested with SacII and StuI restriction enzyme and the linearized plasmid was used for the In-Fusion assembly reaction. Construct number 1190 is an acceptor plasmid intended for "In Fusion" cloning of genes of interest in a CPMV-160-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 11C (SEQ ID NO: 41). The resulting construct was given number 1199 (FIG. 15B, SEQ ID NO: 53). The amino acid sequence of VP7 with truncated signal peptide from Rotavirus A vaccine USA/RotarixA41CB052A/1988/G1P1A[8] strain is presented in FIG. 10E (SEQ ID NO: 38). A representation of plasmid 1199 is presented in FIG. 15C.

10. Double Gene Construct for the Expression of VP6 and VP2 Under CPMV-HT Expression Cassette (Construct Number 1708)

A single vector for the co-expression of VP6 from Rotavirus A WA strain and VP2 from Rotavirus A WA strain under the control of CPMV-HT expression system was assembled using the following restriction enzyme/ligasebased method. Donor plasmid DNA (construct number 1710; 2X35S/CPMV-HT/RVA(WA) VP2(opt)/NOS) (FIG. 7F, SEQ ID NO: 23) was digested with AvrII (located before the 2X35S promoter) and AscI (located after the NOS terminator) restriction enzymes and the fragment corresponding to 2X35S/CPMV-HT/RVA(WA) VP2(opt)/NOS expression cassette was gel-purified. This fragment was then inserted into the acceptor construct number 1713 (2X35S/ CPMV-HT/RVA(WA) VP6(opt)/NOS) (FIG. 8D, SEQ ID NO: 28) linearized using XbaI and AscI restriction enzymes (both sites are located after the NOS terminator of VP6 expression cassette). The resulting construct was given number 1708. A representation of plasmid 1708 is presented in FIG. 16.

11. Double Gene Construct for the Expression of VP7 and VP4 Under CPMV-HT Expression Cassette (Construct Number 1719)

A single vector for the co-expression of VP7 with a truncated version of the native signal peptide from Rotavirus A vaccine USA/Rotarix-A41CB052A/1988/G1P1A[8] strain and VP4 from Rotavirus A vaccine USA/RotarixA41CB052A/1988/G1P1A[8] strain under the control of CPMV-HT expression system was assembled using the following restriction enzyme/ligase-based method. Donor plasmid DNA (construct number 1730; 2X35S/CPMV-HT/ RVA(Rtx) VP4(opt)/NOS) (FIG. 9D, SEQ ID NO: 32) was digested with AvrII (located before the 2X35S promoter) and AscI (located after the NOS terminator) restriction enzymes and the fragment corresponding to 2X35S/CPMVHT/RVA(Rtx) VP4(opt)/NOS expression cassette was gelpurified. This fragment was then inserted into the acceptor construct number 1734 (2X35S/CPMV-HT/TrSp-RVA(Rtx) VP7(opt)/NOS) (FIG. 10D, SEQ ID NO: 37) linearized using XbaI and AscI restriction enzymes (both sites are located after the NOS terminator of VP7 expression cassette). The resulting construct was given number 1719. A representation of plasmid 1719 is presented in FIG. 17.

12. Double Gene Construct for the Expression of VP6 and VP2 Under CPMV-160 Expression Cassette (Construct Number 2400)

A single vector for the co-expression of VP6 from Rotavirus A WA strain and VP2 from Rotavirus A WA strain under the control of CPMV-160 expression system was assembled using the following restriction enzyme/ligasebased method. Donor plasmid DNA (construct number 1108; 2X35S/CPMV-160/RVA(WA) VP2(opt)/NOS) (FIG. 12D, SEQ ID NO: 47) was digested with AvrII (located before the 2X35S promoter) and AscI (located after the NOS terminator) restriction enzymes and the fragment corresponding to 2X35S/CPMV-160/RVA(WA) VP2(opt)/NOS expression cassette was gel-purified. This fragment was then inserted into the acceptor construct number 1128 (2X35S/ CPMV-160/RVA(WA) VP6(opt)/NOS) (FIG. 13B, SEQ ID NO: 49) linearized using XbaI and AscI restriction enzymes (both sites are located after the NOS terminator of VP6 expression cassette). The resulting construct was given number 2400. A representation of plasmid 2400 is presented in FIG. 18.

13. Double Gene Construct for the Expression of VP7 and VP4 Under CPMV-160 Expression Cassette (Construct Number 2408)

A single vector for the co-expression of VP7 with a truncated version of the native signal peptide from Rotavirus A vaccine USA/Rotarix-A41CB052A/1988/G1P1A[8] strain and VP4 from Rotavirus A vaccine USA/RotarixA41CB052A/1988/G1P1A[8] strain under the control of CPMV-160 expression system was assembled using the following restriction enzyme/ligase-based method. Donor plasmid DNA (construct number 1178; 2X35S/CPMV-160/ RVA(Rtx) VP4(opt)/NOS) (FIG. 14B, SEQ ID NO: 51) was digested with AvrII (located before the 2X35S promoter) and AscI (located after the NOS terminator) restriction enzymes and the fragment corresponding to 2X35S/CPMV160/RVA(Rtx) VP4(opt)/NOS expression cassette was gelpurified. This fragment was then inserted into the acceptor construct number 1199 (2X35S/CPMV-160/TrSp-RVA(Rtx) VP7(opt)/NOS) (FIG. 15B, SEQ ID NO: 53) linearized using XbaI and AscI restriction enzymes (both sites are located after the NOS terminator of VP7 expression cassette). The resulting construct was given number 2408. A representation of plasmid 2408 is presented in FIG. 19.

14. Quadruple Gene Construct for the Expression of VP7, VP4, VP6 and VP2 Under CPMV-HT Expression Cassette (Construct Number 1769)

A single vector for the co-expression of VP7 with a truncated version of the native signal peptide from Rotavirus A vaccine USA/Rotarix-A41CB052A/1988/G1P1A[8]

strain, VP4 from Rotavirus A vaccine USA/Rotarix-A41CB052A/1988/G1P1A[8] strain, VP6 from Rotavirus A WA strain and VP2 from Rotavirus A WA strain under the control of CPMV-HT expression system was assembled using the following restriction enzyme/ligase-based method. Donor plasmid DNA (construct number 1730; 2X35S/CPMV-HT/RVA(Rtx) VP4(opt)/NOS) (FIG. 9D, SEQ ID NO: 32) was digested with AvrII (located before the 2X35S promoter) and AscI (located after the NOS terminator) restriction enzymes and the fragment corresponding to 2X35S/CPMV-HT/RVA(Rtx) VP4(opt)/NOS expression cassette was gel-purified. This fragment was then inserted into the acceptor construct number 1734 (2X35S/CPMV-HT/TrSp-RVA(Rtx) VP7(opt)/NOS) (FIG. 10D, SEQ ID NO: 37) linearized using XbaI and AscI restriction enzymes (both sites are located after the NOS terminator of VP7 expression cassette). Ligation of cohesive ends produced by AvrII and XbaI destroyed the original restriction sites producing a temporary acceptor vector with the same unique XbaI and AscI restriction enzyme sites at the end of the NOS terminator of the second expression cassettes (from left to right T-DNA). VP6 (construct number 1713; FIG. 8D, SEQ ID NO: 28) and VP2 (construct number 1710; FIG. 7F, SEQ ID NO: 23) expressed under CPMV-HT expression system were then inserted sequentially in the resulting temporary acceptor vector using the same digestion strategy to give the final VP7/VP4/VP6/VP2 construct. The resulting construct was given number 1769. A representation of plasmid 1769 is presented in FIG. 20.

15. Quintuple Gene Construct for the Expression of VP4, VP7, NSP4, VP6 and VP2 Under CPMV-HT Expression Cassette (Construct Number 2441)

A single vector for the co-expression of VP4 from Rotavirus A vaccine USA/Rotarix-A41CB052A/1988/G1P1A[8] strain, VP7 with a truncated version of the native signal peptide from Rotavirus A vaccine USA/Rotarix-A41CB052A/1988/G1P1A[8] strain, NSP4 from Rotavirus A WA strain, VP6 from Rotavirus A WA strain and VP2 from Rotavirus A WA strain under the control of CPMV-HT expression system was assembled using the following restriction enzyme/ligase-based method. Donor plasmid DNA (construct number 1734; 2X35S/CPMV-HT/TrSp-RVA(Rtx) VP7(opt)/NOS) (FIG. 10D, SEQ ID NO: 37) was digested with AvrII (located before the 2X35S promoter) and AscI (located after the NOS terminator) restriction enzymes and the fragment corresponding to 2X35S/CPMV-HT/TrSp-RVA(Rtx) VP7(opt)/NOS expression cassette was gel-purified. This fragment was then inserted into the acceptor construct number 1730 (2X35S/CPMV-HT/RVA(Rtx) VP4(opt)/NOS) (FIG. 9D, SEQ ID NO: 32) linearized using XbaI and AscI restriction enzymes (both sites are located after the NOS terminator of VP4 expression cassette). Ligation of cohesive ends produced by AvrII and XbaI destroyed the original restriction sites producing a temporary acceptor vector with the same unique XbaI and AscI restriction enzyme sites at the end of the NOS terminator of the second expression cassettes (from left to right T-DNA). NSP4 (construct number 1706; FIG. 11D, SEQ ID NO: 42), VP6 (construct number 1713; FIG. 8D, SEQ ID NO: 28) and VP2 (construct number 1710; FIG. 7F, SEQ ID NO: 23) expressed under CPMV-HT expression system were then inserted sequentially in the resulting temporary acceptor vector using the same digestion strategy to give the final VP4/VP7/NSP4/VP6/VP2 construct. The resulting construct was given number 2441. A representation of plasmid 2441 is presented in FIG. 21.

Example 2

Co-Expression of NSP4 Increases VP4 and VP4 Incorporation into RLPs

Figure 2B:
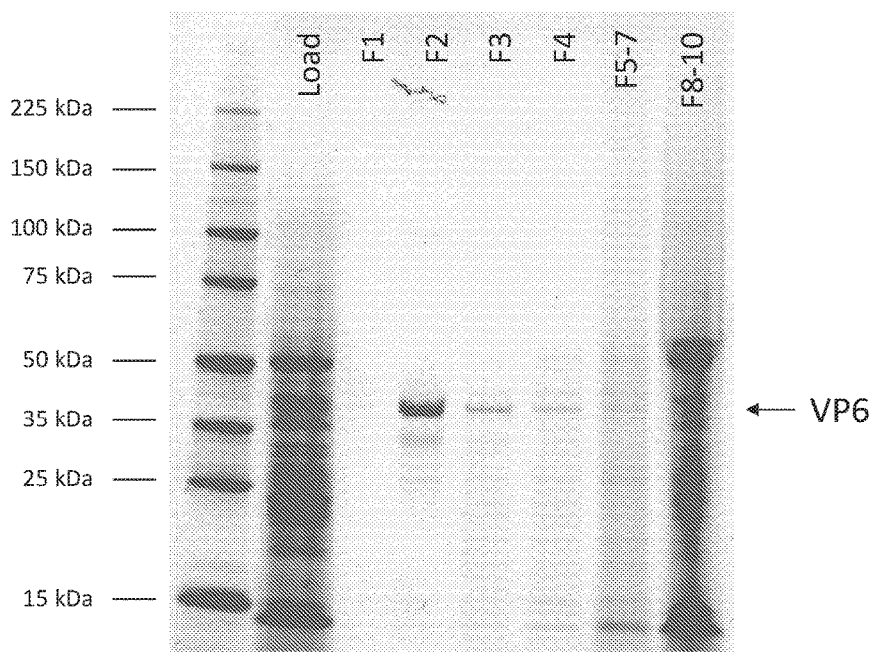
Figure 3A:
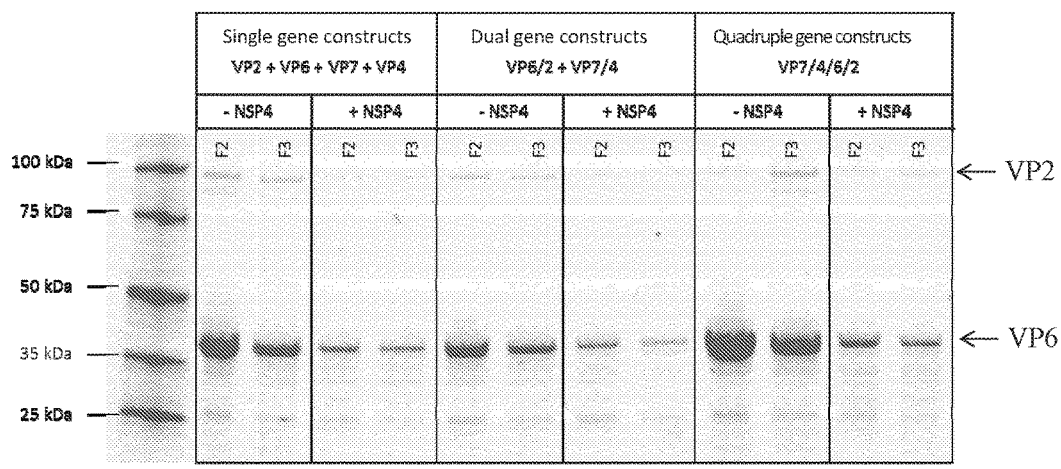

The rotavirus VP2, VP4, VP6 and VP7 structural antigens were transiently co-expressed in Nicotiana benthamiana plants in the presence or absence of a NSP4 expression construct using agroinfiltration as described in example 1. Crude protein extracts from RLP producing plants contain large amounts of host protein as shown by the banding pattern in Coomassie-stained SDS-PAGE (FIG. 2B, load). Rotavirus-like particles can be separated from plant proteins by ultracentrifugation on a iodixanol density gradient. After centrifugation, analysis of the fractions from iodixanol density gradient showed that the RLPs migrated to the 35% iodixanol fraction (F2 and F3 in FIG. 2B) while the majority of the host proteins remained in the 25-30% iodixanol fractions (F4-F10 in FIG. 2B). RLPs from plants co-expressing rotavirus structural antigens were purified on iodixanol density gradients and the analysis of the RLP containing fractions (F2 and F3) showed that RLPs can be produced efficiently, irrespectively of the number of gene per construct as shown in FIG. 3A with single, dual and quadruple gene constructs. The results obtained also showed that the co-expression of NSP4 reduced RLP expression (compare fractions under –NSP4 and +NSP4 in FIG. 3A). Note that equal volumes of each fraction were loaded on the gel to compare RLP content per volume.

Figure 3B:
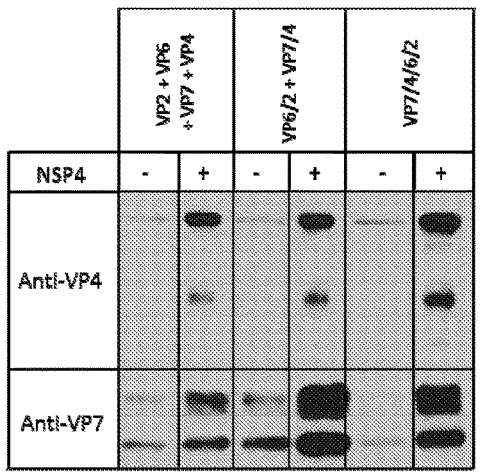

RLP-containing fraction 2 from the same experiments were analyzed by western blot to evaluate the impact of NSP4 co-expression on VP4 and VP7 incorporation. For that comparison, equal amounts of RLPS were loaded on the gel. The western blot results obtained showed stronger signals for VP4 and VP7 on the RLPs produced in the presence of NSP4 (FIG. 3B, compare lanes under –NSP4 and +NSP4). These results clearly indicate that the co-expression of NSP4 increased VP4 and VP7 incorporation on the surface of the RLPs.

Figure 4A:
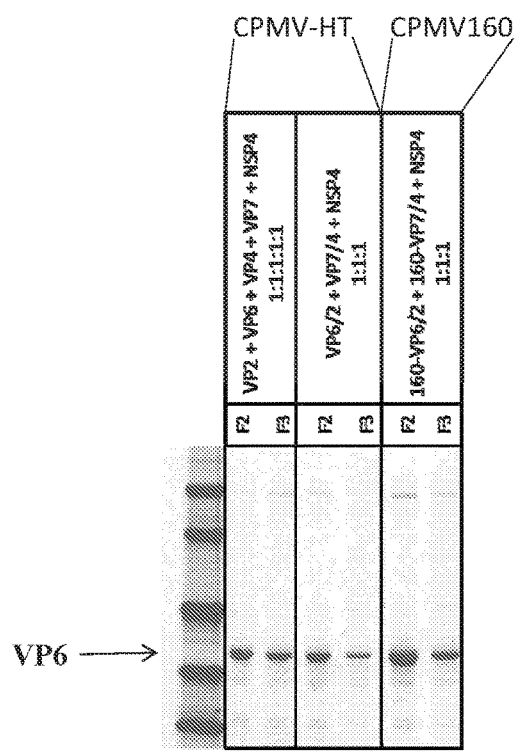
Figure 4B:
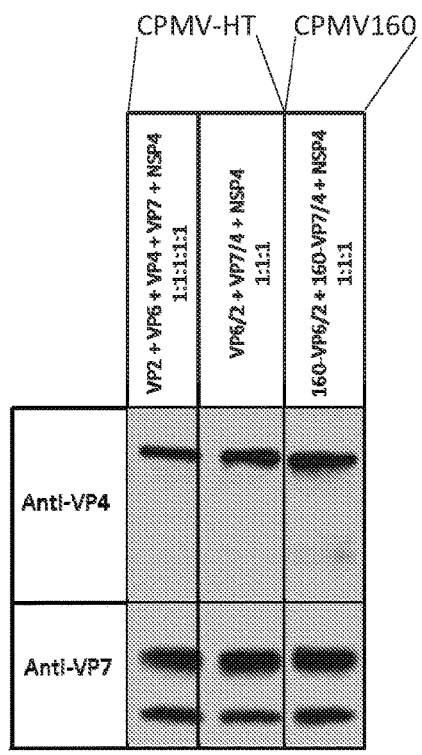

The genes encoding the four rotavirus antigens and the non-structural protein NSP4 were cloned into CPMV-HT and CPMV160 for comparison of expression. Co-expression studies followed by extraction and purification by ultracentrifugation in iodixanol density gradient showed that both expression efficiently produced RLPs, as demonstrated by the amount of VP6 in fractions 2 and 3 of the gradient (FIG. 4A), and the amount of VP4 and VP7 in fraction 2 from the same treatments (FIG. 4B). This study also showed that, when using the CPMV-HT system for expression of the rotavirus proteins, single gene constructs produced as much RLPs as dual gene constructs (FIG. 4A, left panel vs middle panel) and resulted in similar coverage with the surface antigens, VP4 and VP7 (FIG. 4B, left panel vs middle panel).

A quintuple gene construct (comprising 5 genes on the same plasmid) has been evaluated for the co-expression of the four structural antigens with NSP4. As shown in FIG. 5, the use of quintuple gene construct resulted in similar RLP production level as with the use of a quadruple gene construct with the NSP4 gene on a separate plasmid (FIG. 5, top panel), as well as comparable levels of VP4 and VP7 incorporation (FIG. 5, lower panel).

Agrobacterium Transformation

All plasmids were used to transform Agrobacterium tumefaciens (AGL1; ATCC, Manassas, Va. 20108, USA) by electroporation (Mattanovich et al., 1989, Nucleic Acid Res. 17:6747) alternatively, heat shock using CaCl2-prepared competent cells (XU et al., 2008, Plant Methods 4) may be used. The integrity of the plasmids in the *A. tumefaciens* strains created was confirmed by restriction mapping.

Preparation of Plant Biomass, Inoculum, Agroinfiltration, and Harvesting

*Nicotiana benthamiana* plants were grown from seeds in flats filled with a commercial peat moss substrate. The plants were allowed to grow in the greenhouse under a 16/8 photoperiod and a temperature regime of 25° C. day/20° C. night. Three weeks after seeding, individual plantlets were picked out, transplanted in pots and left to grow in the greenhouse for three additional weeks under the same environmental conditions.

Agrobacteria transfected with each construct were grown in a LB medium from vegetal origin and supplemented with 10 mM 2-(N-morpholino)ethanesulfonic acid (MES) and 50 μg/ml kanamycin pH5.6 until they reached an OD600 between 0.6 and 2.5. *Agrobacterium* suspensions were mixed to reach appropriate ratio for each construct and brought to 2.5× OD600 with infiltration medium (10 mM MgCl2 and 10 mM MES pH 5.6). *A. tumefaciens* suspensions were stored overnight at 4° C. On the day of infiltration, culture batches were diluted with infiltration medium and allowed to warm before use. Whole plants of *N. benthamiana* were placed upside down in the bacterial suspension in an air-tight stainless steel tank under a vacuum of 20-40 Torr for 2-min. Following infiltration, plants were returned to the greenhouse for a 9 day incubation period until harvest. Harvested biomass was kept frozen (−80° C.) until use for purification of particles.

Extraction and Screening by Ultracentrifugation of Rotavirus-Like Particles

Proteins were extracted from frozen biomass by mechanical extraction in a blender with 2 volumes of extraction buffer (TNC: 10 mM Tris pH 7.4, 140 mM NaCl, 10 mM CaCl2). The slurry was filtered through a large pore nylon filter to remove large debris and centrifuged 5000 g for 5 min at 4° C. The supernatant was collected and centrifuged again at 5000 g for 30 min (4° C.) to remove additional debris. The supernatant is then loaded on a discontinuous iodixanol density gradient.

Analytical density gradient centrifugation was performed as follows. 38 ml tubes containing discontinuous iodixanol density gradient in TNC buffer (1.2 ml at 45%, 2 ml at 35%, 5 ml at 30% and 5 ml at 25% of iodixanol) were prepared and overlaid with 25 ml of the extracts containing the rotavirus-like particles. The gradients were centrifuged at 120 000 g for 4 hours (4° C.). After centrifugation, 1 ml fractions were collected from the bottom to the top and fractions 2 and 3 (corresponding to 35% iodixanol) were analysed by SDS-PAGE combined to protein staining or Western blot.

SDS-PAGE and Immunoblotting

Protein concentrations were determined by the BCA protein assay (Pierce Biochemicals, Rockport, Ill.). Proteins were separated by SDS-PAGE under reducing conditions using Criterion™ TGX Stain-Free™ precast gels (Bio-Rad Laboratories, Hercules, Calif.) and proteins were visualized with Gel Doc™ EZ imaging system (Bio-Rad Laboratories, Hercules, Calif.).

For immunoblotting, electrophoresed proteins were electrotransferred onto polyvinylene difluoride (PVDF) membranes (Roche Diagnostics Corporation, Indianapolis, Ind.). Prior to immunoblotting, the membranes were blocked with 5% skim milk and 0.1% Tween-20 in Tris-buffered saline (TBS-T) for 16-18 h at 4° C.

Immunoblotting was performed by incubation with a suitable antibody (Table 4) in 2% skim milk in TBS-Tween 20 0.1%. Secondary antibodies used for chemiluminescence detection were as indicated in Table 4, diluted as indicated in 2% skim milk in TBS-Tween 20 0.1% Immunoreactive complexes were detected by chemiluminescence using luminol as the substrate (Roche Diagnostics Corporation, Indianapolis, Ind.).

TABLE 4

Electrophoresis conditions, antibodies, and dilutions for immunoblotting of rotavirus antigens.

| Rotavirus antigen | Electrophoresis condition | Primary antibody | Dilution | Secondary antibody | Dilution |
|---|---|---|---|---|---|
| VP4 | Reducing | Rabbit serum from immunized Rabbit with recombinant VP4 (in house) | 1:30 000 | Goat anti-rabbit (JIR 111-035-144) | 1:10 000 |
| VP7 | Reducing | Rabbit serum from immunized Rabbit with recombinant VP7 (in house) | 1:50 000 | Goat anti-rabbit (JIR 111-035-144) | 1:10 000 |

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A method of producing a rotavirus like particle (RLP) in a host or host cell comprising:

a) providing a host or host cell comprising one or more nucleic acid comprising a first nucleotide sequence encoding a first rotavirus protein, a second nucleotide sequence encoding a second rotavirus protein and a third nucleotide sequence encoding a third rotavirus protein, the first, second and third nucleotide sequence being operatively linked to one or more regulatory region active in the host or host cell; and the first nucleotide sequence encoding rotavirus protein NSP4, the second nucleotide sequence encoding rotavirus protein VP6, and the third nucleotide sequence encoding one of rotavirus protein VP7 or VP4;

b) incubating the host or host cell under conditions that permit the expression of the one or more nucleic acid, so that each of NSP4, VP6 and VP7 or VP4 are expressed, thereby producing the RLP, the RLP comprising rotavirus proteins, the rotavirus proteins consisting of rotavirus structural proteins.

2. The method of claim 1, wherein the one or more nucleic acid further comprises a fourth nucleotide sequence encoding a fourth rotavirus protein, the first, second, third, and fourth nucleotide sequence being operatively linked to one or more regulatory region active in the host or host cell; and the first nucleotide sequence encoding rotavirus protein NSP4, the second nucleotide sequence encoding rotavirus protein VP6, and the third and fourth nucleotide sequence encoding rotavirus protein VP2, VP4 or VP7 and wherein each of NSP4, VP6 and two of VP2, VP4 and VP7 are expressed from the one or more nucleic acid.

3. The method of claim 2, wherein the one or more nucleic acid further comprises a fifth nucleotide sequence encoding a fifth rotavirus protein, the first, second, third, fourth and fifth nucleotide sequence being operatively linked to one or more regulatory region active in the host or host cell; and the first, second, third, fourth and fifth nucleotide sequence encoding one of rotavirus protein VP2, VP4, VP6, VP7 or NSP4 and wherein each of VP2, VP4, VP6, VP7 and NSP4 are expressed from the one or more nucleic acid.

4. The method of claim 1, wherein the host or host cell comprises insect cells, mammalian cells, plant, portion of a plant or plant cells.

5. The method of claim 1, wherein the one or more nucleotide sequence is operatively linked to one or more expression enhancer.

6. The method of claim 5, wherein the expression enhancer is selected from the group consisting of CPMV HT, CPMV 160, CPMV 160+ and CPMV HT+.

7. The method of claim 1, further comprising the steps of:

c) harvesting the host or host cell, and d) purifying the RLPs from the host or host cell, wherein the RLPs range in size from 70-100 nm.

8. A method of producing a rotavirus like particle (RLP) in a host or host cell comprising:

a) introducing into the host or host cell one or more nucleic acid comprising a first nucleotide sequence encoding a first rotavirus protein, a second nucleotide sequence encoding a second rotavirus protein and a third nucleotide sequence encoding a third rotavirus protein, the first, second and third nucleotide sequence being operatively linked to one or more regulatory region active in the host or host cell; and the first nucleotide sequence encoding rotavirus protein NSP4, the second nucleotide sequence encoding rotavirus protein VP6, and the third nucleotide sequence encoding one of rotavirus protein VP7 or VP4;

b) incubating the host or host cell under conditions that permit the expression of the one or more nucleic acid so that each of NSP4, VP6 and VP7 or VP4 are expressed, thereby producing the RLP, the RLP comprising rotavirus proteins, the rotavirus proteins consisting of rotavirus structural proteins.

9. The method of claim 8, wherein the one or more nucleic acid further comprises a fourth nucleotide sequence encoding a fourth rotavirus protein, the first, second, third, and fourth nucleotide sequence being operatively linked to one or more regulatory region active in the host or host cell; and the first nucleotide sequence encoding rotavirus protein NSP4, the second nucleotide sequence encoding rotavirus protein VP6, and the third and fourth nucleotide sequence encoding of rotavirus protein VP2, VP4 or VP7 and wherein each of NSP4, VP6 and two of VP2, VP4 and VP7 are expressed from the one or more nucleic acid.

10. The method of claim 9, wherein the one or more nucleic acid further comprises a fifth nucleotide sequence encoding a fifth rotavirus protein, the first, second, third, fourth and fifth nucleotide sequence being operatively linked to one or more regulatory region active in the host or host cell; and the first, second, third, fourth and fifth nucleotide sequence encoding one of rotavirus protein VP2, VP4, VP6, VP7 or NSP4 and wherein each of VP2, VP4, VP6, VP7 and NSP4 are expressed from the one or more nucleic acid.

11. The method of claim 8, wherein the one or more nucleotide sequence is operatively linked to one or more expression enhancer.

12. The method of claim 11, wherein the expression enhancer is selected from the group consisting of CPMV HT, CPMV 160, CPMV 160+ and CPMV HT+.

13. The method of claim 8, further comprising the steps of:
   c) harvesting the host or host cell, and
   d) purifying the RLPs from the host or host cell, wherein the RLPs range in size from 70-100 nm.

14. An RLP produced by the method of claim 8, wherein the RLP is a triple layered RLP comprising rotavirus protein, the rotavirus protein consisting of VP2, VP4, VP6 and VP7.

15. A composition comprising an effective dose of the RLP of claim 14 for inducing an immune response in a subject, and a pharmaceutically acceptable carrier.

16. A method of inducing immunity to a rotavirus infection in a subject, comprising administering the composition of claim 15 to the subject.

17. The method of claim 16, wherein the composition is administered to a subject orally, intradermally, intranasally, intramuscularly, intraperitoneally, intravenously, or subcutaneously.

18. The method of claim 8, wherein the first rotavirus protein, the second rotavirus protein and the third rotavirus protein are obtained from any one rotavirus strain having a genotype G1 to G27.

19. The method of claim 8, wherein the first rotavirus protein, the second rotavirus protein and the third rotavirus protein are obtained from a rotavirus strain having a genotype G1 or G4.

20. A plant, portion of a plant, a plant cell, a plant matter, or a plant extract comprising an RLP produced by the method of claim 8.

21. The method of claim 1, wherein the host or host cell comprises plant, portion of plant or plant cells.

22. The method of claim 2, wherein the third and fourth nucleotide sequence encoding rotavirus protein VP2 or VP7 and wherein each of VP2, VP6, VP7 and NSP4 are expressed from the one or more nucleic acid.

23. The method of claim 22, wherein the host or host cell comprises *Nicotiana benthamiana*, portion of *Nicotiana benthamiana* or *Nicotiana benthamiana* cells.

24. The method of claim 23, wherein the nucleotide sequence encoding VP2 comprises from 80% to 100% identity with a nucleotide sequence as defined by SEQ ID NO: 21, the nucleotide sequence encoding VP6 comprises from 80% to 100% identity with a nucleotide sequence as defined by SEQ ID NO:27, the nucleotide sequence encoding VP7 comprises from 80% to 100% identity with a nucleotide sequence as defined by SEQ ID NO:37, the nucleotide sequence encoding NSP4 comprises from 80% to 100% identity with a nucleotide sequence as defined by SEQ ID NO:42.

25. The method of claim 23, wherein the VP2 comprises an amino acid sequence having from 80% to 100% identity with the amino acid sequence as defined by SEQ ID NO:24, the VP6 comprises an amino acid sequence having from 80% to 100% identity with the amino acid sequence as defined by SEQ ID NO:29, the VP7 comprises an amino acid sequence having from 80% to 100% identity with the amino acid sequence as defined by SEQ ID NO: 39, the NSP4 comprises an amino acid sequence having from 80% to 100% identity with the amino acid sequence as defined by SEQ ID NO:44.

* * * * *

UNITED STATES PATENT AND TRADEMARK OFFICE
CERTIFICATE OF CORRECTION

PATENT NO.       : 10,287,555 B2
APPLICATION NO.  : 15/545362
DATED            : May 14, 2019
INVENTOR(S)      : Pierre-Olivier Lavoie et al.

It is certified that error appears in the above-identified patent and that said Letters Patent is hereby corrected as shown below:

In the Specification

Column 3, Line 20 Delete "in"
Column 3, Line 24 Replace 'particles' with 'particle'
Column 13, Line 1 Delete repetition of "in the method"
Column 19, Line 25 Add 'be' between 'may...triple'
Column 19, Line 26 Add 'a' after 'proteins in...'
Column 22, Line 33 Add 'in' between 'resulting...co-expression'
Column 23, Line 26 Replace 'maybe also be referred to rotavirus' with 'may also be referred to as rotavirus'
Column 26, Line 35 Move full stop to after '(see FIG. 5)'
Column 27, Line 21 Add space between protein VP2
Column 28, Line 11 Add space between protein VP2
Column 31, Line 10 Remove subscript from 'R' of 'R5'
Column 32, Line 7 Remove subscript from 'P7' of 'VP7'
Column 34, Lines 3, 20, 38, 65 Add ',' between 'R1...R2'
Column 35, Lines 15, 32 & Column 36, Line 35 Add ',' between 'R1...R2'
Column 43, Lines 11 & 12 Replace 'third, fourth and fifth nucleotide sequence' with 'third and fourth nucleotide sequence'
Column 45, Line 54 Replace 'eight' with 'eighth'
Column 55, Line 9 Replace 'o' with 'of'

Signed and Sealed this
Eleventh Day of February, 2020

Andrei Iancu
*Director of the United States Patent and Trademark Office*

SEQUENCE LISTING

```
<160> NUMBER OF SEQ ID NOS: 53

<210> SEQ ID NO 1
<211> LENGTH: 160
<212> TYPE: DNA
<213> ORGANISM: Artificial sequence
<220> FEATURE:
<223> OTHER INFORMATION: Expression enhancer CPMVX

<400> SEQUENCE: 1
tattaaaatc ttaataggtt ttgataaaag cgaacgtggg gaaacccgaa ccaaaccttc      60
ttctaaactc tctctcatct ctcttaaagc aaacttctct cttgtctttc ttgcgtgagc     120
gatcttcaac gttgtcagat cgtgcttcgg caccagtaca                          160
```

```
<210> SEQ ID NO 2
<211> LENGTH: 5
<212> TYPE: DNA
<213> ORGANISM: Artificial Sequence
<220> FEATURE:
<223> OTHER INFORMATION: Plant kozak sequence
<220> FEATURE:
<221> NAME/KEY: misc_feature
<222> LOCATION: (4)..(4)
<223> OTHER INFORMATION: a or c

<400> SEQUENCE: 2 caana                                                              5

<210> SEQ ID NO 3
<211> LENGTH: 5
<212> TYPE: DNA
<213> ORGANISM: Artificial Sequence
<220> FEATURE:
<223> OTHER INFORMATION: Dicot kozak sequence
<220> FEATURE:
<221> NAME/KEY: misc_feature
<222> LOCATION: (4)..(4)
<223> OTHER INFORMATION: a or c

<400> SEQUENCE: 3 aaana                                                              5

<210> SEQ ID NO 4
<211> LENGTH: 5
<212> TYPE: DNA
<213> ORGANISM: Artificial Sequence
<220> FEATURE:
<223> OTHER INFORMATION: Arabidopsis kozak sequence
<220> FEATURE:
<221> NAME/KEY: misc_feature
<222> LOCATION: (3)..(3)
<223> OTHER INFORMATION: a or g
<220> FEATURE:
<221> NAME/KEY: misc_feature
<222> LOCATION: (4)..(4)
<223> OTHER INFORMATION: a or c

<400> SEQUENCE: 4 aanna                                                              5

<210> SEQ ID NO 5
<211> LENGTH: 5
<212> TYPE: DNA
<213> ORGANISM: Artificial Sequence
<220> FEATURE:
<223> OTHER INFORMATION: Plant kozak sequence

<400> SEQUENCE: 5 agaaa                                                              5

<210> SEQ ID NO 6
<211> LENGTH: 5
<212> TYPE: DNA
<213> ORGANISM: Artificial Sequence
<220> FEATURE:
<223> OTHER INFORMATION: Plant kozak sequence

<400> SEQUENCE: 6 agaca                                                              5

<210> SEQ ID NO 7
```

```
<211> LENGTH: 5
<212> TYPE: DNA
<213> ORGANISM: Artificial Sequence
<220> FEATURE:
<223> OTHER INFORMATION: Plant kozak sequence

<400> SEQUENCE: 7 aggaa                                                                    5

<210> SEQ ID NO 8
<211> LENGTH: 5
<212> TYPE: DNA
<213> ORGANISM: Artificial Sequence
<220> FEATURE:
<223> OTHER INFORMATION: Plant kozak sequence

<400> SEQUENCE: 8 aaaaa                                                                    5

<210> SEQ ID NO 9
<211> LENGTH: 5
<212> TYPE: DNA
<213> ORGANISM: Artificial Sequence
<220> FEATURE:
<223> OTHER INFORMATION: Plant kozak sequence

<400> SEQUENCE: 9 aaaca                                                                    5

<210> SEQ ID NO 10
<211> LENGTH: 5
<212> TYPE: DNA
<213> ORGANISM: Artificial Sequence
<220> FEATURE:
<223> OTHER INFORMATION: Plant kozak sequence

<400> SEQUENCE: 10 aagca                                                                    5

<210> SEQ ID NO 11
<211> LENGTH: 5
<212> TYPE: DNA
<213> ORGANISM: Artificial Sequence
<220> FEATURE:
<223> OTHER INFORMATION: Plant kozak sequence

<400> SEQUENCE: 11 aagaa                                                                    5

<210> SEQ ID NO 12
<211> LENGTH: 6
<212> TYPE: DNA
<213> ORGANISM: Artificial Sequence
<220> FEATURE:
<223> OTHER INFORMATION: Plant  kozak sequence

<400> SEQUENCE: 12 aaagaa                                                                   6

<210> SEQ ID NO 13
<211> LENGTH: 6
<212> TYPE: DNA
<213> ORGANISM: Artificial Sequence
<220> FEATURE:
<223> OTHER INFORMATION: Plant kozak sequence

<400> SEQUENCE: 13
``` aaagaa                                                                    6

<210> SEQ ID NO 14
<211> LENGTH: 6
<212> TYPE: DNA
<213> ORGANISM: Artificial Sequence
<220> FEATURE:
<223> OTHER INFORMATION: Kozak consensus sequence
<220> FEATURE:
<221> NAME/KEY: misc_feature
<222> LOCATION: (1)..(1)
<223> OTHER INFORMATION: A or absent
<220> FEATURE:
<221> NAME/KEY: misc_feature
<222> LOCATION: (3)..(4)
<223> OTHER INFORMATION: a or g
<220> FEATURE:
<221> NAME/KEY: misc_feature
<222> LOCATION: (5)..(5)
<223> OTHER INFORMATION: a or c

<400> SEQUENCE: 14 nannna                                                                    6

<210> SEQ ID NO 15
<211> LENGTH: 517
<212> TYPE: DNA
<213> ORGANISM: Artificial Sequence
<220> FEATURE:
<223> OTHER INFORMATION: CPMV HT expression enhancer

<400> SEQUENCE: 15
tattaaaatc ttaataggtt ttgataaaag cgaacgtggg gaaacccgaa ccaaaccttc      60
ttctaaactc tctctcatct ctcttaaagc aaacttctct cttgtctttc ttgcgtgagc     120
gatcttcaac gttgtcagat cgtgcttcgg caccagtaca acgttttctt tcactgaagc     180
gaaatcaaag atctctttgt ggacacgtag tgcggcgcca ttaaataacg tgtacttgtc     240
ctattcttgt cggtgtggtc ttgggaaaag aaagcttgct ggaggctgct gttcagcccc     300
atacattact tgttacgatt ctgctgactt tcggcgggtg caatatctct acttctgctt     360
gacgaggtat tgttgcctgt acttctttct tcttcttctt gctgattggt tctataagaa     420
atctagtatt tctttgaaa cagagttttc ccgtggtttt cgaacttgga gaaagattgt     480
taagcttctg tatattctgc ccaaatttgt cgggccc                              517

<210> SEQ ID NO 16
<211> LENGTH: 534
<212> TYPE: DNA
<213> ORGANISM: Artificial Sequence
<220> FEATURE:
<223> OTHER INFORMATION: CPMV HT plus with a plant kozak consensus
      sequence
<220> FEATURE:
<221> NAME/KEY: misc_feature
<222> LOCATION: (529)..(529)
<223> OTHER INFORMATION: a or absent
<220> FEATURE:
<221> NAME/KEY: misc_feature
<222> LOCATION: (531)..(532)
<223> OTHER INFORMATION: a or g
<220> FEATURE:
<221> NAME/KEY: misc_feature
<222> LOCATION: (533)..(533)
<223> OTHER INFORMATION: a or c

<400> SEQUENCE: 16
tattaaaatc ttaataggtt ttgataaaag cgaacgtggg gaaacccgaa ccaaaccttc      60

```
ttctaaactc tctctcatct ctcttaaagc aaacttctct cttgtctttc ttgcgtgagc    120
gatcttcaac gttgtcagat cgtgcttcgg caccagtaca acgttttctt tcactgaagc    180
gaaatcaaag atctctttgt ggacacgtag tgcggcgcca ttaaataacg tgtacttgtc    240
ctattcttgt cggtgtggtc ttgggaaaag aaagcttgct ggaggctgct gttcagcccc    300
atacattact tgttacgatt ctgctgactt tcggcgggtg caatatctct acttctgctt    360
gacgaggtat tgttgcctgt acttctttct tcttcttctt gctgattggt tctataagaa    420
atctagtatt ttctttgaaa cagagttttc ccgtggtttt cgaacttgga gaaagattgt    480
taagcttctg tatattctgc ccaaatttgt tcgggcccaa taccgcggna nnna            534
```

<210> SEQ ID NO 17
<211> LENGTH: 511
<212> TYPE: DNA
<213> ORGANISM: Cow pea mosaic virus

<400> SEQUENCE: 17

```
tattaaaatc ttaataggtt ttgataaaag cgaacgtggg gaaacccgaa ccaaaccttc     60
ttctaaactc tctctcatct ctcttaaagc aaacttctct cttgtctttc ttgcgtgagc    120
gatcttcaac gttgtcagat cgtgcttcgg caccagtaca acgttttctt tcactgaagc    180
gaaatcaaag atctctttgt ggacacgtag tgcggcgcca ttaaataacg tgtacttgtc    240
ctattcttgt cggtgtggtc ttgggaaaag aaagcttgct ggaggctgct gttcagcccc    300
atacattact tgttacgatt ctgctgactt tcggcgggtg caatatctct acttctgctt    360
gacgaggtat tgttgcctgt acttctttct tcttcttctt gctgattggt tctataagaa    420
atctagtatt ttctttgaaa cagagttttc ccgtggtttt cgaacttgga gaaagattgt    480
taagcttctg tatattctgc ccaaatttga a                                   511
```

<210> SEQ ID NO 18
<211> LENGTH: 534
<212> TYPE: DNA
<213> ORGANISM: Artificial Sequence
<220> FEATURE:
<223> OTHER INFORMATION: CPMV HT plus WT115

<400> SEQUENCE: 18

```
tattaaaatc ttaataggtt ttgataaaag cgaacgtggg gaaacccgaa ccaaaccttc     60
ttctaaactc tctctcatct ctcttaaagc aaacttctct cttgtctttc ttgcatgagc    120
gatcttcaac gttgtcagat cgtgcttcgg caccagtaca acgttttctt tcactgaagc    180
gaaatcaaag atctctttgt ggacacgtag tgcggcgcca ttaaataacg tgtacttgtc    240
ctattcttgt cggtgtggtc ttgggaaaag aaagcttgct ggaggctgct gttcagcccc    300
atacattact tgttacgatt ctgctgactt tcggcgggtg caatatctct acttctgctt    360
gacgaggtat tgttgcctgt acttctttct tcttcttctt gctgattggt tctataagaa    420
atctagtatt ttctttgaaa cagagttttc ccgtggtttt cgaacttgga gaaagattgt    480
taagcttctg tatattctgc ccaaatttgt tcgggcccaa taccgcggag aaaa            534
```

<210> SEQ ID NO 19
<211> LENGTH: 48
<212> TYPE: DNA
<213> ORGANISM: Artificial Sequence
<220> FEATURE:
<223> OTHER INFORMATION: IF WA VP2 opt.s1 plus 3c

<400> SEQUENCE: 19
aaatttgtcg ggcccatggc ataccggaag agaggagcaa agcgcgaa        48

<210> SEQ ID NO 20
<211> LENGTH: 50
<212> TYPE: DNA
<213> ORGANISM: Artificial Sequence
<220> FEATURE:
<223> OTHER INFORMATION: IF WA VP2 opt s1 4r

<400> SEQUENCE: 20
actaaagaaa ataggccttt aaagctcgtt cattattcgc atattgtcga        50

<210> SEQ ID NO 21
<211> LENGTH: 2673
<212> TYPE: DNA
<213> ORGANISM: Artificial Sequence
<220> FEATURE:
<223> OTHER INFORMATION: Optimized coding sequence of Rotavirus A VP2
      from strain WA

<400> SEQUENCE: 21
atggcatacc ggaagagagg agcaaagcgc gaaaacctgc cgcaacagaa cgagagactg       60
caagaaaaag agatagagaa agatgtcgac gtaacaatgg aaaacaagaa taacaatagg      120
aaacaacagc tgtccgacaa agttctgtcc cagaaggagg aaattatcac tgacgcccag      180
gacgatatta aaattgccgg agaaataaag aagagctcga agaagaatc taaacagctg       240
ctcgaaattc tgaaaacaaa agaagaccat cagaaagaga ttcaatatga aattttgcaa       300
aaaacaatac ctacatttga gtccaaagaa agtatcctca gaagcttga agacataaga       360
ccggagcagg caaaaaaaca gatgaaactc tttcgcattt tcgagccaaa acagctccct       420
atatatcgcg ccaatggcga aaggagcta cgcaaccggt ggtactggaa gttgaaaaaa       480
gacacccctg cagatggaga ttatgacgtc cgggagtatt tcctcaatct ctatgatcag       540
atcctcatcg aaatgccgga ctatctgctc ctcaaggaca tggccgtgga gaacaaaaat       600
agcagagacg ccggcaaagt tgtcgactct gagactgcca atatttgtga tgccatcttc       660
caggatgagg agaccgaggg agtcgtccgt agattcatcg ctgatatgcg gcaacaggtc       720
caggctgatc gtaacattgt caattaccct tccatccttc accctattga tcatgcattc       780
aatgagtatt ttcttaacca ccagttggtg agccgctga caatgagat aatcttcaat       840
tacataccag agaggataag gaatgacgtg aattacatcc tgaacatgga tatgaatctg       900
ccatctacag ccaggtatat caggccaaac ttgttgcagg atagactgaa tcttcacgat       960
aattttgagt ccctgtggga taccatcaca acatccaact acattctggc caggtccgtc      1020
gttcccgatt tgaaggagaa ggagctggtc tccaccgaag cacagatcca gaaaatgagc      1080
caggacctgc agctggaggc cctcactatt cagagcgaga cacagttttt agccgggatt      1140
aacagtcagg ctgccaatga ttgtttcaag accctcatag ccgccatgct gtctcaaaga      1200
accatgtctt tggactttgt gaccacgaac tatatgagcc taatctccgg aatgtggcta      1260
cttacagtga ttcccaacga tatgttcctc cgggagtcac tagtggcctg tgagctggcg      1320
atcatcaaca ccatcgtgta tccagcattc ggaatgcaga aatgcatta ccggaatggc      1380
gaccctcaga caccttcca gatcgcagaa cagcagatcc agaatttcca ggtggcgaac      1440
tggctccatt ttattaacaa taacagattc aggcaagttg tgattgatgg agttctgaat      1500
cagactctga acgacaatat acggaatgga caggtcatca accagctgat ggaagcattg      1560

| | |
|---|---|
| atgcaactca gcagacagca gttccccacg atgcctgtgg attacaaacg gagcatccaa | 1620 |
| cggggcattc tgcttctctc caataggctg gggcagcttg tcgacttaac ccgactggtc | 1680 |
| tcctataact acgagacgct aatggcttgt gtgaccatga acatgcagca cgtgcaaacc | 1740 |
| ctgacaactg agaagttgca gctcacttct gtgacttcgc tttgtatgtt aattggtaac | 1800 |
| acaaccgtga ttccgtcccc acagacactg ttccactact acaacatcaa cgtgaatttc | 1860 |
| cactccaatt ataatgagcg gatcaacgac gccgtcgcca taattaccgc agcaaatagg | 1920 |
| ctgaatcttt atcagaaaaa aatgaagtcc atagtggaag actttctgaa acggctccag | 1980 |
| attttcgacg taccacgagt gcctgacgac caaatgtaca ggctgaggga tcgccttcgg | 2040 |
| ctcttacccg ttgaacggag acggcttgac atattcaact tgatcctgat gaatatggag | 2100 |
| cagatcgaac gcgcttctga taagattgct caggggggtta tcatcgcata ccgagatatg | 2160 |
| cagctggaac gcgacgagat gtacggatat gttaatattg cacggaatct tgatggctac | 2220 |
| cagcaaatta acttggagga actcatgcgc accggtgatt acggacaaat tacgaacatg | 2280 |
| cttctcaaca atcaacccgt tgcccttgtg ggtgcattgc ccttcgttac ggactcatcc | 2340 |
| gtgatcagtc taatcgccaa gctcgacgca accgtcttcg ctcagatagt gaagctcagg | 2400 |
| aaagttgaca cactgaagcc catactgtac aaaataaact cggattccaa tgacttttac | 2460 |
| cttgtggcca actacgactg gatccccaca agtacaacta aggtctacaa acaggtgcca | 2520 |
| caaccattcg actttagagc cagcatgcac atgctgactt ctaaccttac gtttaccgtc | 2580 |
| tactctgacc tactgtcatt tgtttcagcg gacacggtag agcccattaa cgcagtcgca | 2640 |
| ttcgacaata tgcgaataat gaacgagctt taa | 2673 |

<210> SEQ ID NO 22
<211> LENGTH: 4875
<212> TYPE: DNA
<213> ORGANISM: Artificial Sequence
<220> FEATURE:
<223> OTHER INFORMATION: Construct 1191

<400> SEQUENCE: 22

| | |
|---|---|
| ttgacgctta gacaacttaa taacacattg cggacgtttt taatgtactg aattaacgcc | 60 |
| gaatcccggg ctggtatatt tatatgttgt caaataactc aaaaaccata aaagtttaag | 120 |
| ttagcaagtg tgtacatttt tacttgaaca aaaatattca cctactactg ttataaatca | 180 |
| ttattaaaca ttagagtaaa gaaatatgga tgataagaac aagagtagtg atattttgac | 240 |
| aacaattttg ttgcaacatt tgagaaaatt ttgttgttct ctcttttcat ggtcaaaaa | 300 |
| caatagagag agaaaaagga agagggagaa taaaaacata atgtgagtat gagagagaaa | 360 |
| gttgtacaaa agttgtacca aaatagttgt acaaatatca ttgaggaatt tgacaaaagc | 420 |
| tacacaaata agggttaatt gctgtaaata aataaggatg acgcattaga gagatgtacc | 480 |
| attagagaat ttttggcaag tcattaaaaa gaaagaataa attatttta aaattaaaag | 540 |
| ttgagtcatt tgattaaaca tgtgattatt taatgaattg atgaaagagt tggattaaag | 600 |
| ttgtattagt aattagaatt tggtgtcaaa tttaatttga catttgatct tttcctatat | 660 |
| attgccccat agagtcagtt aactcatttt tatatttcat agatcaaata agagaaataa | 720 |
| cggtatatta atccctccaa aaaaaaaaaa cggtatattt actaaaaaat ctaagccacg | 780 |
| taggaggata acaggatccc cgtaggagga taacatccaa tccaaccaat cacaacaatc | 840 |
| ctgatgagat aacccacttt aagcccacgc atctgtggca catctacatt atctaaatca | 900 |
| cacattcttc cacacatctg agccacacaa aaaccaatcc acatctttat cacccattct | 960 |

```
ataaaaaatc acactttgtg agtctacact ttgattccct tcaaacacat acaaagagaa    1020
gagactaatt aattaattaa tcatcttgag agaaaatgga acgagctata caaggaaacg    1080
acgctaggga acaagctaac agtgaacgtt gggatggagg atcaggaggt accacttctc    1140
ccttcaaact tcctgacgaa agtccgagtt ggactgagtg gcggctacat aacgatgaga    1200
cgaattcgaa tcaagataat ccccttggtt tcaaggaaag ctggggtttc gggaaagttg    1260
tatttaagag atatctcaga tacgacagga cggaagcttc actgcacaga gtccttggat    1320
cttggacggg agattcggtt aactatgcag catctcgatt tttcggtttc gaccagatcg    1380
gatgtaccta tagtattcgg tttcgaggag ttagtatcac cgtttctgga gggtcgcgaa    1440
ctcttcagca tctctgtgag atggcaattc ggtctaagca agaactgcta cagcttgccc    1500
caatcgaagt ggaaagtaat gtatcaagag gatgccctga aggtactcaa accttcgaaa    1560
aagaaagcga gtaagttaaa atgcttcttc gtctcctatt tataatatgg tttgttattg    1620
ttaattttgt tcttgtagaa gagcttaatt aatcgttgtt gttatgaaat actatttgta    1680
tgagatgaac tggtgtaatg taattcattt acataagtgg agtcagaatc agaatgtttc    1740
ctccataact aactagacat gaagacctgc cgcgtacaat tgtcttatat ttgaacaact    1800
aaaattgaac atcttttgcc acaactttat aagtggttaa tatagctcaa atatatggtc    1860
aagttcaata gattaataat ggaaatatca gttatcgaaa ttcattaaca atcaacttaa    1920
cgttattaac tactaatttt atatcatccc ctttgataaa tgatagtaca ccaattagga    1980
aggagcatgc tcgcctagga gattgtcgtt tcccgccttc agtttgcaag ctgctctagc    2040
cgtgtagcca atacgcaaac cgcctctccc cgcgcgttgg gaattactag cgcgtgtcga    2100
caagcttgca tgccggtcaa catggtggag cacgacacac ttgtctactc caaaaatatc    2160
aaagatacag tctcagaaga ccaaagggca attgagactt ttcaacaaag ggtaaatatcc   2220 ggaaacctcc tcggattcca ttgcccagct atctgtcact ttattgtgaa gatagtggaa    2280
aaggaaggtg gctcctacaa atgccatcat tgcgataaag gaaaggccat cgttgaagat    2340
gcctctgccg acagtggtcc caaagatgga cccccaccca cgaggagcat cgtggaaaaa    2400
gaagacgttc caaccacgtc ttcaaagcaa gtggattgat gtgataacat ggtggagcac    2460
gacacacttg tctactccaa aaatatcaaa gatacagtct cagaagacca aagggcaatt    2520 gagactttc aacaagggt aatatccgga acctcctcg gattccattg cccagctatc    2580
tgtcacttta ttgtgaagat agtggaaaag gaaggtggct cctacaaatg ccatcattgc    2640
gataaaggaa aggccatcgt tgaagatgcc tctgccgaca gtggtcccaa agatggaccc    2700
ccacccacga ggagcatcgt ggaaaaagaa gacgttccaa ccacgtcttc aaagcaagtg    2760
gattgatgtg atatctccac tgacgtaagg gatgacgcac aatcccacta tccttcgcaa    2820
gacccttcct ctatataagg aagttcattt catttggaga ggtattaaaa tcttaatagg    2880
ttttgataaa agcgaacgtg gggaaacccg aaccaaacct tcttctaaac tctctctcat    2940
ctctcttaaa gcaaacttct ctcttgtctt tcttgcgtga gcgatcttca acgttgtcag    3000
atcgtgcttc ggcaccagta caacgttttc tttcactgaa gcgaaatcaa agatctcttt    3060
gtggacacgt agtgcggcgc cattaaataa cgtgtacttg tcctattctt gtcggtgtgg    3120
tcttgggaaa agaaagcttg ctggaggctg ctgttcagcc ccatacatta cttgttacga    3180
ttctgctgac tttcggcggg tgcaatatct ctacttctgc ttgacgaggt attgttgcct    3240
gtacttcttt cttcttcttc ttgctgattg gttctataag aaatctagta ttttctttga    3300
```

```
aacagagttt tcccgtggtt ttcgaacttg gagaaagatt gttaagcttc tgtatattct   3360
gcccaaattt gtcgggcccg cggatggcga aaaacgttgc gattttcggc ttattgtttt   3420
ctcttcttgt gttggttcct tctcagatct tcgcctgcag gctcctcagc caaaacgaca   3480
cccccatctg tctatccact ggcccctgga tctgctgccc aaactaactc catggtgacc   3540
ctgggatgcc tggtcaaggg ctatttccct gagccagtga cagtgacctg gaactctgga   3600
tccctgtcca gcggtgtgca caccttccca gctgtcctgc agtctgacct ctacactctg   3660
agcagctcag tgactgtccc ctccagcacc tggcccagcg agaccgtcac ctgcaacgtt   3720
gcccacccgg ccagcagcac caaggtggac aagaaaattg tgcccaggga ttgtggttgt   3780
aagccttgca tatgtacagt cccagaagta tcatctgtct tcatcttccc cccaaagccc   3840
aaggatgtgc tcaccattac tctgactcct aaggtcacgt gtgttgtggt agacatcagc   3900
aaggatgatc ccgaggtcca gttcagctgg tttgtagatg atgtggaggt gcacacagct   3960
cagacgcaac cccgggagga gcagttcaac agcactttcc gctcagtcag tgaacttccc   4020
atcatgcacc aggactggct caatggcaag gagcgatcgc tcaccatcac catcaccatc   4080
accatcacca ttaaaggcct attttctttta gtttgaattt actgttattc ggtgtgcatt   4140
tctatgtttg gtgagcggtt ttctgtgctc agagtgtgtt tattttatgt aatttaattt   4200
ctttgtgagc tcctgtttag caggtcgtcc cttcagcaag gacacaaaaa gatttaatt   4260 ttattaaaaa aaaaaaaaaa aaagacccggg aattcgatat caagcttatc gacctgcaga   4320
tcgttcaaac atttggcaat aaagtttctt aagattgaat cctgttgccg gtcttgcgat   4380
gattatcata taatttctgt tgaattacgt taagcatgta ataattaaca tgtaatgcat   4440
gacgttattt atgagatggg ttttttatgat tagagtcccg caattataca tttaatacgc   4500
gatagaaaac aaaatatagc gcgcaaacta ggataaatta tcgcgcgcgg tgtcatctat   4560
gttactagat ctctagagtc tcaagcttgg cgcgcccacg tgactagtgg cactggccgt   4620
cgttttacaa cgtcgtgact gggaaaaccc tggcgttacc caacttaatc gccttgcagc   4680
acatccccct ttcgccagct ggcgtaatag cgaagaggcc cgcaccgatc gcccttccca   4740
acagttgcgc agcctgaatg gcgaatgcta gagcagcttg agcttggatc agattgtcgt   4800
ttcccgcctt cagtttaaac tatcagtgtt tgacaggata tattggcggg taaacctaag   4860
agaaaagagc gttta                                                   4875

<210> SEQ ID NO 23
<211> LENGTH: 4413
<212> TYPE: DNA
<213> ORGANISM: Artificial Sequence
<220> FEATURE:
<223> OTHER INFORMATION: Expression cassette number 1710

<400> SEQUENCE: 23
gtcaacatgg tggagcacga cacacttgtc tactccaaaa atatcaaaga tacagtctca     60
gaagaccaaa gggcaattga gacttttcaa caaagggtaa tatccggaaa cctcctcgga    120
ttccattgcc cagctatctg tcactttatt gtgaagatag tggaaaagga aggtggctcc    180
tacaaatgcc atcattgcga taaaggaaag gccatcgttg aagatgcctc tgccgacagt    240
ggtcccaaag atggaccccc acccacgagg agcatcgtgg aaaaagaaga cgttccaacc    300
acgtcttcaa agcaagtgga ttgatgtgat aacatggtgg agcacgacac acttgtctac    360
tccaaaaata tcaagatac agtctcagaa gaccaaaggg caattgagac ttttcaacaa    420
agggtaatat ccggaaacct cctcggattc cattgcccag ctatctgtca ctttattgtg    480
```

```
aagatagtgg aaaaggaagg tggctcctac aaatgccatc attgcgataa aggaaaggcc    540
atcgttgaag atgcctctgc cgacagtggt cccaaagatg accccccacc cacgaggagc    600
atcgtggaaa aagaagacgt tccaaccacg tcttcaaagc aagtggattg atgtgatatc    660
tccactgacg taagggatga cgcacaatcc cactatcctt cgcaagaccc ttcctctata    720
taaggaagtt catttcattt ggagaggtat taaaatctta ataggttttg ataaaagcga    780
acgtggggaa acccgaacca aaccttcttc taaactctct ctcatctctc ttaaagcaaa    840
cttctctctt gtctttcttg cgtgagcgat cttcaacgtt gtcagatcgt gcttcggcac    900
cagtacaacg ttttctttca ctgaagcgaa atcaaagatc tctttgtgga cacgtagtgc    960
ggcgccatta ataacgtgt  acttgtccta ttcttgtcgg tgtggtcttg ggaaaagaaa   1020
gcttgctgga ggctgctgtt cagccccata cattacttgt tacgattctg ctgactttcg   1080
gcgggtgcaa tatctctact tctgcttgac gaggtattgt tgcctgtact tctttcttct   1140
tcttcttgct gattggttct ataagaaatc tagtattttc tttgaaacag agttttcccg   1200
tggttttcga acttggagaa agattgttaa gcttctgtat attctgccca aatttgtcgg   1260
gcccatggca taccggaaga gaggagcaaa gcgcgaaaac ctgccgcaac agaacgagag   1320
actgcaagaa aaagagatag agaaagatgt cgacgtaaca atggaaaaca agaataacaa   1380
taggaaacaa cagctgtccg acaaagttct gtcccagaag gaggaaatta tcactgacgc   1440
ccaggacgat attaaaattg ccggagaaat aaagaagagc tcgaaagaag aatctaaaca   1500
gctgctcgaa attctgaaaa caaaagaaga ccatcagaaa gagattcaat atgaaatttt   1560
gcaaaaaaca atacctacat ttgagtccaa agaaagtatc ctcaagaagc ttgaagacat   1620
aagaccggag caggcaaaaa aacagatgaa actctttcgc attttcgagc caaaacagct   1680
ccctatatat cgcgccaatg gcgagaagga gctacgcaac cggtggtact ggaagttgaa   1740
aaaagacacc ctgccagatg gagattatga cgtccgggag tatttcctca atctctatga   1800
tcagatcctc atcgaaatgc cggactatct gctcctcaag gacatggccg tggagaacaa   1860
aaatagcaga gacgccggca agttgtcga  ctctgagact gccaatattt gtgatgccat   1920
cttccaggat gaggagaccg agggagtcgt ccgtagattc atcgctgata tgcggcaaca   1980
ggtccaggct gatcgtaaca ttgtcaatta cccttccatc cttcacccta ttgatcatgc   2040
attcaatgag tattttctta accaccagtt ggtggagccg ctgaacaatg agataatctt   2100
caattacata ccagagagga taaggaatga cgtgaattac atcctgaaca tggatatgaa   2160
tctgccatct acagccaggt atatcaggcc aaacttgttg caggatagac tgaatcttca   2220
cgataatttt gagtccctgt gggataccat cacaacatcc aactacattc tggccaggtc   2280
cgtcgttccc gatttgaagg agaaggagct ggtctccacc gaagcacaga tccagaaaat   2340
gagccaggac ctgcagctgg aggccctcac tattcagagc gagacacagt ttttagccgg   2400
gattaacagt caggctgcca atgattgttt caagaccctc atagccgcca tgctgtctca   2460
aagaaccatg tctttggact tgtgaccac  gaactatatg agcctaatct ccggaatgtg   2520
gctacttaca gtgattccca acgatatgtt cctccgggag tcactagtgg cctgtgagct   2580
ggcgatcatc aacaccatcg tgtatccagc attcggaatg cagagaatgc attaccggaa   2640
tggcgaccct cagacaccct tccagatcgc agaacagcag atccagaatt ccaggtggc   2700 gaactggctc cattttatta acaataacag attcaggcaa gttgtgattg atggagttct   2760
gaatcagact ctgaacgaca atatacggaa tggacaggtc atcaaccagc tgatggaagc   2820
```

```
attgatgcaa ctcagcagac agcagttccc cacgatgcct gtggattaca aacggagcat    2880
ccaacgggc attctgcttc tctccaatag gctggggcag cttgtcgact taacccgact     2940
ggtctcctat aactacgaga cgctaatggc ttgtgtgacc atgaacatgc agcacgtgca    3000
aaccctgaca actgagaagt tgcagctcac ttctgtgact tcgctttgta tgttaattgg    3060
taacacaacc gtgattccgt ccccacagac actgttccac tactacaaca tcaacgtgaa    3120
tttccactcc aattataatg agcggatcaa cgacgccgtc gccataatta ccgcagcaaa    3180
taggctgaat ctttatcaga aaaaaatgaa gtccatagtg aagactttc tgaaacggct     3240
ccagattttc gacgtaccac gagtgcctga cgaccaaatg tacaggctga gggatcgcct    3300
tcggctctta cccgttgaac ggagacggct tgacatattc aacttgatcc tgatgaatat    3360
ggagcagatc gaacgcgctt ctgataagat tgctcagggg gttatcatcg cataccgaga    3420
tatgcagctg aacgcgacg agatgtacgg atatgttaat attgcacgga atcttgatgg     3480
ctaccagcaa attaacttgg aggaactcat gcgcaccggt gattacgac aaattacgaa     3540
catgcttctc aacaatcaac ccgttgccct tgtgggtgca ttgcccttcg ttacggactc    3600
atccgtgatc agtctaatcg ccaagctcga cgcaaccgtc ttcgctcaga tagtgaagct    3660
caggaaagtt gacacactga agcccatact gtacaaaata aactcggatt ccaatgactt    3720
ttaccttgtg ccaactacg actggatccc cacaagtaca actaaggtct acaaacaggt    3780
gccacaacca ttcgacttta gagccagcat gcacatgctg acttctaacc ttacgtttac    3840
cgtctactct gacctactgt catttgtttc agcggacacg gtagagccca ttaacgcagt    3900
cgcattcgac aatatgcgaa taatgaacga gctttaaagg cctatttct ttagtttgaa     3960
tttactgtta ttcggtgtgc atttctatgt ttggtgagcg gttttctgtg ctcagagtgt    4020
gtttatttta tgtaatttaa tttctttgtg agctcctgtt tagcaggtcg tcccttcagc    4080
aaggacacaa aagattttta attttattaa aaaaaaaaa aaaaagacc gggaattcga      4140
tatcaagctt atcgacctgc agatcgttca acatttggc aataaagttt cttaagattg     4200
aatcctgttg ccggtcttgc gatgattatc atataatttc tgttgaatta cgttaagcat    4260
gtaataatta acatgtaatg catgacgtta tttatgagat gggtttttat gattagagtc    4320
ccgcaattat acatttaata cgcgatagaa aacaaatat agcgcgcaaa ctaggataaa     4380
ttatcgcgcg cggtgtcatc tatgttacta gat                                 4413
```

<210> SEQ ID NO 24
<211> LENGTH: 890
<212> TYPE: PRT
<213> ORGANISM: Rotavirus

<400> SEQUENCE: 24

```
Met Ala Tyr Arg Lys Arg Gly Ala Lys Arg Glu Asn Leu Pro Gln Gln
1               5                   10                  15

Asn Glu Arg Leu Gln Glu Lys Glu Ile Glu Lys Asp Val Asp Val Thr
            20                  25                  30

Met Glu Asn Lys Asn Asn Asn Arg Lys Gln Gln Leu Ser Asp Lys Val
        35                  40                  45

Leu Ser Gln Lys Glu Glu Ile Ile Thr Asp Ala Gln Asp Asp Ile Lys
    50                  55                  60

Ile Ala Gly Glu Ile Lys Lys Ser Ser Lys Glu Glu Ser Lys Gln Leu
65                  70                  75                  80

Leu Glu Ile Leu Lys Thr Lys Glu Asp His Gln Lys Glu Ile Gln Tyr
                85                  90                  95
```

-continued

Glu Ile Leu Gln Lys Thr Ile Pro Thr Phe Glu Ser Lys Glu Ser Ile
            100                 105                 110

Leu Lys Lys Leu Glu Asp Ile Arg Pro Glu Gln Ala Lys Lys Gln Met
            115                 120                 125

Lys Leu Phe Arg Ile Phe Glu Pro Lys Gln Leu Pro Ile Tyr Arg Ala
        130                 135                 140

Asn Gly Glu Lys Glu Leu Arg Asn Arg Trp Tyr Trp Lys Leu Lys Lys
145                 150                 155                 160

Asp Thr Leu Pro Asp Gly Asp Tyr Asp Val Arg Glu Tyr Phe Leu Asn
                165                 170                 175

Leu Tyr Asp Gln Ile Leu Ile Glu Met Pro Asp Tyr Leu Leu Leu Lys
            180                 185                 190

Asp Met Ala Val Glu Asn Lys Asn Ser Arg Asp Ala Gly Lys Val Val
        195                 200                 205

Asp Ser Glu Thr Ala Asn Ile Cys Asp Ala Ile Phe Gln Asp Glu Glu
    210                 215                 220

Thr Glu Gly Val Val Arg Arg Phe Ile Ala Asp Met Arg Gln Gln Val
225                 230                 235                 240

Gln Ala Asp Arg Asn Ile Val Asn Tyr Pro Ser Ile Leu His Pro Ile
                245                 250                 255

Asp His Ala Phe Asn Glu Tyr Phe Leu Asn His Gln Leu Val Glu Pro
            260                 265                 270

Leu Asn Asn Glu Ile Ile Phe Asn Tyr Ile Pro Glu Arg Ile Arg Asn
        275                 280                 285

Asp Val Asn Tyr Ile Leu Asn Met Asp Met Asn Leu Pro Ser Thr Ala
290                 295                 300

Arg Tyr Ile Arg Pro Asn Leu Leu Gln Asp Arg Leu Asn Leu His Asp
305                 310                 315                 320

Asn Phe Glu Ser Leu Trp Asp Thr Ile Thr Thr Ser Asn Tyr Ile Leu
                325                 330                 335

Ala Arg Ser Val Val Pro Asp Leu Lys Glu Lys Glu Leu Val Ser Thr
            340                 345                 350

Glu Ala Gln Ile Gln Lys Met Ser Gln Asp Leu Gln Leu Glu Ala Leu
        355                 360                 365

Thr Ile Gln Ser Glu Thr Gln Phe Leu Ala Gly Ile Asn Ser Gln Ala
    370                 375                 380

Ala Asn Asp Cys Phe Lys Thr Leu Ile Ala Ala Met Leu Ser Gln Arg
385                 390                 395                 400

Thr Met Ser Leu Asp Phe Val Thr Thr Asn Tyr Met Ser Leu Ile Ser
                405                 410                 415

Gly Met Trp Leu Leu Thr Val Ile Pro Asn Asp Met Phe Leu Arg Glu
            420                 425                 430

Ser Leu Val Ala Cys Glu Leu Ala Ile Ile Asn Thr Ile Val Tyr Pro
        435                 440                 445

Ala Phe Gly Met Gln Arg Met His Tyr Arg Asn Gly Asp Pro Gln Thr
    450                 455                 460

Pro Phe Gln Ile Ala Glu Gln Ile Gln Asn Phe Gln Val Ala Asn
465                 470                 475                 480

Trp Leu His Phe Ile Asn Asn Arg Phe Arg Gln Val Val Ile Asp
                485                 490                 495

Gly Val Leu Asn Gln Thr Leu Asn Asp Asn Ile Arg Asn Gly Gln Val
            500                 505                 510

```
Ile Asn Gln Leu Met Glu Ala Leu Met Gln Leu Ser Arg Gln Gln Phe
515                 520                 525

Pro Thr Met Pro Val Asp Tyr Lys Arg Ser Ile Gln Arg Gly Ile Leu
530                 535                 540

Leu Leu Ser Asn Arg Leu Gly Gln Leu Val Asp Leu Thr Arg Leu Val
545                 550                 555                 560

Ser Tyr Asn Tyr Glu Thr Leu Met Ala Cys Val Thr Met Asn Met Gln
                565                 570                 575

His Val Gln Thr Leu Thr Thr Glu Lys Leu Gln Leu Thr Ser Val Thr
            580                 585                 590

Ser Leu Cys Met Leu Ile Gly Asn Thr Thr Val Ile Pro Ser Pro Gln
        595                 600                 605

Thr Leu Phe His Tyr Tyr Asn Ile Asn Val Asn Phe His Ser Asn Tyr
    610                 615                 620

Asn Glu Arg Ile Asn Asp Ala Val Ala Ile Thr Ala Ala Asn Arg
625                 630                 635                 640

Leu Asn Leu Tyr Gln Lys Lys Met Lys Ser Ile Val Glu Asp Phe Leu
                645                 650                 655

Lys Arg Leu Gln Ile Phe Asp Val Pro Arg Val Pro Asp Asp Gln Met
            660                 665                 670

Tyr Arg Leu Arg Asp Arg Leu Arg Leu Pro Val Glu Arg Arg Arg
        675                 680                 685

Leu Asp Ile Phe Asn Leu Ile Leu Met Asn Met Glu Gln Ile Glu Arg
    690                 695                 700

Ala Ser Asp Lys Ile Ala Gln Gly Val Ile Ile Ala Tyr Arg Asp Met
705                 710                 715                 720

Gln Leu Glu Arg Asp Glu Met Tyr Gly Tyr Val Asn Ile Ala Arg Asn
                725                 730                 735

Leu Asp Gly Tyr Gln Gln Ile Asn Leu Glu Glu Leu Met Arg Thr Gly
            740                 745                 750

Asp Tyr Gly Gln Ile Thr Asn Met Leu Leu Asn Asn Gln Pro Val Ala
        755                 760                 765

Leu Val Gly Ala Leu Pro Phe Val Thr Asp Ser Ser Val Ile Ser Leu
    770                 775                 780

Ile Ala Lys Leu Asp Ala Thr Val Phe Ala Gln Ile Val Lys Leu Arg
785                 790                 795                 800

Lys Val Asp Thr Leu Lys Pro Ile Leu Tyr Lys Ile Asn Ser Asp Ser
                805                 810                 815

Asn Asp Phe Tyr Leu Val Ala Asn Tyr Asp Trp Ile Pro Thr Ser Thr
            820                 825                 830

Thr Lys Val Tyr Lys Gln Val Pro Gln Pro Phe Asp Phe Arg Ala Ser
        835                 840                 845

Met His Met Leu Thr Ser Asn Leu Thr Phe Thr Val Tyr Ser Asp Leu
    850                 855                 860

Leu Ser Phe Val Ser Ala Asp Thr Val Glu Pro Ile Asn Ala Val Ala
865                 870                 875                 880

Phe Asp Asn Met Arg Ile Met Asn Glu Leu
                885                 890

<210> SEQ ID NO 25
<211> LENGTH: 49
<212> TYPE: DNA
<213> ORGANISM: Artificial Sequence
<220> FEATURE:
<223> OTHER INFORMATION: IF WA VP6 opt.s1 plus 3c
```

<400> SEQUENCE: 25
aaatttgtcg ggcccatgga ggtcctttat agtctctcca aaacgctga        49

<210> SEQ ID NO 26
<211> LENGTH: 52
<212> TYPE: DNA
<213> ORGANISM: Artificial Sequence
<220> FEATURE:
<223> OTHER INFORMATION: IF WA VP6 opt.s1 4r

<400> SEQUENCE: 26
actaaagaaa ataggcctct acttgatcaa catactccgg atagaggcca ca        52

<210> SEQ ID NO 27
<211> LENGTH: 1194
<212> TYPE: DNA
<213> ORGANISM: Artificial Sequence
<220> FEATURE:
<223> OTHER INFORMATION: Optimized coding sequence of Rotavirus A VP6
      from strain WA

<400> SEQUENCE: 27
atggaggtcc tttatagtct ctccaaaacg ctgaaggacg ctagggacaa gatcgtggag        60
ggtacacttt atagcaatgt cagcgaccta atacagcagt ttaatcaaat gatcgttaca       120
atgaatggga tgatttcca aactggcggt attggtaatc tgcccgtgag aactggaca        180 ttcgatttcg gcctgctggg cacgactctc cttaatctcg atgcaaatta tgtagaaaac       240
gccagaacga ttatcgagta ctttatcgat ttcattgata cgtttgtat ggatgagatg        300 gcccgcgagt cacaacggaa cggagttgct ccacagtccg aggcccttcg gaaactcgcc       360
ggcattaagt tcaagcgtat taatttcgac aactcctccg aatatataga gaactggaac       420
ttgcagaatc gtcgacagag aaccggcttc gtgttccata acctaatat ctttccgtat        480 agcgcctcat tcaccctgaa taggagtcag cccatgcacg acaacctcat gggtacaatg       540
tggctgaatg cggggagtga atacaggtc gccgggttcg attactcctg tgccattaat        600
gcacccgcaa acatccagca gttcgaacat atcgtgcaac taagacgggc tctcacgacc       660
gcgacaatta cactcctgcc cgacgccgag cgcttctcct ttccccgcgt aatcaactca       720
gctgatggcg ccaccacttg gttcttcaac cctgttatat gcgcccctaa caacgtagag       780
gtggagtttc tcttaaacgg acagatcatc aatacctacc aagccaggtt cggcacgatt       840
attgcaagaa atttcgacgc tatcaggctg ctcttccaac tgatgaggcc cccaatatg       900 actcccgctg tgaacgcttt gtttccgcag gctcagcctt ccagcacca cgccaccgtc       960 ggcttgactc ttcgaataga gagcgcggtc tgcgaatcag tgctggcaga cgccaacgag     1020
acgctgctgg caaacgttac cgccgtgcgg caagagtatg ccatcccagt agggcctgtg     1080
tttccacccg gcatgaactg gactgaacta attactaact atagcccatc cagagaagac     1140
aacttgcagc gggtcttcac tgtggcctct atccggagta tgttgatcaa gtag         1194

<210> SEQ ID NO 28
<211> LENGTH: 2934
<212> TYPE: DNA
<213> ORGANISM: Artificial Sequence
<220> FEATURE:
<223> OTHER INFORMATION: Expression cassette number 1713

<400> SEQUENCE: 28
gtcaacatgg tggagcacga cacacttgtc tactccaaaa atatcaaaga tacagtctca        60

```
gaagaccaaa gggcaattga gacttttcaa caaagggtaa tatccggaaa cctcctcgga    120
ttccattgcc cagctatctg tcactttatt gtgaagatag tggaaaagga aggtggctcc    180
tacaaatgcc atcattgcga taaggaaag gccatcgttg aagatgcctc tgccgacagt    240
ggtcccaaag atggaccccc acccacgagg agcatcgtgg aaaagaaga cgttccaacc    300 acgtcttcaa agcaagtgga ttgatgtgat aacatggtgg agcacgacac acttgtctac    360
tccaaaaata tcaagatac agtctcagaa gaccaaaggg caattgagac ttttcaacaa    420
agggtaatat ccggaaacct cctcggattc cattgcccag ctatctgtca ctttattgtg    480
aagatagtgg aaaaggaagg tggctcctac aaatgccatc attgcgataa ggaaaggcc    540 atcgttgaag atgcctctgc cgacagtggt cccaaagatg acccccacc cacgaggagc    600 atcgtggaaa agaagacgt tccaaccacg tcttcaaagc aagtggattg atgtgatatc    660
tccactgacg taagggatga cgcacaatcc cactatcctt cgcaagaccc ttcctctata    720
taaggaagtt catttcattt ggagaggtat taaaatctta ataggttttg ataaaagcga    780
acgtggggaa acccgaacca aaccttcttc taaactctct ctcatctctc ttaaagcaaa    840
cttctctctt gtcttttcttg cgtgagcgat cttcaacgtt gtcagatcgt gcttcggcac    900
cagtacaacg ttttctttca ctgaagcgaa atcaaagatc tctttgtgga cacgtagtgc    960
ggcgccatta ataacgtgt acttgtccta ttccttgtcgg tgtggtcttg ggaaaagaaa   1020
gcttgctgga ggctgctgtt cagccccata cattacttgt tacgattctg ctgactttcg   1080
gcgggtgcaa tatctctact tctgcttgac gaggtattgt tgcctgtact tctttctttct   1140 tcttcttgct gattggttct ataagaaatc tagtattttc tttgaaacag agttttcccg   1200
tggttttcga acttggagaa agattgttaa gcttctgtat attctgccca aatttgtcgg   1260
gcccatggag gtcctttata gtctctccaa aacgctgaag gacgctaggg acaagatcgt   1320
ggagggtaca ctttatagca atgtcagcga cctaatacag cagtttaatc aaatgatcgt   1380
tacaatgaat gggaatgatt ccaaactgg cggtattggt aatctgcccg tgaggaactg   1440
gacattcgat ttcggcctgc tgggcacgac tctccttaat ctcgatgcaa attatgtaga   1500
aaacgccaga acgattatcg agtactttat cgatttcatt gataacgttt gtatggatga   1560
gatggcccgc gagtcacaac ggaacggagt tgctccacag tccgaggccc ttcggaaact   1620
cgccggcatt aagttcaagc gtattaattt cgacaactcc tccgaatata tagagaactg   1680
gaacttgcag aatcgtcgac agagaaccgg cttcgtgttc cataaaccta atatctttcc   1740
gtatagcgcc tcattcaccc tgaataggag tcagcccatg cacgacaacc tcatgggtac   1800
aatgtggctg aatgcgggga gtgaaataca ggtcgccggg ttcgattact cctgtgccat   1860
taatgcaccc gcaaacatcc agcagttcga acatatcgtg caactaagac gggctctcac   1920
gaccgcgaca attacactcc tgcccgacgc cgagcgcttc tcctttcccc gcgtaatcaa   1980
ctcagctgat ggcgccacca cttggttctt caaccctgtt atattgcgcc taacaacgt   2040 agaggtggag tttctcttaa acggacagat catcaatacc taccaagcca ggttcggcac   2100
gattattgca agaaatttcg acgctatcag gctgctcttc caactgatga ggccccccaa   2160
tatgactccc gctgtgaacg cttgttttcc gcaggctcag cctttccagc accacgccac   2220
cgtcggcttg actcttcgaa tagagagcgc ggtctgcgaa tcagtgctgg cagacgccaa   2280
cgagacgctc ctggcaaacg ttaccgccgt gcggcaagag tatgccatcc cagtagggcc   2340
tgtgtttcca cccggcatga actggactga actaattact aactatagcc catccagaga   2400
```

-continued

```
agacaacttg cagcgggtct tcactgtggc ctctatccgg agtatgttga tcaagtagag    2460 gcctatttc tttagtttga atttactgtt attcggtgtg catttctatg tttggtgagc    2520
ggttttctgt gctcagagtg tgtttatttt atgtaattta atttctttgt gagctcctgt    2580
ttagcaggtc gtcccttcag caaggacaca aaaagatttt aattttatta aaaaaaaaa    2640 aaaaaaagac cgggaattcg atatcaagct tatcgacctg cagatcgttc aaacatttgg    2700
caataaagtt tcttaagatt gaatcctgtt gccggtcttg cgatgattat catataattt    2760
ctgttgaatt acgttaagca tgtaataatt aacatgtaat gcatgacgtt atttatgaga    2820
tgggttttta tgattagagt cccgcaatta tacatttaat acgcgataga aaacaaaata    2880
tagcgcgcaa actaggataa attatcgcgc gcggtgtcat ctatgttact agat          2934
```

<210> SEQ ID NO 29
<211> LENGTH: 397
<212> TYPE: PRT
<213> ORGANISM: Rotavirus

<400> SEQUENCE: 29

```
Met Glu Val Leu Tyr Ser Leu Ser Lys Thr Leu Lys Asp Ala Arg Asp
1               5                   10                  15

Lys Ile Val Glu Gly Thr Leu Tyr Ser Asn Val Ser Asp Leu Ile Gln
            20                  25                  30

Gln Phe Asn Gln Met Ile Val Thr Met Asn Gly Asn Asp Phe Gln Thr
        35                  40                  45

Gly Gly Ile Gly Asn Leu Pro Val Arg Asn Trp Thr Phe Asp Phe Gly
    50                  55                  60

Leu Leu Gly Thr Thr Leu Leu Asn Leu Asp Ala Asn Tyr Val Glu Asn
65                  70                  75                  80

Ala Arg Thr Ile Ile Glu Tyr Phe Ile Asp Phe Ile Asp Asn Val Cys
                85                  90                  95

Met Asp Glu Met Ala Arg Glu Ser Gln Arg Asn Gly Val Ala Pro Gln
            100                 105                 110

Ser Glu Ala Leu Arg Lys Leu Ala Gly Ile Lys Phe Lys Arg Ile Asn
        115                 120                 125

Phe Asp Asn Ser Ser Glu Tyr Ile Glu Asn Trp Asn Leu Gln Asn Arg
    130                 135                 140

Arg Gln Arg Thr Gly Phe Val Phe His Lys Pro Asn Ile Phe Pro Tyr
145                 150                 155                 160

Ser Ala Ser Phe Thr Leu Asn Arg Ser Gln Pro Met His Asp Asn Leu
                165                 170                 175

Met Gly Thr Met Trp Leu Asn Ala Gly Ser Glu Ile Gln Val Ala Gly
            180                 185                 190

Phe Asp Tyr Ser Cys Ala Ile Asn Ala Pro Ala Asn Ile Gln Gln Phe
        195                 200                 205

Glu His Ile Val Gln Leu Arg Arg Ala Leu Thr Thr Ala Thr Ile Thr
    210                 215                 220

Leu Leu Pro Asp Ala Glu Arg Phe Ser Phe Pro Arg Val Ile Asn Ser
225                 230                 235                 240

Ala Asp Gly Ala Thr Thr Trp Phe Phe Asn Pro Val Ile Leu Arg Pro
                245                 250                 255

Asn Asn Val Glu Val Glu Phe Leu Leu Asn Gly Gln Ile Ile Asn Thr
            260                 265                 270

Tyr Gln Ala Arg Phe Gly Thr Ile Ile Ala Arg Asn Phe Asp Ala Ile
        275                 280                 285
```

```
Arg Leu Leu Phe Gln Leu Met Arg Pro Pro Asn Met Thr Pro Ala Val
    290                 295                 300
Asn Ala Leu Phe Pro Gln Ala Gln Pro Phe Gln His His Ala Thr Val
305                 310                 315                 320
Gly Leu Thr Leu Arg Ile Glu Ser Ala Val Cys Glu Ser Val Leu Ala
                325                 330                 335
Asp Ala Asn Glu Thr Leu Leu Ala Asn Val Thr Ala Val Arg Gln Glu
            340                 345                 350
Tyr Ala Ile Pro Val Gly Pro Val Phe Pro Pro Gly Met Asn Trp Thr
        355                 360                 365
Glu Leu Ile Thr Asn Tyr Ser Pro Ser Arg Glu Asp Asn Leu Gln Arg
    370                 375                 380
Val Phe Thr Val Ala Ser Ile Arg Ser Met Leu Ile Lys
385                 390                 395

<210> SEQ ID NO 30
<211> LENGTH: 53
<212> TYPE: DNA
<213> ORGANISM: Artificial Sequence
<220> FEATURE:
<223> OTHER INFORMATION: IF Rtx VP4 opt.s1 plus 3c

<400> SEQUENCE: 30
aaatttgtcg ggcccatggc tagcctgatc tacagacaac tcttgaccaa ttc        53

<210> SEQ ID NO 31
<211> LENGTH: 55
<212> TYPE: DNA
<213> ORGANISM: Artificial Sequence
<220> FEATURE:
<223> OTHER INFORMATION: IF Rtx VP4 opt.s1 4r

<400> SEQUENCE: 31
actaaagaaa ataggccttc agagtttaca ttgcaggatt aattgctcaa tccta      55

<210> SEQ ID NO 32
<211> LENGTH: 2328
<212> TYPE: DNA
<213> ORGANISM: Artificial Sequence
<220> FEATURE:
<223> OTHER INFORMATION: Optimized coding sequence of Rotavirus A VP4

<400> SEQUENCE: 32
atggctagcc tgatctacag acaactcttg accaattcat attctgtgga tcttcatgac    60
gaaatcgagc agattgggtc cgagaagacc agaacgtga ccatcaaccc tggacctttt    120
gctcagaccc gctatgcccc tgtgaattgg gatcacggag aaatcaacga cagtacgacc    180
gtcgaaccca ttctggacgg gccataccaa cccaccacct tcaccccacc taatgattat    240 tggatttttaa tcaactccaa cacaaacgga gtggtctacg agtccactaa taactccgat    300
ttttggaccg ccgttgtagc catcgagcca cacgtcaatc tgtcgatcg ccagtatatg    360 atattcggcg agtccaaaca gtttaacgtt ccaatgaca gcaacaaatg gaagtttctg    420
gagatgtttc gcagctcctc tcagaacgaa ttctataata gacggaccct tacctccgat    480
acacgactcg tgggtatttt taagtacggc ggcagggtgt ggacatttca cggtgaaacc    540
cctcgagcaa ccactgactc cagtagcact gcaaacctga acaatatatc tattaccatc    600
cacagcgaat ctacacataat cccaagatct caggaaagta agtgtaacga atatatcaac    660
aacggactcc ccccaattca gaatacacgg aacgtggtgc ctctcccact cagttctcgg    720
```

```
tctatccagt ataagagagc acaagtgaat gaggacatta ttgtgagcaa gactagcctt      780
tggaaagaaa tgcagtacaa cagagacatt atcatccggt ttaagtttgg gaactctatc      840
gtgaagatgg gcggcctggg gtacaaatgg tcagaaatct catataaagc cgccaactat      900
cagtataact acttgagaga cggcgagcag gtaaccgccc acacaacatg ctctgtcaac      960
ggcgttaata actttagcta caacggaggc ttccttccca ccgacttcgg tatcagccgg     1020
tatgaagtca tcaaggaaaa ttcttatgtg tacgtagatt actgggatga tagcaaagcg     1080
ttccgcaaca tggtgtatgt taggagcctg gctgctaatc tcaattctgt gaagtgtact     1140
ggtggatcat attatttctc aattcccgtg ggggcttggc cagtcatgaa tggcggggca     1200
gtctccctcc attttgctgg cgtgacgttg agcactcagt ttaccgattt cgtgtctctg     1260
aactccctga ggttccggtt ttcccttact gtcgacgagc ccccattcag cattctgcgt     1320
acaagaactg tcaacctcta cgggttacct gccgcgaatc caaacaacgg caatgaatac     1380
tatgaaattt cggccgcgtt ctctttgata agtctggtac caactaatga cgactatcag     1440
acacccatca tgaacagcgt gactgtcaga caggacctgg aaagacaact tacagatctg     1500
cgggaagaat tcaattctct cagtcaggag attgcaatgg cccaattgat agatcttgcc     1560
ctactgcctc tcgatatgtt tagtatgttc tccggcatca aatcaactat agatctgaca     1620
aagagcatgg ctacttctgt gatgaagaag ttcaggaaat caaaacttgc cacgagcata     1680
tcagaaatga cgaactctct gagtgatgca gcatcatcag cgtcacgcaa cgtttccatt     1740
cggtcgaatc tcagcgccat cagcaactgg acaaacgtgt ccaacgacgt cagcaacgtg     1800
accaactcct tgaacgatat ttctacccag acgtcaacga tcagtaagaa actccgcttg     1860
aaagaaatga tcacccagac tgagggaatg tctttcgacg acatttccgc cgccgtgcta     1920
aaaaccaaaa tcgatatgtc tactcagatc ggcaagaaca ctctgccgga tatcgtaacc     1980
gaagcctccg aaaagtttat ccctaagcgc agctacagaa tattgaaaga tgacgaggtc     2040
atggagatca acacagaagg gaagttcttc gcttataaga tcaacaccct tgacgaggtt     2100
ccgtttgacg tcaataagtt tgcagagctc gtgacagata gtccagtgat ttctgccatc     2160
attgacttta agactttgaa gaacctgaac gacaactatg aataacacg gaccgaagcg     2220 ttgaacctca ttaagtccaa tcccaatatg ttgcgcaatt tcattaacca gaacaatcca     2280
atcataagaa ataggattga gcaattaatc ctgcaatgta aactctga                  2328
```

<210> SEQ ID NO 33
<211> LENGTH: 4068
<212> TYPE: DNA
<213> ORGANISM: Artificial Sequence
<220> FEATURE:
<223> OTHER INFORMATION: Expression cassette number 1730

<400> SEQUENCE: 33

```
gtcaacatgg tggagcacga cacacttgtc tactccaaaa atatcaaaga tacagtctca       60
gaagaccaaa gggcaattga gacttttcaa caaagggtaa tatccggaaa cctcctcgga      120
ttccattgcc cagctatctg tcactttatt gtgaagatag tggaaaagga aggtggctcc      180
tacaaatgcc atcattgcga taaaggaaag gccatcgttg aagatgcctc tgccgacagt      240
ggtcccaaag atggaccccc acccacgagg agcatcgtgg aaaaagaaga cgttccaacc      300
acgtcttcaa gcaagtgga ttgatgtgat aacatggtgg agcacgacac acttgtctac      360
tccaaaaata tcaaagatac agtctcagaa gaccaaaggg caattgagac ttttcaacaa      420
```

```
agggtaatat ccggaaacct cctcggattc cattgcccag ctatctgtca ctttattgtg    480
aagatagtgg aaaaggaagg tggctcctac aaatgccatc attgcgataa aggaaaggcc    540
atcgttgaag atgcctctgc cgacagtggt cccaaagatg accccccacc cacgaggagc    600
atcgtggaaa aagaagacgt tccaaccacg tcttcaaagc aagtggattg atgtgatatc    660
tccactgacg taagggatga cgcacaatcc cactatcctt cgcaagaccc ttcctctata    720
taaggaagtt catttcattt ggagaggtat aaaatctta ataggttttg ataaaagcga     780
acgtggggaa acccgaacca aaccttcttc taaactctct ctcatctctc ttaaagcaaa    840
cttctctctt gtcttctt cgtgagcgat cttcaacgtt gtcagatcgt gcttcggcac      900
cagtacaacg ttttctttca ctgaagcgaa atcaaagatc tctttgtgga cacgtagtgc    960
ggcgccatta ataacgtgt acttgtccta ttcttgtcgg tgtggtcttg ggaaaagaaa     1020
gcttgctgga ggctgctgtt cagccccata cattacttgt tacgattctg ctgactttcg    1080
gcgggtgcaa tatctctact tctgcttgac gaggtattgt tgcctgtact tctttcttct    1140
tcttcttgct gattggttct ataagaaatc tagtattttc tttgaaacag agttttcccg    1200
tggttttcga acttggagaa agattgttaa gcttctgtat attctgccca aatttgtcgg    1260
gcccatggct agcctgatct acagacaact cttgaccaat tcatattctg tggatcttca    1320
tgacgaaatc gagcagattg ggtccgagaa gacccagaac gtgaccatca accctggacc    1380
ttttgctcag acccgctatg cccctgtgaa ttgggatcac ggagaaatca acgacagtac    1440
gaccgtcgaa cccattctgg acgggccata ccaacccacc accttcaccc cacctaatga    1500
ttattggatt ttaatcaact ccaacacaaa cggagtggtc tacgagtcca ctaataactc    1560
cgatttttgg accgccgttg tagccatcga gccacacgtc aatcctgtcg atcgccagta    1620
tatgatattc ggcgagtcca aacagtttaa cgtttccaat gacagcaaca aatgaaagtt    1680
tctggagatg tttcgcagct cctctcagaa cgaattctat aatagacgga cccttacctc    1740
cgatacacga ctcgtgggta tttttaagta cggcggcagg gtgtggacat ttcacggtga    1800
aacccctcga gcaaccactg actccagtag cactgcaaac ctgaacaata tatctattac    1860
catccacagc gaattctaca taatcccaag atctcaggaa agtaagtgta acgaatatat    1920
caacaacgga ctccccccaa ttcagaatac acggaacgtg gtgcctctcc cactcagttc    1980
tcggtctatc cagtataaga gagcacaagt gaatgaggac attattgtga gcaagactag    2040
cctttggaaa gaaatgcagt acaacagaga cattatcatc cggtttaagt ttgggaactc    2100
tatcgtgaag atgggcggcc tggggtacaa atggtcagaa atctcatata aagccgccaa    2160
ctatcagtat aactacttga gagacggcga gcaggtaacc gcccacacaa catgctctgt    2220
caacggcgtt aataacttta gctacaacgg aggcttcctt cccaccgact tcggtatcag    2280
ccggtatgaa gtcatcaagg aaaattctta tgtgtacgta gattactggg atgatagcaa    2340
agcgttccgc aacatggtgt atgttaggag cctggctgct aatctcaatt ctgtgaagtg    2400
tactggtgga tcatattatt tctcaattcc cgtgggggct tggccagtca tgaatggcgg    2460
ggcagtctcc ctccatttttg ctggcgtgac gttgagcact cagtttaccg atttcgtgtc    2520
tctgaactcc ctgaggttcc ggttttccct tactgtcgac gagcccccat tcagcattct    2580
gcgtacaaga actgtcaacc tctacggggtt acctgccgcg aatccaaaca cggcaatga    2640 atactatgaa atttcgggcc gcttctcttt gataagtctg gtaccaacta atgacgacta    2700
tcagacaccc atcatgaaca gcgtgactgt cagacaggac ctggaaagac aacttacaga    2760
tctgcgggaa gaattcaatt ctctcagtca ggagattgca atggcccaat tgatagatct    2820
```

-continued

```
tgccctactg cctctcgata tgtttagtat gttctccggc atcaaatcaa ctatagatct    2880
gacaaagagc atggctactt ctgtgatgaa gaagttcagg aaatcaaaac ttgccacgag    2940
catatcagaa atgacgaact ctctgagtga tgcagcatca tcagcgtcac gcaacgtttc    3000
cattcggtcg aatctcagcg ccatcagcaa ctggacaaac gtgtccaacg acgtcagcaa    3060
cgtgaccaac tccttgaacg atatttctac ccagacgtca acgatcagta agaaactccg    3120
cttgaaagaa atgatcaccc agactgaggg aatgtctttc gacgacattt ccgccgccgt    3180
gctaaaaacc aaaatcgata tgtctactca gatcggcaag aacactctgc cggatatcgt    3240
aaccgaagcc tccgaaaagt ttatccctaa gcgcagctac agaatattga agatgacga    3300 ggtcatggag atcaacacag aagggaagtt cttcgcttat aagatcaaca cctttgacga    3360
ggttccgttt gacgtcaata agtttgcaga gctcgtgaca gatagtccag tgatttctgc    3420
catcattgac tttaagactt tgaagaacct gaacgacaac tatggaataa cacggaccga    3480
agcgttgaac ctcattaagt ccaatcccaa tatgttgcgc aatttcatta accagaacaa    3540
tccaatcata agaaatagga ttgagcaatt aatcctgcaa tgtaaactct gaaggcctat    3600
tttctttagt ttgaatttac tgttattcgg tgtgcatttc tatgtttggt gagcggtttt    3660
ctgtgctcag agtgtgttta ttttatgtaa tttaatttct ttgtgagctc ctgtttagca    3720
ggtcgtccct tcagcaagga cacaaaaaga ttttaattt attaaaaaaa aaaaaaaaa    3780 agaccgggaa ttcgatatca agcttatcga cctgcagatc gttcaaacat ttggcaataa    3840
agtttcttaa gattgaatcc tgttgccggt cttgcgatga ttatcatata atttctgttg    3900
aattacgtta agcatgtaat aattaacatg taatgcatga cgttatttat gagatgggtt    3960
tttatgatta gagtcccgca attatacatt taatacgcga tagaaaacaa aatatagcgc    4020
gcaaactagg ataaattatc gcgcgcggtg tcatctatgt tactagat            4068
```

<210> SEQ ID NO 34  
<211> LENGTH: 775  
<212> TYPE: PRT  
<213> ORGANISM: Rotavirus

<400> SEQUENCE: 34

```
Met Ala Ser Leu Ile Tyr Arg Gln Leu Leu Thr Asn Ser Tyr Ser Val
 1               5                  10                  15

Asp Leu His Asp Glu Ile Glu Gln Ile Gly Ser Glu Lys Thr Gln Asn
                20                  25                  30

Val Thr Ile Asn Pro Gly Pro Phe Ala Gln Thr Arg Tyr Ala Pro Val
            35                  40                  45

Asn Trp Asp His Gly Glu Ile Asn Asp Ser Thr Thr Val Glu Pro Ile
        50                  55                  60

Leu Asp Gly Pro Tyr Gln Pro Thr Thr Phe Thr Pro Pro Asn Asp Tyr
65                  70                  75                  80

Trp Ile Leu Ile Asn Ser Asn Thr Asn Gly Val Val Tyr Glu Ser Thr
                85                  90                  95

Asn Asn Ser Asp Phe Trp Thr Ala Val Val Ala Ile Glu Pro His Val
            100                 105                 110

Asn Pro Val Asp Arg Gln Tyr Met Ile Phe Gly Glu Ser Lys Gln Phe
        115                 120                 125

Asn Val Ser Asn Asp Ser Asn Lys Trp Lys Phe Leu Glu Met Phe Arg
    130                 135                 140

Ser Ser Ser Gln Asn Glu Phe Tyr Asn Arg Arg Thr Leu Thr Ser Asp
```

-continued

```
           145                 150                 155                 160
     Thr Arg Leu Val Gly Ile Phe Lys Tyr Gly Gly Arg Val Trp Thr Phe
                         165                 170                 175
     His Gly Glu Thr Pro Arg Ala Thr Thr Asp Ser Ser Ser Thr Ala Asn
                         180                 185                 190
     Leu Asn Asn Ile Ser Ile Thr Ile His Ser Glu Phe Tyr Ile Ile Pro
                         195                 200                 205
     Arg Ser Gln Glu Ser Lys Cys Asn Glu Tyr Ile Asn Asn Gly Leu Pro
                         210                 215                 220
     Pro Ile Gln Asn Thr Arg Asn Val Val Pro Leu Pro Leu Ser Ser Arg
     225                 230                 235                 240
     Ser Ile Gln Tyr Lys Arg Ala Gln Val Asn Glu Asp Ile Ile Val Ser
                         245                 250                 255
     Lys Thr Ser Leu Trp Lys Glu Met Gln Tyr Asn Arg Asp Ile Ile Ile
                         260                 265                 270
     Arg Phe Lys Phe Gly Asn Ser Ile Val Lys Met Gly Gly Leu Gly Tyr
                         275                 280                 285
     Lys Trp Ser Glu Ile Ser Tyr Lys Ala Ala Asn Tyr Gln Tyr Asn Tyr
                         290                 295                 300
     Leu Arg Asp Gly Glu Gln Val Thr Ala His Thr Cys Ser Val Asn
     305                 310                 315                 320
     Gly Val Asn Asn Phe Ser Tyr Asn Gly Gly Phe Leu Pro Thr Asp Phe
                         325                 330                 335
     Gly Ile Ser Arg Tyr Glu Val Ile Lys Glu Asn Ser Tyr Val Tyr Val
                         340                 345                 350
     Asp Tyr Trp Asp Asp Ser Lys Ala Phe Arg Asn Met Val Tyr Val Arg
                         355                 360                 365
     Ser Leu Ala Ala Asn Leu Asn Ser Val Lys Cys Thr Gly Gly Ser Tyr
                         370                 375                 380
     Tyr Phe Ser Ile Pro Val Gly Ala Trp Pro Val Met Asn Gly Gly Ala
     385                 390                 395                 400
     Val Ser Leu His Phe Ala Gly Val Thr Leu Ser Thr Gln Phe Thr Asp
                         405                 410                 415
     Phe Val Ser Leu Asn Ser Leu Arg Phe Arg Phe Ser Leu Thr Val Asp
                         420                 425                 430
     Glu Pro Pro Phe Ser Ile Leu Arg Thr Arg Thr Val Asn Leu Tyr Gly
                         435                 440                 445
     Leu Pro Ala Ala Asn Pro Asn Asn Gly Asn Glu Tyr Tyr Glu Ile Ser
                         450                 455                 460
     Gly Arg Phe Ser Leu Ile Ser Leu Val Pro Thr Asn Asp Asp Tyr Gln
     465                 470                 475                 480
     Thr Pro Ile Met Asn Ser Val Thr Val Arg Gln Asp Leu Glu Arg Gln
                         485                 490                 495
     Leu Thr Asp Leu Arg Glu Glu Phe Asn Ser Leu Ser Gln Glu Ile Ala
                         500                 505                 510
     Met Ala Gln Leu Ile Asp Leu Ala Leu Leu Pro Leu Asp Met Phe Ser
                         515                 520                 525
     Met Phe Ser Gly Ile Lys Ser Thr Ile Asp Leu Thr Lys Ser Met Ala
                         530                 535                 540
     Thr Ser Val Met Lys Lys Phe Arg Lys Ser Lys Leu Ala Thr Ser Ile
     545                 550                 555                 560
     Ser Glu Met Thr Asn Ser Leu Ser Asp Ala Ala Ser Ser Ala Ser Arg
                         565                 570                 575
```

```
Asn Val Ser Ile Arg Ser Asn Leu Ser Ala Ile Ser Asn Trp Thr Asn
            580                 585                 590

Val Ser Asn Asp Val Ser Asn Val Thr Asn Ser Leu Asn Asp Ile Ser
        595                 600                 605

Thr Gln Thr Ser Thr Ile Ser Lys Lys Leu Arg Leu Lys Glu Met Ile
    610                 615                 620

Thr Gln Thr Glu Gly Met Ser Phe Asp Asp Ile Ser Ala Ala Val Leu
625                 630                 635                 640

Lys Thr Lys Ile Asp Met Ser Thr Gln Ile Gly Lys Asn Thr Leu Pro
                645                 650                 655

Asp Ile Val Thr Glu Ala Ser Glu Lys Phe Ile Pro Lys Arg Ser Tyr
            660                 665                 670

Arg Ile Leu Lys Asp Asp Glu Val Met Glu Ile Asn Thr Glu Gly Lys
        675                 680                 685

Phe Phe Ala Tyr Lys Ile Asn Thr Phe Asp Glu Val Pro Phe Asp Val
    690                 695                 700

Asn Lys Phe Ala Glu Leu Val Thr Asp Ser Pro Val Ile Ser Ala Ile
705                 710                 715                 720

Ile Asp Phe Lys Thr Leu Lys Asn Leu Asn Asp Asn Tyr Gly Ile Thr
                725                 730                 735

Arg Thr Glu Ala Leu Asn Leu Ile Lys Ser Asn Pro Asn Met Leu Arg
            740                 745                 750

Asn Phe Ile Asn Gln Asn Asn Pro Ile Ile Arg Asn Arg Ile Glu Gln
        755                 760                 765

Leu Ile Leu Gln Cys Lys Leu
    770                 775

<210> SEQ ID NO 35
<211> LENGTH: 50
<212> TYPE: DNA
<213> ORGANISM: Artificial Sequence
<220> FEATURE:
<223> OTHER INFORMATION: IF TrSP plus Rtx VP7 opt. s1 plus 3c

<400> SEQUENCE: 35
aaatttgtcg ggcccatgga ttatattatc tatcgtagcc tcctcatcta                50

<210> SEQ ID NO 36
<211> LENGTH: 54
<212> TYPE: DNA
<213> ORGANISM: Artificial Sequence
<220> FEATURE:
<223> OTHER INFORMATION: IF Rtx VP7 opt s1 4r

<400> SEQUENCE: 36
actaaagaaa ataggcctct aaacgcgata atagaaggct gctgagttca ggga           54

<210> SEQ ID NO 37
<211> LENGTH: 981
<212> TYPE: DNA
<213> ORGANISM: Artificial Sequence
<220> FEATURE:
<223> OTHER INFORMATION: Optimized coding sequence of Rotavirus A VP7

<400> SEQUENCE: 37
atgtacggca tcgagtatac aacaatttta attttcctga tttccatcat tctgttaaac     60
tacatcctta agtccgtgac cagaattatg gattatatta tctatcgtag cctcctcatc    120
tacgtggccc tttttgccct gaccagggcc cagaactatg gcctgaactt accaatcacc    180
```

```
ggttcaatgg ataccgttta cgctaattcc actcaagagg ggatatttct gacaagtacc      240
ctgtgcctgt attatccaac agaagcctct acccagatca atgatgggga gtggaaggat      300
agtctctcac agatgttcct aaccaagggc tggcccaccg gttccgtcta cttcaaggaa      360
tactctagta ttgtcgactt ctcagttgac ccccagcttt attgcgacta caacctggta      420
cttatgaaat acgaccagaa cctggagctg atatgtccg agctggctga cctgatcctc       480
aatgagtggc tgtgcaaccc catggacatc acattatatt actaccagca gtctggagaa      540
tccaacaagt ggatcagtat gggctcaagt tgcaccgtga aggtgtgtcc cttgaacacc      600
caaatgctgg gcattggttg tcagacaact aatgtggatt cgtttgaaat ggtagccgaa      660
aacgagaagc tggctatagt ggacgtagtc gatgggatta accacaagat caatctgact      720
accaccactt gtaccatcag aaactgtaaa aagctcggcc cccggggagaa cgtcgccgtg     780 atccaggtgg gggggagcaa tgtgctcgac attactgccg accctaccac caatccacag      840
acggaacgga tgatgagagt caactggaag aaatggtggc aggtcttta taccattgtg       900 gactacatta accagattgt gcaagtcatg agtaaacggt ccagatccct gaactcagca      960
gccttctatt atcgcgttta g                                                 981

<210> SEQ ID NO 38
<211> LENGTH: 2634
<212> TYPE: DNA
<213> ORGANISM: Artificial Sequence
<220> FEATURE:
<223> OTHER INFORMATION: Expression cassette number 1734

<400> SEQUENCE: 38
gtcaacatgg tggagcacga cacacttgtc tactccaaaa atatcaaaga tacagtctca       60
gaagaccaaa gggcaattga acttttcaa caaagggtaa tatccggaaa cctcctcgga      120
ttccattgcc cagctatctg tcactttatt gtgaagatag tggaaaagga aggtggctcc      180
tacaaatgcc atcattgcga taaggaaag gccatcgttg aagatgcctc tgccgacagt       240
ggtcccaaag atggaccccc acccacgagg agcatcgtgg aaaagaaga cgttccaacc       300 acgtcttcaa gcaagtggga ttgatgtgat aacatggtgg agcacgacac acttgtctac      360
tccaaaaata tcaaagatac agtctcagaa gaccaagggg caattgagac ttttcaacaa      420
agggtaatat ccggaaacct cctcggattc cattgcccag ctatctgtca ctttattgtg      480
aagatagtgg aaaaggaagg tggctcctac aaatgccatc attgcgataa aggaaaggcc     540
atcgttgaag atgcctctgc cgacagtggt cccaaagatg accccccacc cacgaggagc     600
atcgtggaaa agaagacgt tccaaccacg tcttcaaagc aagtggattg atgtgatatc       660
tccactgacg taagggatga cgcacaatcc cactatcctt cgcaagaccc ttcctctata      720
taaggaagtt catttcattt ggagaggtat taaatctta ataggttttg ataaaagcga       780
acgtggggaa acccgaacca aaccttcttc taaactctct ctcatctctc ttaaagcaaa      840
cttctctctt gtctttcttg cgtgagcgat cttcaacgtt gtcagatcgt gcttcggcac      900
cagtacaacg ttttctttca ctgaagcgaa atcaaagatc tctttgtgga cacgtagtgc      960
ggcgccatta ataacgtgt acttgtccta ttcttgtcgg tgtggtcttg ggaaaagaaa      1020
gcttgctgga ggctgctgtt cagccccata cattacttgt tacgattctg ctgactttcg     1080
gcgggtgcaa tatctctact tctgcttgac gaggtattgt tgcctgtact tctttcttct     1140
tcttcttgct gattggttct ataagaaatc tagtattttc tttgaaacag agttttcccg     1200
```

-continued

```
tggttttcga acttggagaa agattgttaa gcttctgtat attctgccca aatttgtcgg    1260
gcccatggat tatattatct atcgtagcct cctcatctac gtggccctt ttgccctgac    1320
```

```
tggttttcga acttggagaa agattgttaa gcttctgtat attctgccca aatttgtcgg    1260
gcccatggat tatattatct atcgtagcct cctcatctac gtggcccttt ttgccctgac    1320
cagggcccag aactatggcc tgaacttacc aatcaccggt tcaatggata ccgtttacgc    1380
taattccact caagagggga tatttctgac aagtaccctg tgcctgtatt atccaacaga    1440
agcctctacc cagatcaatg atggggagtg aaggatagt ctctcacaga tgttcctaac     1500
caagggctgg cccaccggtt ccgtctactt caaggaatac tctagtattg tcgacttctc    1560
agttgacccc cagctttatt gcgactacaa cctggtactt atgaaatacg accagaacct    1620
ggagctggat atgtccgagc tggctgacct gatcctcaat gagtggctgt gcaaccccat    1680
ggacatcaca ttatattact accagcagtc tggagaatcc aacaagtgga tcagtatggg    1740
ctcaagttgc accgtgaagg tgtgtcccct gaacacccaa atgctgggca ttggttgtca    1800
gacaactaat gtggattcgt ttgaaatggt agccgaaaac gagaagctgg ctatagtgga    1860
cgtagtcgat gggattaacc acaagatcaa tctgactacc accacttgta ccatcagaaa    1920
ctgtaaaaag ctcggccccc gggagaacgt cgccgtgatc caggtggggg ggagcaatgt    1980
gctcgacatt actgccgacc ctaccaccaa tccacagacg gaacggatga tgagagtcaa    2040
ctggaagaaa tggtggcagg tcttttatac cattgtggac tacattaacc agattgtgca    2100
agtcatgagt aaacggtcca gatccctgaa ctcagcagcc ttctattatc gcgtttagag    2160
gcctattttc tttagtttga atttactgtt attcggtgtg catttctatg tttggtgagc    2220
ggttttctgt gctcagagtg tgtttatttt atgtaattta atttctttgt gagctcctgt    2280
ttagcaggtc gtcccttcag caaggacaca aaaagatttt aatttattta aaaaaaaaaa    2340
aaaaaaagac cgggaattcg atatcaagct tatcgacctg cagatcgttc aaacatttgg    2400
caataaagtt tcttaagatt gaatcctgtt gccggtcttg cgatgattat catataattt    2460
ctgttgaatt acgttaagca tgtaataatt aacatgtaat gcatgacgtt atttatgaga    2520
tgggtttttta tgattagagt cccgcaatta tacatttaat acgcgataga aaacaaaata    2580
tagcgcgcaa actaggataa attatcgcgc gcggtgtcat ctatgttact agat         2634
```

<210> SEQ ID NO 39
<211> LENGTH: 297
<212> TYPE: PRT
<213> ORGANISM: Rotavirus

<400> SEQUENCE: 39

```
Met Asp Tyr Ile Ile Tyr Arg Ser Leu Leu Ile Tyr Val Ala Leu Phe
1               5                   10                  15

Ala Leu Thr Arg Ala Gln Asn Tyr Gly Leu Asn Leu Pro Ile Thr Gly
            20                  25                  30

Ser Met Asp Thr Val Tyr Ala Asn Ser Thr Gln Glu Gly Ile Phe Leu
        35                  40                  45

Thr Ser Thr Leu Cys Leu Tyr Tyr Pro Thr Glu Ala Ser Thr Gln Ile
    50                  55                  60

Asn Asp Gly Glu Trp Lys Asp Ser Leu Ser Gln Met Phe Leu Thr Lys
65                  70                  75                  80

Gly Trp Pro Thr Gly Ser Val Tyr Phe Lys Glu Tyr Ser Ser Ile Val
                85                  90                  95

Asp Phe Ser Val Asp Pro Gln Leu Tyr Cys Asp Tyr Asn Leu Val Leu
            100                 105                 110

Met Lys Tyr Asp Gln Asn Leu Glu Leu Asp Met Ser Glu Leu Ala Asp
        115                 120                 125
```

Leu Ile Leu Asn Glu Trp Leu Cys Asn Pro Met Asp Ile Thr Leu Tyr
    130                 135                 140

Tyr Tyr Gln Gln Ser Gly Glu Ser Asn Lys Trp Ile Ser Met Gly Ser
145                 150                 155                 160

Ser Cys Thr Val Lys Val Cys Pro Leu Asn Thr Gln Met Leu Gly Ile
                165                 170                 175

Gly Cys Gln Thr Thr Asn Val Asp Ser Phe Glu Met Val Ala Glu Asn
            180                 185                 190

Glu Lys Leu Ala Ile Val Asp Val Val Asp Gly Ile Asn His Lys Ile
        195                 200                 205

Asn Leu Thr Thr Thr Thr Cys Thr Ile Arg Asn Cys Lys Lys Leu Gly
    210                 215                 220

Pro Arg Glu Asn Val Ala Val Ile Gln Val Gly Gly Ser Asn Val Leu
225                 230                 235                 240

Asp Ile Thr Ala Asp Pro Thr Thr Asn Pro Gln Thr Glu Arg Met Met
                245                 250                 255

Arg Val Asn Trp Lys Lys Trp Trp Gln Val Phe Tyr Thr Ile Val Asp
            260                 265                 270

Tyr Ile Asn Gln Ile Val Gln Val Met Ser Lys Arg Ser Arg Ser Leu
        275                 280                 285

Asn Ser Ala Ala Phe Tyr Tyr Arg Val
    290                 295

<210> SEQ ID NO 40
<211> LENGTH: 52
<212> TYPE: DNA
<213> ORGANISM: Artificial Sequence
<220> FEATURE:
<223> OTHER INFORMATION: IF WA NSP4 s1 plus 3c

<400> SEQUENCE: 40
aaatttgtcg ggcccatgga taagcttgcc gacctcaact acacattgag tg 52

<210> SEQ ID NO 41
<211> LENGTH: 55
<212> TYPE: DNA
<213> ORGANISM: Artificial Sequence
<220> FEATURE:
<223> OTHER INFORMATION: IF WA NSP4 s1 4r

<400> SEQUENCE: 41
actaaagaaa ataggccttc acatggatgc agtcacttct gacggttcat atgga 55

<210> SEQ ID NO 42
<211> LENGTH: 528
<212> TYPE: DNA
<213> ORGANISM: Rotavirus

<400> SEQUENCE: 42
atggataagc ttgccgacct caactacaca ttgagtgtaa tcacttcaat gaatgacaca 60
ttgcattcta taattcaaga tcctggaatg gcgtattttc tatatattgc atctgttcta 120
acagttttgt tcacattaca taaagcttca attccaacca tgaaaatagc attgaaaaca 180
tcaaaatgtt catataaagt gattaaatat tgtatagtca cgatcattaa tactctttta 240
aaattggctg gatataaaga gcaggttact acaaaagacg aaattgagca acagatggac 300
agaattgtga aagagatgag acgtcagctg gagatgattg ataaactaac tactcgtgaa 360
attgaacagg ttgaattgct taaacgtata catgacaacc tgataactag accagttgac 420

```
gttatagata tgtcgaagga attcaatcag aaaaacatca aaacgctaga tgaatgggag    480
agtggaaaaa atccatatga accgtcagaa gtgactgcat ccatgtga               528
```

<210> SEQ ID NO 43
<211> LENGTH: 2268
<212> TYPE: DNA
<213> ORGANISM: Artificial Sequence
<220> FEATURE:
<223> OTHER INFORMATION: Expression cassette number 1706

<400> SEQUENCE: 43

```
gtcaacatgg tggagcacga cacacttgtc tactccaaaa atatcaaaga tacagtctca    60
gaagaccaaa gggcaattga dcttttcaa caaagggtaa tatccggaaa cctcctcgga   120
ttccattgcc cagctatctg tcactttatt gtgaagatag tggaaaagga aggtggctcc   180
tacaaatgcc atcattgcga taaggaaag gccatcgttg aagatgcctc tgccgacagt    240
ggtcccaaag atggaccccc acccacgagg agcatcgtgg aaaagaaga cgttccaacc    300 acgtcttcaa agcaagtgga ttgatgtgat aacatggtgg agcacgacac acttgtctac   360
tccaaaaata tcaaagatac agtctcagaa gaccaaaggg caattgagac ttttcaacaa   420
agggtaatat ccggaaacct cctcggattc cattgcccag ctatctgtca ctttattgtg   480
aagatagtgg aaaaggaagg tggctcctac aaatgccatc attgcgataa ggaaaggcc    540 atcgttgaag atgcctctgc cgacagtggt cccaaagatg gacccccacc cacgaggagc   600
atcgtggaaa agaagacgt tccaaccacg tcttcaaagc aagtggattg atgtgatatc    660
tccactgacg taagggatga cgcacaatcc cactatcctt cgcaagaccc ttcctctata   720
taaggaagtt catttcattt ggagaggtat taaaatctta ataggttttg ataaaagcga   780
acgtggggaa acccgaacca aaccttcttc taaactctct ctcatctctc ttaaagcaaa   840
cttctctctt gtctttcttg cgtgagcgat cttcaacgtt gtcagatcgt gcttcggcac   900
cagtacaacg ttttctttca ctgaagcgaa atcaaagatc tctttgtgga cacgtagtgc   960
ggcgccatta ataacgtgt acttgtccta ttccttgtcgg tgtggtcttg ggaaaagaaa   1020
gcttgctgga ggctgctgtt cagccccata cattacttgt tacgattctg ctgactttcg   1080
gcgggtgcaa tatctctact tctgcttgac gaggtattgt tgcctgtact tctttcttct   1140
tcttcttgct gattggttct ataagaaatc tagtatttc tttgaaacag agttttcccg    1200
tggttttcga acttggagaa agattgttaa gcttctgtat attctgccca aatttgtcgg   1260
gcccatggat aagcttgccg acctcaacta cacattgagt gtaatcactt caatgaatga   1320
cacattgcat tctataattc aagatcctgg aatggcgtat tttctatata ttgcatctgt   1380
tctaacagtt tgttcacat tacataaagc ttcaattcca accatgaaaa tagcattgaa    1440
aacatcaaaa tgttcatata aagtgattaa atattgtata gtcacgatca ttaatactct   1500
tttaaaattg gctggatata aagagcaggt tactacaaaa gacgaaattg agcaacagat   1560
ggacagaatt gtgaaagaga tgagacgtca gctggagatg attgataaac taactactcg   1620
tgaaattgaa caggttgaat tgcttaaacg tatacatgac aacctgataa ctagaccagt   1680
tgacgttata gatatgtcga aggaattcaa tcagaaaaac atcaaaacgc tagatgaatg   1740
ggagagtgga aaaaatccat atgaaccgtc agaagtgact gcatccatgt gaaggcctat   1800
tttctttagt ttgaatttac tgttattcgg tgtgcatttc tatgttttggt gagcggtttt   1860 ctgtgctcag agtgtgttta tttatgtaa tttaatttct ttgtgagctc ctgtttagca    1920
```

```
ggtcgtccct tcagcaagga cacaaaaaga tttaattttt attaaaaaaa aaaaaaaaaa      1980
agaccgggaa ttcgatatca agcttatcga cctgcagatc gttcaaacat ttggcaataa      2040
agtttcttaa gattgaatcc tgttgccggt cttgcgatga ttatcatata atttctgttg      2100
aattacgtta agcatgtaat aattaacatg taatgcatga cgttatttat gagatgggtt      2160
tttatgatta gagtcccgca attatacatt taatacgcga tagaaaacaa aatatagcgc      2220
gcaaactagg ataaattatc gcgcgcggtg tcatctatgt tactagat                  2268

<210> SEQ ID NO 44
<211> LENGTH: 175
<212> TYPE: PRT
<213> ORGANISM: Rotavirus

<400> SEQUENCE: 44

Met Asp Lys Leu Ala Asp Leu Asn Tyr Thr Leu Ser Val Ile Thr Ser
1               5                   10                  15

Met Asn Asp Thr Leu His Ser Ile Ile Gln Asp Pro Gly Met Ala Tyr
                20                  25                  30

Phe Leu Tyr Ile Ala Ser Val Leu Thr Val Leu Phe Thr Leu His Lys
            35                  40                  45

Ala Ser Ile Pro Thr Met Lys Ile Ala Leu Lys Thr Ser Lys Cys Ser
        50                  55                  60

Tyr Lys Val Ile Lys Tyr Cys Ile Val Thr Ile Ile Asn Thr Leu Leu
65                  70                  75                  80

Lys Leu Ala Gly Tyr Lys Glu Gln Val Thr Thr Lys Asp Glu Ile Glu
                85                  90                  95

Gln Gln Met Asp Arg Ile Val Lys Glu Met Arg Arg Gln Leu Glu Met
                100                 105                 110

Ile Asp Lys Leu Thr Thr Arg Glu Ile Glu Gln Val Glu Leu Leu Lys
            115                 120                 125

Arg Ile His Asp Asn Leu Ile Thr Arg Pro Val Asp Val Ile Asp Met
        130                 135                 140

Ser Lys Glu Phe Asn Gln Lys Asn Ile Lys Thr Leu Asp Glu Trp Glu
145                 150                 155                 160

Ser Gly Lys Asn Pro Tyr Glu Pro Ser Glu Val Thr Ala Ser Met
                165                 170                 175

<210> SEQ ID NO 45
<211> LENGTH: 54
<212> TYPE: DNA
<213> ORGANISM: Artificial Sequence
<220> FEATURE:
<223> OTHER INFORMATION: IF C160 WA VP2 opt c

<400> SEQUENCE: 45
tcgtgcttcg gcaccagtac aatggcatac cggaagagag gagcaaagcg cgaa            54

<210> SEQ ID NO 46
<211> LENGTH: 4540
<212> TYPE: DNA
<213> ORGANISM: Artificial Sequence
<220> FEATURE:
<223> OTHER INFORMATION: Construct 1190

<400> SEQUENCE: 46
tggcaggata tattgtggtg taaacaaatt gacgcttaga caacttaata acacattgcg      60
gacgttttta atgtactgaa ttaacgccga atcccgggct ggtatattta tatgttgtca     120
```

```
aataactcaa aaaccataaa agtttaagtt agcaagtgtg tacattttta cttgaacaaa    180
aatattcacc tactactgtt ataaatcatt attaaacatt agagtaaaga aatatggatg    240
ataagaacaa gagtagtgat attttgacaa caattttgtt gcaacatttg agaaaatttt    300
gttgttctct cttttcattg gtcaaaaaca atagagagag aaaaaggaag agggagaata    360
aaaacataat gtgagtatga gagagaaagt tgtacaaaag ttgtaccaaa atagttgtac    420
aaatatcatt gaggaatttg acaaaagcta cacaaataag ggttaattgc tgtaaataaa    480
taaggatgac gcattagaga gatgtaccat tagagaattt ttggcaagtc attaaaaaga    540
aagaataaat tatttttaaa attaaaagtt gagtcatttg attaaacatg tgattattta    600
atgaattgat gaaagagttg gattaaagtt gtattagtaa ttagaatttg gtgtcaaatt    660
taatttgaca tttgatcttt tcctatatat tgccccatag agtcagttaa ctcattttta    720
tatttcatag atcaaataag agaaataacg gtatattaat ccctccaaaa aaaaaaaacg    780
gtatatttac taaaaaatct aagccacgta ggaggataac aggatccccg taggaggata    840
acatccaatc caaccaatca caacaatcct gatgagataa cccactttaa gcccacgcat    900
ctgtggcaca tctacattat ctaaatcaca cattcttcca cacatctgag ccacacaaaa    960
accaatccac atctttatca cccattctat aaaaaatcac actttgtgag tctacacttt   1020
gattcccttc aaacacatac aaagagaaga gactaattaa ttaattaatc atcttgagag   1080
aaaatggaac gagctataca aggaaacgac gctagggaac aagctaacag tgaacgttgg   1140
gatggaggat caggaggtac cacttctccc ttcaaacttc ctgacgaaag tccgagttgg   1200
actgagtggc ggctacataa cgatgagacg aattcgaatc aagataatcc ccttggtttc   1260
aaggaaagct gggggtttcgg gaaagttgta tttaagagat atctcagata cgacaggacg   1320
gaagcttcac tgcacagagt ccttggatct tggacgggag attcggttaa ctatgcagca   1380
tctcgatttt tcggtttcga ccagatcgga tgtacctata gtattcggtt tcgaggagtt   1440
agtatcaccg tttctggagg gtcgcgaact cttcagcatc tctgtgagat ggcaattcgg   1500
tctaagcaag aactgctaca gcttgcccca atcgaagtgg aaagtaatgt atcaagagga   1560
tgccctgaag gtactcaaac cttcgaaaaa gaaagcgagt aagttaaaat gcttcttcgt   1620
ctcctatttta taatatggtt tgttattgtt aattttgttc ttgtagaaga gcttaattaa   1680
tcgttgttgt tatgaaatac tatttgtatg agatgaactg gtgtaatgta attcattac    1740
ataagtggag tcagaatcag aatgtttcct ccataactaa ctagacatga agacctgccg   1800
cgtacaattg tcttatattt gaacaactaa aattgaacat cttttgccac aactttataa   1860
gtggttaata tagctcaaat atatggtcaa gttcaataga ttaataatgg aaatatcagt   1920
tatcgaaatt cattaacaat caacttaacg ttattaacta ctaatttttat atcatcccct   1980
ttgataaatg atagtacacc aattaggaag gagcatgctc gcctaggaga ttgtcgtttc   2040
ccgccttcag tttgcaagct gctctagccg tgtagccaat acgcaaaccg cctctccccg   2100
cgcgttggga attactagcg cgtgtcgaca agcttgcatg ccggtcaaca tggtggagca   2160
cgacacactt gtctactcca aaaatatcaa agatacagtc tcagaagacc aaagggcaat   2220
tgagactttt caacaaaggg taatatccgg aaacctcctc ggattccatt gcccagctat   2280
ctgtcacttt attgtgaaga tagtggaaaa ggaaggtggc tcctacaaat gccatcattg   2340
cgataaagga aaggccatcg ttgaagatgc ctctgccgac agtggtccca agatggacc    2400
cccacccacg aggagcatcg tggaaaaaga agacgttcca accacgtctt caaagcaagt   2460
ggattgatgt gataacatgg tggagcacga cacacttgtc tactccaaaa atatcaaaga   2520
```

```
tacagtctca gaagaccaaa gggcaattga gacttttcaa caaagggtaa tatccggaaa    2580
cctcctcgga ttccattgcc cagctatctg tcactttatt gtgaagatag tggaaaagga    2640
aggtggctcc tacaaatgcc atcattgcga taaaggaaag gccatcgttg aagatgcctc    2700
tgccgacagt ggtcccaaag atggaccccc acccacgagg agcatcgtgg aaaaagaaga    2760
cgttccaacc acgtcttcaa agcaagtgga ttgatgtgat atctccactg acgtaaggga    2820
tgacgcacaa tcccactatc cttcgcaaga cccttcctct atataaggaa gttcatttca    2880
tttggagagg tattaaaatc ttaataggtt ttgataaaag cgaacgtggg gaaacccgaa    2940
ccaaaccttc ttctaaactc tctctcatct ctcttaaagc aaacttctct cttgtctttc    3000
ttgcgtgagc gatcttcaac gttgtcagat cgtgcttcgg caccgcggat ggcgaaaaac    3060
gttgcgattt tcggcttatt gttttctctt cttgtgttgg ttccttctca gatcttcgcc    3120
tgcaggctcc tcagccaaaa cgacaccccc atctgtctat ccactggccc ctggatctgc    3180
tgcccaaact aactccatgg tgaccctggg atgcctggtc aagggctatt ccctgagcc     3240 agtgacagtg acctggaact ctggatccct gtccagcggt gtgcacacct tcccagctgt    3300
cctgcagtct gacctctaca ctctgagcag ctcagtgact gtcccctcca gcacctggcc    3360
cagcgagacc gtcacctgca acgttgccca cccggccagc agcaccaagg tggacaagaa    3420
aattgtgccc agggattgtg gttgtaagcc ttgcatatgt acagtcccag aagtatcatc    3480
tgtcttcatc ttccccccaa agcccaagga tgtgctcacc attactctga ctcctaaggt    3540
cacgtgtgtt gtggtagaca tcagcaagga tgatcccgag gtccagttca gctggtttgt    3600
agatgatgtg gaggtgcaca cagctcagac gcaacccgg gaggagcagt tcaacagcac     3660
tttccgctca gtcagtgaac ttcccatcat gcaccaggac tggctcaatg gcaaggagcg    3720
atcgctcacc atcaccatca ccatcaccat caccattaaa ggcctatttt ctttagtttg    3780
aatttactgt tattcggtgt gcatttctat gtttggtgag cggttttctg tgctcagagt    3840
gtgtttattt tatgtaattt aatttctttg tgagctcctg tttagcaggt cgtcccttca    3900
gcaaggacac aaaaagattt taattttatt aaaaaaaaaa aaaaaaaga ccggaattc     3960 gatatcaagc ttatcgacct gcagatcgtt caaacatttg gcaataaagt ttcttaagat    4020
tgaatcctgt tgccggtctt gcgatgatta tcatataatt tctgttgaat tacgttaagc    4080
atgtaataat taacatgtaa tgcatgacgt tatttatgag atgggttttt atgattagag    4140
tcccgcaatt atacatttaa tacgcgatag aaaacaaaat atagcgcgca aactaggata    4200
aattatcgcg cgcggtgtca tctatgttac tagatctcta gagtctcaag cttggcgcgc    4260
ccacgtgact agtggcactg gccgtcgttt tacaacgtcg tgactgggaa accctggcg    4320 ttacccaact taatcgcctt gcagcacatc cccctttcgc cagctggcgt aatagcgaag    4380
aggcccgcac cgatcgccct tcccaacagt tgcgcagcct gaatggcgaa tgctagagca    4440
gcttgagctt ggatcagatt gtcgtttccc gccttcagtt taaactatca gtgtttgaca    4500
ggatatattg gcgggtaaac ctaagagaaa agagcgttta                          4540
```

<210> SEQ ID NO 47
<211> LENGTH: 4056
<212> TYPE: DNA
<213> ORGANISM: Artificial Sequence
<220> FEATURE:
<223> OTHER INFORMATION: Expression cassette number 1108

<400> SEQUENCE: 47

```
gtcaacatgg tggagcacga cacacttgtc tactccaaaa atatcaaaga tacagtctca      60
gaagaccaaa gggcaattga gacttttcaa caaagggtaa tatccggaaa cctcctcgga     120
ttccattgcc cagctatctg tcactttatt gtgaagatag tggaaaagga aggtggctcc     180
tacaaatgcc atcattgcga taaggaaag gccatcgttg aagatgcctc tgccgacagt     240
ggtcccaaag atggaccccc acccacgagg agcatcgtgg aaaagaaga cgttccaacc     300 acgtcttcaa agcaagtgga ttgatgtgat aacatggtgg agcacgacac acttgtctac     360
tccaaaaata tcaaagatac agtctcagaa gaccaaaggg caattgagac ttttcaacaa     420
agggtaatat ccggaaacct cctcggattc cattgcccag ctatctgtca ctttattgtg     480
aagatagtgg aaaaggaagg tggctcctac aaatgccatc attgcgataa aggaaaggcc     540
atcgttgaag atgcctctgc cgacagtggt cccaaagatg acccccacc cacgaggagc     600 atcgtggaaa agaagacgt tccaaccacg tcttcaaagc aagtggattg atgtgatatc     660
tccactgacg taaggcgatga cgcacaatcc cactatcctt cgcaagaccc ttcctctata     720
taaggaagtt catttcattt ggagaggtat taaaatctta ataggttttg ataaaagcga     780
acgtggggaa acccgaacca aaccttcttc taaactctct ctcatctctc ttaaagcaaa     840
cttctctctt gtctttcttg cgtgagcgat cttcaacgtt gtcagatcgt gcttcggcac     900
cagtacaatg gcataccgga agagaggagc aaagcgcgaa acctgccgc aacagaacga     960 gagactgcaa gaaaaagaga tagagaaaga tgtcgacgta acaatggaaa acaagaataa    1020
caataggaaa aacagctgt ccgacaaagt tctgtcccag aaggaggaaa ttatcactga    1080
cgcccaggac gatattaaaa ttgccggaga aataaagaag agctcgaaag aagaatctaa    1140
acagctgctc gaaattctga aaacaaaaga agaccatcag aaagagattc aatatgaaat    1200
tttgcaaaaa acaatacta catttgagtc caaagaaagt atcctcaaga agcttgaaga    1260
cataagaccg gagcaggcaa aaaacagat gaaactcttt cgcattttcg agccaaaaca    1320
gctccctata tatcgcgcca atggcgagaa ggagctacgc aaccggtggt actgaagtt    1380 gaaaaaagac accctgccag atggagatta tgacgtccgg gagtatttcc tcaatctcta    1440
tgatcagatc ctcatcgaaa tgccggacta tctgctcctc aaggacatgg ccgtggagaa    1500
caaaaatagc agagacgccg gcaaagttgt cgactctgag actgccaata tttgtgatgc    1560
catcttccag gatgaggaga ccgagggagt cgtccgtaga ttcatcgctg atatgcggca    1620
acaggtccag gctgatcgta acattgtcaa ttacccttcc atccttcacc ctattgatca    1680
tgcattcaat gagtattttc ttaaccacca gttggtggag ccgctgaaca atgagataat    1740
cttcaattac ataccagaga ggataaggaa tgacgtgaat tacatcctga acatggatat    1800
gaatctgcca tctacagcca ggtatatcag gccaaacttg ttgcaggata gactgaatct    1860
tcacgataat tttgagtccc tgtgggatac catcacaaca tccaactaca ttctggccag    1920
gtccgtcgtt cccgatttga aggagaagga gctggtctcc accgaagcac agatccagaa    1980
aatgagccag gacctgcagc tggaggccct cactattcag agcgagacac agttttttagc    2040 cgggattaac agtcaggctg ccaatgattg tttcaagacc ctcatagccg ccatgctgtc    2100
tcaaagaacc atgtctttgg actttgtgac cacgaactat atgagcctaa tctccggaat    2160
gtggctactt acagtgattc ccaacgatat gttcctccgg gagtcactag tggcctgtga    2220
gctggcgatc atcaacacca tcgtgtatcc agcattcgga atgcagagaa tgcattaccg    2280
gaatggcgac cctcagacac ccttccgat cgcagaacag cagatccaga atttccaggt    2340
ggcgaactgg ctccattttta ttaacaataa cagattcagg caagttgtga ttgatggagt    2400
```

```
tctgaatcag actctgaacg acaatatacg gaatggacag gtcatcaacc agctgatgga    2460
agcattgatg caactcagca gacagcagtt ccccacgatg cctgtggatt acaaacggag    2520
catccaacgg ggcattctgc ttctctccaa taggctgggg cagcttgtcg acttaacccg    2580
actggtctcc tataactacg agacgctaat ggcttgtgtg accatgaaca tgcagcacgt    2640
gcaaaccctg acaactgaga agttgcagct cacttctgtg acttcgcttt gtatgttaat    2700
tggtaacaca accgtgattc cgtccccaca gacactgttc cactactaca acatcaacgt    2760
gaatttccac tccaattata atgagcggat caacgacgcc gtcgccataa ttaccgcagc    2820
aaataggcta atctttatc agaaaaaaat gaagtccata gtggaagact ttctgaaacg    2880
gctccagatt ttcgacgtac cacgagtgcc tgacgaccaa atgtacaggc tgagggatcg    2940
ccttcggctc ttacccgttg aacggagacg gcttgacata ttcaacttga tcctgatgaa    3000
tatggagcag atcgaacgcg cttctgataa gattgctcag ggggttatca tcgcataccg    3060
agatatgcag ctggaacgcg acgagatgta cggatatgtt aatattgcac ggaatcttga    3120
tggctaccag caaattaact tggaggaact catgcgcacc ggtgattacg gacaaattac    3180
gaacatgctt ctcaacaatc aacccgttgc ccttgtgggt gcattgccct tcgttacgga    3240
ctcatccgtg atcagtctaa tcgccaagct cgacgcaacc gtcttcgctc agatagtgaa    3300
gctcaggaaa gttgacacac tgaagcccat actgtacaaa ataaactcgg attccaatga    3360
cttttacctt gtggccaact acgactggat ccccacaagt acaactaagg tctacaaaca    3420
ggtgccacaa ccattcgact ttagagccag catgcacatg ctgacttcta accttacgtt    3480
taccgtctac tctgacctac tgtcatttgt ttcagcggac acggtagagc ccattaacgc    3540
agtcgcattc gacaatatgc gaataatgaa cgagctttaa aggcctattt tctttagttt    3600
gaatttactg ttattcggtg tgcatttcta tgtttggtga gcggttttct gtgctcagag    3660
tgtgtttatt ttatgtaatt taatttcttt gtgagctcct gtttagcagg tcgtcccttc    3720
agcaaggaca caaaagatt ttaattttat taaaaaaaaa aaaaaaaag accgggaatt    3780 cgatatcaag cttatcgacc tgcagatcgt tcaaacattt ggcaataaag tttcttaaga    3840
ttgaatcctg ttgccggtct tgcgatgatt atcatataat ttctgttgaa ttacgttaag    3900
catgtaataa ttaacatgta atgcatgacg ttatttatga gatgggtttt tatgattaga    3960
gtcccgcaat tatacattta atacgcgata gaaaacaaaa tatagcgcgc aaactaggat    4020
aaattatcgc gcgcggtgtc atctatgtta ctagat                              4056
```

<210> SEQ ID NO 48
<211> LENGTH: 55
<212> TYPE: DNA
<213> ORGANISM: Artificial Sequence
<220> FEATURE:
<223> OTHER INFORMATION: IF C160 WA VP6 opt c

<400> SEQUENCE: 48

```
tcgtgcttcg gcaccagtac aatggaggtc ctttatagtc tctccaaaac gctga    55
```

<210> SEQ ID NO 49
<211> LENGTH: 2577
<212> TYPE: DNA
<213> ORGANISM: Artificial Sequence
<220> FEATURE:
<223> OTHER INFORMATION: Expression cassette number 1128

<400> SEQUENCE: 49

-continued

```
gtcaacatgg tggagcacga cacacttgtc tactccaaaa atatcaaaga tacagtctca    60
gaagaccaaa gggcaattga gacttttcaa caaagggtaa tatccggaaa cctcctcgga   120
ttccattgcc cagctatctg tcactttatt gtgaagatag tggaaaagga aggtggctcc   180
tacaaatgcc atcattgcga taaaggaaag gccatcgttg aagatgcctc tgccgacagt   240
ggtcccaaag atggaccccc acccacgagg agcatcgtgg aaaaagaaga cgttccaacc   300
acgtcttcaa agcaagtgga ttgatgtgat aacatggtgg agcacgacac acttgtctac   360
tccaaaaata tcaaagatac agtctcagaa gaccaaaggg caattgagac ttttcaacaa   420
agggtaatat ccgaaaacct cctcggattc cattgcccag ctatctgtca ctttattgtg   480
aagatagtgg aaaaggaagg tggctcctac aaatgccatc attgcgataa aggaaaggcc   540
atcgttgaag atgcctctgc cgacagtggt cccaaagatg gaccccccacc cacgaggagc   600 atcgtggaaa aagaagacgt tccaaccacg tcttcaaagc aagtggattg atgtgatatc   660
tccactgacg taaggatgac gcacaatcc cactatcctt cgcaagaccc ttcctctata   720
taaggaagtt catttcattt ggagaggtat taaaatctta ataggttttg ataaaagcga   780
acgtggggaa acccgaacca aaccttcttc taaactctct ctcatctctc ttaaagcaaa   840
cttctctctt gtctttcttg cgtgagcgat cttcaacgtt gtcagatcgt gcttcggcac   900
cagtacaatg gaggtccttt atagtctctc caaaacgctg aaggacgcta gggacaagat   960
cgtggagggt acactttata gcaatgtcag cgacctaata cagcagttta tcaaatgat   1020 cgttacaatg aatgggaatg atttccaaac tggcggtatt ggtaatctgc ccgtgaggaa   1080
ctggacattc gatttcggcc tgctgggcac gactctcctt aatctcgatg caaattatgt   1140
agaaaacgcc agaacgatta tcgagtactt tatcgatttc attgataacg tttgtatgga   1200
tgagatggcc cgcgagtcac aacggaacgg agttgctcca cagtccgagg cccttcggaa   1260
actcgccggc attaagttca agcgtattaa tttcgacaac tcctccgaat atatagagaa   1320
ctggaacttg cagaatcgtc gacagagaac cggcttcgtg ttccataaac ctaatatctt   1380
tccgtatagc gcctcattca ccctgaatag gagtcagccc atgcacgaca acctcatggg   1440
tacaatgtgg ctgaatgcgg ggagtgaaat acaggtcgcc gggttcgatt actcctgtgc   1500
cattaatgca cccgcaaaca tccagcagtt cgaacatatc gtgcaactaa gacgggctct   1560
cacgaccgcg acaattacac tcctgcccga cgccgagcgc ttctcctttc ccgcgtaat   1620 caactcagct gatggcgcca ccacttggtt cttcaaccct gttatattgc gccctaacaa   1680
cgtagaggtg gagtttctct taaacggaca gatcatcaat acctaccaag ccaggttcgg   1740
cacgattatt gcaagaaatt tcgacgctat caggctgctc ttccaactga tgaggccccc   1800
caatatgact cccgctgtga acgctttgtt tccgcaggct cagcctttcc agcaccacgc   1860
caccgtcggc ttgactcttc gaatagagag cgcggtctgc gaatcagtgc tggcagacgc   1920
caacgagacg ctgctggcaa acgttaccgc cgtgcggcaa gagtatgcca tcccagtagg   1980
gcctgtgttt ccacccggca tgaactggac tgaactaatt actaactata gcccatccag   2040
agaagacaac ttgcagcggg tcttcactgt ggcctctatc cggagtatgt tgatcaagta   2100
gaggcctatt tcttttagtt tgaatttact gttattcggt gtgcatttct atgtttggtg   2160
agcggttttc tgtgctcaga gtgtgtttat tttatgtaat ttaatttctt tgtgagctcc   2220
tgtttagcag gtcgtccctt cagcaaggac acaaaaagat tttaatttta ttaaaaaaaa   2280
aaaaaaaaaa gaccgggaat tcgatatcaa gcttatcgac ctgcagatcg ttcaaacatt   2340
tggcaataaa gtttcttaag attgaatcct gttgccggtc ttgcgatgat tatcatataa   2400
```

```
tttctgttga attacgttaa gcatgtaata attaacatgt aatgcatgac gttatttatg    2460
agatgggttt ttatgattag agtcccgcaa ttatacattt aatacgcgat agaaaacaaa    2520
atatagcgcg caaactagga taaattatcg cgcgcggtgt catctatgtt actagat       2577

<210> SEQ ID NO 50
<211> LENGTH: 59
<212> TYPE: DNA
<213> ORGANISM: Artificial Sequence
<220> FEATURE:
<223> OTHER INFORMATION: IF C160 Rtx VP4 opt c

<400> SEQUENCE: 50
tcgtgcttcg gcaccagtac aatggctagc ctgatctaca gacaactctt gaccaattc    59

<210> SEQ ID NO 51
<211> LENGTH: 3711
<212> TYPE: DNA
<213> ORGANISM: Artificial Sequence
<220> FEATURE:
<223> OTHER INFORMATION: Expression cassette number 1178

<400> SEQUENCE: 51
gtcaacatgg tggagcacga cacacttgtc tactccaaaa atatcaaaga tacagtctca    60
gaagaccaaa gggcaattga gacttttcaa caaagggtaa tatccggaaa cctcctcgga   120
ttccattgcc cagctatctg tcactttatt gtgaagatag tggaaaagga aggtggctcc   180
tacaaatgcc atcattgcga taaggaaag gccatcgttg aagatgcctc tgccgacagt    240
ggtcccaaag atgaccccc acccacgagg agcatcgtgg aaaagaaga cgttccaacc    300 acgtcttcaa gcaagtggat tgatgtgat aacatggtgg agcacgacac acttgtctac    360
tccaaaaata tcaaagatac agtctcagaa gaccaaaggg caattgagac ttttcaacaa   420
agggtaatat ccggaaacct cctcggattc cattgcccag ctatctgtca ctttattgtg   480
aagatagtgg aaaaggaagg tggctcctac aaatgccatc attgcgataa ggaaaggcc    540 atcgttgaag atgcctctgc cgacagtggt cccaaagatg acccccacc cacgaggagc    600 atcgtggaaa agaagacgt tccaaccacg tcttcaaagc aagtggattg atgtgatatc    660
tccactgacg taaggatga cgcacaatcc cactatcctt cgcaagaccc ttcctctata   720
taaggaagtt catttcattt ggagaggtat taaaatctta ataggttttg ataaaagcga    780
acgtggggaa acccgaacca aaccttcttc taaactctct ctcatctctc ttaaagcaaa    840
cttctctctt gtctttcttg cgtgagcgat cttcaacgtt gtcagatcgt gcttcggcac   900
cagtacaatg gctagcctga tctacagaca actcttgacc aattcatatt ctgtggatct   960
tcatgacgaa atcgagcaga ttgggtccga agaccccag aacgtgacca tcaaccctgg   1020 acctttttgct cagacccgct atgcccctgt gaattgggat cacggagaaa tcaacgacag   1080
tacgaccgtc gaaccattc tggacgggcc ataccaaccc accaccttca ccccacctaa    1140
tgattattgg attttaatca actccaacac aaacggagtg gtctacgagt ccactaataa   1200
ctccgatttt tggaccgccg ttgtagccat cgagccacac gtcaatcctg tcgatcgcca   1260
gtatatgata ttcggcgagt ccaaacagtt taacgttttcc aatgacagca caaatggaa    1320 gtttctggag atgtttcgca gctcctctca gaacgaattc tataatagac ggaccctttac   1380 ctccgataca cgactcgtgg gtatttttaa gtacggcggc agggtgtgga catttcacgg   1440 tgaaaccct cgagcaacca ctgactccag tagcactgca aacctgaaca atatatctat   1500
```

| | |
|---|---:|
| taccatccac agcgaattct acataatccc aagatctcag gaaagtaagt gtaacgaata | 1560 |
| tatcaacaac ggactccccc caattcagaa tacacggaac gtggtgcctc tcccactcag | 1620 |
| ttctcggtct atccagtata agagagcaca agtgaatgag gacattattg tgagcaagac | 1680 |
| tagcctttgg aaagaaatgc agtacaacag agacattatc atccggttta agtttgggaa | 1740 |
| ctctatcgtg aagatgggcg gcctggggta caaatggtca gaaatctcat ataaagccgc | 1800 |
| caactatcag tataactact tgagagacgg cgagcaggta accgcccaca caacatgctc | 1860 |
| tgtcaacggc gttaataact ttagctacaa cggaggcttc cttcccaccg acttcggtat | 1920 |
| cagccggtat gaagtcatca aggaaaaattc ttatgtgtac gtagattact gggatgatag | 1980 |
| caaagcgttc cgcaacatgg tgtatgttag gagcctggct gctaatctca attctgtgaa | 2040 |
| gtgtactggt ggatcatatt atttctcaat tcccgtgggg gcttggccag tcatgaatgg | 2100 |
| cggggcagtc tccctccatt ttgctggcgt gacgttgagc actcagttta ccgatttcgt | 2160 |
| gtctctgaac tccctgaggt tccggttttc ccttactgtc gacgagcccc cattcagcat | 2220 |
| tctgcgtaca agaactgtca acctctacgg gttacctgcc gcgaatccaa acaacggcaa | 2280 |
| tgaatactat gaaatttcgg gccgcttctc tttgataagt ctggtaccaa ctaatgacga | 2340 |
| ctatcagaca cccatcatga acagcgtgac tgtcagacag gacctggaaa gacaacttac | 2400 |
| agatctgcgg gaagaattca attctctcag tcaggagatt gcaatggccc aattgataga | 2460 |
| tcttgcccta ctgcctctcg atatgtttag tatgttctcc ggcatcaaat caactataga | 2520 |
| tctgacaaag agcatggcta cttctgtgat gaagaagttc aggaaatcaa aacttgccac | 2580 |
| gagcatatca gaaatgacga actctctgag tgatgcagca tcatcagcgt cacgcaacgt | 2640 |
| ttccattcgg tcgaatctca gcgccatcag caactggaca aacgtgtcca acgacgtcag | 2700 |
| caacgtgacc aactccttga acgatatttc tacccagacg tcaacgatca gtaagaaact | 2760 |
| ccgcttgaaa gaaatgatca cccagactga gggaatgtct ttcgacgaca tttccgccgc | 2820 |
| cgtgctaaaa accaaaatcg atatgtctac tcagatcggc aagaacactc tgccggatat | 2880 |
| cgtaaccgaa gcctccgaaa agtttatccc taagcgcagc tacagaatat tgaaagatga | 2940 |
| cgaggtcatg gagatcaaca cagaagggaa gttcttcgct tataagatca acacctttga | 3000 |
| cgaggttccg tttgacgtca ataagtttgc agagctcgtg acagatagtc cagtgatttc | 3060 |
| tgccatcatt gactttaaga ctttgaagaa cctgaacgac aactatggaa taacacggac | 3120 |
| cgaagcgttg aacctcatta agtccaatcc caatatgttg cgcaatttca ttaaccagaa | 3180 |
| caatccaatc ataagaaata ggattgagca attaatcctg caatgtaaac tctgaaggcc | 3240 |
| tattttcttt agtttgaatt tactgttatt cggtgtgcat ttctatgttt ggtgagcggt | 3300 |
| tttctgtgct cagagtgtgt ttattttatg taatttaatt tctttgtgag ctcctgttta | 3360 |
| gcaggtcgtc ccttcagcaa ggacacaaaa agatttaat tttattaaaa aaaaaaaaa | 3420 |
| aaaagaccgg gaattcgata tcaagcttat cgacctgcag atcgttcaaa catttggcaa | 3480 |
| taaagtttct taagattgaa tcctgttgcc ggtcttgcga tgattatcat ataatttctg | 3540 |
| ttgaattacg ttaagcatgt aataattaac atgtaatgca tgacgttatt tatgagatgg | 3600 |
| gtttttatga ttagagtccc gcaattatac atttaatacg cgatagaaaa caaaatatag | 3660 |
| cgcgcaaact aggataaatt atcgcgcgcg gtgtcatcta tgttactaga t | 3711 |

<210> SEQ ID NO 52
<211> LENGTH: 56
<212> TYPE: DNA
<213> ORGANISM: Artificial Sequence
<220> FEATURE:
<223> OTHER INFORMATION: IF C160 TrSP plus Rtx VP7 opt c

<400> SEQUENCE: 52
tcgtgcttcg gcaccagtac aatggattat attatctatc gtagcctcct catcta 56

<210> SEQ ID NO 53
<211> LENGTH: 2277
<212> TYPE: DNA
<213> ORGANISM: Artificial Sequence
<220> FEATURE:
<223> OTHER INFORMATION: Expression cassette number 1199

<400> SEQUENCE: 53
gtcaacatgg tggagcacga cacacttgtc tactccaaaa atatcaaaga tacagtctca 60
gaagaccaaa gggcaattga gacttttcaa caaagggtaa tatccggaaa cctcctcgga 120
ttccattgcc cagctatctg tcactttatt gtgaagatag tggaaaagga aggtggctcc 180
tacaaatgcc atcattgcga taaaggaaag gccatcgttg aagatgcctc tgccgacagt 240
ggtcccaaag atggaccccc acccacgagg agcatcgtgg aaaaagaaga cgttccaacc 300
acgtcttcaa agcaagtgga ttgatgtgat aacatggtgg agcacgacac acttgtctac 360
tccaaaaata tcaaagatac agtctcagaa gaccaaaggg caattgagac ttttcaacaa 420
agggtaatat ccggaaacct cctcggattc cattgcccag ctatctgtca ctttattgtg 480
aagatagtgg aaaaggaagg tggctcctac aaatgccatc attgcgataa aggaaaggcc 540
atcgttgaag atgcctctgc cgacagtggt cccaaagatg gacccccacc cacgaggagc 600
atcgtggaaa aagaagacgt tccaaccacg tcttcaaagc aagtggattg atgtgatatc 660
tccactgacg taagggatga cgcacaatcc cactatcctt cgcaagaccc ttcctctata 720
taaggaagtt catttcattt ggagaggtat taaaatctta ataggttttg ataaaagcga 780
acgtggggaa acccgaacca aaccttcttc taaactctct ctcatctctc ttaaagcaaa 840
cttctctctt gtctttcttg cgtgagcgat cttcaacgtt gtcagatcgt gcttcggcac 900
cagtacaatg gattatatta tctatcgtag cctcctcatc tacgtggccc tttttgccct 960
gaccagggcc cagaactatg gcctgaactt accaatcacc ggttcaatgg ataccgttta 1020
cgctaattcc actcaagagg ggatatttct gacaagtacc ctgtgcctgt attatccaac 1080
agaagcctct acccagatca atgatgggga gtggaaggat agtctctcac agatgttcct 1140
aaccaagggc tggcccaccg gttccgtcta cttcaaggaa tactctagta ttgtcgactt 1200
ctcagttgac ccccagcttt attgcgacta caacctggta cttatgaaat acgaccagaa 1260
cctggagctg gatatgtccg agctggctga cctgatcctc aatgagtggc tgtgcaaccc 1320
catggacatc acattatatt actaccagca gtctggagaa tccaacaagt ggatcagtat 1380
gggctcaagt tgcaccgtga aggtgtgtcc cttgaacacc caaatgctgg gcattggttg 1440
tcagacaact aatgtggatt cgtttgaaat ggtagccgaa aacgagaagc tggctatagt 1500
ggacgtagtc gatgggatta accacaagat caatctgact accaccactt gtaccatcag 1560
aaactgtaaa aagctcggcc cccgggagaa cgtcgccgtg atccaggtgg gggggagcaa 1620
tgtgctcgac attactgccg accctaccac caatccacag acggaacgga tgatgagagt 1680
caactggaag aaatggtggc aggtctttta taccattgtg gactacatta accagattgt 1740
gcaagtcatg agtaaacggt ccagatccct gaactcagca gccttctatt atcgcgttta 1800
gaggcctatt ttctttagtt tgaatttact gttattcggt gtgcatttct atgtttggtg 1860

-continued

```
agcggttttc tgtgctcaga gtgtgtttat tttatgtaat ttaatttctt tgtgagctcc  1920
tgtttagcag gtcgtccctt cagcaaggac acaaaaagat tttaatttta ttaaaaaaaa  1980
aaaaaaaaaa gaccgggaat tcgatatcaa gcttatcgac ctgcagatcg ttcaaacatt  2040
tggcaataaa gtttcttaag attgaatcct gttgccggtc ttgcgatgat tatcatataa  2100
tttctgttga attacgttaa gcatgtaata attaacatgt aatgcatgac gttatttatg  2160
agatgggttt ttatgattag agtcccgcaa ttatacattt aatacgcgat agaaaacaaa  2220
atatagcgcg caaactagga taaattatcg cgcgcggtgt catctatgtt actagat     2277
```